(12) United States Patent
Delgado Oyarzo et al.

(10) Patent No.: US 11,318,133 B2
(45) Date of Patent: May 3, 2022

(54) MODULATORS OF INTEGRATED STRESS RESPONSE PATHWAY

(71) Applicant: Praxis Biotech LLC, San Francisco, CA (US)

(72) Inventors: Luz Marina Delgado Oyarzo, Santiago (CL); Gonzalo Andrés Ureta Díaz, Santiago (CL); Brahmam Pujala, Greater Noida (IN); Dayanand Panpatil, Noida (IN); Sebastian Bernales, Piedmont, CA (US)

(73) Assignee: PRAXIS BIOTECH LLC, San Francisco, CA (US)

( * ) Notice: Subject to any disclaimer, the term of this patent is extended or adjusted under 35 U.S.C. 154(b) by 23 days.

(21) Appl. No.: 16/899,521

(22) Filed: Jun. 11, 2020

(65) Prior Publication Data

US 2020/0390759 A1    Dec. 17, 2020

Related U.S. Application Data

(60) Provisional application No. 62/860,683, filed on Jun. 12, 2019.

(51) Int. Cl.

| | | |
|---|---|---|
| *C07D 401/12* | (2006.01) | |
| *A61K 31/496* | (2006.01) | |
| *A61K 31/4709* | (2006.01) | |
| *A61K 31/47* | (2006.01) | |
| *C07K 14/435* | (2006.01) | |
| *A61K 45/06* | (2006.01) | |
| *A01N 43/60* | (2006.01) | |
| *A01N 43/42* | (2006.01) | |
| *C07D 215/06* | (2006.01) | |

(52) U.S. Cl.
CPC ............ *A61K 31/496* (2013.01); *A01N 43/42* (2013.01); *A01N 43/60* (2013.01); *A61K 31/47* (2013.01); *A61K 31/4709* (2013.01); *A61K 45/06* (2013.01); *C07D 215/06* (2013.01); *C07D 401/12* (2013.01); *C07K 14/435* (2013.01)

(58) Field of Classification Search
CPC .. A61K 31/496; A61K 31/47; A61K 31/4709; C07D 215/06; C07D 401/12; C07D 14/435; C07K 14/435; A01N 43/42; A01N 43/60
See application file for complete search history.

(56) References Cited

U.S. PATENT DOCUMENTS

| | | | |
|---|---|---|---|
| 5,096,901 A | 3/1992 | Ward | |
| 9,382,232 B2 * | 7/2016 | Gong | ............ A61K 31/5377 |
| 10,683,278 B2 * | 6/2020 | Ding | ............ A61P 35/00 |
| 11,166,942 B2 | 11/2021 | Delgado Oyarzo et al. | |
| 2004/0138286 A1 | 7/2004 | Imazaki | |
| 2005/0197350 A1 | 9/2005 | Sekiguchi | |
| 2010/0035898 A1 | 2/2010 | Beattie | |
| 2011/0039860 A1 | 2/2011 | Yang | |
| 2011/0300575 A1 | 12/2011 | Imataka | |
| 2015/0314018 A1 | 11/2015 | Sahin | |
| 2016/0318931 A1 | 11/2016 | Hadida-ruah | |
| 2017/0342020 A1 | 11/2017 | Walter | |
| 2019/0177310 A1 | 6/2019 | Bernales | |
| 2020/0101047 A1 | 4/2020 | Delgado Oyarzo | |
| 2020/0270232 A1 | 8/2020 | Bernales | |
| 2021/0317102 A1 | 10/2021 | Delgado Oyarzo et al. | |

FOREIGN PATENT DOCUMENTS

| | | |
|---|---|---|
| WO | 199906387 A2 | 2/1999 |
| WO | 2010068881 A1 | 6/2010 |
| WO | 2011095450 A1 | 8/2011 |
| WO | 2014144952 A2 | 9/2014 |
| WO | 2017193030 A1 | 11/2017 |
| WO | 2017193034 A1 | 11/2017 |
| WO | 2017193041 A1 | 11/2017 |
| WO | 2017193063 A1 | 11/2017 |
| WO | 2017212423 A1 | 12/2017 |
| WO | 2017212425 A1 | 12/2017 |
| WO | 2018225093 A1 | 12/2018 |
| WO | 2019008506 A1 | 1/2019 |
| WO | 2019008507 A1 | 1/2019 |
| WO | 2019032743 A1 | 2/2019 |
| WO | 2019046779 A1 | 3/2019 |
| WO | 2019090074 A1 | 5/2019 |
| WO | 2019090076 A1 | 5/2019 |
| WO | 2019090078 A1 | 5/2019 |
| WO | 2019090081 A1 | 5/2019 |
| WO | 2019090082 A1 | 5/2019 |
| WO | 2019090085 A1 | 5/2019 |
| WO | 2019090088 A1 | 5/2019 |
| WO | 2019090090 A1 | 5/2019 |
| WO | 2919090069 A1 | 5/2019 |
| WO | 2019118785 A2 | 6/2019 |
| WO | 2019183589 A1 | 9/2019 |
| WO | 2019193540 A1 | 10/2019 |
| WO | 2019193541 A1 | 10/2019 |
| WO | 2020012339 A1 | 1/2020 |
| WO | 2020031107 A1 | 2/2020 |
| WO | 2020077217 A1 | 4/2020 |
| WO | 2020167994 A1 | 8/2020 |
| WO | 2020168011 A | 8/2020 |
| WO | 2020176428 A1 | 9/2020 |
| WO | 2020181247 A1 | 9/2020 |
| WO | 2020216764 A1 | 10/2020 |
| WO | 2020216766 A1 | 10/2020 |
| WO | 2020223536 A1 | 11/2020 |
| WO | 2020223538 A1 | 11/2020 |
| WO | 2020252205 A1 | 12/2020 |
| WO | 2020252207 A1 | 12/2020 |

OTHER PUBLICATIONS

US 11,198,688 B2, 12/2021, Bernales (withdrawn)
Wei, Cell Death andDisease, (2021)12:334, 1-14, 2021. (Year: 2021).*

(Continued)

*Primary Examiner* — D Margaret M Seaman
(74) *Attorney, Agent, or Firm* — Morrison & Foerster LLP

(57) ABSTRACT

The present disclosure relates generally to therapeutic agents that may be useful as modulators of Integrated Stress Response (ISR) pathway.

45 Claims, 6 Drawing Sheets

(56) References Cited

OTHER PUBLICATIONS

Pitale, Frontiers in Cellular Neuroscience, Dec. 2017, vol. 11, article 410, 1-8. (Year: 2017).*
Colla, Frontiers in Clellular Neuroscience, Dec. 2017, vol. 8, article 2202, 1-14. (Year: 2017).*
Adams, C.M. et al. (May 2017). "Role of ATF4 in Skeletal Muscle Atrophy," Curr Opin. Clin. Nutr. Metab. Care 20 (3):164-168.
Adomavicius, T. et al. (e-pub. Dec. 20, 2018). "The Structural Basis of Translational Control by eIF2 Phosphorylation", Article, 46 pages (including Supplementary Material begins at p. 30 of 46).
Al-Chalabi, A. et al. (2012). "The Genetics and Neuropathology of Amyotrophic Lateral Sclerosis," Acta Neuropathol 124(3):339-352.
Anastassiadis, T. et al. (2011). "Comprehensive Assay of Kinase Catalytic Activity Reveals Features of Kinase Inhibitor Selectivity," Nat Biotechnol. 29(11):1039-1045.
Ardiles, A.O. et al., (Oct. 15, 2014), "Pannexin 1 Regulates Bidirectional Hippocampal Synaptic Plasticity In Adult Mice," Front Cell Neurosci. 8(326):1-11.
ATCC Product Sheet (2 018). "CT26.WT (ATCC CRL-2638)", located at www.atc.org, last visited on Jun. 27, 2019, 3 pages.
Axten, J.M. et al. (2012). "Discovery of 7-methyl-5-(1-{[3-(trifluoromethyl)phenyl]acetyl}2,3-dihydro-1H-indol-5-yl)-7H-p yrrolo[2,3-d]pyrimidin-4-amine (GSK2606414), a potent and selective first-in-class inhibitor of protein kinase R (PKR)-like endoplasmic reticulum kinase (PERK)," J Med Chem. 55(16):7193-7207.
Bain, J. et al. (2003). "The Specificities of Protein Kinase Inhibitors: An Update," Biochem J. 371(Pt 1):199-204.
Baird, T.D. et al. (2012). "Eukaryotic Initiation Factor 2 Phosphorylation and Translationai Control in Metabolism," Adv Nutr. 3(3):307-321.
Bartsch, D. et al. (1995). "Aplysia CREB2 Represses Long-Term Facilitation: Relief of Repression Converts Transient Facilitation Into Long-Term Functional and Structural Change," Cell 83(6):979-992.
Beck, D. et al. (2013). "Vemurafenib Potently Induces Endoplasmic Reticulum Stress-Mediated Apoptosis in BRAFV600E Melanoma Cells," Sci Signal. 6(260):ra7, 12 pages.
BI, M. et al. (2005). "ER Stress-Regulated Translation Increases Tolerance to Extreme Hypoxia and Promotes Tumor Growth," EMBO J. 24(19):3470-3481.
BioCare Medical, MM620L "Mouse-on-Mouse HRP-Polymer: Mouse Antibodies on Mouse Tissues Polymer Detection Component, Control No. 902-MM620-090617", Biocare Medical, located at https://biocare.net/wp-content/uploads/MM620.pdf, lasted visited Feb. 28, 2019, 2 pages.
Bogorad, A.M. et al. (Feb. 9, 2018). "eIF2B Mechanisms of Action and Regulation: A Thermodynamic View", Biochemistry 57:1426-1435.
Borck, G. et al. (2012). "Eif2gamma Mutation That Disrupts Eif2 Complex Integrity Links Intellectual Disability To Impaired Translation Initiation," Mol Cell 48(4):641-646.
Brazeau, J.F. (2014). "Triazolo[4,5-d]pyrimidine Derivatives as Inhibitors of GCN2m," ACS Med Chem Lett. 5 (4):282-283.
Cao, Y. et al. (2019). "ER Stress-Induced Mediator C/EBP Homologous Protein Thwarts Effector T Ceil Activity In Tumors Through T-Bet Repression," Nature Communications 10:1280, 15 pages.
Cell Signaling Technology, catalog No. 11815 (Nov. 26, 2018). "ATF-4 (D4B8) Rabbit mAb", located at www.cellsignal.com, last visited on Jun. 27, 2019, 2 pages.
Chang, R.C. et al. (2002). "involvement of Double-Stranded RNA-Dependent Protein Kinase and Phosphorylation of Eukaryotic Initiation Factor-2alpha in Neuronal Degeneration," J Neurochem 83(5):1215-1225.
Chen, A. et al. (2003), "Inducible Enhancement of Memory Storage and Synaptic Plasticity in Transgenic Mice Expressing an Inhibitor of ATF4 (CREB-2) and C/EBP Proteins," Neuron 39(4):655-669.
Chen, H.M. et al. (2008). "A Chemical Compound Commonly Used to inhibit PKR, {8-(imidazol-4-ylmethylene)-6H-azolidino[5,4-g] benzothiazol-7-one}. Protects Neurons By Inhibiting Cyolin-Dependent Kinase," Eur J Neurosci. 28 (10):2003-2016, 26 pages.

Chen, L. et al. (Aug. 25, 2012). "Tumor Suppression By Small Molecule Inhibitors of Translation Initiation," Oncotarget 3(8):869-881.
Chou, A. et al. (e-pub. Jul. 10, 2017). "Inhibition of the Integrated Stress Response Reverses Cognitive Deficits After Traumatic Brain Injury", PNAS USA 114(31):E6420-E6426.
Clavarino, G. et al. (2016). "Unfolded Protein Response Gene GADD34 is Overexpressed in Rheumatoid Arthritis and Related to the Presence of Circulating Anti-Citrullinated Protein Antibodies," Autoimmunity 49(3):172-178.
Cnop, M. et al. (Feb. 9, 2007). "Selective Inhibition of Eukaryotic Translation Initiation Factor 2 Alpha Dephosphorylation Potentiates Fatty Acid-Induced Endoplasmic Reticulum Stress and Causes Pancreatic Beta-Cell Dysfunction and Apoptosis," J. Biol. Chem. 282(6): 3989-3997.
Costa-Mattioli, M. et al. (2005). "Translational Control of Hippocampal Synaptic Plasticity and Memory by the eIF2alpha Kinase GCN2," Nature 436(7054):1166-1173, (includes Supplementary Material), 28 pages.
Costa-Mattioli, M. et al. (2007). "eIF2alpha Phosphorylation Bidirectionally Regulates The Switch From Short- To Long-Term Synaptic Plasticity and Memory," Ceil 129(1):195-206, (includes Supplementary Material), 23 pages.
Costa-Mattioli, M. et al. (2009). "Translational Control of Long-Lasting Synaptic Plasticity and Memory," Neuron 61(1):10-26.
Costa-Mattioli, M. et al. (2009). "Translational Regulatory Mechanisms in Synaptic Plasticity and Memory Storage," Prog Mol Biol Transl Sci 90:293-311.
Couturier, J. et al. (2012). "Pharmacological Inhibition of PKR in Appsweps1de9 Mice Transiently Prevents Inflammation at 12 Months of Age But Increases Abeta42 Levels in the Late Stages of the Alzheimer's Disease," Curr Alzheimer Res. 9(3):344-360.
Couturier, J. et al. (Jan. 8, 2010). "interaction of Double-Stranded RNA-Dependent Protein Kinase (PKR) with the Death Receptor Signaling Pathway in Amyloid Beta (Abeta)-Treated Cells and in APPSLPS1 Knock-in Mice," J Biol Chem. 285(2):1272-1282.
De Benedetti, A. (2004). "EIF-4E Expression and its Role In Malignancies and Metastases," Oncogene 23 (18):3189-3199.
Deng, J. et al. (2004). "Translational Repression Mediates Activation of Nuclear Factor Kappa B By Phosphorylated Translation Initiation Factor 2," Mol. Cell Biol. 24(23):10161-10168.
Dermer, G.B. et al. (Mar. 1994). "Another Anniversary for the War on Cancer," Bio/Technology 12:320, 1 page.
Dey, S et al. (2015). "ATF4-Dependent Induction of Heme Oxygenase 1 Prevents Anoikis and Promotes Metastasis," J Clin. invest. 125(7):2592-2608.
Dezwaan-McCabe, D. et al. (2013). "The Stress-Regulated Transcription Factor CHOP Promotes Hepatic Inflammatory Gene Expression, Fibrosis, and Oncogenesis," PLoS Genet. 9(12):e1003937, 12 pages.
Di Marco, S. et al. (Jun. 12, 2012). "The Translation Inhibitor Pateamine A Prevents Cachexia-Induced Muscle Wasting in Mice," Nature Communications 3(896):1-12.
Di Prisco, G.V. et al., (Aug. 2014). "Translational Control of MGluR-Dependent Long-Term Depression and Object-Place Learning by eIF2α," Nat Neurosci. 17(8): 1073-1082, 29 pages.
Ebert, S.M. (Oct. 16, 2015, Published, JBC Papers in Press, Sep. 3, 2015). "Identification and Small Molecule Inhibition of an Activating Transcription Factor 4 (ATF4)-dependent Pathway to Age-Related Skeletal Muscle Weakness and Atrophy," 290(42):25497-25511.
Ebert, S.M. et al. (Apr. 2010, e-pub. Mar. 2, 2010). "The Transcription Factor ATF4 Promotes Skeletal Myofiber Atrophy During Fasting," Mol. Endocrinol. 24(4):790-799.
Ebert, S.M. et al. (Aug. 10, 2012). "Stress-induced Skeletal Muscle Gadd45a Expression Reprograms Myonuclei and Causes Muscle Atrophy," Journal of Biology Chemistry 287(33):27290-27301.
Ebert, S.M. et al. (Feb. 28, 2020, e-pub. Jan. 17, 2020). "Activating Transcription Factor 4 (ATF4) Promotes Skeletal Muscle Atrophy By Forming A Heterodimer With The Transcriptional Regulator C/EBPb," JBC (The Journal of Biological Chemistry) 295:2787-2803, 30 pages.

(56) References Cited

OTHER PUBLICATIONS

Eley, H.L. (2008, e-pub. Dec. 18, 2007). "Increased Expression of Phosphorylated Forms of RNA-Dependent Protein Kinase and Eukaryotic Initiation Factor 2α May Signal Skeletal Muscle Atrophy in Weight-Losing Cancer Patients," British Journal of Cancer 98:443-449.
Farook, J.M. et al. (2013). "GADD34 Induces Cell Death Through Inactivation of Akt Following Traumatic Brain Injury," Cell Death Dis 4:e754, 9 pages.
Fels, D.R. et al. (2006). "The PERK/eIF2alpha/ATF4 Module of the UPR in Hypoxia Resistance and Tumor Growth," Cancer Biol Ther 5(7):723-728.
Freshney, R.I. et al. (1983). Culture of Animal Cells, A Manual of Basic Technique, Alan R. Liss, Inc., 1983, New York, p. 4. and pp. 129-133, 9 pages.
Fuster, J. J. et al. (Mar. 19, 2019). "Integrated Stress Response Inhibition in Atherosclerosis", JACC 73 (10):1170-1172.
Gelman, M.S. et al. (2002). "A Principal Role For The Proteasome in Endoplasmic Reticulum-Associated Degradation of Misfolded Intracellular Cystic Fibrosis Transmembrane Conductance Regulator," J Biol Chem. 277 (14):11709-11714.
Golub, T.R. et al. (1999). "Molecular Classification of Cancer: Class Discovery and Class Prediction by Gene Expression Monitoring," Science 286:531-537.
Gordiyenko, Y. et al. (e-pub. Dec. 21, 2018). "Structural Basis for the inhibition of Translation Through eiF2α Phosphorylation", Article, 37 pages.
Grolleau, A. et al. (2000). "Impaired Translational Response and Increased Protein Kinase PKR Expression In T Cells From Lupus Patients," J. Clin. Invest. 106(12):1561-1568.
Guppy, M. et al. (2005). "Metabolic Depression: A Response of Cancer Cells to Hypoxia?," Comp. Biochem. Physiol. B Biochem. Mol. Biol. 140(2): 233-239.
Halliday, M. et al. (2015, e-pub. Mar. 5, 2015). "Partial Restoration of Protein Synthesis Rates by the Small Molecule ISRIB Prevents Neurodegeneration without Pancreatic Toxicity", Cell Death Dis 6:e1672, 9 pages.
Halliday, M. et al. (2017). "Repurposed Drugs Targeting eIF2a-P-Mediated Translational Repression Prevent Neurodegeneration in Mice", Brain 16 pages.
Han, S. et al. (2006). "Macrophage insulin Receptor Deficiency increases ER Stress-Induced Apoptosis and Necrotic Core Formation in Advanced Atherosclerotic Lesions," Cell Metab. 3(4):257-266.
Harding, H.P. et al. (2000). "Perk is Essential for Translational Regulation and Cell Survival During the Unfolded Protein Response," Mol. Cell 5(5):897-904.
Harding, H.P. et al. (2000). "Regulated Translation initiation Controls Stress-induced Gene Expression in Mammalian Cells," Mol. Cell 6(5):1099-1108.
Harding, H.P. et al. (Mar. 2003). "An Integrated Stress Response Regulates Amino Acid Metabolism and Resistance to Oxidative Stress," Mol. Cell 11(3):619-633.
Hearn, B.R. et al. (2016). "Structure-Activity Studies of Bis-O-Arylglycolamides: Inhibitors of the Integrated A Stress Response," Chem. Med. Chem. 11:870-880.
Hernandez, G. et al. (Jan. 8, 2020). "Pancreatitis is an FGF21-Deficient State That is Corrected by Replacement Therapy," Sci. Transl. Med. 12:eaay5186, 12 pages.
Hinnebusch, A.G. (2005). "Translational Regulation of GCN4 and the General Amino Acid Control of Yeast," Annu. Rev Microbiol. 59:407-450.
Hinnebusch, A.G. et al. (May 5, 2015). "Blocking Stress Response for Better Memory?," Science 348 (6238):967-968.
Hodgson, R.E. (Apr. 1, 2019, e-pub. Feb. 6, 2019). "Cellular eIF2B Subunit Localization: Implications for the Integrated Stress Response and its Control by Small Molecule Drugs", Mol. Biol. Cell 30:942-958.

Hosoi, T. et al. (2016, e-pub. Aug. 12, 2016), "Unique Pharmacological Property of ISRIB in Inhibition of AB-Induced Neuronal Cell Death", J. Pharm. Sci. 131(2016):292-295.
Igarashi, T. et al. (2007, e-pub. Feb. 12, 2007). "Clock and ATF4 Transcription System Regulates Drug Resistance in Human Cancer Cell Lines," Oncogene 26:4749-4760.
Jackson, R.J. et al. (2010). "The Mechanism of Eukaryotic Translation Initiation and Principles of its Regulation," Nat. Rev. Mol. Cell Biol. 11(2):113-127.
Jammi, N.V. et al. (2003). Small Molecule Inhibitors of the RNA-Dependent Protein Kinase, Biochem. Biophys. Res. Commun. 308(1):50-57.
Jiang, H.Y. et al. (2005). "GCN2 Phosphorylation of eIF2alpha Activates NF-kappaB in Response to UV Irradiation," Biochem. J. 385(Pt 2):371-380.
Jiang, Z. et al. (Feb. 17, 2010). "eIF2α Phosphorylation-Dependent Translation in CA1 Pyramidal Ceils Impairs Hippocampal Memory Consolidation Without Affecting General Translation," J. Neurosci. 30(7):2582-2594.
Kaidanovich-Belinin, O. et al. (2011). "Assessment of Social Interaction Behaviors," J. Vis. Exp. 48:e2473, 6 pages.
Kammer, G.M., et al. (May 2002). "Abnormal T Cell Signal Transduction in Systemic Lupus Erythematosus," Arthritis Rheum. 46(5):1139-1154.
Kashiwagi, K et al. (2016). "Crystal Structure of Eukaryotic Translation Initiation Factor 2B", Nature 000(00):1-17.
Kashiwagi, K et al. (May 3, 2019). "Structural Basis for eIF2B Inhibition in Integrated Stress Response", Science 364 (6439):495-499.
Kim, H.J., et al. (2014). "Therapeutic Modulation of Eif2alpha Phosphorylation Rescues TDP-43 Toxicity in Amyotrophic Lateral Sclerosis Disease Models," Nat Genet. 46(2):152-160, 25 pages.
Kim, S.H. et al. (2000). "Human Breast Cancer Cells Contain Elevated Levels and Activity of The Protein Kinase, PKR," Oncogene 19(27):3086-3094.
Kim, S.H., et al. (2002). "Neoplastic Progression in Melanoma and Colon Cancer is Associated With Increased Expression and Activity of The Interferon-Inducible Protein Kinase, PKR," Oncogene 21(57):8741-8748.
Krishnamoorthy, T. et al. (Aug. 2001). "Tight Binding of The Phosphorylated Alpha Subunit of Initiation Factor 2 (eIF2alpha) to the Regulatory Subunits of Guanine Nucleotide Exchange Factor eIF2B is Required For Inhibition of Translation Initiation," Mol. Cell Biol. 21(15):5018-5030.
Kusio-Kobialka, M. et al. (Nov. 1, 2012). "The PERK-eIF2alpha Phosphorylation Arm is A Pro-Survival Pathway of BCR-ABL Signaling and Confers Resistance to Imatinib Treatment in Chronic Myeloid Leukemia Cells," Cell Cycle 11(21):4069-4078.
Lawrence De Koning, A.B., et al. (2003). "Hyperhomocysteinemia and Its Role in The Development of Atherosclerosis," Clin. Biochem. 36(6):431-441.
Layzer (1996). "Degenerative Diseases of the Nervous System," Cecil Textbook of Medicine, 20th Edition, vol. 2, pp. 2050-2057.
Lehman, S.L. et al. (Jun. 30, 2015). "Signaling Through Alternative Integrated Stress Response Pathways Compensates for GCN2 Loss in a Mouse Model of Soft Tissue Sarcoma", Sci Rep 5(11781):1-13.
Li, J. et al. (2018). "Deletion of Tmtc4 Activates The Unfolded Protein Response and Causes Postnatal Hearing Loss," J. Clin. Invest 128(11):5150-5162.
Li, K. et al. (2016). "Liver-Specific Gene Inactivation of the Transcription Factor ATF4 Alleviates Alcoholic Liver Steatosis in Mice," J. Biol Chem. 291 (35):18536-18546.
Lin, Y. et al. (Sep. 3, 2014). "impaired Eukaryotic Translation Initiation Factor 2B Activity Specifically in Oligodendrocytes Reproduces the Pathology of Vanishing White Matter Disease in Mice", J Neurosci 34(36):12182-12191.
Lobo, M.V. et al. (2000). "Levels, Phosphorylation Status and Cellular Localization of Translational Factor eIF2 in Gastrointestinal Carcinomas," Histochem. J. 32(3):139-150.
Lopez, J. et al. (Feb. 11, 2015). "Memory Retrieval Requires Ongoing Protein Synthesis and NMDA Receptor Activity-Mediated AMPA Receptor Trafficking," J. Neurosci. 35(6):2465-2475.

(56) References Cited

OTHER PUBLICATIONS

Lu, M., et al. (2014). "Opposing Unfolded-Protein-Response Signals Converge on Death Receptor 5 to Control Apoptosis," Science 345(6192):98-101.
Lu, P.D. et al. (2004, e-pub. Oct. 11, 2004). "Translation Reinitiation at Alternative Open Reading Frames Regulates Gene Expression in an Integrated Stress Response," J. Cell Biol. 167(1):27-33.
Ma, T., et al. (2013). "Suppression of elF2alpha Kinases Alleviates Alzheimer's Disease-Related Plasticity and Memory Deficits," Nat. Neurosci. 16(9):1299-1305.
Ma, X.H., et al. (2014). "Targeting ER Stress-Induced Autophagy Overcomes BRAF Inhibitor Resistance in Melanoma," J. Clin. Invest. 124(3):1406-1417.
Marco, S.D. et al. (2012, e-pub. Jun. 12, 2012) "The Translation Inhibitor Pateamine A Prevents Cachexia-Induced Muscle Wasting in Mice," Nat. Commun. 12(3):896, 12 pages.
Mihailovich, M., et al. (2007, e-pub. Apr. 16, 2007). "Complex Translational Regulation of BACE1 Involves Upstream Augs and Stimulatory Elements Within the 5' Untranslated Region," Nucleic Acids Res. 35(9):2975-2985.
Milani, M. et al. (May 15, 2009). "The Role of ATF4 Stabilization and Autophagy in Resistance of Breast Cancer Cells Treated with Bortezomib," Cancer Res. 69(10):4415-4423.
Moller, J.T. et al. (Mar. 21, 1998). "Long-Term Postoperative Cognitive Dysfunction in The Elderly ISPOCD1 Study. ISPOCD investigators, International Study of Post-Operative Cognitive Dysfunction," Lancet 351(9106):857-861.
Moreno, J.A. et al. (2013). "Oral Treatment Targeting The Unfolded Protein Response Prevents Neurodegeneration and Clinical Disease in Prion-Infected Mice," Sci. Transl. Med. 5(206):206ra138, 11 pages.
Moreno, J.A. et al. (May 24, 2012). "Sustained Translational Repression By elF2alpha-P Mediates Prion Neurodegeneration," Nature 485(7399):507-511.
Munn, D.H., et al. (May 2005). "GCN2 kinase in T Cells Mediates Proliferative Arrest and Anergy Induction in Response To Indoleamine 2,3-Dioxygenase," Immunity 22(5):633-642.
Nagaraju, K. et al. (Jun. 2005). "Activation of the Endoplasmic Reticulum Stress Response in Autoimmune Myositis: Potential Role in Muscle Fiber Damage and Dysfunction," Arthritis Rheum. 52(6):1824-1835.
Nagasawa, I. et al. (2017). "BRAF-Mutated Cells Activate GCN2-Mediated Integrated Stress Response as A Cytoprotective Mechanism in Response to Vemurafenib," Biochem. Biophys. Res. Commun. 482(4):1491-1497.
Nakamura, T. et al. (Feb. 2014). "Small-Molecule Inhibitors of PKR Improve Glucose Homeostasis in Obese Diabetic Mice," Diabetes 63(2):526-534.
Namba, T. et al. (2007). "Up-Regulation of 150-kDa Oxygen-Regulated Protein by Celecoxib in Human Gastric Carcinoma Cells," Mol. Pharmacol. 71(3):860-870.
Nguyen, H.G. (May 2, 2018). "Development of A Stress Response Therapy Targeting Aggressive Prostate Cancer," Sci. Transl. Med. 10(439):1-24, 24 pages.
Novoa, I. et al. (2003). "Stress-Induced Gene Expression Requires Programmed Recovery From Translational Repression," EMBO J. 22(5):1180-1187.
O'Connor, T. et al. (Dec. 26, 2008). "Phosphorylation of the Translation Initiation Factor Eif2alpha Increases BACE1 Levels and Promotes Amyloidogenesis," Neuron 60(6):988-1009, 42 pages.
Ohno, M. (Apr. 2014). "Roles of elF2alpha Kinases in the Pathogenesis of Alzheimer's Disease", Front Mol Neurosci 7(22):1-8.
Oliveira, M.M. et al. (2019). "The elF2B Stimulating Drug ISRIB Alleviates Brain Translational Repression and Rescues Long-Term Memory in Alzheimer's Disease Models", Article, 44 pages,
Onat, U.I. et al. (Mar. 19, 2019), "Intercepting the Lipid-Induced Integrated Stress Response Reduces Atherosclerosis," JACC 73(10):1149-1169.

Oyadomari, S. et al. (2008). "Dephosphorylation of Translation Initiation Factor 2alpha Enhances Glucose Tolerance and Attenuates Hepatosteatosis in Mice," Cell Metab. 7(6):520-532.
Page, G. et al. (2006). Activated Double-Stranded RNA-Dependent Protein Kinase and Neuronal Death in Models of Alzheimer's Disease, Neuroscience 139(4):1343-1354.
Pakos-Zebrucka, K. et al. (2016, e-pub. Sep. 14, 2016). "The Integrated Stress Response", EMBO Reports 17(10):1374-1395.
Palam, L.R. et al. (2015, e-pub. Oct. 15, 2015), "integrated Stress Response is Critical for Gemcitabine Resistance in Pancreatic Ductal Adenocarcinoma", Cell Death and Disease 6(e1913):1-13.
Palam, L.R. et al. (Apr. 1, 2011). "Phosphorylation of elF2 Facilitates Ribosomal Bypass of an Inhibitory Upstream ORF to Enhance CHOP Translation", J Biol Chem. 286(13):10939-10949.
Peel, A.L. et al. (2001). "Double-Stranded RNA-Dependent Protein Kinase, PKR, Binds Preferentially to Huntington's Disease (HD) Transcripts and is Activated in HD Tissue," Hum Mol Genet. 10(15):1531-1518.
Pike, L.R. et al. (2013). "Transcriptional Up-Regulation of ULK1 By ATF4 Contributes to Cancer Cell Survival," Biochem J 449(2):389-400.
PubChem (Aug. 6, 2016)."N-[[4-[[2-(4-Chlorophenoxy)acetyl]amino]cyclohexyl]methyl]-2-(4-chlorophenyl) acetamide," PubChem-CID: 121258884; 9 pages.
PubChem (Jan. 25, 2012). "AKOS007163870 (N-[2-(4-Chlorophenoxy)ethyl]-1-(3-phenoxypropanoyl)piperidine-4-carboxamide) (PubChemCID:55856026)," located at https://pubchem.ncbi.nlm.nih.gov/compound/55856026, last visited Jun. 27, 2019, 10 pages.
PubChem (Jul. 30, 2007). "N-(1-Benzylpiperidin-4-yl)-1-cyclopropyl-6,7-difluoro-8-methoxy-4-oxoquinoline-3-carboxamide," PubChem CID 16417729, 13 pages.
PubChem (Jul. 9, 2005). "ISRIB (PubChemCID:1011240)," located at: https://pubchem.ncbi.nlm.nih.gov/compound/1011240, lasted visited Jun. 27, 2019, 17 pages.
PubChem (Nov. 29, 2013). "ZINC10313554 MCULE-8385854081 (N-[2-[[2-(2,4-Dichlorophenoxy)acetyl]amino]ethyl]quinoline-2-carboxamide) (PubChemCID:71946601)", 4 pages.
PUBCHEM-CID: 125480315 Create Date: Apr. 10, 2017 pp. 1-5; p. 2 structure.
PUBCHEM-CID: 86000498 Create Date: Nov. 3, 2014 pp. 1-5; p. 2 structure.
Rabouw, H.H. et al. (Feb. 5, 2019). "Small Molecule ISRIB Suppresses the Integrated Stress Response within a Defined Window of Activation", PNAS 116(6):2097-2102.
Radford, H. et al. (2015). "PERK Inhibition Prevents Tau-Mediated Neurodegeneration in A Mouse Model of Frontotemporal Dementia," Acta Neuropathol. 130(5):633-642.
Raught, B. et al. (Oct. 1, 1996). "Expression of a Translationally Regulated, Dominant-Negative CCAAT/Enhancer-Binding Protein Beta Isoform and Up-Regulation of The Eukaryotic Translation Initiation Factor 2alpha Are Correlated With Neoplastic Transformation of Mammary Epithelial Cells," Cancer Res. 56(19):4382-4386.
Remission. (obtained on Jan. 13, 2021) Definition of REMISSION. Medical Dictionary from Harvard located at: https://www.health.harvard.edu/medical-dictionary-of-health-terms/q-through-z#R-terms, last visited on Jan. 13, 2021, 2 pages.
Remission, (obtained on Jan. 13, 2021) Definition of Remission. NIH: Dictionary of Cancer Terms located at: https://www.cancer.gov/publications/dictionaries/cancer-terms/def/remission, last visited on Jan. 13, 2021, 1 page.
Richardson, J.P. et al., (Mar. 2004). "Mutations Causing Childhood Ataxia With Central Nervous System Hypomyelination Reduce Eukaryotic Initiation Factor 2B Complex Formation and Activity," Mol Cell Biol. 24(6):2352-2363.
Robert, F. et al. (2009). Blocking UV-Induced Eif2alpha Phosphorylation With Small Molecule Inhibitors of GCN2, Chem Biol Drug Des 74(1):57-67.
Rodriguez, P.C. et al. (2010). "L-Arginine Deprivation Regulates Cyclin D3 mRNA Stability in Human T Cells by Controlling HuR Expression," J Immunol. 185(9):5198-5204.

(56) References Cited

OTHER PUBLICATIONS

Romero-Ramirez, L. et al. (Apr. 27, 2017). "integrated Stress Response as a Therapeutic Target for CNS Injuries", HINDAWI 2017(6953156):1-7.

Ron, D. et al. (Jul. 2007). "Signal Integration in The Endoplasmic Reticulum Unfolded Protein Response," Nat Rev Mol Cell Biol. 8(7):519-529.

Rosenwald, I.B. et al. (2001). "Expression of Eukaryotic Translation Initiation Factors 4E and 2alpha is Increased Frequently in Bronchioloalveolar But Not in Squamous Ceil Carcinomas of The Lung," Cancer 92(8):2164-2171.

Ryoo, H.D. et al. (2017). "Two Distinct Nodes of Translational Inhibition in The integrated Stress Response", BMP Rep. 50(11):539-545.

Sacheck, J. M. (2007). "Rapid Disuse and Denervation Atrophy Involve Transcriptional Changes Similar to Those of Muscle Wasting During Systemic Diseases," FASEB J. 21:140-155.

Scaiewicz, V. et al. (2013). "CCAAT/Enhancer-Binding Protein Homologous (CHOP) Protein Promotes Carcinogenesis in The DEN-Induced Hepatocellular Carcinoma Model," PLoS One 8(12):e81065.

Scheuner, D., et al. (Jun. 2001). "Translational Control is Required for The Unfolded Protein Response and In Vivo Glucose Homeostasis," Mol Cell 7(6):1165-1176.

Sekine, Y. et al. (Apr. 9, 2015). "Mutations in a Translation Initiation Factor identify the Target of a Memory-Enhancing Compound", Science aaa6986:1-6.

Sharma, D.K. et al. (2016). "Role of Eukaryotic Initiation Factors during Cellular Stress and Cancer Progression," J Nucleic Acids 2016:8235121.

Shrestha, N. et al. (Aug. 17, 2012). "Eukaryotic Initiation Factor 2 (eIF2) Signaling Regulates Proinflammatory Cytokine Expression and Bacterial Invasion," J Biol Chem. 287(34):28738-28744.

Sidrauski, C. et al. (Apr. 15, 2015), "Pharmacological Dimerization and Activation of the Exchange Factor eIF2B Antagonizes the Integrated Stress Response", Elite 4(e07314):1-27.

Sidrauski, C. et al. (Feb. 26, 2015). "The Small Molecule ISRIB Reverses the Effects of eIF2α Phosphorylation on Translation and Stress Granule Assembly", eLIFE 4(e05033):1-16.

Sidrauski, C. et al. (May 28, 2013). "Pharmacological Brake-Release of mRNA Translation Enhances Cognitive Memory", eLIFE 2(e00498):1-22.

Simone, J.V. et al. (1996). "Oncology," Part XIV in Cecil Textbook of Medicine, 20th edition, Bennet, J.C. et al. eds., W.B. Saunders Company, pp. 1004-1010.

Southwood, C.M. et al. (Nov. 14, 2002). "The Unfolded Protein Response Modulates Disease Severity in Pelizaeus-Merzbacher Disease," Neuron 36(4):585-596.

Stone, S. et al. (Jul. 29, 2015). "The Unfolded Protein Response In Multiple Sclerosis," 9(264):1-11, 11 pages.

Stutzbach, L.D. et al. (2013). "The Unfolded Protein Response is Activated in Disease-Affected Brain Regions in Progressive Supranuclear Palsy and Alzheimer's Disease," Acta Neuropathoi Commun. 1(31):1-13.

Tabas, I. et al. (2011). "Integrating The Mechanisms of Apoptosis induced by Endoplasmic Reticulum Stress," Nat Cell Biol. 13(3):184-190.

Taylor, S.S. et al. (2005). "PKR and eIF2alpha: Integration of Kinase Dimerization, Activation, and Substrate Docking," Cell 122(6):823-825.

Thevenot, P.T. et al. (Sep. 18, 2014). "The Stress-Response Sensor Chop Regulates The Function and Accumulation of Myeloid-Derived Suppressor Cells in Tumors," 41(3):389-401.

Trinh, M.A. et al. (Jun. 28, 2012). Brain-specific disruption of the eIF2alpha kinase PERK decreases ATF4 expression and impairs behavioral flexibility. Cell Rep. 1(6):676-688.

Trinh, M.A. et al. (Oct. 2013). "Translational Control by eIF2α Kinases in Long-lasting Synaptic Plasticity and Long-term Memory", Neurobiol Learn Mem. 105:93-99, 16 pages.

Tsai, J.C. et al. (Mar. 30, 2018). "Structure of the Nucleotide Exchange Factor eIF2B Reveals Mechanism of Memory-Enhancing Molecule", Science 359(6383):1-20.

U.S. Appl. No. 17/398,862, filed Aug. 10, 2021 for Sebastian Bernales, et al. (A U.S. Patent Application is not submitted herewith pursuant to the waiver of 37 C.F.R. § 1.98(a)(2)(iii) issued by the Office on Sep. 21, 2004.).

U.S. Appl. No. 17/398,902, filed Aug. 10, 2021 for Luz Marina Delgado Oyarzo, et al. (A U.S. Patent Application is not submitted herewith pursuant to the waiver of 37 C.F.R. § 1.98(a)(2)(iii) issued by the Office on Sep. 21, 2004.).

Van Der Knaap, M.S. et al. (2006). "Vanishing White Matter Disease," Lancet Neurol. 5(5):413-423.

Van Der Voorn, J.P. et al. (Sep. 2005). "The Unfolded Protein Response in Vanishing White Matter Disease," J Neuropathol Exp Neurol. 64(9):770-775.

Vattem, K.M. et al. (2004). "Reinitiation Involving Upstream ORFS Regulates ATF4 Mrna Translation in Mammalian Celis," Proc Natl Acad Sci U S A 101(31):11269-11274.

Vilas-Boas, F. et al., (2016). "Impairment of Stress Granule Assembly Via Inhibition of The EifSalpha Phosphorylation Sensitizes Glioma Cells to Chemotherapeutic Agents," J Neurooncol. 127(2):253-260.

Walter, P. et al. (2011). "The Unfolded Protein Response: From Stress Pathway to Homeostatic Regulation," Science 334(6059):1081-1086.

Wang, C. et al. (Jul. 19, 2018). "Inhibiting the integrated Stress Response Pathway Prevents Aberrant Chondrocyte Differentiation Thereby Alleviating Chondrodysplasia", eLIFE 7(e37673):1-35.

Wang, S. et al. (2001). "Expression of Eukaryotic Translation initiation Factors 4E and 2alpha Correlates With The Progression of Thyroid Carcinoma," Thyroid 11 (12):1101-1107.

Wang, S. et al. (Jul. 1999). "Expression of the Eukaryotic Translation Initiation Factors 4E and 2alpha in Non-Hodgkin's Lymphomas," Am J Pathol. 155(1):247-255.

Wang, Y. et al. (Aug. 2013). "Amino Acid Deprivation Promotes Tumor Angiogenesis Through The GCN2/ATF4 Pathway," Neoplasia 15(8)989-997.

Watanabe, S. et al. (pre-print. Feb. 27, 2020). "Resetting Proteostasls With ISRIB Prevents Pulmonary Fibrosis," located at: https://www.biorxiv.org/content/10.1101/2020.02.26.965566v1.article-info, last visted on Jul. 30, 2020, 42 pages.

Way, S. et al. (Apr. 2016). "Harnessing the Integrated Stress Response for The Treatment of Multiple Sclerosis", Lancet Neurol. 15(4):434-443, 20 pages.

Wek, R.C. et al. (2006). "Coping with Stress: eIF2 Kinases and Translational Control," Biochem Soc Trans 34(Pt 1):7-11.

Wek, S.A. et al. (Aug. 1995). "The Histidyl-tRNA Synthetase-Related Sequence in The Eif-2 Alpha Protein Kinase GCN2 Interacts With Trna and is Required For Activation in Response To Starvation For Different Amino Acids," Mol Cell Biol. 15(8):4497-506.

Wong, Y. L. (Jan. 9, 2019). "eIF2B Activator Prevents Neurological Defects Caused by a Chronic Integrated Stress Response", eLIFE 8(e42940):1-31.

Wong, Y. L. et al. (Feb. 28, 2018). "The Small Molecule ISRIB Rescues the Stability and Activity of Vanishing White Matter Disease eIF2B Mutant Complexes", eLIFE 7(e32733):1-23.

Wortham, N.C. (2015). "eIF2B: Recent Structural and Functional Insights into a Key Regulator of Translation", Biochemical Society Transactions 43(6):1234-1240.

Yang, L.B. et al. (Jan. 2003). "Elevated β-Secretase Expression and Enzymatic Activity Detected in Sporadic Alzheimer Disease," Nat Med. 9(1):3-4.

Ye, J. et al. (2010). "The GCN2-ATF4 Pathway is Critical For Tumour Cell Survival and Proliferation in Response to Nutrient Deprivation," EMBO J. 29(12):2082-2096, including Supplemental Material, 24 pages.

(56) References Cited

OTHER PUBLICATIONS

Yefidoff-Freedman, R. et al. (e-pub. Jun. 7, 2017). "Development of 1-((1,4-trans)-4-aryloxycyclohexyl)-3-arylurea Activators of the Heme Regulated Inhibitor as Selective Activators of Eucaryotic Translation initiation Factor 2 Alpha (elF2#) Phosphorylation Arm of the Integrated Endoplasmic Reticulum Stress Response", J. Med. Chem. X(X):1-54.

Young-Baird, S.K. et al. (Feb. 20, 2020, e-pub, Dec. 10, 2019). "Suppression of MEHMO Syndrome Mutation in elF2 by Smail Molecule ISRIB," Mol. Cell. 77(4):875-886.e7, 66 pages.

Zhan, K. et al. (2002). "Phosphorylation of Eukaryotic Initiation Factor 2 By Heme-Regulated Inhibitor Kinase-Related Protein Kinases in Schizosaccharomyces Pombe is Important for Resistance to Environmental Stresses," Mol Cell Biol. 22(201:7134-7146.

Zhu, P. J. et al. (Nov. 15, 2019). "Activation of The ISR Mediates The Behavioral and Neurophysiological Abnormalities in Down Syndrome," Science 366:843-849, 8 pages.

Zhu, P.J. et al. (Dec. 2011). "Suppression of PKR Promotes Network Excitability and Enhanced Cognition by Interferon-Gamma-Mediated Disinhibition," Cell 147(6):1384-1396, 26 pages.

Zyryanova, A.F. (Mar. 30, 2018). "Binding of ISRIB Reveals a Regulatory Site in the Nucleotide Exchange Factor, elF2B", Science 359(6383):1533-1536, 13 pages.

\* cited by examiner

MODULATORS OF INTEGRATED STRESS RESPONSE PATHWAY

CROSS REFERENCE TO RELATED APPLICATIONS

This application claims the priority benefit of U.S. Provisional Patent Application No. 62/860,683, filed Jun. 12, 2019, the disclosure of which is hereby incorporated herein by reference in its entirety.

FIELD

The present disclosure relates generally to therapeutic agents that may be useful as modulators of Integrated Stress Response (ISR) pathway.

BACKGROUND

Genetically modifying plants to express heterologous proteins or increase the expression of endogenous proteins has become an important tool for a large number of business. Plants can be modified to express an increased amount of essential amino acids, to achieve greater yields of the plants or the proteins express therein, or to produce recombinant proteins such as biopolymers, industrial proteins/enzymes, and therapeutic proteins. However, there is a need to further increase the expression of plant proteins, which may require methods other than genetic modification.

In addition, given the resistance to genetically modifying plants by some people, it may be desirable to increase protein production in plants using other methods. Increased protein production by plants will likely be essential for ensuring the availability of enough protein to feed an increasing world population under changing environmental conditions. Further, increased protein production in plants promote plant growth, because additional proteins can be released through the roots into the surrounding area to attract microorganisms, such as bacteria that can in turn improve plant development.

One potential method of increasing protein production in plants is by modulating Integrated Stress Response (ISR) pathway. Diverse cellular conditions and stresses activate this widely conserved signaling pathway. The ISR pathway is activated in response to intrinsic and extrinsic stresses, such as viral infections, hypoxia, glucose and amino acid deprivation, oncogene activation, UV radiation, and endoplasmic reticulum stress. Upon activation of ISR by one or more of these factors, the eukaryotic initiation factor 2 (eIF2, which is comprised of three subunits, $\alpha$, $\beta$, and $\gamma$) becomes phosphorylated in its $\alpha$-subunit and rapidly reduces overall protein translation by binding to the eIF2B complex. This phosphorylation inhibits the eIF2B-mediated exchange of GDP for GTP (i.e., a guanine nucleotide exchange factor (GEF) activity), sequestering eIF2B in a complex with eIF2 and reducing general protein translation of most mRNA in the cell. Paradoxically, eIF2$\alpha$ phosphorylation also increases translation of a subset of mRNAs that contain one or more upstream open reading frames (uORFs) in their 5' untranslated region (UTR). These transcripts include the transcriptional modulator activating transcription factor 4 (ATF4), the transcription factor CHOP, the growth arrest and DNA damage-inducible protein GADD34 and the $\beta$-secretase BACE-1.

Additionally, compounds useful in modulating the ISR pathway may also be useful in treating a large number of diseases. In animals, the ISR pathway modulates a broad translational and transcriptional program involved in diverse processes such as learning memory, immunity, intermediary metabolism, insulin production and resistance to unfolded protein stress in the endoplasmic reticulum, among others. Activation of the ISR pathway has also been associated with numerous pathological conditions including cancer, neurodegenerative diseases, metabolic diseases (metabolic syndrome), autoimmune diseases, inflammatory diseases, musculoskeletal diseases (such as myopathy), vascular diseases, ocular diseases, and genetic disorders. Aberrant protein synthesis through eIF2$\alpha$ phosphorylation is also characteristic of several other human genetic disorders, cystic fibrosis, amyotrophic lateral sclerosis, Huntington disease and prion disease.

BRIEF SUMMARY

Modulators of the Integrated Stress Response (ISR) pathway are described, as are methods of making and using the compounds, or salts thereof.

DETAILED DESCRIPTION

Definitions

Figure 1:
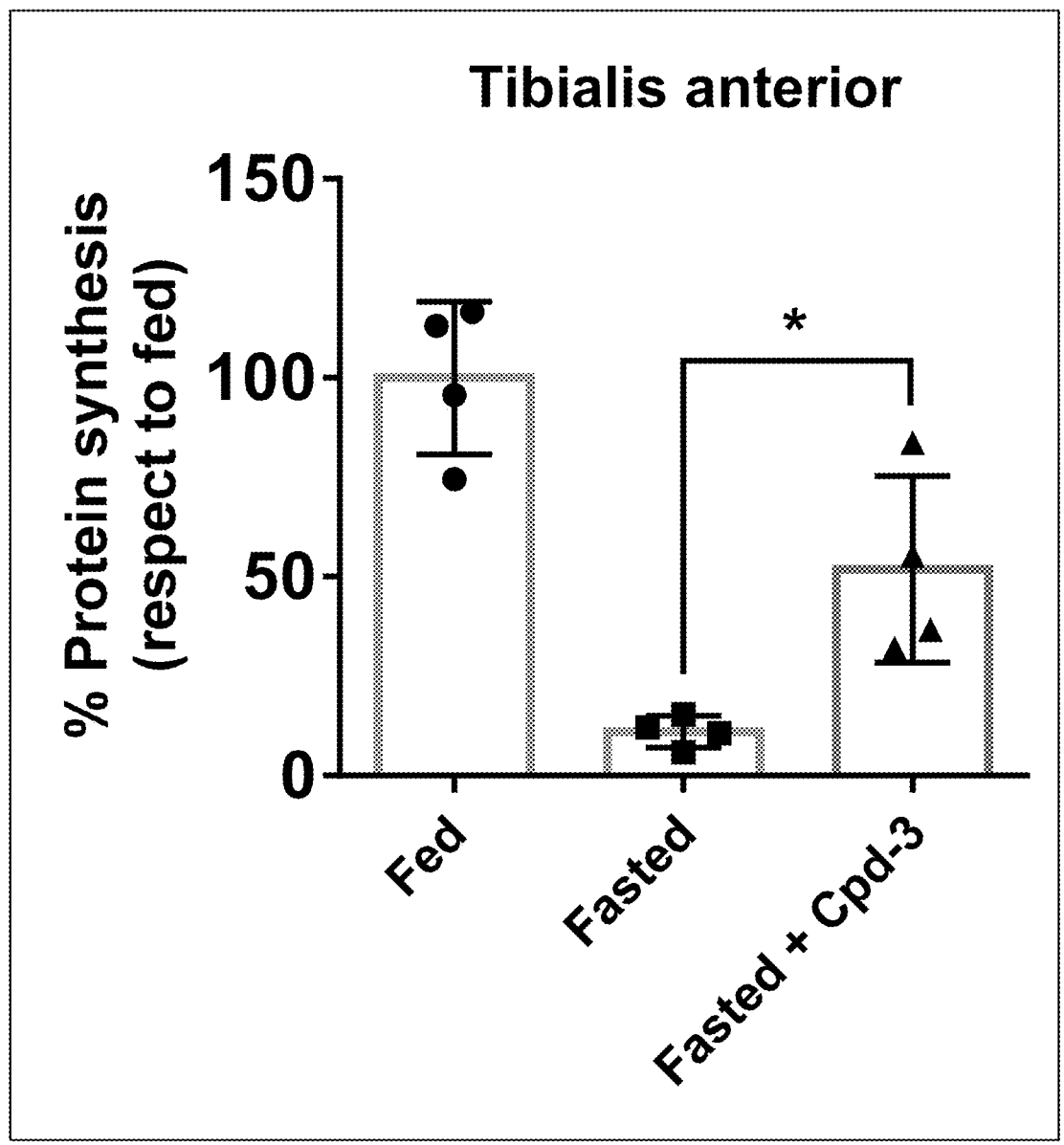
FIG. 1 shows percent of protein synthesis in tibialis anterior of each mouse from fed or fasted animals treated with vehicle or compound 3.

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkenylene" as used herein refers to the same residues as alkenyl, but having bivalency. Particular alkenylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH=CH—), propenylene (—CH=CHCH_2$—), 1,4-but-1-enylene (—CH=CH—$CH_2CH_2$—), 1,4-but-2-enylene (—$CH_2$CH=CHCH$_2$—), 1,6-hex-1-enylene (—CH=CH—$(CH_2)_3CH_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Alkynylene" as used herein refers to the same residues as alkynyl, but having bivalency. Particular alkynylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_1$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH$_2$—), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C=C) and having the number of carbon atoms designated (i.e., $C_2$-$C_{10}$ means two to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen, and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen, and sulfur, 5 to 10-membered rings having 1 to 8 annular carbon atoms and 1 to 4 annular heteroatoms independently selected from nitrogen, oxygen, and sulfur, or 5, 6 or 7-membered rings having 1 to 5 annular carbon atoms and 1 to 4 annular heteroatoms independently selected from nitrogen, oxygen, and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen, and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. The methods of the present disclosure contemplate any one or more of these aspects of treatment.

As used herein, the term "agriculturally effective amount" refers to an amount of a compound or salt thereof sufficient to produce a desired agricultural outcome in a plant. Accordingly, in some embodiments, an agriculturally effective amount may increase protein expression, increase growth, and/or alter the microbial environment adjacent to the plant.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the present disclosure in its free acid or base form with a suitable organic or inorganic base or acid, respectively, and isolating the salt thus formed during subsequent purification.

The term "agriculturally acceptable salt" refers to a salt which retains at least some of the biological activity of the free (non-salt) compound and which can be administered to plants. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Agriculturally acceptable salts can be prepared in situ in the manufacturing process, or by separately reacting a purified compound of the present disclosure in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the present disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that aspects and embodiments described herein as "comprising" include "consisting of" and "consisting essentially of" embodiments.

When a composition is described as "consisting essentially of" the listed components, the composition contains the components expressly listed, and may contain other components which do not substantially affect the disease or condition being treated such as trace impurities. However, the composition either does not contain any other components which do substantially affect the disease or condition being treated other than those components expressly listed; or, if the composition does contain extra components other than those listed which substantially affect the disease or condition being treated, the composition does not contain a sufficient concentration or amount of those extra components to substantially affect the disease or condition being treated. When a method is described as "consisting essentially of" the listed steps, the method contains the steps listed, and may contain other steps that do not substantially affect the disease or condition being treated, but the method does not contain any other steps which substantially affect the disease or condition being treated other than those steps expressly listed.

When a moiety is indicated as substituted by "at least one" substituent, this also encompasses the disclosure of exactly one substituent.

Compounds

In one aspect, provided is a compound of formula (I):

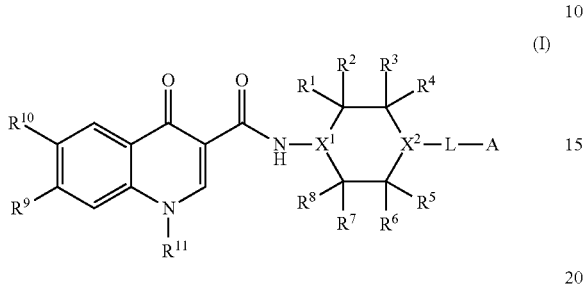

(I)

or a salt thereof,
wherein:
$X^1$ is N or $CR^{X1}$;
$X^2$ is N or $CR^{X2}$.
when present, $R^{X1}$ is selected from the group consisting of hydrogen, $C_1$-$C_6$ alkyl, $C_1$-$C_6$ haloalkyl, —C(O)OH, —C(O)O($C_1$-$C_6$ alkyl), —C(O)O($C_1$-$C_6$ haloalkyl), and halogen;
when present, $R^{X2}$ is selected from the group consisting of hydrogen, $C_1$-$C_6$ alkyl, $C_1$-$C_6$ haloalkyl, —C(O)OH, —C(O)O($C_1$-$C_6$ alkyl), —C(O)O($C_1$-$C_6$ haloalkyl), and halogen; $R^1$, $R^2$, $R^3$, $R^4$, $R^5$, $R^6$, $R^7$, and $R^8$, independently from each other, are selected from the group consisting of hydrogen, $C_1$-$C_6$ alkyl, $C_1$-$C_6$ haloalkyl, —C(O)OH, —C(O)O($C_1$-$C_6$ alkyl), —C(O)O($C_1$-$C_6$ haloalkyl), and halogen;
or, one of $R^1$, $R^2$, $R^3$, $R^4$, $R^5$, $R^6$, $R^7$, and $R^8$, and another one of $R^1$, $R^2$, $R^3$, $R^4$, $R^5$, $R^6$, $R^7$, and $R^8$, are taken together to form a $C_1$-$C_6$ alkylene moiety;
or, two geminal substituents selected from the group consisting of $R^1$, $R^2$, $R^3$, $R^4$, $R^5$, $R^6$, $R^7$, and $R^8$ are taken together to form an oxo group;
or, one of $R^1$, $R^2$, $R^3$, $R^4$, $R^5$, $R^6$, $R^7$, and $R^8$, and $R^{X1}$, when present, are taken together to form a $C_1$-$C_6$ alkylene moiety;
$R^9$ and $R^{10}$, independently from each other, are selected from the group consisting of hydrogen, halogen, $NO_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{B-a}R^{B-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{B-a}R^{B-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{B-a}R^{B-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{B-a}$ and $R^{B-b}$ are taken together with the nitrogen atom to which they are attached to form a 3-10 membered heterocycle;
$R^{11}$ is selected from the group consisting of $C_3$-$C_{10}$ cycloalkyl optionally substituted with 1 to 17 $R^{12}$ substituents and 3-10 membered heterocycloalkyl optionally substituted with 1 to 17 $R^{12}$ substituents;
$R^{12}$, independently at each occurrence, is selected from the group consisting of oxo, halogen, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{C-a}R^{C-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{C-a}R^{C-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{C-a}R^{C-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{C-a}$ and $R^{C-b}$ are taken together with the nitrogen atom to which they are attached to form a 3-10 membered heterocycle;
L is a linker selected from the group consisting of @-$C_1$-$C_6$ alkylene-#, @—$NR^N$—($C_1$-$C_6$ alkylene)-#, @—$NR^N$—$NR^N$—($C_1$-$C_6$ alkylene)-#, @-$CH_2$—$NR^N$—($C_{1-6}$ alkylene)-#, @-$CH_2$—$NR^N$—$NR^N$—($C_{1-6}$ alkylene)-#, @—$NR^N$—($C_1$-$C_6$ alkylene)-O-#, @—$NR^N$—$NR^N$—($C_1$-$C_6$ alkylene)-O-#, @-$CH_2$—$NR^N$—($C_1$-$C_6$ alkylene)-O-#, @-$CH_2$—$NR^N$—$NR^N$—($C_1$-$C_6$ alkylene)-O-#, and @—($C_1$-$C_6$ alkylene)-O-#;
wherein @ represents the attachment point to $X^2$ and # represents the attachment point to A;
the $C_1$-$C_6$ alkylene moiety of each of the @-$C_1$-$C_6$ alkylene-#, @—$NR^N$—($C_1$-$C_6$ alkylene)-#, @—$NR^N$—$NR^N$—($C_1$-$C_6$ alkylene)-#, @-$CH_2$—$NR^N$—($C_1$-$C_6$ alkylene)-#, @-$CH_2$—$NR^N$—$NR^N$—($C_{1-6}$ alkylene)-#, @—$NR^N$—($C_1$-$C_6$ alkylene)-O-#, @—$NR^N$—$NR^N$—($C_1$-$C_6$ alkylene)-O-#, @-$CH_2$—$NR^N$—($C_1$-$C_6$ alkylene)-O-#, @-$CH_2$—$NR^N$—$NR^N$—($C_1$-$C_6$ alkylene)-O-#, and @—($C_1$-$C_6$ alkylene)-O-# is optionally substituted with 1 to 12 $R^{13}$;

$R^N$, independently at each occurrence, is selected from the group consisting of hydrogen, $C_1$-$C_6$ alkyl, and $C_1$-$C_6$ haloalkyl, $R^{13}$, independently at each occurrence, is selected from the group consisting of oxo, halogen, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{L-a}$R$^{L-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{L-a}$R$^{L-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{L-a}$R$^{L-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{L-a}$ and $R^{L-b}$ are taken together with the nitrogen atom to which they are attached to form a 3-10 membered heterocycle;

A is selected from the group consisting of:
a substituent of formula (A-1)

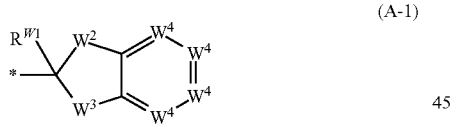

(A-1)

$W^2$ is selected from the group consisting of —C($R^{W2-1}R^{W2-2}$)—, —N($R^{W2-2}$)—, —C($R^{W2-1}R^{W2-1}$)N($R^{W2-2}$)—, —N($R^{W2-1}$)C($R^{W2-1}R^{W2-2}$)—, —C($R^{W2-1}$)=N—, —N=C($R^{W2-1}$)—, —O—, —C($R^{W2-1}R^{W2-1}$)O—, —OC($R^{W2-1}R^{W2-2}$)—, —S—, —C($R^{W2-1}R^{W2-1}$)S—, —SC($R^{W2-1}R^{W2-2}$)—, —C($R^{W2-1}R^{W2-1}$)C($R^{W2-1}R^{W2-2}$)—, and —CR$^{W2-1}$=CR$^{W2-1}$—, wherein $R^{W2-1}$ is H or $R^A$, and $R^{W2-2}$ is H or $R^A$;

$W^3$ is selected from the group consisting of —C($R^{W3-1}R^{W3-2}$)—, —N($R^{W3-2}$)—, —C($R^{W3-1}R^{W3-1}$)N($R^{3-2}$)—, —N($R^{W3-1}$)C($R^{W3-1}R^{W3-2}$)—, —C($R^{W3-1}$)=N—, —N=C($R^{W3-1}$), —O—, —C($R^{W3-1}R^{W3-1}$)O—, —OC($R^{W3-1}R^{3-2}$)—, —S—, —C($R^{W3-1}R^{W3-1}$)S—, —SC($R^{W3-1}R^{W3-2}$)—, —C($R^{W3-1}R^{W3-1}$)C($R^{W3-1}R^{W3-2}$)—, and —CR$^{W3-1}$=CR$^{W3-1}$—, wherein $R^{W3-1}$ is H or $R^A$, and $R^{W3-2}$ is H or $R^A$;

$W^4$, independently at each occurrence, is CR$^{W4}$ or N, wherein $R^{W4}$ is H or $R^A$;

$R^{W1}$ is hydrogen or $R^A$, or $R^{W1}$ and $R^{W2-2}$ are taken together to form a double bond between the carbon atom bearing $R^{W1}$ and the atom bearing $R^{W2-2}$, or $R^{W1}$ and $R^{W3-2}$ are taken together to form a double bond between the carbon atom bearing $R^{W1}$ and the atom bearing $R^{W3-2}$;

$C_6$-$C_{14}$ aryl optionally substituted with 1, 2, 3, 4, 5, 6, 7, 8, or 9 $R^A$ substituents; and 5-14 membered heteroaryl optionally substituted with 1, 2, 3, 4, 5, 6, 7, 8, or 9 $R^A$ substituents;

$R^A$, independently at each occurrence, is selected from the group consisting of halogen, NO$_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{A-a}$R$^{A-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{A-a}$R$^{A-b}$, —S(O)$_2$H, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{A-a}$R$^{A-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{A-a}$ and $R^{A-b}$ are taken together with the nitrogen atom to which they are attached to form a 3-10 membered heterocycle;

provided that when $X^2$ is N, then L is a linker selected from the group consisting of @-$C_1$-$C_6$ alkylene-#, @—NR$^N$—($C_1$-$C_6$ alkylene)-#, @—NR$^N$—($C_1$-$C_6$ alkylene)-O-#, and @—($C_1$-$C_6$ alkylene)-O-#.

In some embodiments, the compound of formula (I), or the salt thereof, is a compound of formula (II):

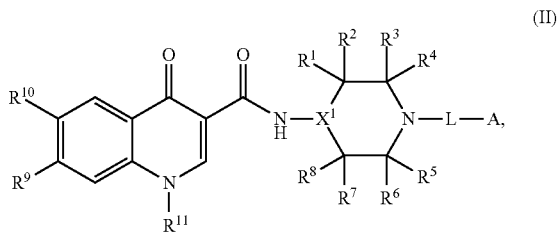

(II)

or a salt thereof, wherein $R^1$, $R^2$, $R^3$, $R^4$, $R^5$, $R^6$, $R^7$, $R^8$, $R^9$, $R^{10}$, $R^{11}$, $X^1$, L, and A are as defined in compounds of formula (I); provided that L is a linker selected from the group consisting of @-$C_1$-$C_6$ alkylene-#, @—NR$^N$—($C_1$-$C_6$ alkylene)-#, @—NR$^N$—($C_1$-$C_6$ alkylene)-O-#, and @—($C_1$-$C_6$ alkylene)-O-#.

In some embodiments, the compound of formula (I), or the salt thereof, is a compound of formula (III):

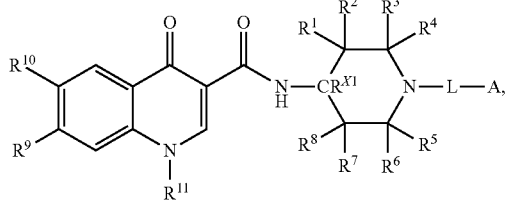
(III)

or a salt thereof, wherein $R^1$, $R^2$, $R^3$, $R^4$, $R^5$, $R^6$, $R^7$, $R^8$, $R^9$, $R^{10}$, $R^{11}$, $R^{X1}$, L, and A are as defined in compounds of formula (I); provided that L is a linker selected from the group consisting of @-$C_1$-$C_6$ alkylene-#, @—$NR^N$—($C_1$-$C_6$ alkylene)-#, @—$NR^N$—($C_1$-$C_6$ alkylene)-O-#, and @—($C_1$-$C_6$ alkylene)-O-#.

In some embodiments, the compound of formula (I), or the salt thereof, is a compound of formula (IV):

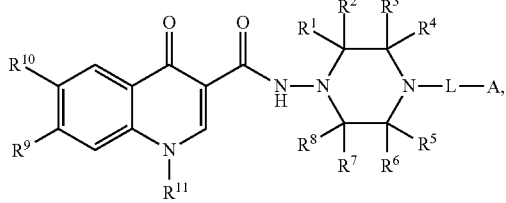
(IV)

or a salt thereof, wherein $R^1$, $R^2$, $R^3$, $R^4$, $R^5$, $R^6$, $R^7$, $R^8$, $R^9$, $R^{10}$, $R^{11}$, L, and A are as defined in compounds of formula (I); provided that L is a linker selected from the group consisting of @-$C_1$-$C_6$ alkylene-#, @—$NR^N$—($C_1$-$C_6$ alkylene)-#, @—$NR^N$—($C_1$-$C_6$ alkylene)-O-#, and @—($C_1$-$C_6$ alkylene)-O-#.

In some embodiments, the compound of formula (I), or the salt thereof, is a compound of formula (V):

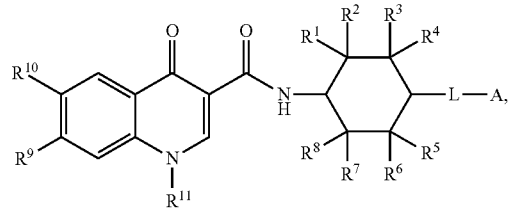
(V)

or a salt thereof, wherein $R^1$, $R^2$, $R^3$, $R^4$, $R^5$, $R^6$, $R^7$, $R^8$, $R^9$, $R^{10}$, $R^{11}$, L, and A are as defined in compounds of formula (I).

In some embodiments, the compound of formula (I), or the salt thereof, is a compound of formula (V):

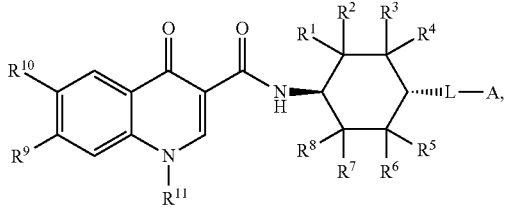
(VI)

or a salt thereof, wherein $R^1$, $R^2$, $R^3$, $R^4$, $R^5$, $R^6$, $R^7$, $R^8$, $R^9$, $R^{10}$, $R^{11}$, L, and A are as defined in compounds of formula (I).

In some embodiments, the compound of formula (I), or the salt thereof, is a compound of formula (VII):

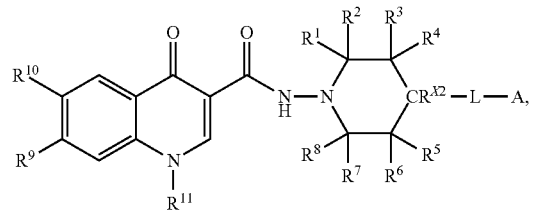
(VII)

or a salt thereof, wherein $R^1$, $R^2$, $R^3$, $R^4$, $R^5$, $R^6$, $R^7$, $R^8$, $R^9$, $R^{10}$, $R^{11}$, $R^{X2}$, L, and A are as defined in compounds of formula (I).

In some embodiments, the compound of formula (I), or the salt thereof, is a compound of formula (VIII):

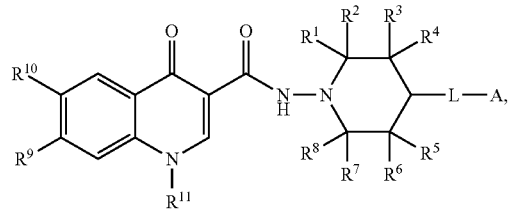
(VIII)

or a salt thereof, wherein $R^1$, $R^2$, $R^3$, $R^4$, $R^5$, $R^6$, $R^7$, $R^8$, $R^9$, $R^{10}$, $R^{11}$, L, and A are as defined in compounds of formula (I).

In some embodiments of the compounds of formulae (I), (II), (III), (IV), (V), (VI), (VII), and (VIII), or the salts thereof, $R^1$, $R^2$, $R^3$, $R^4$, $R^5$, $R^6$, $R^7$, and $R^8$ are each hydrogen. In such embodiments, the compound of formula (I), or the salt thereof, is a compound of formula (IX), or a salt thereof. In such embodiments, the compound of formula (II), or the salt thereof, is a compound of formula (X), or a salt thereof. In such embodiments, the compound of formula (III), or the salt thereof, is a compound of formula (XI), or a salt thereof. In such embodiments, the compound of formula (IV), or the salt thereof, is a compound of formula (XII), or a salt thereof. In such embodiments, the compound of formula (V), or the salt thereof, is a compound of formula (XIII), or a salt thereof. In such embodiments, the compound of formula (VI), or the salt thereof, is a compound of formula (XIV), or a salt thereof. In such embodiments, the compound of formula (VII), or the salt thereof, is a compound of formula (XV), or a salt thereof. In such embodiments, the compound of formula (VIII), or the salt thereof, is a compound of formula (XVI), or a salt thereof.

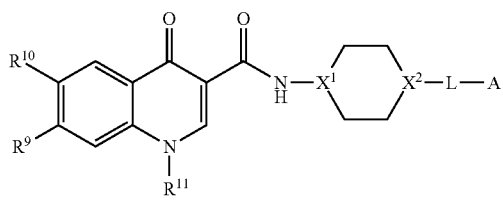
(IX)

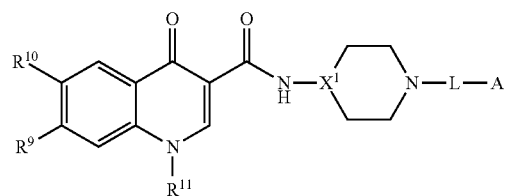
(X)

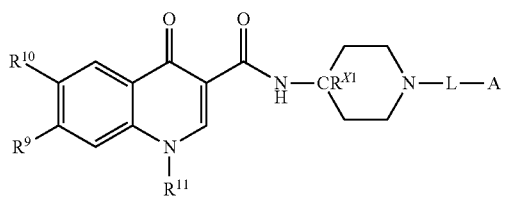
(XI)

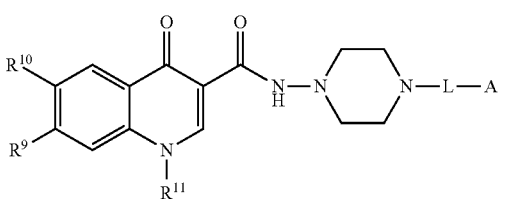
(XII)

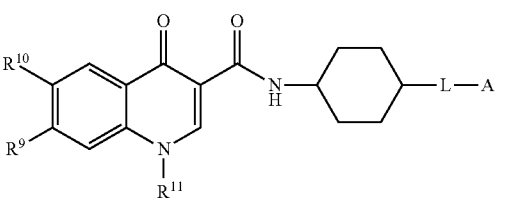
(XIII)

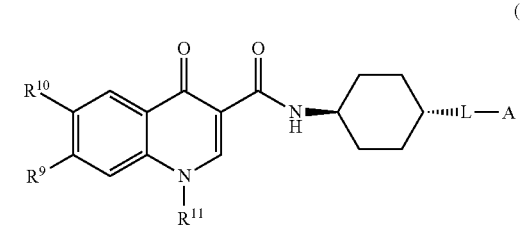
(XIV)

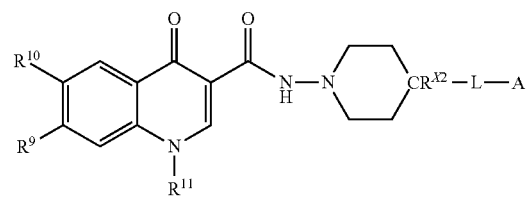
(XV)

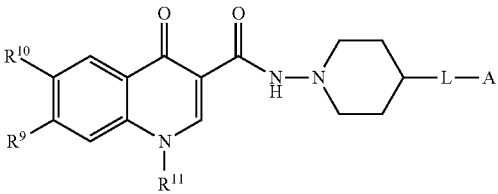
(XVI)

In some embodiments of the compound of formula (XI), or the salt thereof, the compound of formula (XI), or the salt thereof, is a compound of formula (XV):

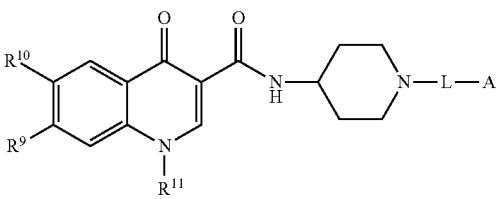
(XVII)

or a salt thereof,
wherein $R^9$, $R^{10}$, $R^{11}$, L, and A are as defined in compounds of formula (XI).

In some embodiments of the compounds of formulae (I), (II), (III), (IV), (V), (VI), (VII), (VIII), (IX), (X), (XI), (XII), (XIII), (XIV), and (XV), or the salts thereof, $R^{11}$ is selected from the group consisting of $R^{11}$ is $C_3$-$C_{10}$ cycloalkyl optionally substituted with 1 to 17 $R^{12}$ substituents. In some embodiments, $R^{11}$ is unsubstituted $C_3$-$C_{10}$ cycloalkyl. In some embodiments, $R^{11}$ is $C_3$-$C_{10}$ cycloalkyl substituted with 1 to 17 $R^{12}$ substituents. In some embodiments, $R^{11}$ is selected from the group consisting of cyclopropyl, cyclobutyl, and cyclopentyl, wherein each of the cyclopropyl, cyclobutyl, and cyclopentyl is optionally substituted by 1 to 4 $R^{12}$ substituents. In some embodiments, $R^{11}$ is cyclopropyl optionally substituted by 1 to 4 $R^{12}$ substituents. In some embodiments, $R^{11}$ is cyclopropyl. In some embodiments, $R^{11}$ is cyclopropyl substituted by 1 to 4 $R^{12}$ substituents. In some embodiments, $R^{11}$ is cyclopropyl substituted by —$NH_2$. In some embodiments, $R^{11}$ is 1-aminocycloprop-1-yl. In some embodiments, $R^{11}$ is cyclopropyl optionally substituted by —CH=$CH_2$. In some embodiments, $R^{11}$ is 2-vinylcycloprop-1-yl. In some embodiments, $R^{11}$ is cyclopropyl optionally substituted by a halogen substituent. In some embodiments, $R^{11}$ is cyclopropyl optionally substituted by a fluoro substituent. In some embodiments, $R^{11}$ is 2-fluorocycloprop-1-yl. In some embodiments, $R^{11}$ is cyclobutyl optionally substituted by 1 to 4 $R^{12}$ substituents. In some embodiments, $R^{11}$ is cyclopentyl optionally substituted by 1 to 4 $R^{12}$ substituents.

In some embodiments of the compounds of formulae (I), (II), (III), (IV), (V), (VI), (VII), (VIII), (IX), (X), (XI), (XII), (XIII), (XIV), and (XV), or the salts thereof, $R^{11}$ is selected from the group consisting of $R^{11}$ is 3-10 membered heterocycloalkyl optionally substituted with 1 to 17 $R^{12}$ substituents.

In some embodiments of the compounds of formulae (I), (II), (III), (IV), (V), (VI), (VII), (VIII), (IX), (X), (XI), (XII), (XIII), (XIV), (XV), (XVI), and (XVII), or the salts thereof, $R^{11}$ is cyclopropyl. In such embodiments, the compound of formula (I), or the salt thereof, is a compound of formula (I-1), or a salt thereof. In such embodiments, the compound of formula (II) is a compound of formula (II-1), or a salt thereof. In such embodiments, the compound of formula (III) is a compound of formula (II-1), or a salt thereof. In such embodiments, the compound of formula (IV), or the salt thereof, is a compound of formula (IV-1), or a salt thereof. In such embodiments, the compound of formula (V), or the salt thereof, is a compound of formula (V-1), or a salt thereof. In such embodiments, the compound of formula (VI), or the salt thereof, is a compound of formula (VI-1), or a salt thereof. In such embodiments, the compound of formula (VII), or the salt thereof, is a compound of formula (VII-1), or a salt thereof. In such embodiments, the compound of formula (VIII), or the salt thereof, is a compound of formula (VIII-1), or a salt thereof. In such embodiments, the compound of formula (IX), or the salt thereof, is a compound of formula (IX-1), or a salt thereof. In such embodiments, the compound of formula (X), or the salt thereof, is a compound of formula (X-1), or a salt thereof. In such embodiments, the compound of formula (XI), or the salt thereof, is a compound of formula (XI-1), or a salt thereof. In such embodiments, the compound of formula (XII), or the salt thereof, is a compound of formula (XII-1), or a salt thereof. In such embodiments, the compound of formula (XIII), or the salt thereof, is a compound of formula (XIII-1), or a salt thereof. In such embodiments, the compound of formula (XIV), or the salt thereof, is a compound of formula (XIV-1), or a salt thereof. In such embodiments, the compound of formula (XV), or the salt thereof, is a compound of formula (XV-1), or a salt thereof. In such embodiments, the compound of formula (XVI), or the salt thereof, is a compound of formula (XVI-1), or a salt thereof. In such embodiments, the compound of formula (XVII), or the salt thereof, is a compound of formula (XVII-1), or a salt thereof.

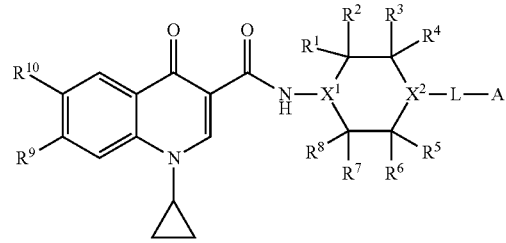

(I-1)

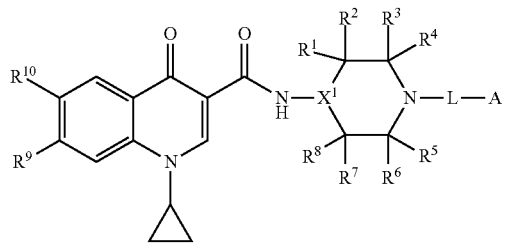

(II-1)

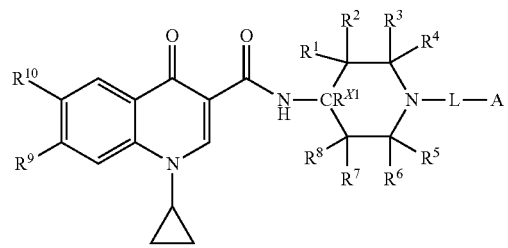

(III-1)

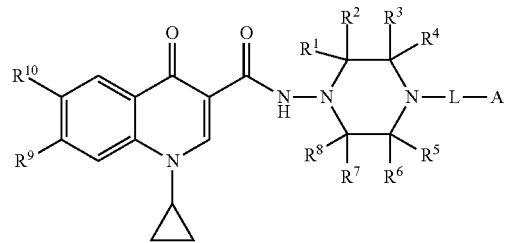

(IV-1)

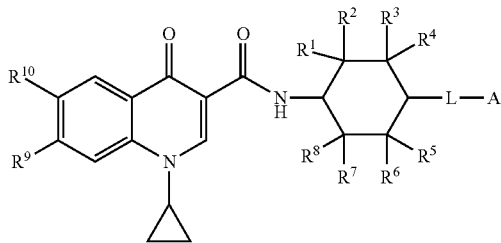

(V-1)

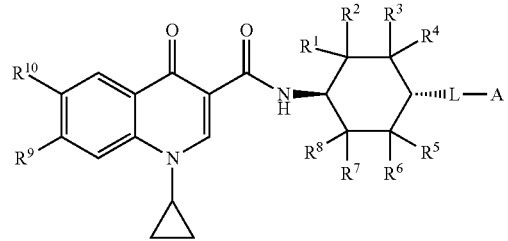

(VI-1)

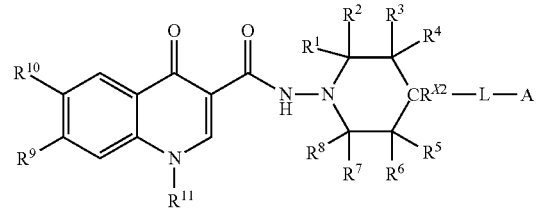

(VII-1)

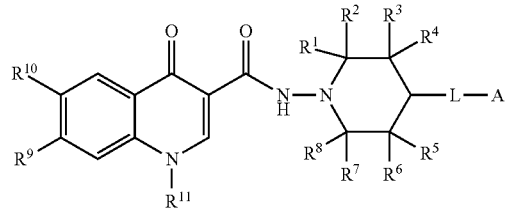

(VIII-1)

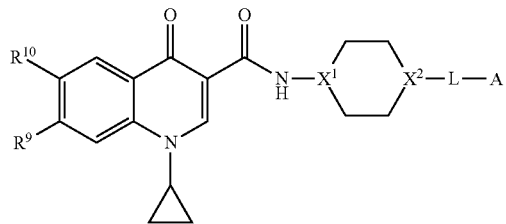
(IX-1)
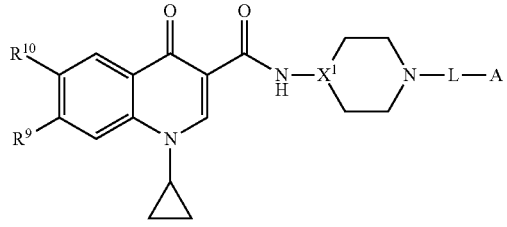
(X-1)
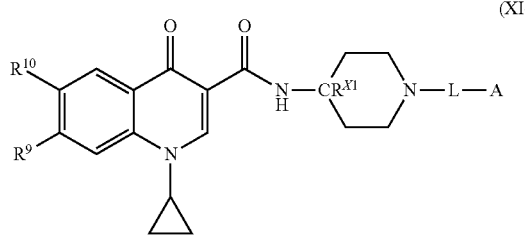
(XI-1)
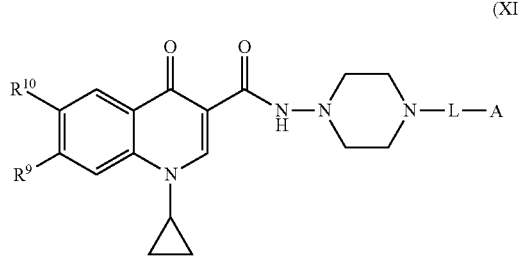
(XII-1)
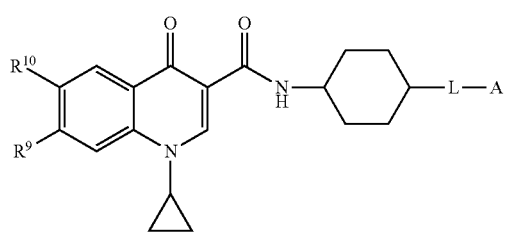
(XIII-1)
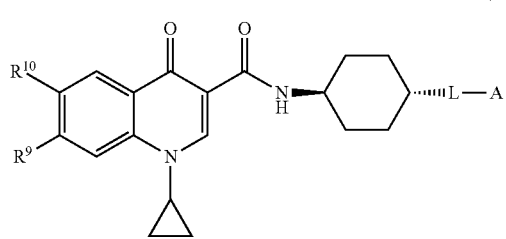
(XIV-1)
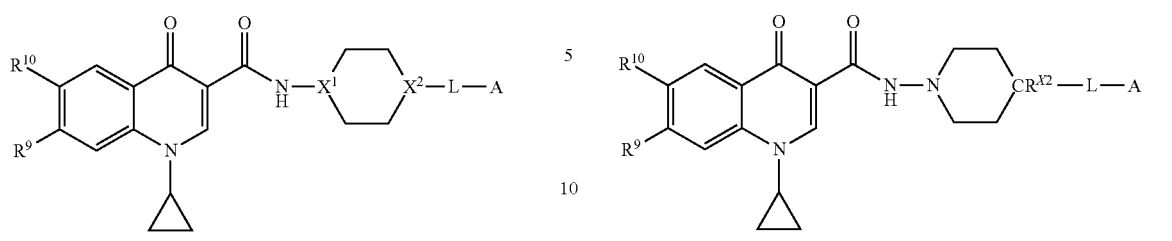
(XV-1)
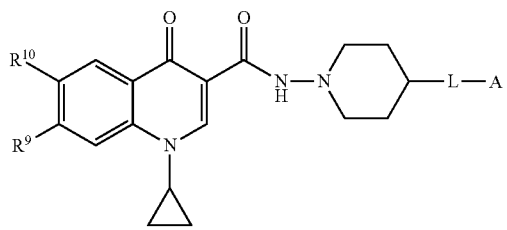
(XVI-1)
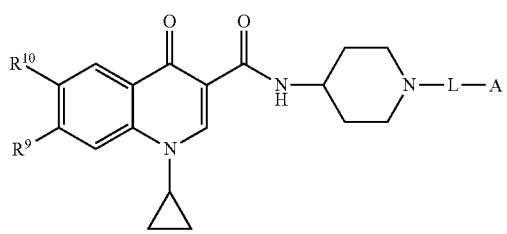
(XVII-1)
In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), and (XVII-1), or the salts thereof, L is selected from the group consisting of
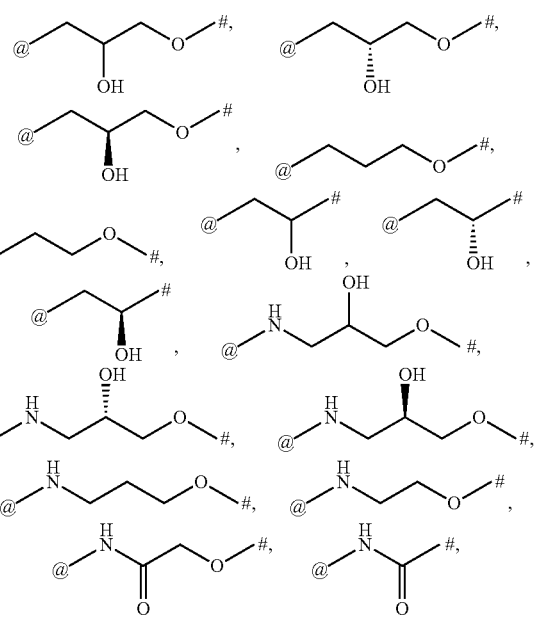

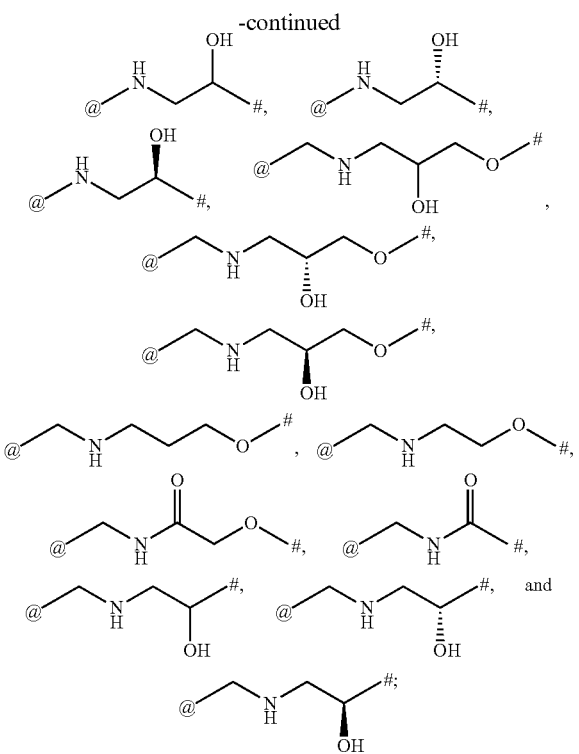

wherein # represents the attachment point to A and @ represents the attachment point to the remainder of the molecule.

In some embodiments of the compounds of formulae (I), (V), (VI), (VII), (VIII), (IX), (XIII), (XIV), (XV), (XVI), (I-1), (V-1), (VI-1), (VII-1), (VIII-1), (IX-1), (XIII-1), (XIV-1), (XV-1), and (XVI-1), or the salts thereof, L is selected from the group consisting of

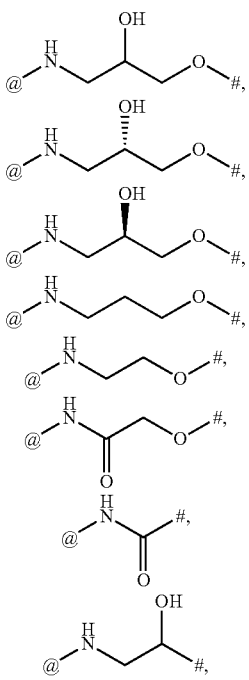

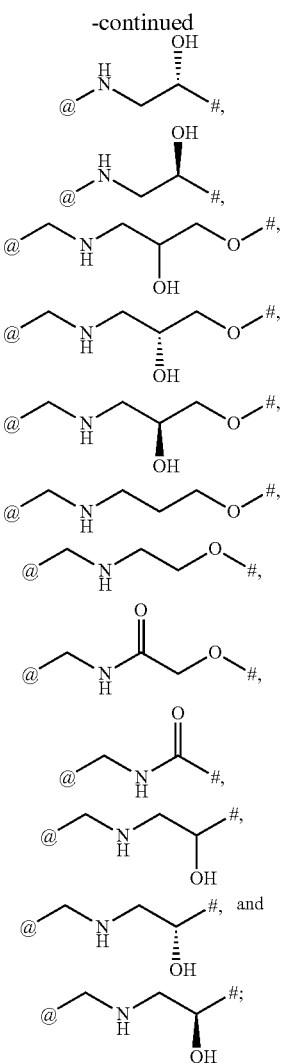

wherein # represents the attachment point to A and @ represents the attachment point to the remainder of the molecule.

In some embodiments of the compounds of formulae (I), (II), (III), (IV), (IX), (X), (XI), (XII), (XVII), (I-1), (II-1), (III-1), (IV-1), (IX-1), (X-1), (XI-1), (XII-1), and (XVII-1), or the salts thereof, L is selected from the group consisting of

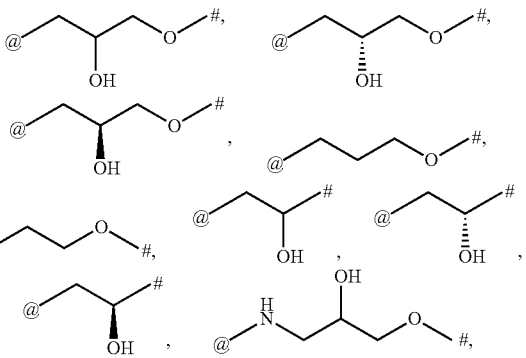

-continued

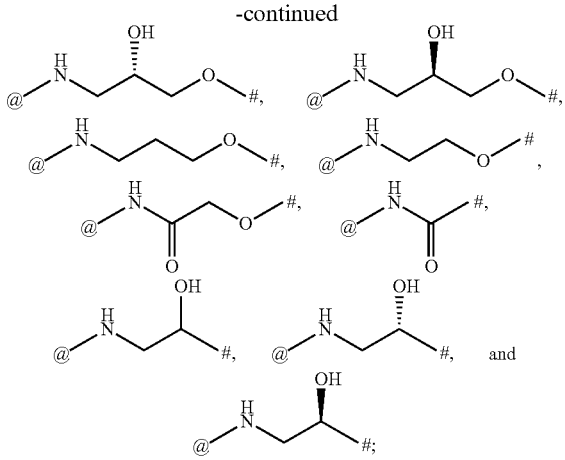

wherein # represents the attachment point to A and @ represents the attachment point to the remainder of the molecule.

In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), and (XVII-1), or the salts thereof, L is

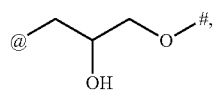

wherein # represents the attachment point to A and @ represents the attachment point to the remainder of the molecule. In such embodiments, the compound of formula (I-1), or the salt thereof, is a compound of formula (I-2), or a salt thereof. In such embodiments, the compound of formula (II-1) is a compound of formula (II-2), or a salt thereof. In such embodiments, the compound of formula (III-1) is a compound of formula (III-2), or a salt thereof. In such embodiments, the compound of formula (IV-1), or the salt thereof, is a compound of formula (IV-2), or a salt thereof. In such embodiments, the compound of formula (V-1), or the salt thereof, is a compound of formula (V-2), or a salt thereof. In such embodiments, the compound of formula (VI-1), or the salt thereof, is a compound of formula (VI-2), or a salt thereof. In such embodiments, the compound of formula (VII-1), or the salt thereof, is a compound of formula (VII-2), or a salt thereof. In such embodiments, the compound of formula (VIII-1), or the salt thereof, is a compound of formula (VIII-2), or a salt thereof. In such embodiments, the compound of formula (IX-1), or the salt thereof, is a compound of formula (IX-2), or a salt thereof. In such embodiments, the compound of formula (X-1), or the salt thereof, is a compound of formula (X-2), or a salt thereof. In such embodiments, the compound of formula (XI-1), or the salt thereof, is a compound of formula (XI-2), or a salt thereof. In such embodiments, the compound of formula (XII-1), or the salt thereof, is a compound of formula (XII-2), or a salt thereof. In such embodiments, the compound of formula (XIII-1), or the salt thereof, is a compound of formula (XIII-2), or a salt thereof. In such embodiments, the compound of formula (XIV-1), or the salt thereof, is a compound of formula (XIV-2), or a salt thereof.

In such embodiments, the compound of formula (XV-1), or the salt thereof, is a compound of formula (XV-2), or a salt thereof. In such embodiments, the compound of formula (XVI-1), or the salt thereof, is a compound of formula (XVI-2), or a salt thereof. In such embodiments, the compound of formula (XVII-1), or the salt thereof, is a compound of formula (XVII-2), or a salt thereof.

(I-2)

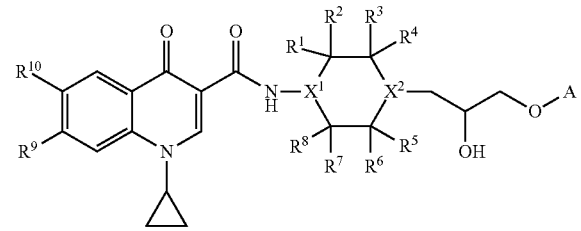

(II-2)

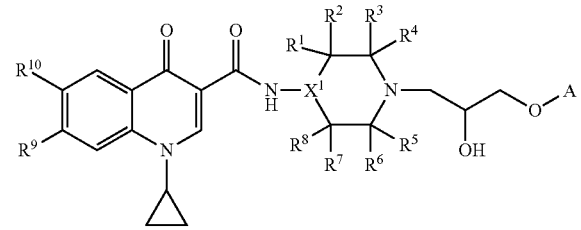

(III-2)

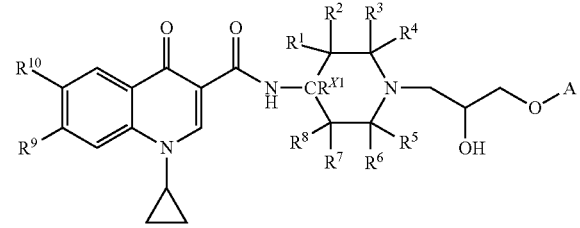

(IV-2)

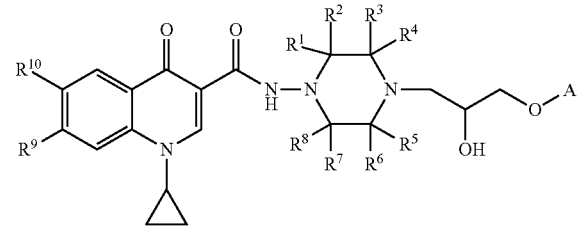

(V-2)

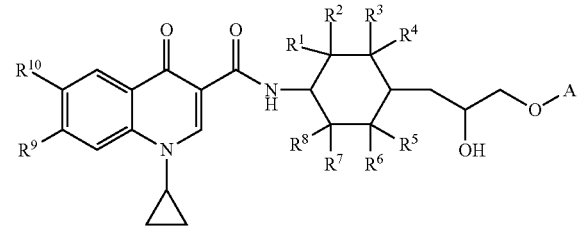

(VI-2)
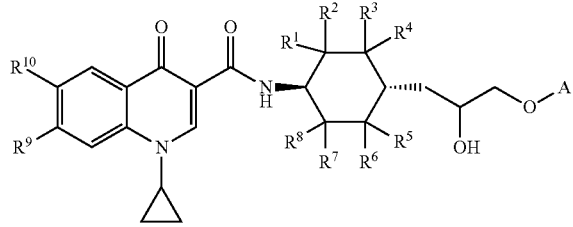
(XII-2)
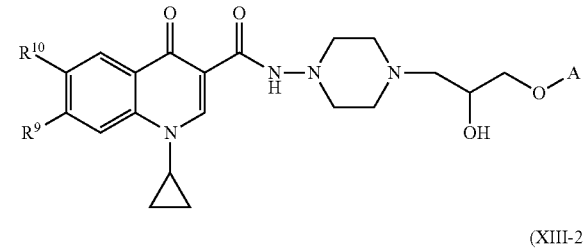
(VII-2)
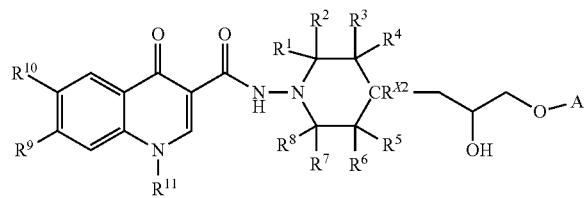
(XIII-2)
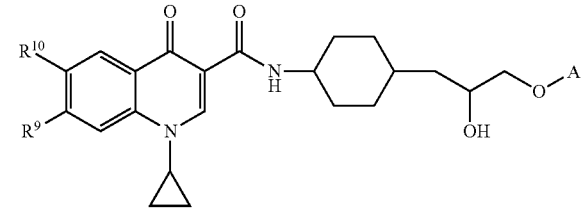
(VIII-2)
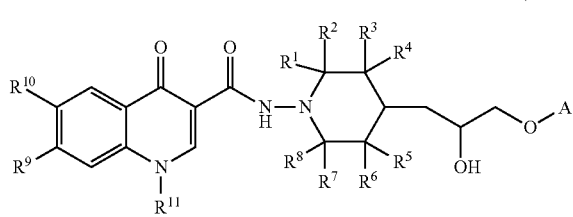
(XIV-2)
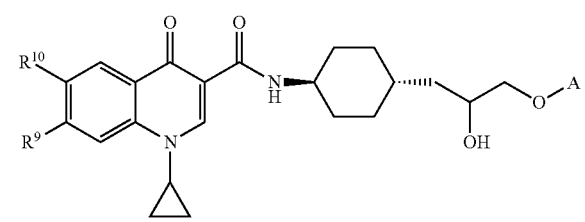
(IX-2)
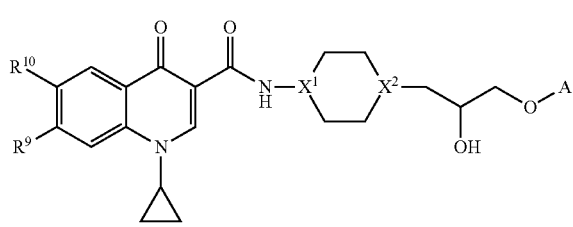
(XV-2)
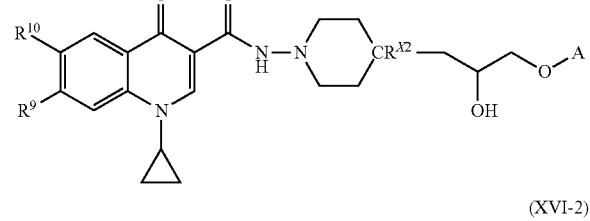
(X-2)
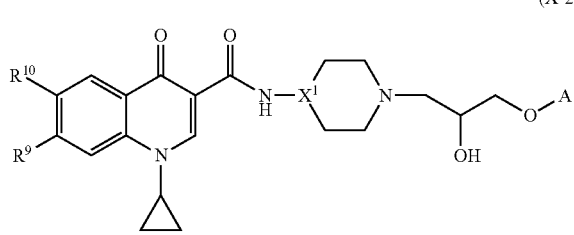
(XVI-2)
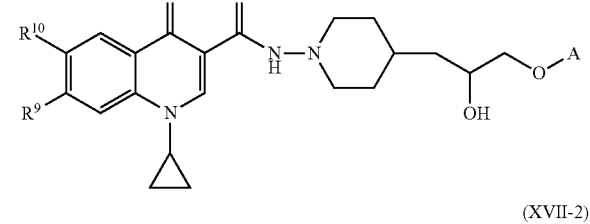
(XVII-2)
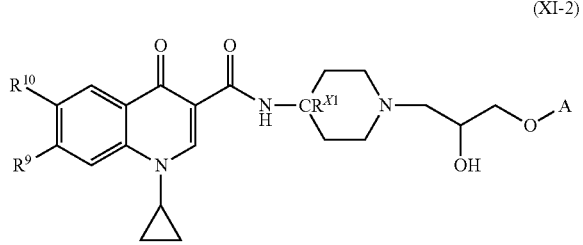
(XI-2)
In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (II-1), (IV-1), (V-1), (VI-1), (VII-1), (VIII-1), (IX-1), (X-1), (XI-1), (XII-1), (XIII-1), (XIV-1), (XV-1), (XVI-1), and (XVII-1), or the salts thereof, L is

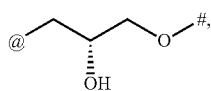

wherein # represents the attachment point to A and @ represents the attachment point to the remainder of the molecule. In such embodiments, the compound of formula (I-1), or the salt thereof, is a compound of formula (I-3), or a salt thereof. In such embodiments, the compound of formula (II-1) is a compound of formula (II-3), or a salt thereof. In such embodiments, the compound of formula (III-1) is a compound of formula (II-3), or a salt thereof. In such embodiments, the compound of formula (IV-1), or the salt thereof, is a compound of formula (IV-3), or a salt thereof. In such embodiments, the compound of formula (V-1), or the salt thereof, is a compound of formula (V-3), or a salt thereof. In such embodiments, the compound of formula (VI-1), or the salt thereof, is a compound of formula (VI-3), or a salt thereof. In such embodiments, the compound of formula (VII-1), or the salt thereof, is a compound of formula (VII-3), or a salt thereof. In such embodiments, the compound of formula (VIII-1), or the salt thereof, is a compound of formula (VIII-3), or a salt thereof. In such embodiments, the compound of formula (IX-1), or the salt thereof, is a compound of formula (IX-3), or a salt thereof. In such embodiments, the compound of formula (X-1), or the salt thereof, is a compound of formula (X-3), or a salt thereof. In such embodiments, the compound of formula (XI-1), or the salt thereof, is a compound of formula (XI-3), or a salt thereof. In such embodiments, the compound of formula (XII-1), or the salt thereof, is a compound of formula (XII-3), or a salt thereof. In such embodiments, the compound of formula (XIII-1), or the salt thereof, is a compound of formula (XIII-3), or a salt thereof. In such embodiments, the compound of formula (XIV-1), or the salt thereof, is a compound of formula (XIV-3), or a salt thereof. In such embodiments, the compound of formula (XV-1), or the salt thereof, is a compound of formula (XV-3), or a salt thereof. In such embodiments, the compound of formula (XVI-1), or the salt thereof, is a compound of formula (XVI-3), or a salt thereof. In such embodiments, the compound of formula (XVII-1), or the salt thereof, is a compound of formula (XVII-3), or a salt thereof.

(I-3)

(II-3)

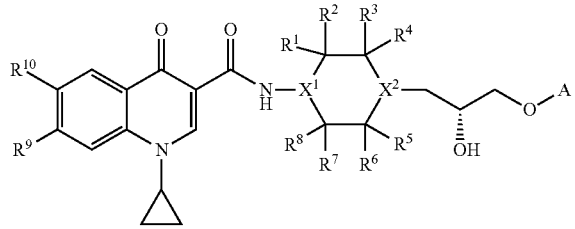

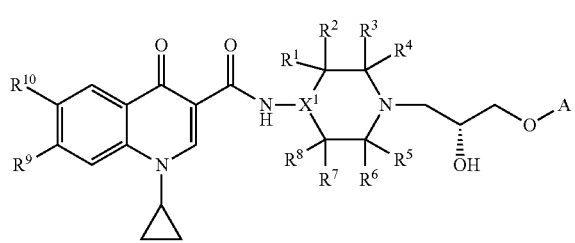

(III-3)

(IV-3)

(V-3)

(VI-3)

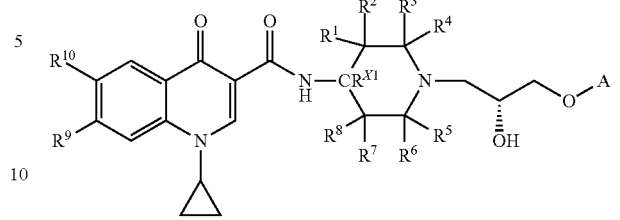

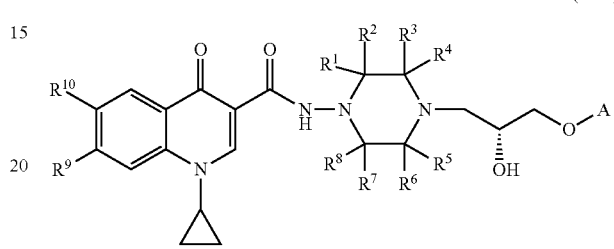

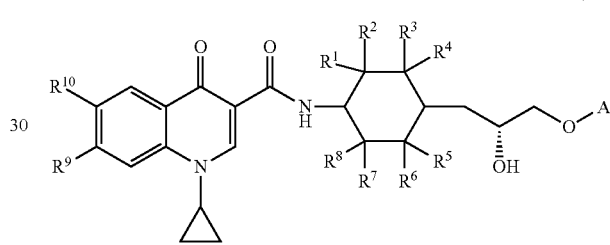

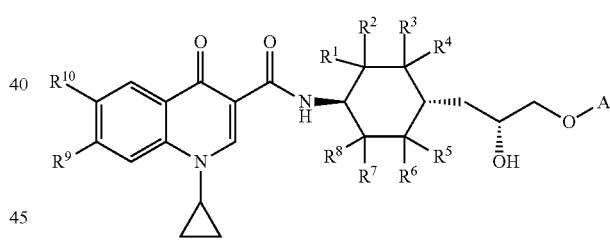

(VII-3)

(VIII-3)

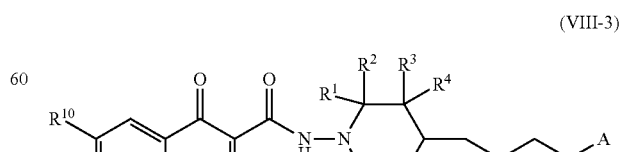

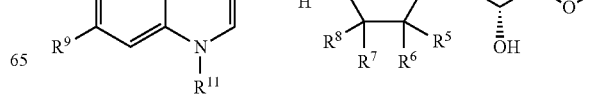

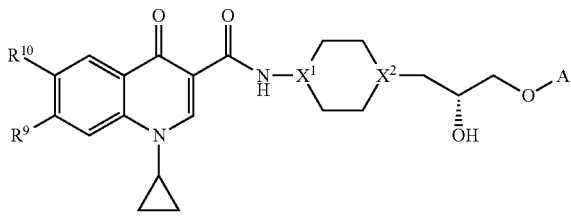
(IX-3)

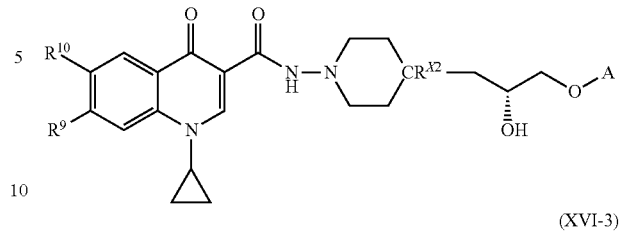
(XV-3)

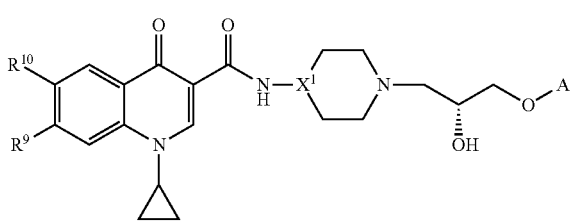
(X-3)

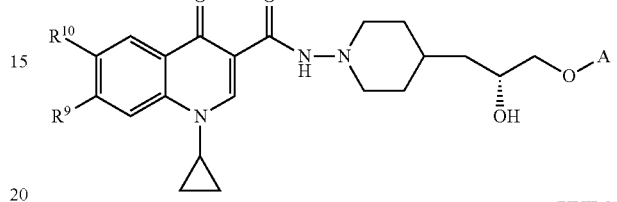
(XVI-3)

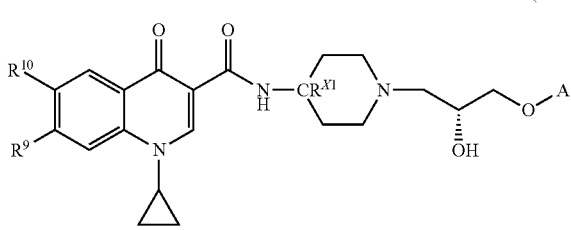
(XI-3)

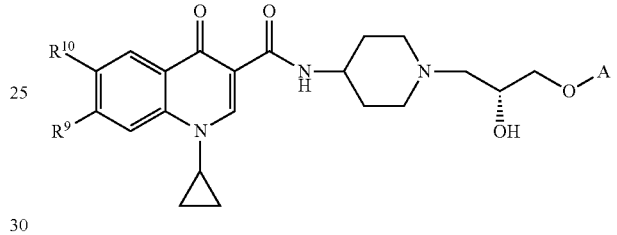
(XVII-3)

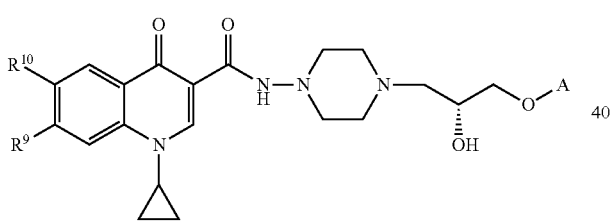
(XII-3)

In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), and (XVII-1), or the pharmaceutically acceptable salts thereof, L is

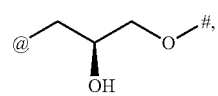

wherein # represents the attachment point to A and @ represents the attachment point to the remainder of the molecule. In such embodiments, the compound of formula (I-1), or the salt thereof, is a compound of formula (I-4), or a salt thereof. In such embodiments, the compound of formula (II-1) is a compound of formula (II-4), or a salt thereof. In such embodiments, the compound of formula (III-1) is a compound of formula (III-4), or a salt thereof. In such embodiments, the compound of formula (IV-1), or the salt thereof, is a compound of formula (IV-4), or a salt thereof. In such embodiments, the compound of formula (V-1), or the salt thereof, is a compound of formula (V-4), or a salt thereof. In such embodiments, the compound of formula (VI-1), or the salt thereof, is a compound of formula (VI-4), or a salt thereof. In such embodiments, the compound of formula (VII-1), or the salt thereof, is a compound of formula (VII-4), or a salt thereof. In such embodiments, the compound of formula (VIII-1), or the salt thereof, is a compound of formula (VIII-4), or a salt thereof. In such embodiments, the compound of formula (IX-1), or the salt thereof, is a compound of formula (IX-4), or a salt thereof. In such embodiments, the compound of formula (X-1), or the salt thereof, is a compound of formula (X-4), or a salt

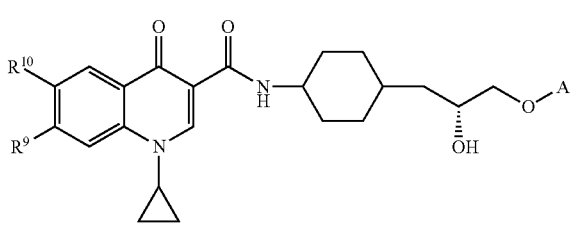
(XIII-3)

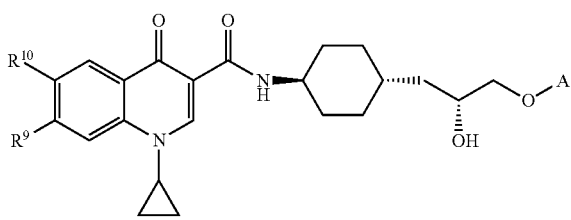
(XIV-3)

thereof. In such embodiments, the compound of formula (XI-1), or the salt thereof, is a compound of formula (XI-4), or a salt thereof. In such embodiments, the compound of formula (XII-1), or the salt thereof, is a compound of formula (XII-4), or a salt thereof. In such embodiments, the compound of formula (XIII-1), or the salt thereof, is a compound of formula (XIII-4), or a salt thereof. In such embodiments, the compound of formula (XIV-1), or the salt thereof, is a compound of formula (XIV-4), or a salt thereof. In such embodiments, the compound of formula (XV-1), or the salt thereof, is a compound of formula (XV-4), or a salt thereof. In such embodiments, the compound of formula (XVI-1), or the salt thereof, is a compound of formula (XVI-4), or a salt thereof. In such embodiments, the compound of formula (XVII-1), or the salt thereof, is a compound of formula (XVII-4), or a salt thereof.

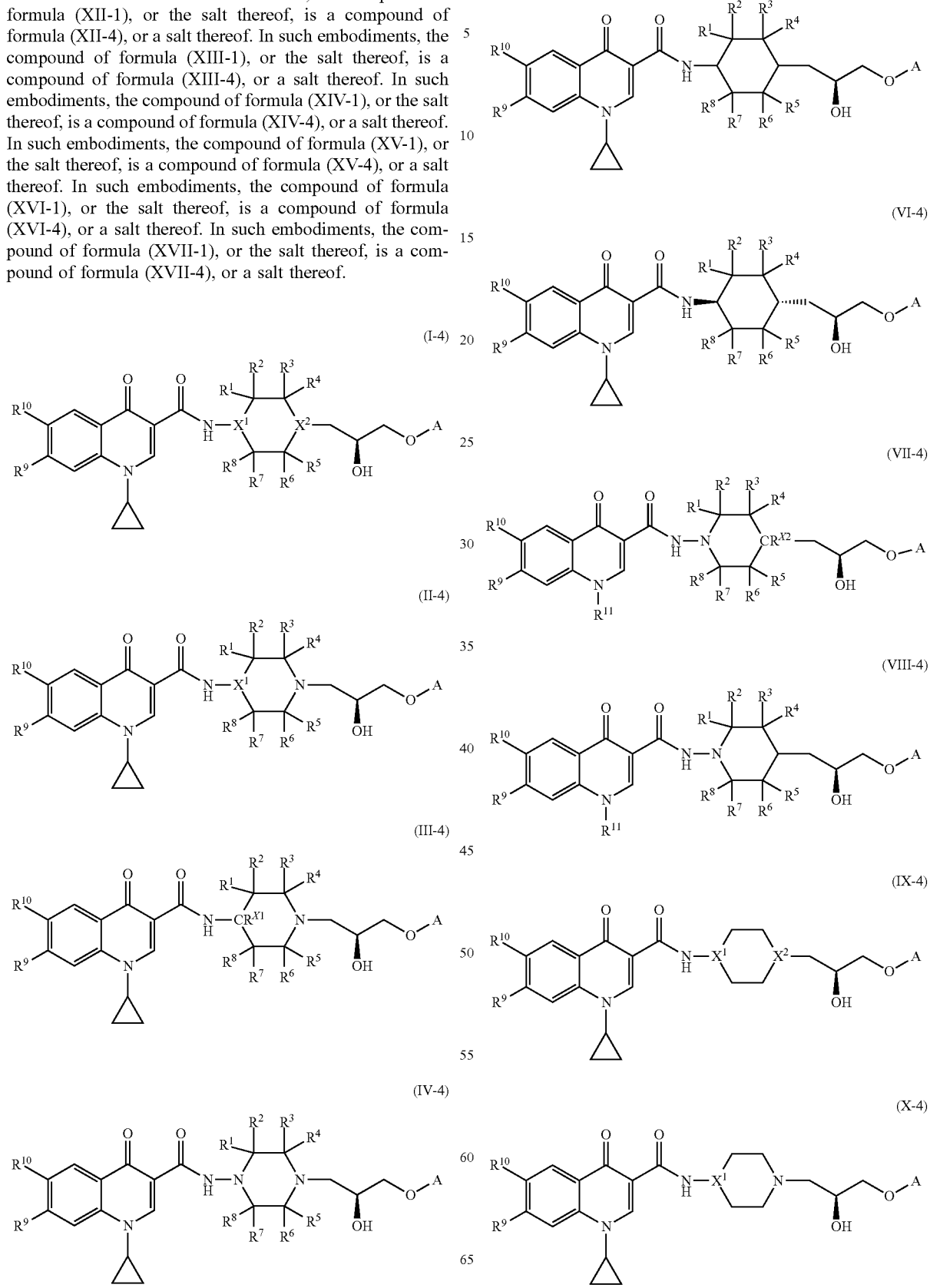

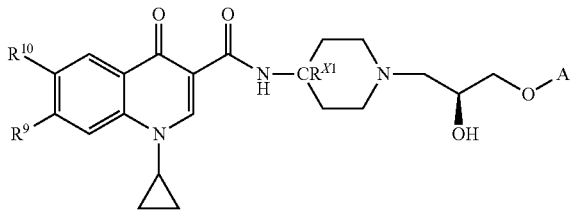

(XI-4)

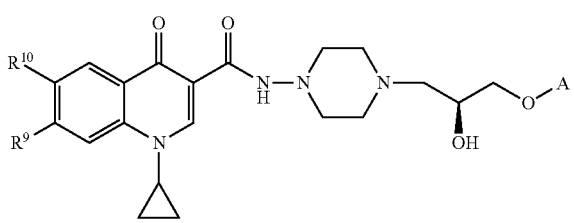

(XII-4)

(XIII-4)

(XIV-4)

(XV-4)

(XVI-4)

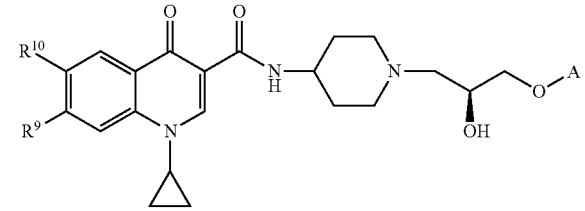

(XVII-4)

In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), (XVII-1), (I-2), (II-2), (III-2), (IV-2), (V-2), (VI-2), (VII-2), (VIII-2), (IX-2), (X-2), (XI-2), (XII-2), (XIII-2), (XIV-2), (XV-2), (XVI-2), (XVII-2), (I-3), (II-3), (III-3), (IV-3), (V-3), (VI-3), (VII-3), (VIII-3), (IX-3), (X-3), (XI-3), (XII-3), (XIII-3), (XIV-3), (XV-3), (XVI-3), (XVII-3), (I-4), (II-4), (III-4), (IV-4), (V-4), (VI-4), (VII-4), (VIII-4), (IX-4), (X-4), (XI-4), (XII-4), (XIII-4) (XIV-4), (XV-4), (XVI-4), and (XVII-4), or the salts thereof, $R^9$ and $R^{10}$ are each halogen. In some embodiments, $R^9$ is selected from the group consisting of fluoro, chloro, bromo, and iodo. In some embodiments, $R^9$ is fluoro. In some embodiments, $R^9$ is chloro. In some embodiments, $R^9$ is bromo. In some embodiments, $R^9$ is iodo. In some embodiments, $R^{10}$ is selected from the group consisting of fluoro, chloro, bromo, and iodo. In some embodiments, $R^{10}$ is fluoro. In some embodiments, $R^{10}$ is chloro. In some embodiments, $R^{10}$ is bromo. In some embodiments, $R^{10}$ is iodo. In some embodiments, $R^9$ and $R^{10}$, independently of each other, are selected from the group consisting of fluoro, chloro, bromo, and iodo. In some embodiments, $R^9$ is chloro and $R^{10}$ is fluoro.

In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), (XVII-1), (I-2), (II-2), (III-2), (IV-2), (V-2), (VI-2), (VII-2), (VIII-2), (IX-2), (X-2), (XI-2), (XII-2), (XIII-2), (XIV-2), (XV-2), (XVI-2), (XVII-2), (I-3), (II-3), (III-3), (IV-3), (V-3), (VI-3), (VII-3), (VIII-3), (IX-3), (X-3), (XI-3), (XII-3), (XIII-3), (XIV-3), (XV-3), (XVI-3), (XVII-3), (I-4), (II-4), (III-4), (IV-4), (V-4), (VI-4), (VII-4), (VIII-4), (IX-4), (X-4), (XI-4), (XII-4), (XIII-4) (XIV-4), (XV-4), (XVI-4), and (XVII-4), or the salts thereof, A is a substituent of formula (A-1)

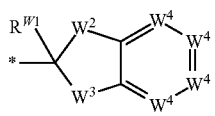

(A-1)

wherein $W^2$ is selected from the group consisting of $-C(R^{W2-1}R^{W2-2})-$, $-N(R^{W2-2})-$, $-C(R^{W2-1}R^{W2-1})N(R^{W2-2})-$, $-N(R^{W2-1})C(R^{W2-1}R^{W2-2})-$, $-C(R^{W2-1})=N-$, $-N=C(R^{W2-1})-$, $-O-$, $-C(R^{W2-1}R^{W2-1})O-$, $-OC(R^{W2-1}R^{W2-2})-$, $-S-$, $-C(R^{W2-1}R^{W2-1})S-$, $-SC(R^{W2-1}R^{W2-2})-$, $-C(R^{W2-1}R^{W2-1})C(R^{W2-1}R^{W2-2})-$, and $-CR^{W2-1}=CR^{W2-1}-$;

wherein $R^{W2-1}$ is H or $R^A$, and $R^{W2-2}$ is H or $R^A$;

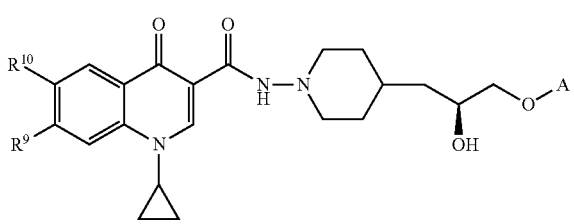

$W^3$ is selected from the group consisting of —C($R^{W3-1}$ $R^{W3-2}$)—, —N($R^{W3-2}$)—, —C($R^{W3-1}R^{W3-1}$)N($R^{W3-2}$)—, —N($R^{W3-1}$)C($R^{W3-1}R^{W3-2}$)—, —C($R^{W3-1}$)=N—, —N=C($R^{W3-1}$)—, —O—, —C($R^{W3-1}R^{W3-1}$)O—, —OC($R^{W3-1}$ $R^{W3-2}$)—, —S—, —C($R^{W3-1}R^{W3-1}$)S—, —SC($R^{W3-1}$ $R^{W3-2}$)—, —C($R^{W3-1}R^{W3-1}$)C($R^{W3-1}R^{W3-2}$)—, and —C$R^{W3-1}$=C$R^{W3-1}$—, wherein $R^{W3-1}$ is H or $R^A$, and $R^{W3-2}$ is H or $R^A$;

$W^4$, independently at each occurrence, is C$R^{W4}$ or N, wherein $R^{W4}$ is H or $R^A$;

$R^{W1}$ is hydrogen or $R^A$, or $R^{W1}$ and $R^{W2-2}$ are taken together to form a double bond between the carbon atom bearing $R^{W1}$ and the atom bearing $R^{W2-2}$, or $R^{W1}$ and $R^{W3-2}$ are taken together to form a double bond between the carbon atom bearing $R^{W1}$ and the atom bearing $R^{W3-2}$. In some embodiments, (A-1) is selected from the group consisting of

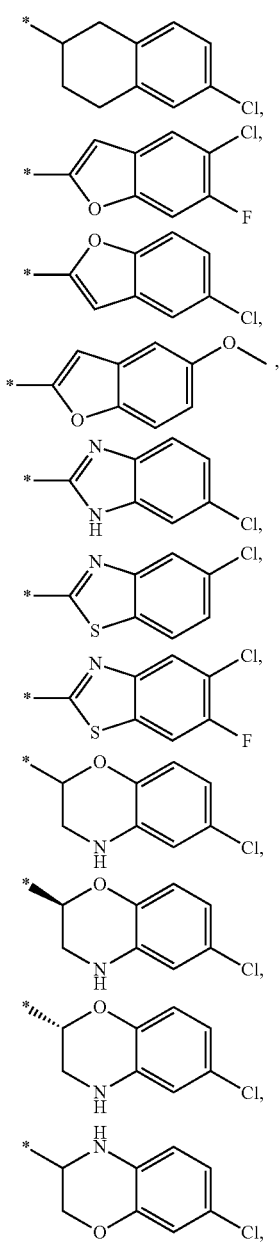

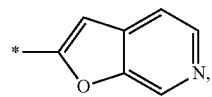

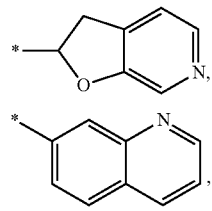

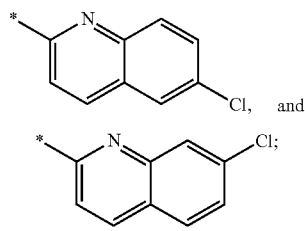

wherein * represents the attachment point to the remainder of the molecule. In some embodiments, (A-1) is

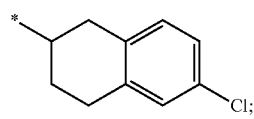

wherein * represents the attachment point to the remainder of the molecule. In some embodiments, (A-1) is

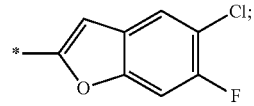 [SMILES: *c1cc2cc(Cl)c(F)cc2o1]

wherein * represents the attachment point to the remainder of the molecule. In some embodiments, (A-1) is

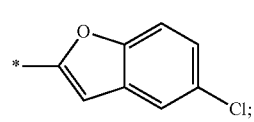 [SMILES: *c1cc2cc(Cl)ccc2o1]

wherein * represents the attachment point to the remainder of the molecule. In some embodiments, (A-1) is

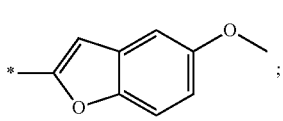

wherein * represents the attachment point to the remainder of the molecule. In some embodiments, (A-1) is

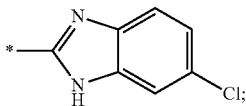 [SMILES: *c1nc2ccc(Cl)cc2[nH]1]

wherein * represents the attachment point to the remainder of the molecule. In some embodiments, (A-1) is

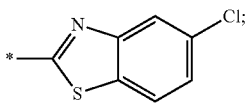 [SMILES: *c1nc2cc(Cl)ccc2s1]

wherein * represents the attachment point to the remainder of the molecule. In some embodiments, (A-1) is

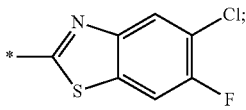

wherein * represents the attachment point to the remainder of the molecule. In some embodiments, (A-1) is

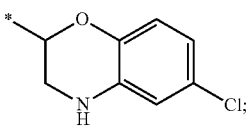 [SMILES: *C1CNc2cc(Cl)ccc2O1]

wherein * represents the attachment point to the remainder of the molecule. In some embodiments, (A-1) is

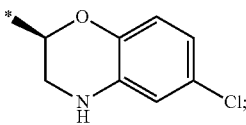 [SMILES: *[C@@H]1CNc2cc(Cl)ccc2O1]

wherein * represents the attachment point to the remainder of the molecule. In some embodiments, (A-1) is

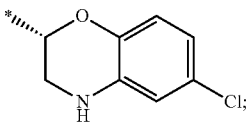 [SMILES: *[C@H]1CNc2cc(Cl)ccc2O1]

wherein * represents the attachment point to the remainder of the molecule. In some embodiments, (A-1) is

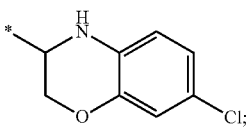 [SMILES: *C1COc2cc(Cl)ccc2N1]

wherein * represents the attachment point to the remainder of the molecule. In some embodiments, (A-1) is

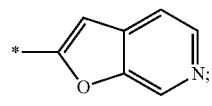 [SMILES: *c1cc2ccncc2o1]

wherein * represents the attachment point to the remainder of the molecule. In some embodiments, (A-1) is

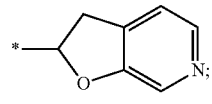

wherein * represents the attachment point to the remainder of the molecule. In some embodiments, (A-1) is

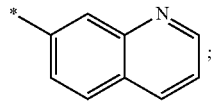 [SMILES: *c1ccc2cccnc2c1]

wherein * represents the attachment point to the remainder of the molecule. In some embodiments, (A-1) is

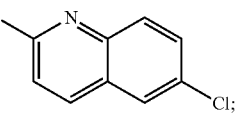

wherein * represents the attachment point to the remainder of the molecule. In some embodiments, (A-1) is

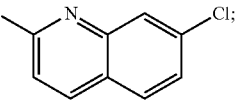

wherein * represents the attachment point to the remainder of the molecule.

In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), (XVII-1), (I-2), (II-2), (III-2), (IV-2), (V-2), (VI-2), (VII-2), (VIII-2), (IX-2), (X-2), (XI-2), (XII-2), (XIII-2), (XIV-2), (XV-2), (XVI-2), (XVII-2), (I-3), (II-3), (111-3), (IV-3), (V-3), (VI-3), (VII-3), (VIII-3), (IX-3), (X-3), (XI-3), (XII-3), (XIII-3), (XIV-3), (XV-3), (XVI-3), (XVII-3), (I-4), (II-4), (III-4), (IV-4), (V-4), (VI-4), (VII-4), (VIII-4), (IX-4), (X-4), (XI-4), (XII-4), (XIII-4) (XIV-4), (XV-4), (XVI-4), and (XVII-4), or the salts thereof, A is $C_6$-$C_{14}$ aryl optionally substituted with 1, 2, 3, 4, 5, 6, 7, 8, or 9 $R^A$ substituents. In some embodiments, A is phenyl optionally substituted with 1, 2, 3, 4, or 5 $R^A$ substituents. In some embodiments, A is phenyl substituted with two $R^A$ substituents. In some embodiments, A is phenyl substituted with two $R^A$ substituents and $R^A$, independently at each occurrence, is halogen. In embodiments, A is phenyl substituted with two $R^A$ substituents and $R^A$, independently at each occurrence, is selected from the group consisting of fluoro, chloro, bromo, and iodo. In some embodiments, A is phenyl substituted with two $R^A$ substituents and one $R^A$ is fluoro and the other $R^A$ is chloro. In some embodiments, A is 1-chloro-2-fluoro-benz-4-yl. In some embodiments, A is selected from the group consisting of

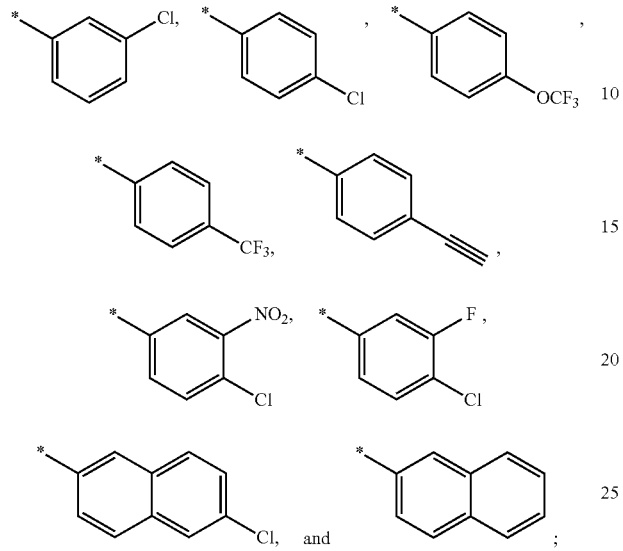

wherein * represents the attachment point to the remainder of the molecule. In some embodiments, A is

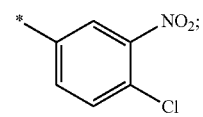 [SMILES: *c1ccc(Cl)c([N+](=O)[O-])c1]

wherein * represents the attachment point to the remainder of the molecule. In some embodiments, A is

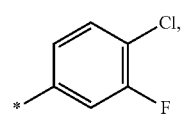 [SMILES: *c1ccc(Cl)c(F)c1]

wherein * represents the attachment point to the remainder of the molecule. In some embodiments, A is

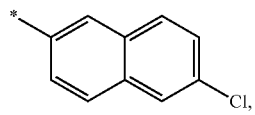 [SMILES: *c1ccc2cc(Cl)ccc2c1]

wherein * represents the attachment point to the remainder of the molecule. In some embodiments, A is

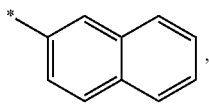 [SMILES: *c1ccc2ccccc2c1]

wherein * represents the attachment point to the remainder of the molecule. In some embodiments, A is

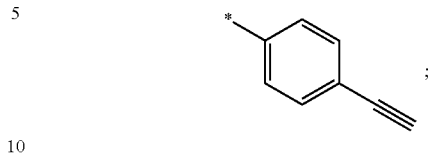

wherein * represents the attachment point to the remainder of the molecule. In some embodiments, A is wherein * represents the attachment point to the remainder of the molecule. In some embodiments, A is wherein * represents the attachment point to the remainder of the molecule. In some embodiments, A is wherein * represents the attachment point to the remainder of the molecule. In some embodiments, A is wherein * represents the attachment point to the remainder of the molecule.

In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), (XVII-1), (I-2), (II-2), (III-2), (IV-2), (V-2), (VI-2), (VII-2), (VIII-2), (IX-2), (X-2), (XI-2), (XII-2), (XIII-2), (XIV-2), (XV-2), (XVI-2), (XVII-2), (I-3), (II-3), (III-3), (IV-3), (V-3), (VI-3), (VII-3), (VIII-3), (IX-3), (X-3), (XI-3), (XII-3), (XIII-3), (XIV-3), (XV-3), (XVI-3), (XVII-3), (I-4), (II-4), (III-4), (IV-4), (V-4), (VI-4), (VII-4), (VIII-4), (IX-4), (X-4), (XI-4), (XII-4), (XIII-4) (XIV-4), (XV-4), (XVI-4), and (XVII-4), or the salts thereof, A is (A-2)

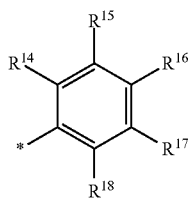

(A-2)

wherein * represents the attachment point to the remainder of the molecule, and each of $R^{14}$, $R^{15}$, $R^{16}$, $R^{17}$, and $R^{18}$, independently of each other is hydrogen or $R^A$. In some embodiments, each of $R^{14}$, $R^{15}$, $R^{16}$, $R^{17}$, and $R^{18}$, independently of each other is hydrogen or halogen. In some embodiments, $R^{14}$ is hydrogen, $R^{15}$ is halogen, $R^{16}$ is halogen, $R^{17}$ is hydrogen, and $R^{18}$ is hydrogen. In some embodiments, (A-2) is selected from the group consisting of

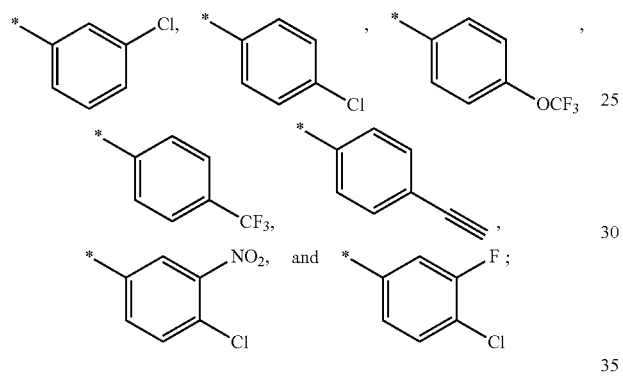

wherein * represents the attachment point to the remainder of the molecule. In some embodiments, (A-2) is

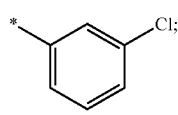 [SMILES: *c1cccc(Cl)c1]

wherein * represents the attachment point to the remainder of the molecule. In some embodiments, (A-2) is

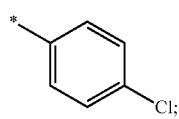

wherein * represents the attachment point to the remainder of the molecule. In some embodiments, (A-2) is

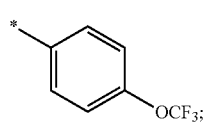 [SMILES: *c1ccc(OC(F)(F)F)cc1]

wherein * represents the attachment point to the remainder of the molecule. In some embodiments, (A-2) is

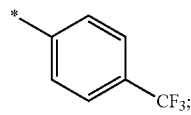

wherein * represents the attachment point to the remainder of the molecule. In some embodiments, (A-2) is

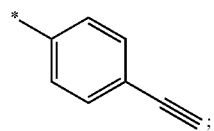 [SMILES: *c1ccc(C#C)cc1]

wherein * represents the attachment point to the remainder of the molecule. In some embodiments, (A-2) is

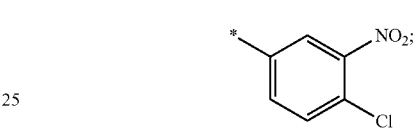

wherein * represents the attachment point to the remainder of the molecule. In some embodiments, (A-2) is

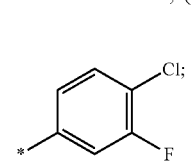

wherein * represents the attachment point to the remainder of the molecule.

In some embodiments of the compounds of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), (XVII-1), (I-2), (II-2), (II-2), (IV-2), (V-2), (VI-2), (VII-2), (VIII-2), (IX-2), (X-2), (XI-2), (XII-2), (XIII-2), (XIV-2), (XV-2), (XVI-2), (XVII-2), (I-3), (II-3), (III-3), (IV-3), (V-3), (VI-3), (VII-3), (VIII-3), (IX-3), (X-3), (XI-3), (XII-3), (XIII-3), (XIV-3), (XV-3), (XVI-3), (XVII-3), (I-4), (II-4), (III-4), (IV-4), (V-4), (VI-4), (VII-4), (VIII-4), (IX-4), (X-4), (XI-4), (XII-4), (XIII-4) (XIV-4), (XV-4), (XVI-4), and (XVII-4), or the salts thereof, 5-14 membered heteroaryl optionally substituted with 1, 2, 3, 4, 5, 6, 7, 8, or 9 $R^A$ substituents. In some embodiments, A is pyridyl optionally substituted with 1, 2, 3, 4, or 5 $R^A$ substituents. In some embodiments, A is pyrazinyl optionally substituted with 1, 2, 3, 4, or 5 $R^A$ substituents. In some embodiments, A is quinolinyl optionally substituted with 1, 2, 3, 4, or 5 $R^A$ substituents. In some embodiments, A is selected from the group consisting of

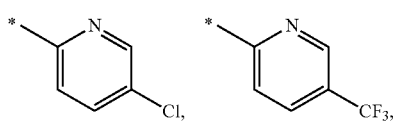

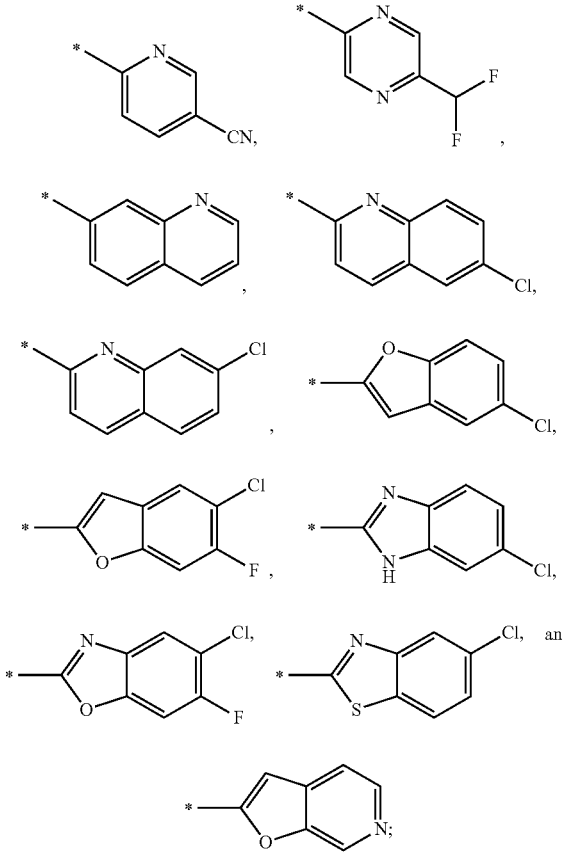, and wherein * represents the attachment point to the remainder of the molecule. In some embodiments, A is

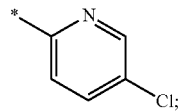

wherein * represents the attachment point to the remainder of the molecule. In some embodiments, A is

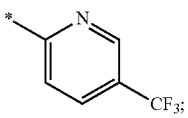

wherein * represents the attachment point to the remainder of the molecule. In some embodiments, A is

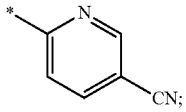 [SMILES: *c1ccc(C#N)cn1]

wherein * represents the attachment point to the remainder of the molecule. In some embodiments, A is

wherein * represents the attachment point to the remainder of the molecule. In some embodiments, A is

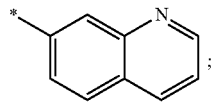

wherein * represents the attachment point to the remainder of the molecule. In some embodiments, A is

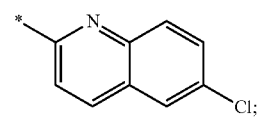 [SMILES: *c1ccc2cc(Cl)ccc2n1]

wherein * represents the attachment point to the remainder of the molecule. In some embodiments, A is

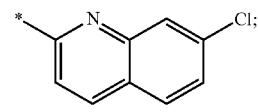 [SMILES: *c1ccc2ccc(Cl)cc2n1]

wherein * represents the attachment point to the remainder of the molecule. In some embodiments, A is

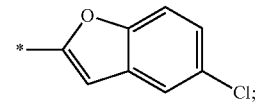 [SMILES: *c1cc2cc(Cl)ccc2o1]

wherein * represents the attachment point to the remainder of the molecule. In some embodiments, A is

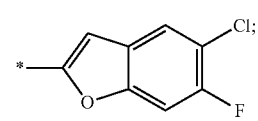 [SMILES: *c1cc2cc(Cl)c(F)cc2o1]

wherein * represents the attachment point to the remainder of the molecule. In some embodiments, A is

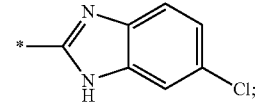 [SMILES: *c1nc2ccc(Cl)cc2[nH]1]

wherein * represents the attachment point to the remainder of the molecule. In some embodiments, A is

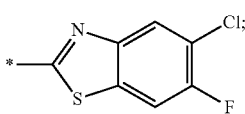 [SMILES: *c1nc2cc(Cl)c(F)cc2s1]

wherein * represents the attachment point to the remainder of the molecule. In some embodiments, A is

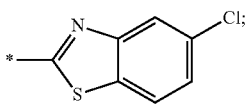 [SMILES: *c1nc2cc(Cl)ccc2s1]

wherein * represents the attachment point to the remainder of the molecule. In some embodiments, A is

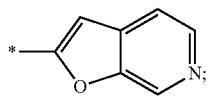

wherein * represents the attachment point to the remainder of the molecule.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to A of formula (I) may be combined with every description, variation, embodiment or aspect of $X^1$, $X^2$, L, $R^1$, $R^2$, $R^3$, $R^4$, $R^5$, $R^6$, $R^7$, R, $R^9$, $R^{10}$, and $R^{11}$, the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae (I), (II), (III), (IV), (V), (VI), (VII), (VIII), (IX), (X), (XI), (XII), (XIII), (XIV), (XV), (XVI), (XVII), (I-1), (II-1), (III-1), (IV-1), (V-1), (VI-1), (VII-1), (VIII-1), (IX-1), (X-1), (XI-1), (XII-1), (XIII-1), (XIV-1), (XV-1), (XVI-1), (XVII-1), (I-2), (II-2), (II-2), (IV-2), (V-2), (VI-2), (VII-2), (VIII-2), (IX-2), (X-2), (XI-2), (XII-2), (XIII-2), (XIV-2), (XV-2), (XVI-2), (XVII-2), (I-3), (II-3), (III-3), (IV-3), (V-3), (VI-3), (VII-3), (VIII-3), (IX-3), (X-3), (XI-3), (XII-3), (XIII-3), (XIV-3), (XV-3), (XVI-3), (XVII-3), (I-4), (II-4), (III-4), (IV-4), (V-4), (VI-4), (VII-4), (VIII-4), (IX-4), (X-4), (XI-4), (XII-4), (XIII-4) (XIV-4), (XV-4), (XVI-4), and (XVII-4), detailed herein, and are equally described, the same as if each and every description, variation, embodiment or aspect were separately and individually listed for all formulae.

Also provided are salts of compounds referred to herein, such as pharmaceutically acceptable salts and agriculturally acceptable salts. The present disclosure also includes any or all of the stereochemical forms, including any enantiomeric or diastereomeric forms, and any tautomers or other forms of the compounds described. Thus, if a particular stereochemical form, such as a specific enantiomeric form or diastereomeric form, is depicted for a given compound, then it is understood that any or all stereochemical forms, including any enantiomeric or diastereomeric forms, and any tautomers or other forms of any of that same compound are herein described and embraced by the invention.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

In some embodiments, provided is compound selected from compounds in Table 1, or a stereoisomer, tautomer, solvate, prodrug or salt thereof. Although certain compounds described in Table 1 are presented as specific stereoisomers and/or in a non-stereochemical form, it is understood that any or all stereochemical forms, including any enantiomeric or diastereomeric forms, and any tautomers or other forms of any of the compounds of Table 1 are herein described.

TABLE 1

| Cpd No. | Structure |
| --- | --- |
| 1 | 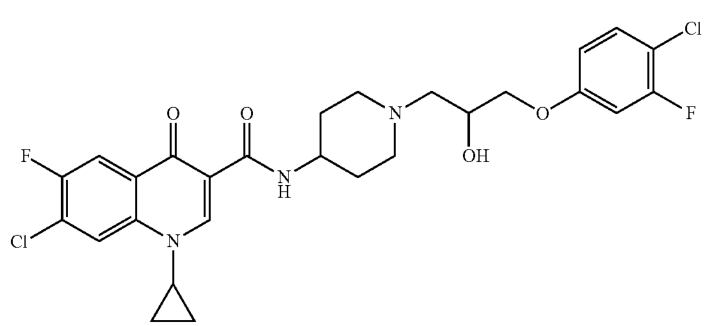 [SMILES: O=C(NC1CCN(CC(O)COc2ccc(Cl)c(F)c2)CC1)c1cn(C2CC2)c2cc(Cl)c(F)cc2c1=O] |

TABLE 1-continued
| Cpd No. | Structure |
|---|---|
| 2 | 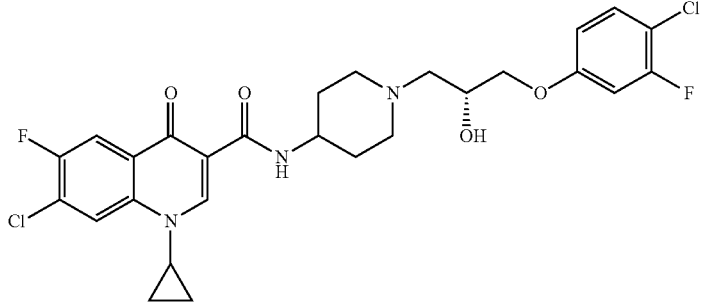 [SMILES: O=C(NC1CCN(C[C@@H](O)COc2ccc(Cl)c(F)c2)CC1)c1cn(C2CC2)c2cc(Cl)c(F)cc2c1=O] |
| 3 | 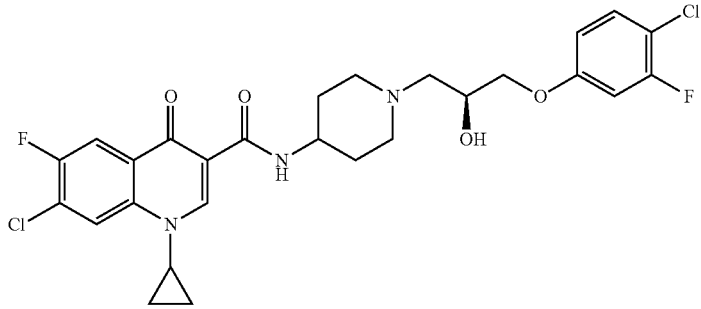 [SMILES: O=C(NC1CCN(C[C@H](O)COc2ccc(Cl)c(F)c2)CC1)c1cn(C2CC2)c2cc(Cl)c(F)cc2c1=O] |
| 4 | 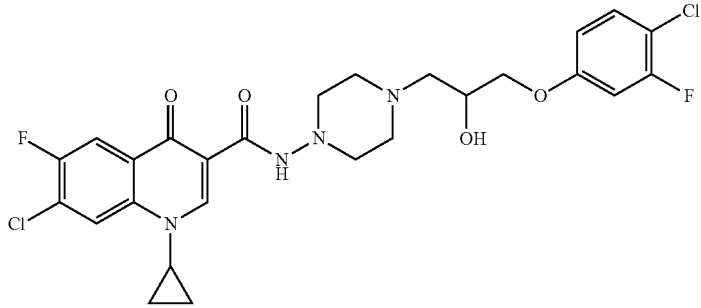 [SMILES: O=C(NN1CCN(CC(O)COc2ccc(Cl)c(F)c2)CC1)c1cn(C2CC2)c2cc(Cl)c(F)cc2c1=O] |
| 5 | 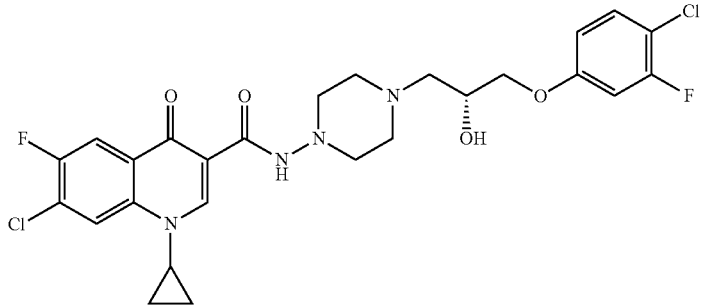 [SMILES: O=C(NN1CCN(C[C@@H](O)COc2ccc(Cl)c(F)c2)CC1)c1cn(C2CC2)c2cc(Cl)c(F)cc2c1=O] |
| 6 | 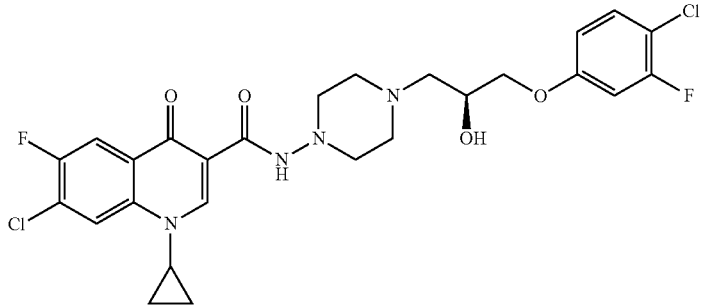 [SMILES: O=C(NN1CCN(C[C@H](O)COc2ccc(Cl)c(F)c2)CC1)c1cn(C2CC2)c2cc(Cl)c(F)cc2c1=O] |

TABLE 1-continued
| Cpd No. | Structure |
|---|---|
| 7 | 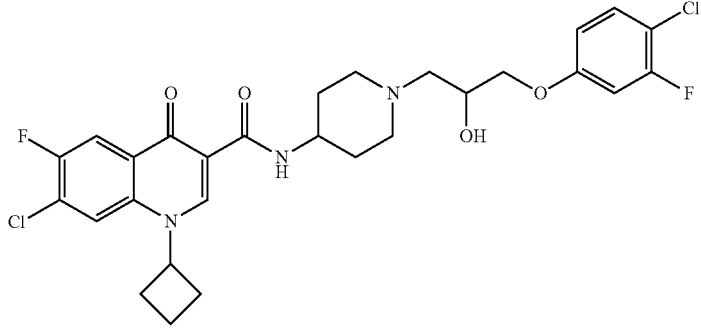 [SMILES: O=C(NC1CCN(CC(O)COc2ccc(Cl)c(F)c2)CC1)c1cn(C2CCC2)c2cc(Cl)c(F)cc2c1=O] |
| 8 | 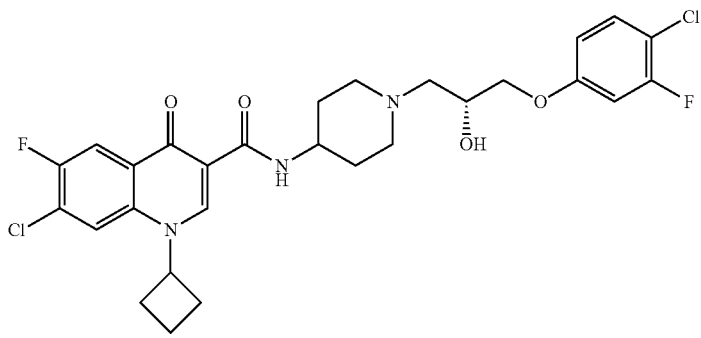 [SMILES: O=C(NC1CCN(C[C@@H](O)COc2ccc(Cl)c(F)c2)CC1)c1cn(C2CCC2)c2cc(Cl)c(F)cc2c1=O] |
| 9 | 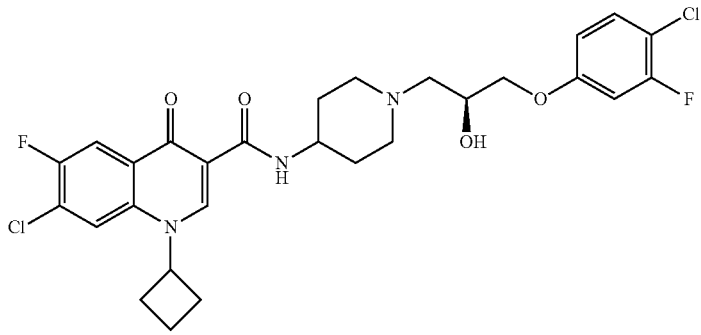 [SMILES: O=C(NC1CCN(C[C@H](O)COc2ccc(Cl)c(F)c2)CC1)c1cn(C2CCC2)c2cc(Cl)c(F)cc2c1=O] |
| 10 | 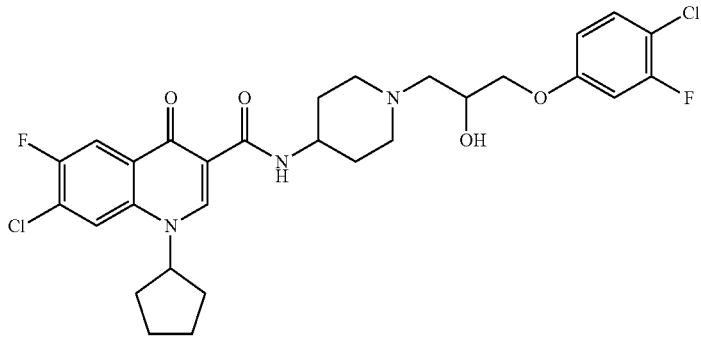 [SMILES: O=C(NC1CCN(CC(O)COc2ccc(Cl)c(F)c2)CC1)c1cn(C2CCCC2)c2cc(Cl)c(F)cc2c1=O] |

TABLE 1-continued

| Cpd No. | Structure |
|---|---|
| 11 | 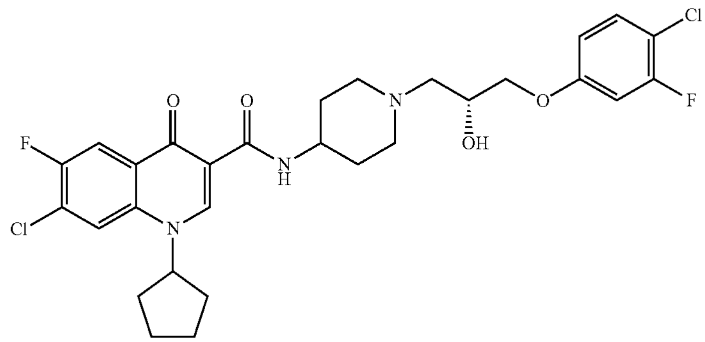 [SMILES: O=C(NC1CCN(C[C@@H](O)COc2ccc(Cl)c(F)c2)CC1)c1cn(C2CCCC2)c2cc(Cl)c(F)cc2c1=O] |
| 12 | 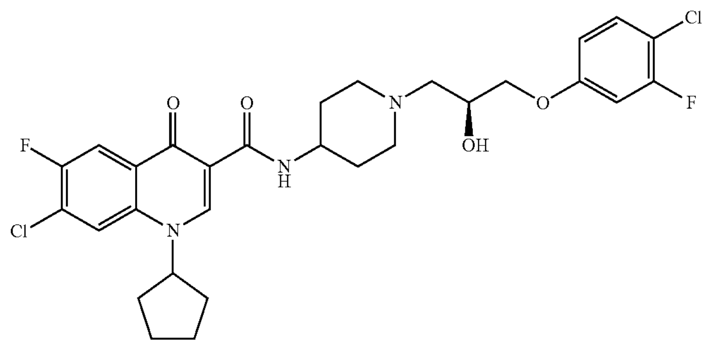 [SMILES: O=C(NC1CCN(C[C@H](O)COc2ccc(Cl)c(F)c2)CC1)c1cn(C2CCCC2)c2cc(Cl)c(F)cc2c1=O] |
| 13 | 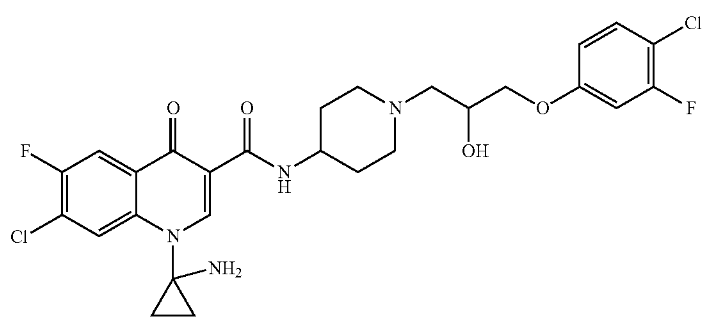 [SMILES: NC1(n2cc(C(=O)NC3CCN(CC(O)COc4ccc(Cl)c(F)c4)CC3)c(=O)c3cc(F)c(Cl)cc32)CC1] |
| 14 | 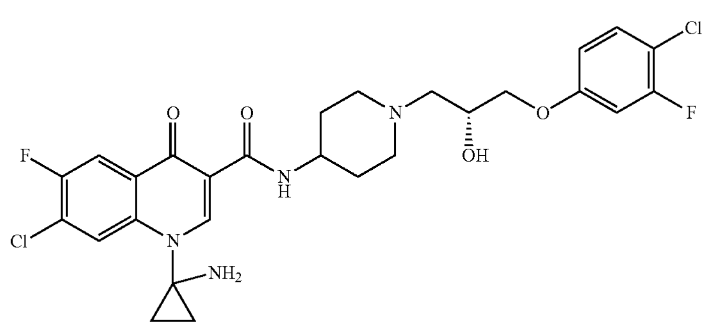 [SMILES: NC1(n2cc(C(=O)NC3CCN(C[C@@H](O)COc4ccc(Cl)c(F)c4)CC3)c(=O)c3cc(F)c(Cl)cc32)CC1] |

TABLE 1-continued

| Cpd No. | Structure |
|---|---|
| 15 | 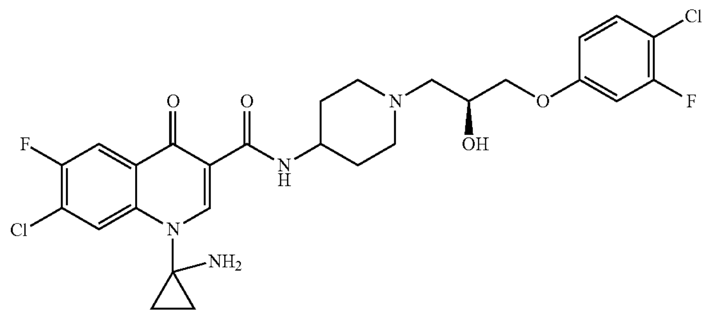 [SMILES: NC1(n2cc(C(=O)NC3CCN(C[C@H](O)COc4ccc(Cl)c(F)c4)CC3)c(=O)c3cc(F)c(Cl)cc32)CC1] |
| 16 | 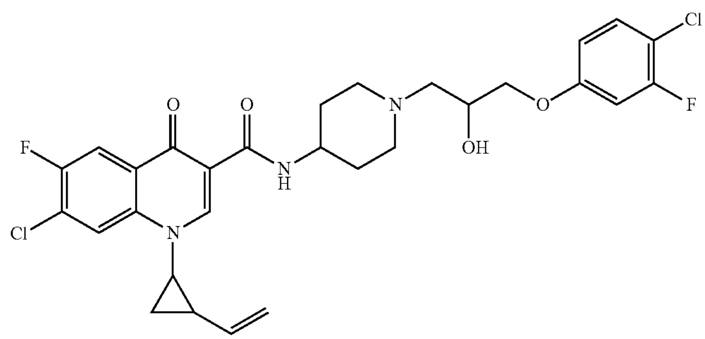 [SMILES: C=CC1CC1n1cc(C(=O)NC2CCN(CC(O)COc3ccc(Cl)c(F)c3)CC2)c(=O)c2cc(F)c(Cl)cc21] |
| 17 | 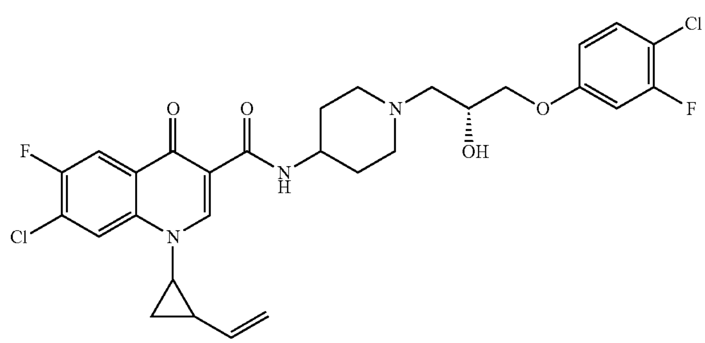 [SMILES: C=CC1CC1n1cc(C(=O)NC2CCN(C[C@@H](O)COc3ccc(Cl)c(F)c3)CC2)c(=O)c2cc(F)c(Cl)cc21] |
| 18 | 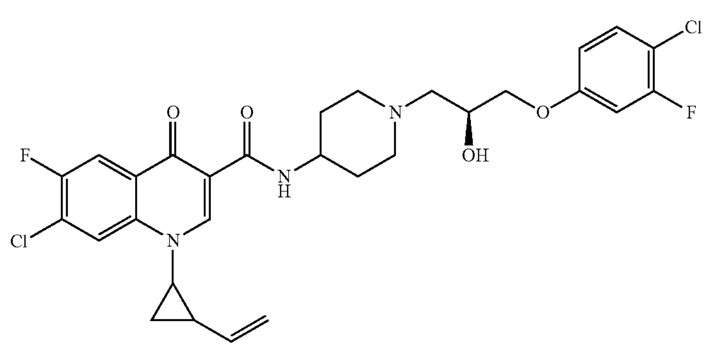 [SMILES: C=CC1CC1n1cc(C(=O)NC2CCN(C[C@H](O)COc3ccc(Cl)c(F)c3)CC2)c(=O)c2cc(F)c(Cl)cc21] |

TABLE 1-continued
| Cpd No. | Structure |
|---|---|
| 19 | 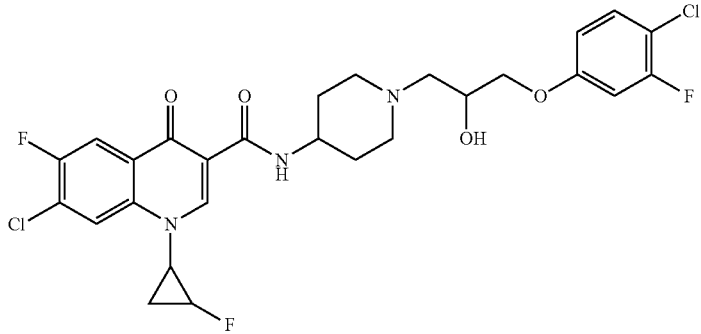 [SMILES: O=C(NC1CCN(CC(O)COc2ccc(Cl)c(F)c2)CC1)c1cn(C2CC2F)c2cc(Cl)c(F)cc2c1=O] |
| 20 | 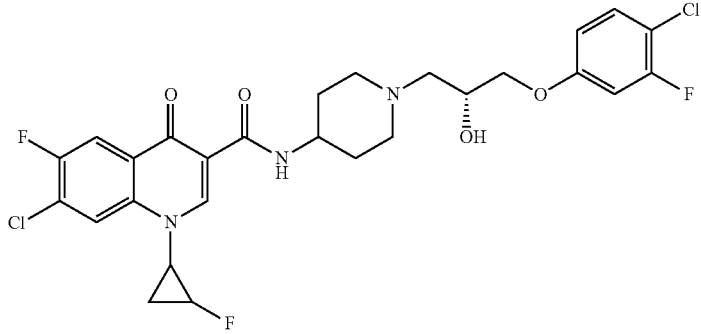 [SMILES: O=C(NC1CCN(C[C@@H](O)COc2ccc(Cl)c(F)c2)CC1)c1cn(C2CC2F)c2cc(Cl)c(F)cc2c1=O] |
| 21 | 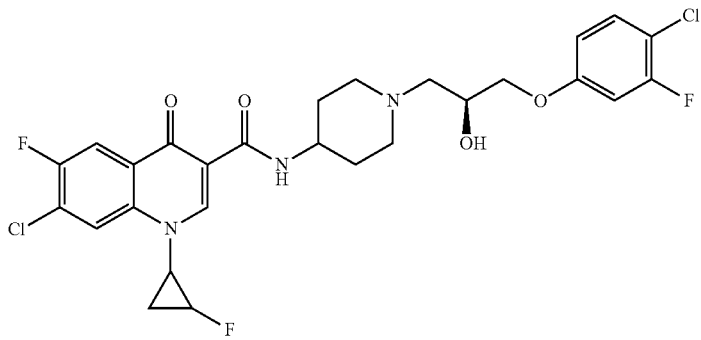 [SMILES: O=C(NC1CCN(C[C@H](O)COc2ccc(Cl)c(F)c2)CC1)c1cn(C2CC2F)c2cc(Cl)c(F)cc2c1=O] |
| 22 | 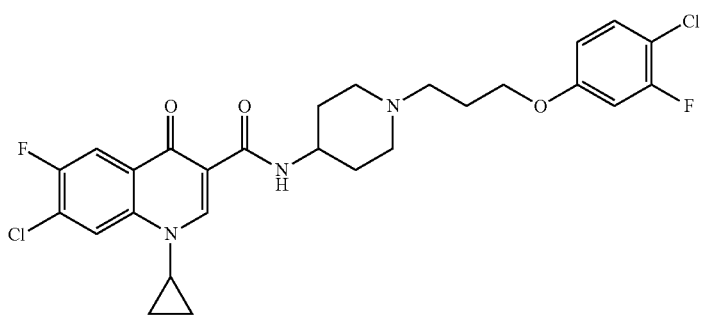 [SMILES: O=C(NC1CCN(CCCOc2ccc(Cl)c(F)c2)CC1)c1cn(C2CC2)c2cc(Cl)c(F)cc2c1=O] |

TABLE 1-continued

| Cpd No. | Structure |
|---|---|
| 23 | 7-chloro-1-cyclopropyl-6-fluoro-4-oxo-N-(1-(2-hydroxy-3-(4-(trifluoromethyl)phenoxy)propyl)piperidin-4-yl)-1,4-dihydroquinoline-3-carboxamide |
| 24 | 7-chloro-1-cyclopropyl-6-fluoro-N-(1-((S)-2-hydroxy-3-(4-(trifluoromethyl)phenoxy)propyl)piperidin-4-yl)-4-oxo-1,4-dihydroquinoline-3-carboxamide |
| 25 | 7-chloro-1-cyclopropyl-6-fluoro-N-(1-((R)-2-hydroxy-3-(4-(trifluoromethyl)phenoxy)propyl)piperidin-4-yl)-4-oxo-1,4-dihydroquinoline-3-carboxamide |
| 26 | 7-chloro-N-(1-(3-(4-cyanophenoxy)-2-hydroxypropyl)piperidin-4-yl)-1-cyclopropyl-6-fluoro-4-oxo-1,4-dihydroquinoline-3-carboxamide |

TABLE 1-continued

| Cpd No. | Structure |
|---|---|
| 27 | (6-fluoro-7-chloro-1-cyclopropyl-4-oxo-1,4-dihydroquinoline-3-carboxamide)-N-(1-((2S)-2-hydroxy-3-(4-cyanophenoxy)propyl)piperidin-4-yl) |
| 28 | (6-fluoro-7-chloro-1-cyclopropyl-4-oxo-1,4-dihydroquinoline-3-carboxamide)-N-(1-((2R)-2-hydroxy-3-(4-cyanophenoxy)propyl)piperidin-4-yl) |
| 29 | (6-fluoro-7-chloro-1-cyclopropyl-4-oxo-1,4-dihydroquinoline-3-carboxamide)-N-(1-(2-hydroxy-2-(4-(trifluoromethoxy)phenyl)ethyl)piperidin-4-yl) |
| 30 | (6-fluoro-7-chloro-1-cyclopropyl-4-oxo-1,4-dihydroquinoline-3-carboxamide)-N-(1-((2S)-2-hydroxy-2-(4-(trifluoromethoxy)phenyl)ethyl)piperidin-4-yl) |
| 31 | (6-fluoro-7-chloro-1-cyclopropyl-4-oxo-1,4-dihydroquinoline-3-carboxamide)-N-(1-((2R)-2-hydroxy-2-(4-(trifluoromethoxy)phenyl)ethyl)piperidin-4-yl) |

TABLE 1-continued

| Cpd No. | Structure |
|---|---|
| 32 | *[chemical structure: 7-chloro-1-cyclopropyl-6-fluoro-4-oxo-1,4-dihydroquinoline-3-carboxamide linked via trans-cyclohexyl-NH to C(=O)CH2O-(4-chloro-3-fluorophenyl)]* |
| 33 | *[chemical structure: 7-chloro-1-cyclopropyl-6-fluoro-4-oxo-1,4-dihydroquinoline-3-carboxamide linked via trans-cyclohexyl-CH2-NH-C(=O)CH2O-(3-fluoro-4-chlorophenyl)]* |
| 34 | *[chemical structure: quinolone carboxamide - trans-cyclohexyl-NH-CH2-CH(OH)-CH2-O-(3-fluoro-4-chlorophenyl)]* |
| 35 | *[chemical structure: same as 34 with (S)-OH stereochemistry]* |
| 36 | *[chemical structure: same as 34 with (R)-OH stereochemistry]* |

TABLE 1-continued

| Cpd No. | Structure |
|---|---|
| 37 | 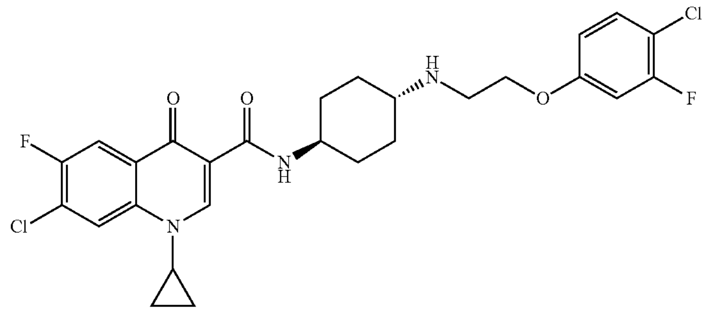 [SMILES: O=C(N[C@H]1CC[C@H](NCCOc2ccc(Cl)c(F)c2)CC1)c1cn(C2CC2)c2cc(Cl)c(F)cc2c1=O] |
| 38 | 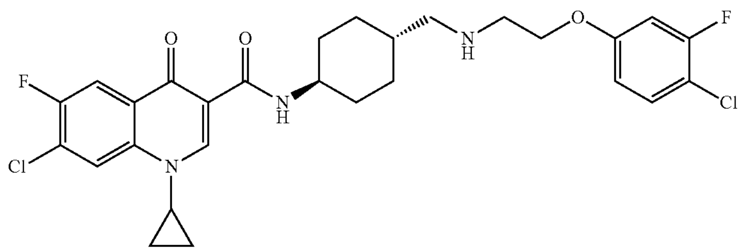 [SMILES: O=C(N[C@H]1CC[C@H](CNCCOc2ccc(Cl)c(F)c2)CC1)c1cn(C2CC2)c2cc(Cl)c(F)cc2c1=O] |
| 39 | 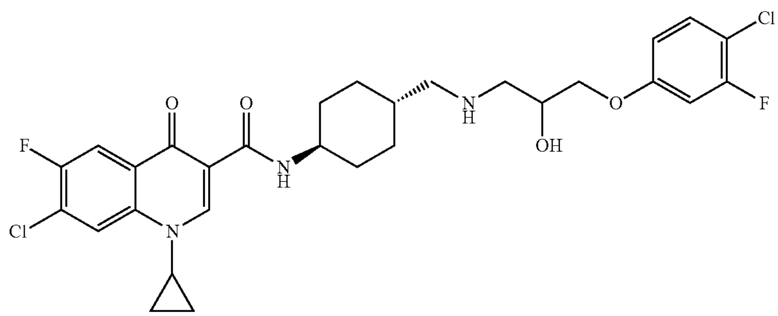 [SMILES: O=C(N[C@H]1CC[C@H](CNCC(O)COc2ccc(Cl)c(F)c2)CC1)c1cn(C2CC2)c2cc(Cl)c(F)cc2c1=O] |
| 40 | 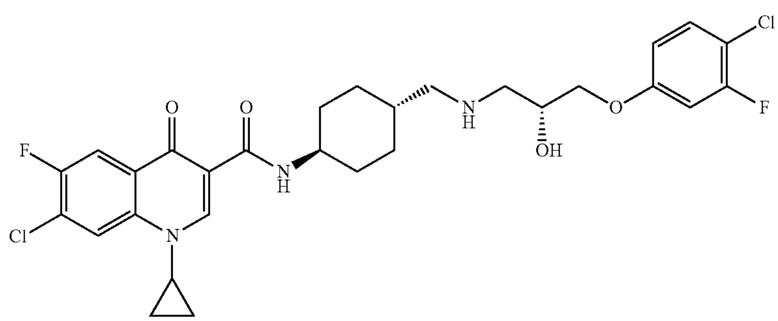 [SMILES: O=C(N[C@H]1CC[C@H](CNC[C@@H](O)COc2ccc(Cl)c(F)c2)CC1)c1cn(C2CC2)c2cc(Cl)c(F)cc2c1=O] |
| 41 | 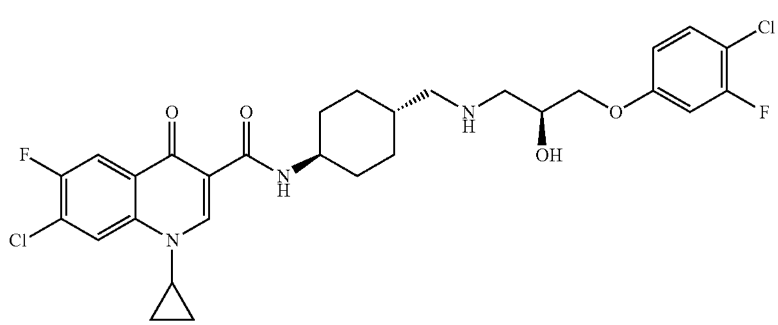 [SMILES: O=C(N[C@H]1CC[C@H](CNC[C@H](O)COc2ccc(Cl)c(F)c2)CC1)c1cn(C2CC2)c2cc(Cl)c(F)cc2c1=O] |

TABLE 1-continued

| Cpd No. | Structure |
|---|---|
| 42 | (structure) |
| 43 | (structure) |
| 44 | (structure) |
| 45 | (structure) |
| 46 | (structure) |

TABLE 1-continued

| Cpd No. | Structure |
|---|---|
| 47 | 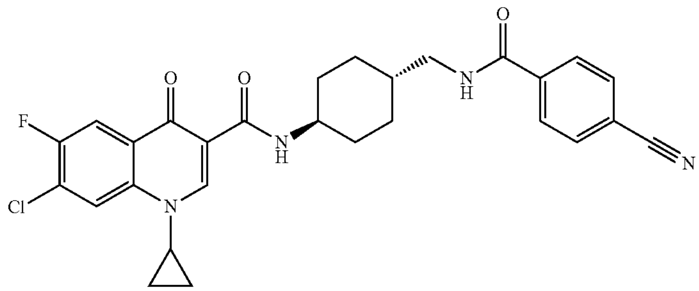 [SMILES: N#Cc1ccc(C(=O)NC[C@H]2CC[C@H](NC(=O)c3cn(C4CC4)c4cc(Cl)c(F)cc4c3=O)CC2)cc1] |
| 48 | 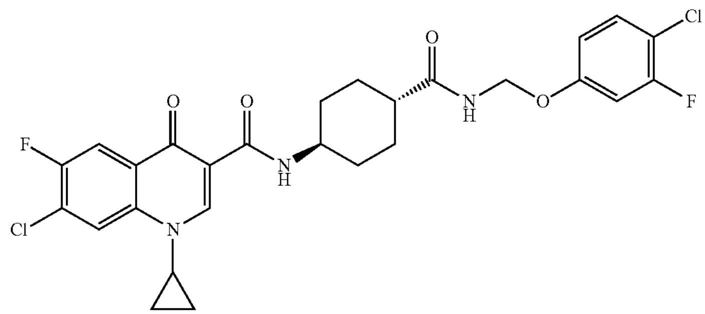 [SMILES: O=C(N[C@H]1CC[C@H](C(=O)NCOc2ccc(Cl)c(F)c2)CC1)c1cn(C2CC2)c2cc(Cl)c(F)cc2c1=O] |
| 49 | 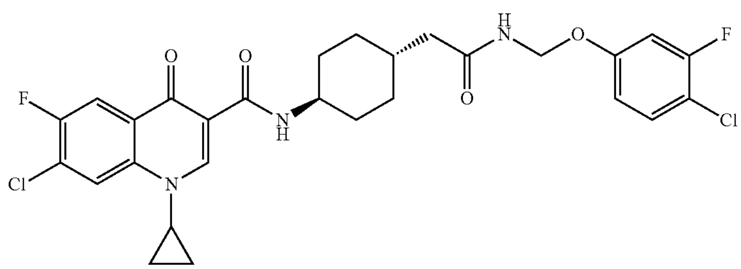 [SMILES: O=C(C[C@H]1CC[C@H](NC(=O)c2cn(C3CC3)c3cc(Cl)c(F)cc3c2=O)CC1)NCOc1ccc(Cl)c(F)c1] |
| 50 | 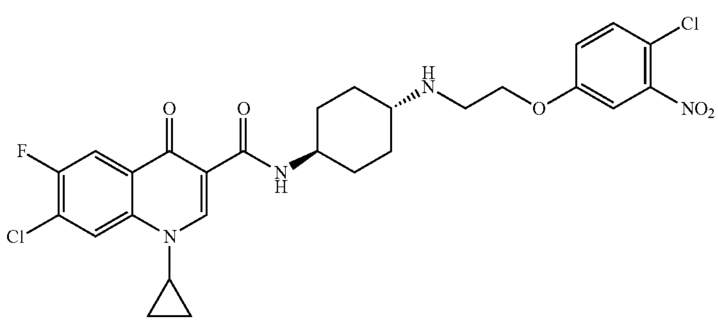 [SMILES: O=C(N[C@H]1CC[C@H](NCCOc2ccc(Cl)c([N+](=O)[O-])c2)CC1)c1cn(C2CC2)c2cc(Cl)c(F)cc2c1=O] |
| 51 | 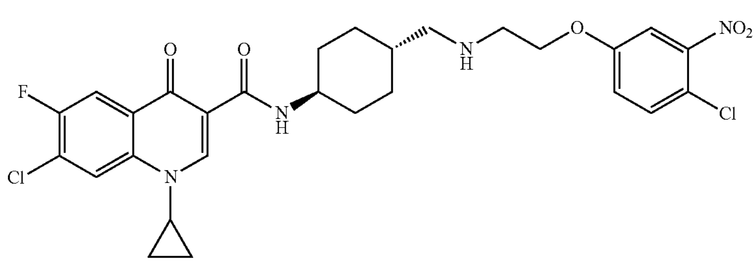 [SMILES: O=C(N[C@H]1CC[C@H](CNCCOc2ccc(Cl)c([N+](=O)[O-])c2)CC1)c1cn(C2CC2)c2cc(Cl)c(F)cc2c1=O] |

TABLE 1-continued

| Cpd No. | Structure |
|---|---|
| 52 | 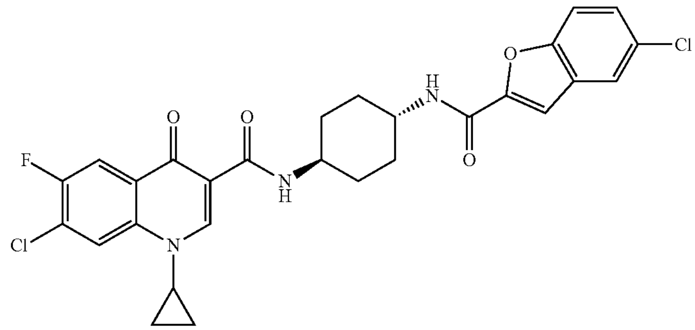 [SMILES: O=C(N[C@H]1CC[C@H](NC(=O)c2cn(C3CC3)c3cc(Cl)c(F)cc3c2=O)CC1)c1cc2cc(Cl)ccc2o1] |
| 53 | 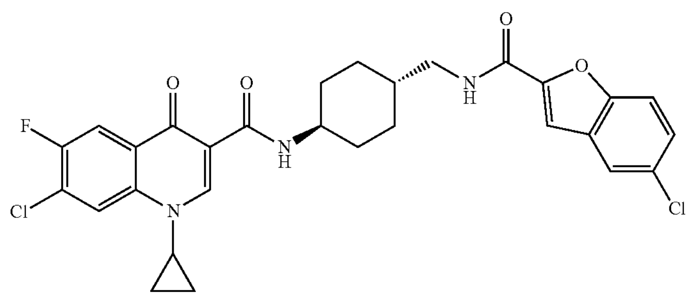 [SMILES: O=C(NC[C@H]1CC[C@H](NC(=O)c2cn(C3CC3)c3cc(Cl)c(F)cc3c2=O)CC1)c1cc2cc(Cl)ccc2o1] |
| 54 | 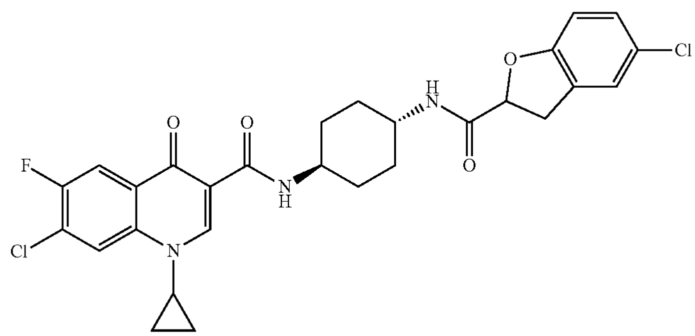 [SMILES: O=C(N[C@H]1CC[C@H](NC(=O)C2Cc3cc(Cl)ccc3O2)CC1)c1cn(C2CC2)c2cc(Cl)c(F)cc2c1=O] |
| 55 | 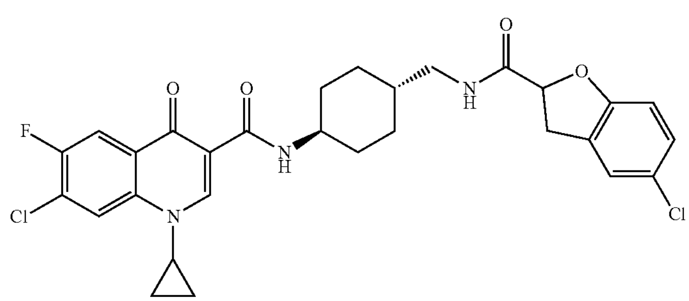 [SMILES: O=C(N[C@H]1CC[C@H](CNC(=O)C2Cc3cc(Cl)ccc3O2)CC1)c1cn(C2CC2)c2cc(Cl)c(F)cc2c1=O] |
| 56 | 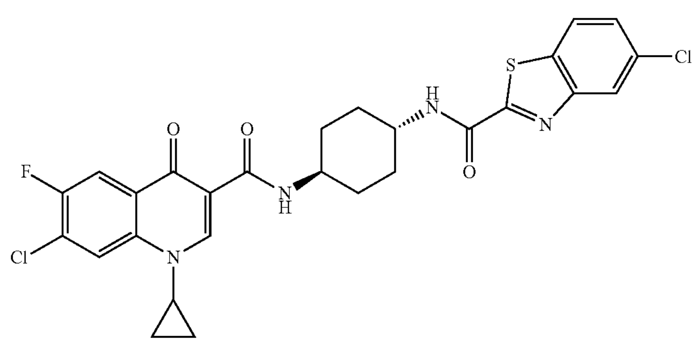 [SMILES: O=C(N[C@H]1CC[C@H](NC(=O)c2cn(C3CC3)c3cc(Cl)c(F)cc3c2=O)CC1)c1nc2cc(Cl)ccc2s1] |

TABLE 1-continued

| Cpd No. | Structure |
|---|---|
| 57 | 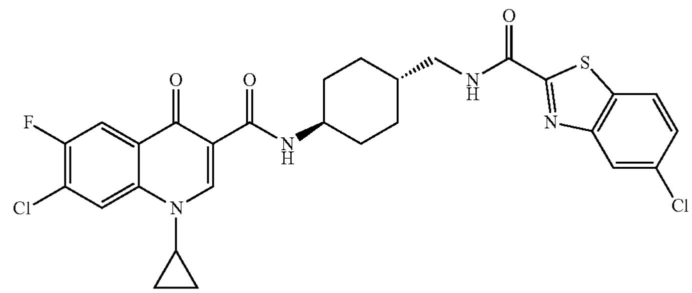 [SMILES: O=C(NC[C@H]1CC[C@H](NC(=O)c2cn(C3CC3)c3cc(Cl)c(F)cc3c2=O)CC1)c1nc2cc(Cl)ccc2s1] |
| 58 | 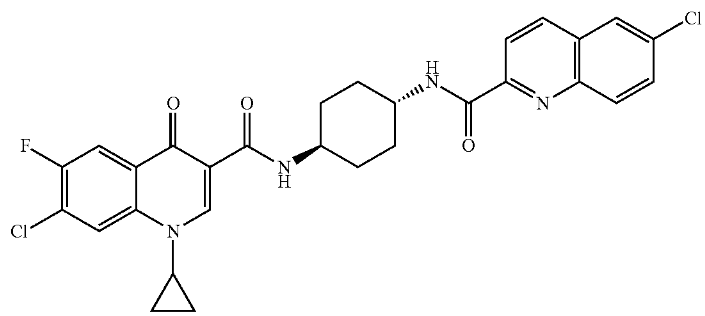 [SMILES: O=C(N[C@H]1CC[C@H](NC(=O)c2cn(C3CC3)c3cc(Cl)c(F)cc3c2=O)CC1)c1ccc2cc(Cl)ccc2n1] |
| 59 | 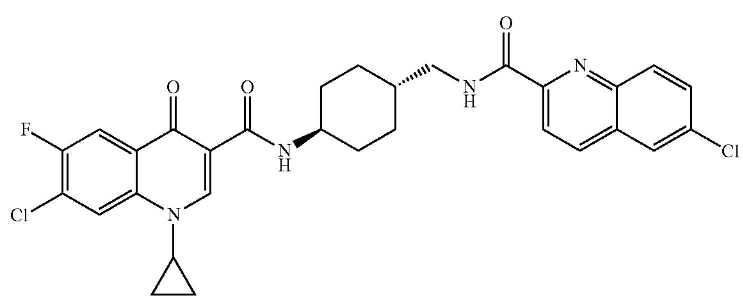 [SMILES: O=C(NC[C@H]1CC[C@H](NC(=O)c2cn(C3CC3)c3cc(Cl)c(F)cc3c2=O)CC1)c1ccc2cc(Cl)ccc2n1] |
| 60 | 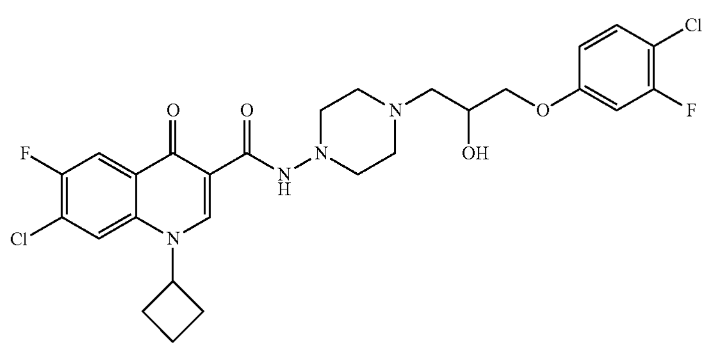 |
| 61 | 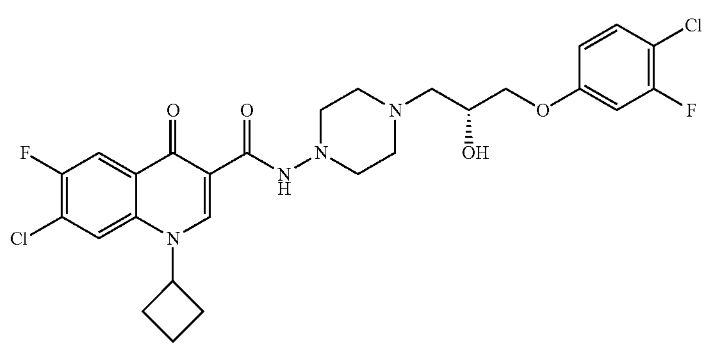 |

TABLE 1-continued

| Cpd No. | Structure |
|---|---|
| 62 | 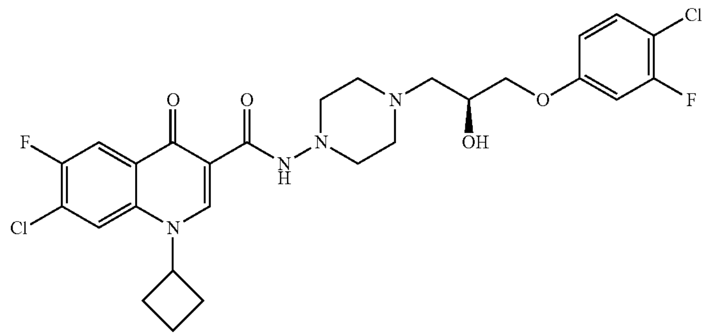 |
| 63 | 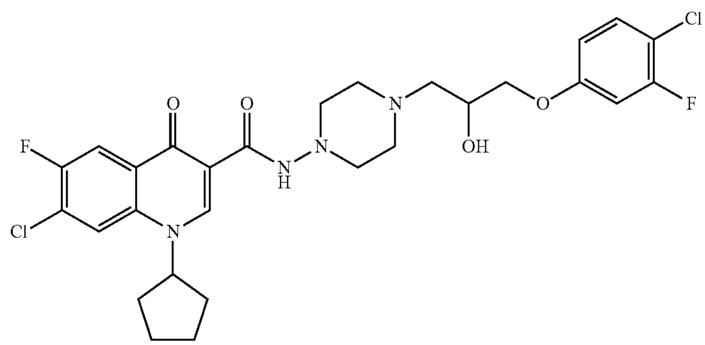 |
| 64 | 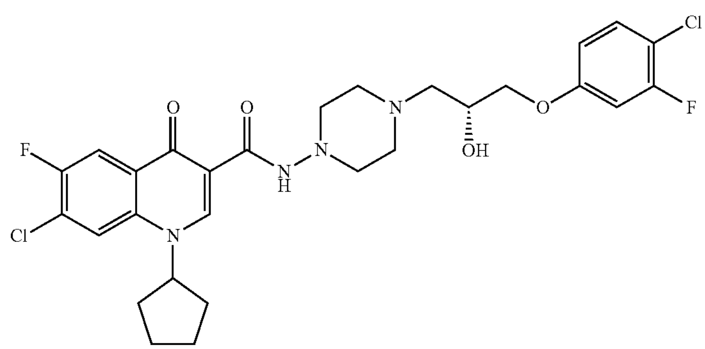 |
| 65 | 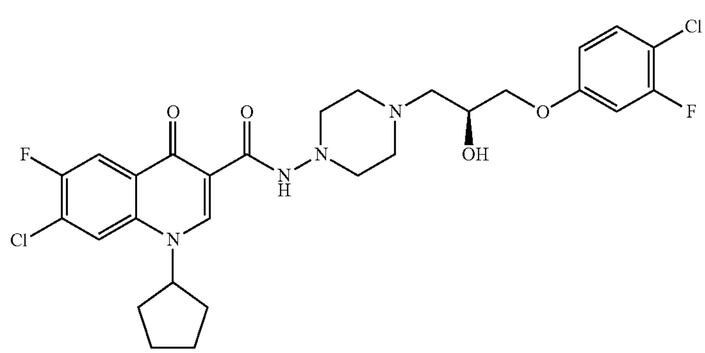 [SMILES: O=C(NN1CCN(C[C@H](O)COc2ccc(Cl)c(F)c2)CC1)c1cn(C2CCCC2)c2cc(Cl)c(F)cc2c1=O] |

TABLE 1-continued
| Cpd No. | Structure |
|---|---|
| 66 | 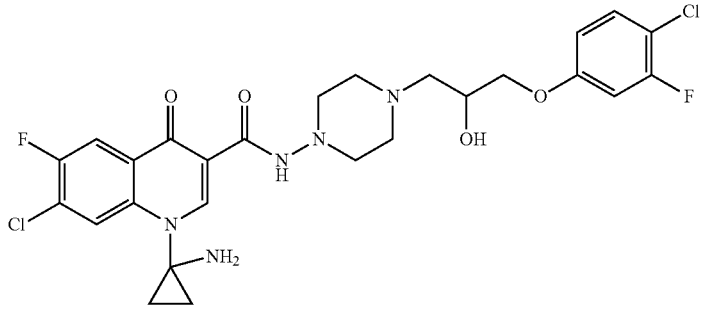 [SMILES: NC1(n2cc(C(=O)NN3CCN(CC(O)COc4ccc(Cl)c(F)c4)CC3)c(=O)c3cc(F)c(Cl)cc32)CC1] |
| 67 | 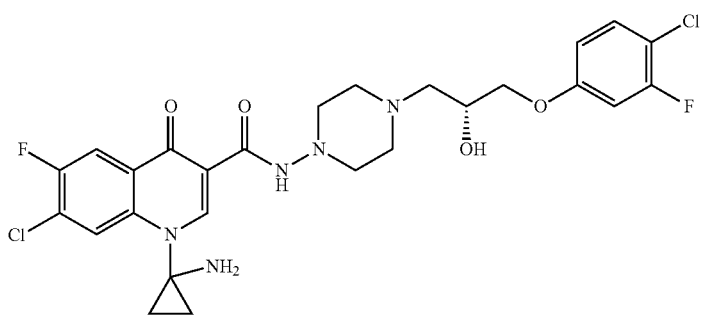 [SMILES: NC1(n2cc(C(=O)NN3CCN(C[C@@H](O)COc4ccc(Cl)c(F)c4)CC3)c(=O)c3cc(F)c(Cl)cc32)CC1] |
| 68 | 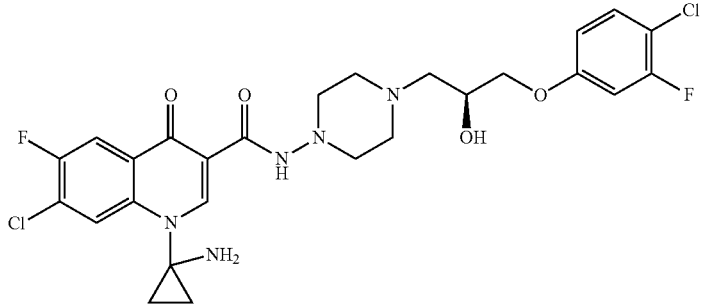 |
| 69 | 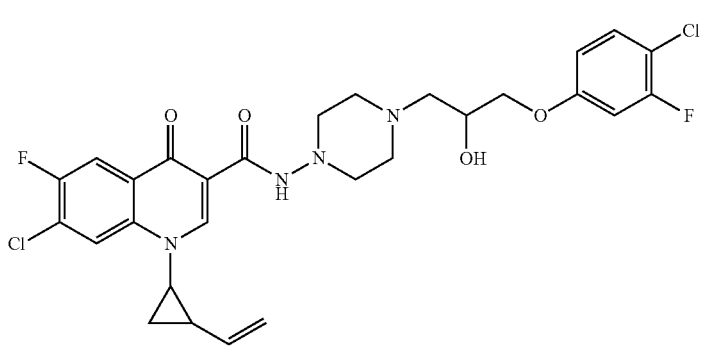 |

TABLE 1-continued
| Cpd No. | Structure |
|---|---|
| 70 | 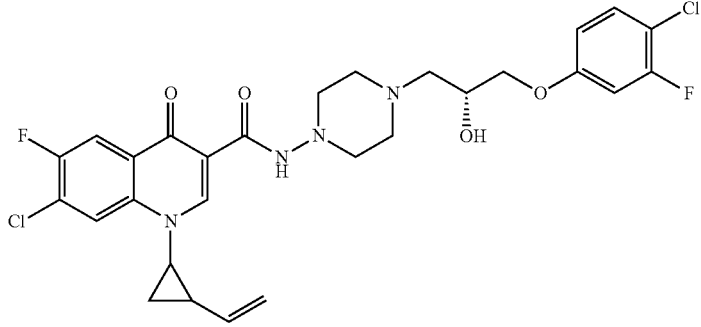 |
| 71 | 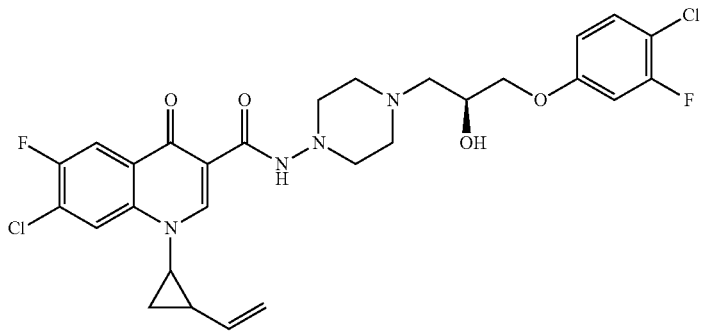 |
| 72 | 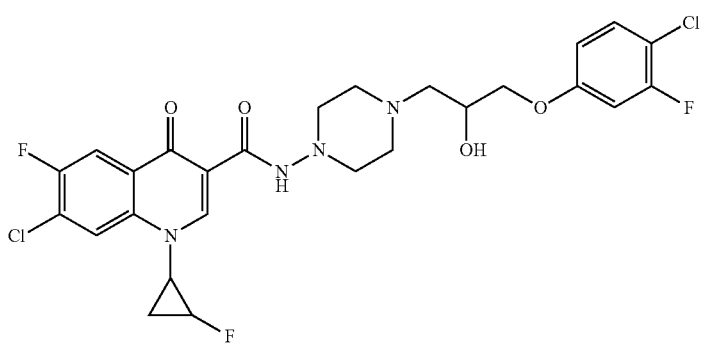 |
| 73 | 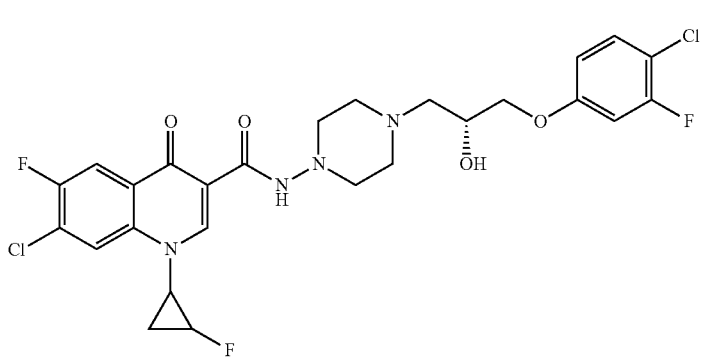 [SMILES: O=C(NN1CCN(C[C@@H](O)COc2ccc(Cl)c(F)c2)CC1)c1cn(C2CC2F)c2cc(Cl)c(F)cc2c1=O] |

TABLE 1-continued

| Cpd No. | Structure |
|---|---|
| 74 | 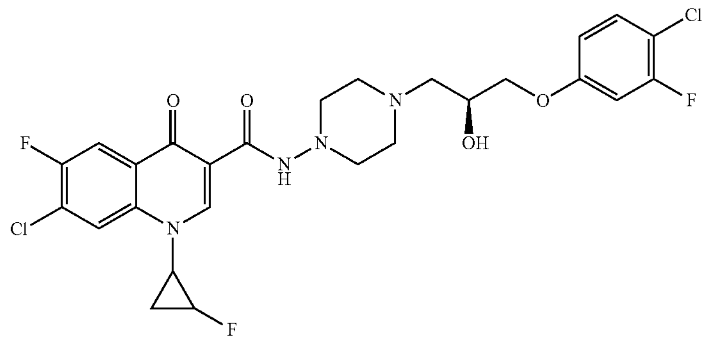 |
| 75 | 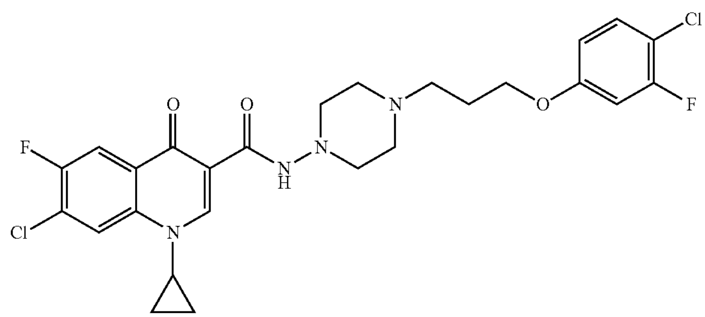 |
| 76 | 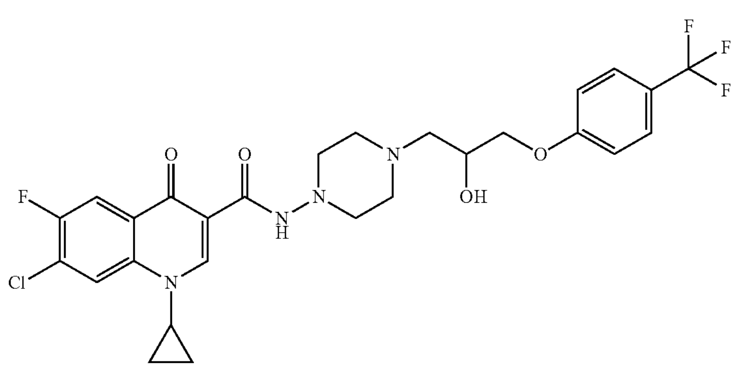 [SMILES: O=C(NN1CCN(CC(O)COc2ccc(C(F)(F)F)cc2)CC1)c1cn(C2CC2)c2cc(Cl)c(F)cc2c1=O] |
| 77 | 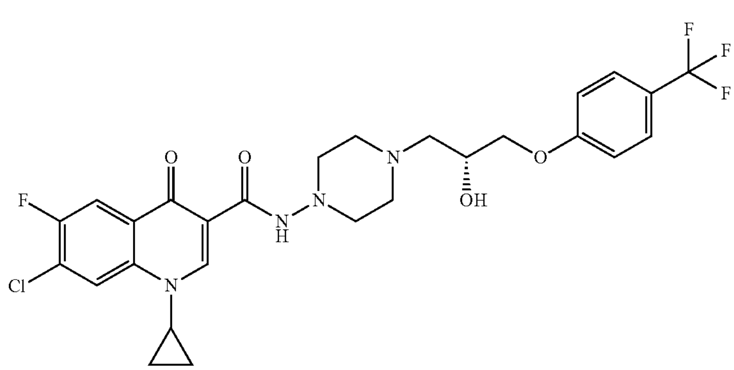 [SMILES: O=C(NN1CCN(C[C@@H](O)COc2ccc(C(F)(F)F)cc2)CC1)c1cn(C2CC2)c2cc(Cl)c(F)cc2c1=O] |

TABLE 1-continued

| Cpd No. | Structure |
|---|---|
| 78 | 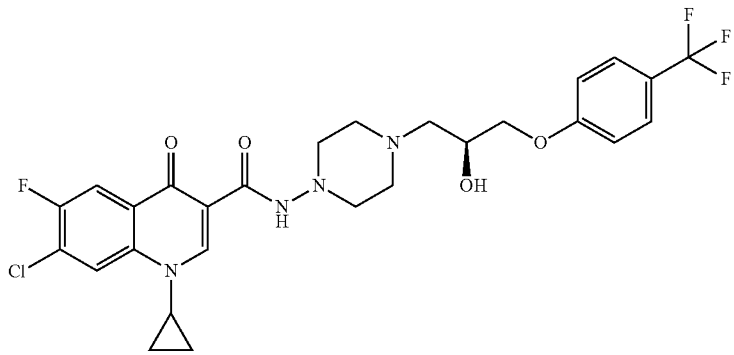 [SMILES: O=C(NN1CCN(C[C@H](O)COc2ccc(C(F)(F)F)cc2)CC1)c1cn(C2CC2)c2cc(Cl)c(F)cc2c1=O] |
| 79 | 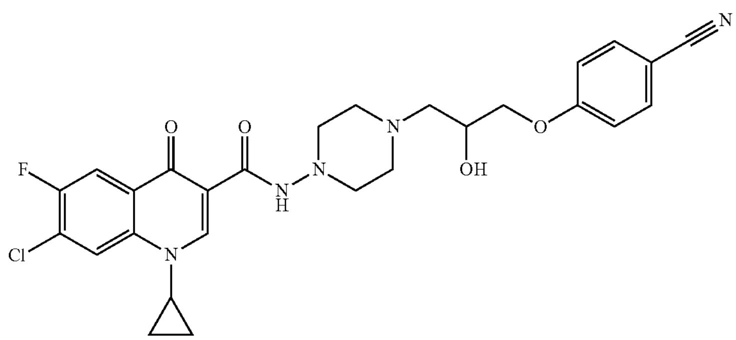 [SMILES: N#Cc1ccc(OCC(O)CN2CCN(NC(=O)c3cn(C4CC4)c4cc(Cl)c(F)cc4c3=O)CC2)cc1] |
| 80 | 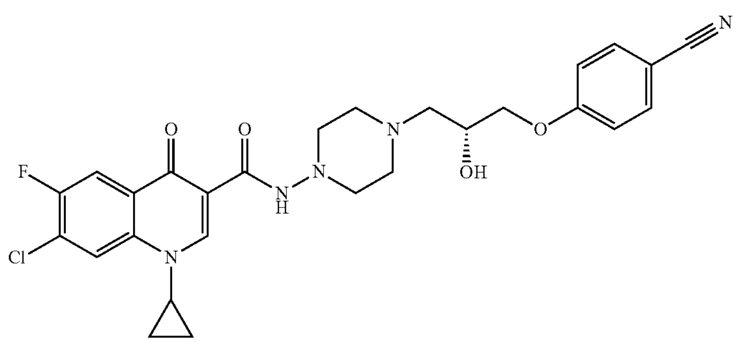 [SMILES: N#Cc1ccc(OC[C@H](O)CN2CCN(NC(=O)c3cn(C4CC4)c4cc(Cl)c(F)cc4c3=O)CC2)cc1] |
| 81 | 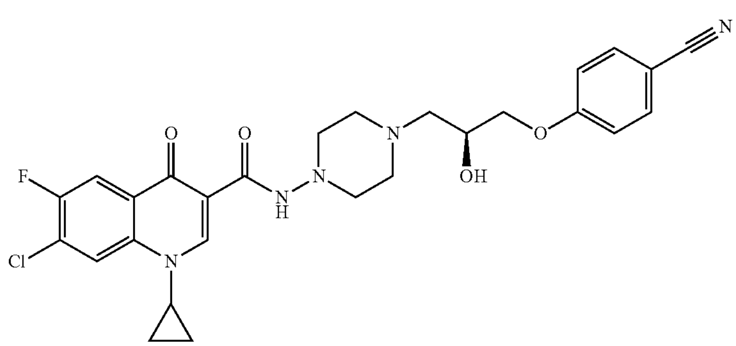 |

TABLE 1-continued
| Cpd No. | Structure |
|---|---|
| 82 | 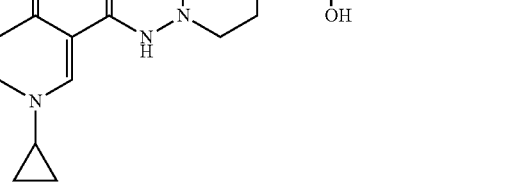 |
| 83 | 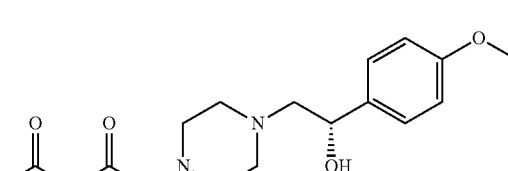 |
| 84 | 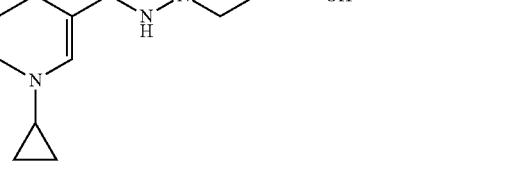 |
| 85 | 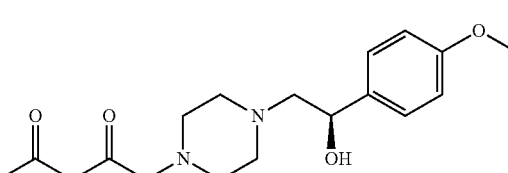 |
| 86 | 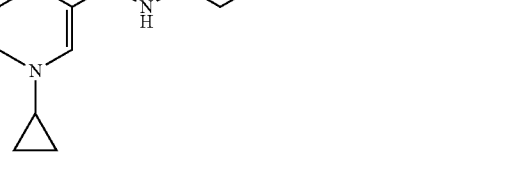 |

TABLE 1-continued

| Cpd No. | Structure |
|---|---|
| 87 | 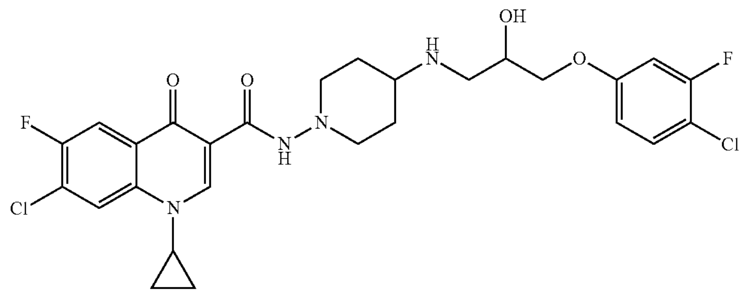 [SMILES: O=C(NN1CCC(NCC(O)COc2ccc(Cl)c(F)c2)CC1)c1cn(C2CC2)c2cc(Cl)c(F)cc2c1=O] |
| 88 | 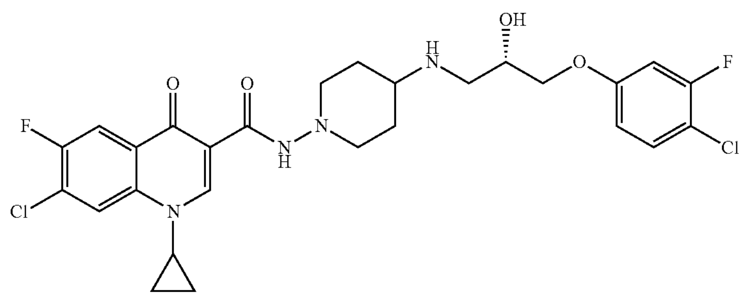 [SMILES: O=C(NN1CCC(NC[C@H](O)COc2ccc(Cl)c(F)c2)CC1)c1cn(C2CC2)c2cc(Cl)c(F)cc2c1=O] |
| 89 | 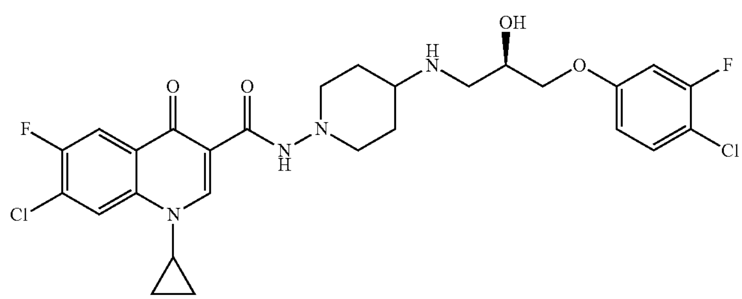 [SMILES: O=C(NN1CCC(NC[C@@H](O)COc2ccc(Cl)c(F)c2)CC1)c1cn(C2CC2)c2cc(Cl)c(F)cc2c1=O] |
| 90 | 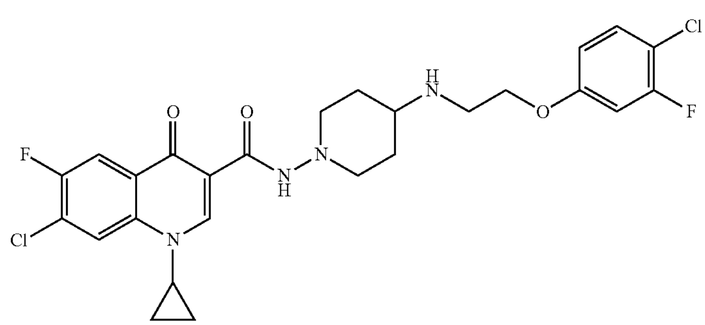 [SMILES: O=C(NN1CCC(NCCOc2ccc(Cl)c(F)c2)CC1)c1cn(C2CC2)c2cc(Cl)c(F)cc2c1=O] |
| 91 | 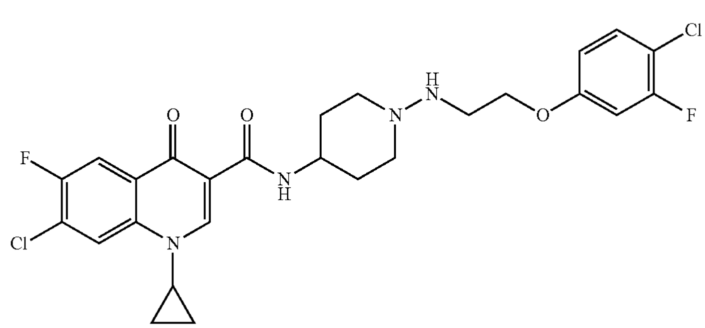 [SMILES: O=C(NC1CCN(NCCOc2ccc(Cl)c(F)c2)CC1)c1cn(C2CC2)c2cc(Cl)c(F)cc2c1=O] |

TABLE 1-continued

| Cpd No. | Structure |
| --- | --- |
| 92 | 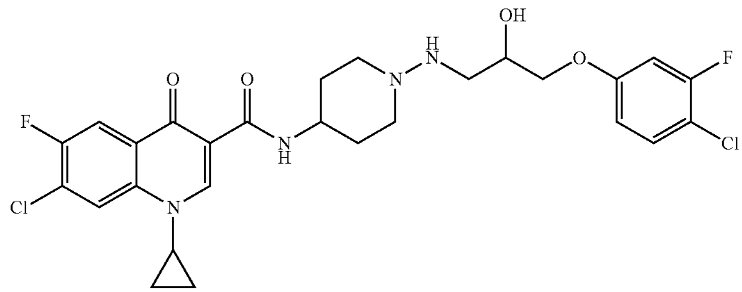 [SMILES: O=C(NC1CCN(NCC(O)COc2ccc(Cl)c(F)c2)CC1)c1cn(C2CC2)c2cc(Cl)c(F)cc2c1=O] |
| 93 | 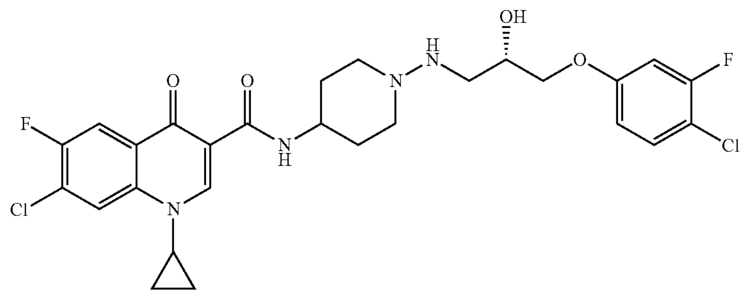 [SMILES: O=C(NC1CCN(NC[C@H](O)COc2ccc(Cl)c(F)c2)CC1)c1cn(C2CC2)c2cc(Cl)c(F)cc2c1=O] |
| 94 | 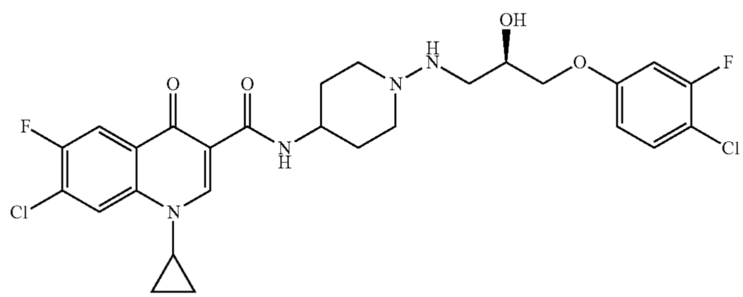 [SMILES: O=C(NC1CCN(NC[C@@H](O)COc2ccc(Cl)c(F)c2)CC1)c1cn(C2CC2)c2cc(Cl)c(F)cc2c1=O] |
| 95 | 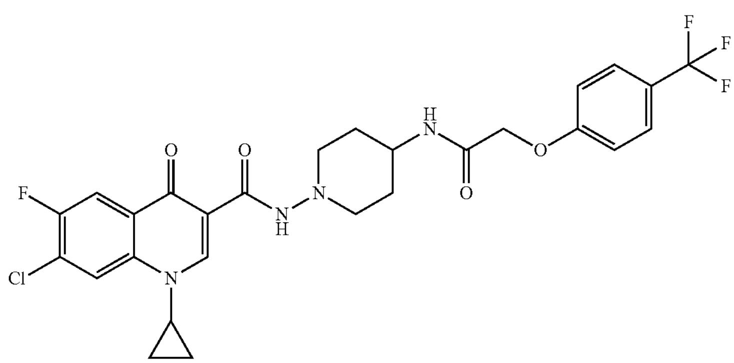 [SMILES: O=C(COc1ccc(C(F)(F)F)cc1)NC1CCN(NC(=O)c2cn(C3CC3)c3cc(Cl)c(F)cc3c2=O)CC1] |
| 96 | 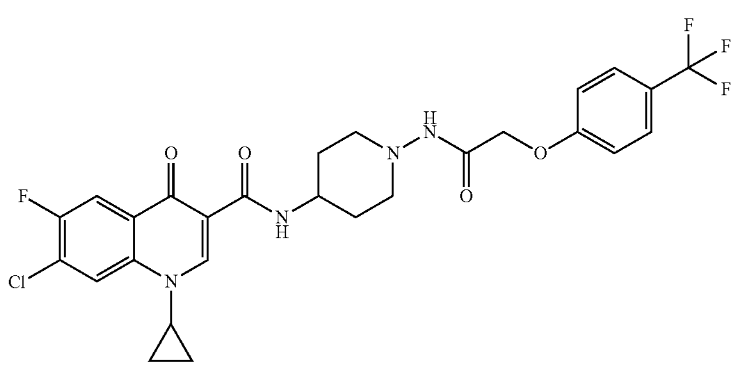 [SMILES: O=C(COc1ccc(C(F)(F)F)cc1)NN1CCC(NC(=O)c2cn(C3CC3)c3cc(Cl)c(F)cc3c2=O)CC1] |

TABLE 1-continued
| Cpd No. | Structure |
|---|---|
| 97 | 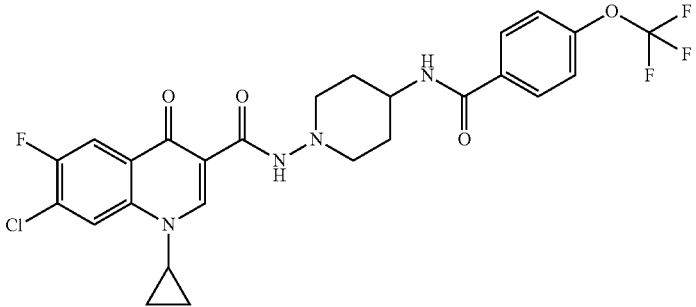 [SMILES: O=C(NC1CCN(NC(=O)c2cn(C3CC3)c3cc(Cl)c(F)cc3c2=O)CC1)c1ccc(OC(F)(F)F)cc1] |
| 98 | 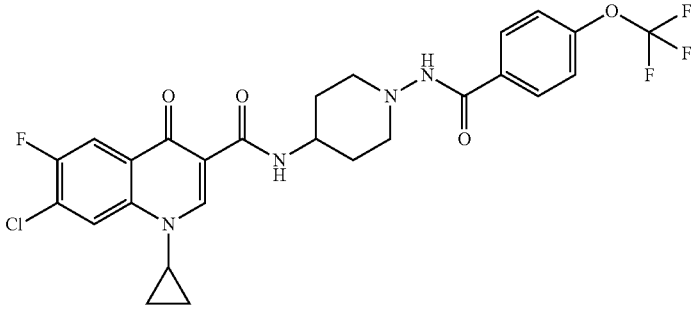 [SMILES: O=C(NN1CCC(NC(=O)c2cn(C3CC3)c3cc(Cl)c(F)cc3c2=O)CC1)c1ccc(OC(F)(F)F)cc1] |
| 99 | 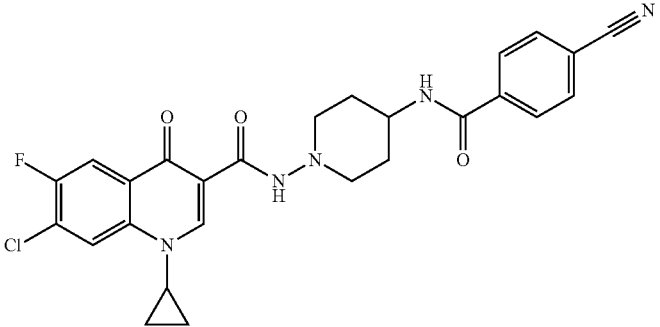 [SMILES: N#Cc1ccc(C(=O)NC2CCN(NC(=O)c3cn(C4CC4)c4cc(Cl)c(F)cc4c3=O)CC2)cc1] |
| 100 | 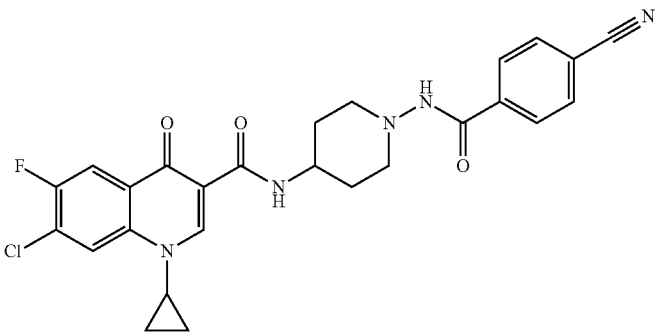 [SMILES: N#Cc1ccc(C(=O)NN2CCC(NC(=O)c3cn(C4CC4)c4cc(Cl)c(F)cc4c3=O)CC2)cc1] |
| 101 | 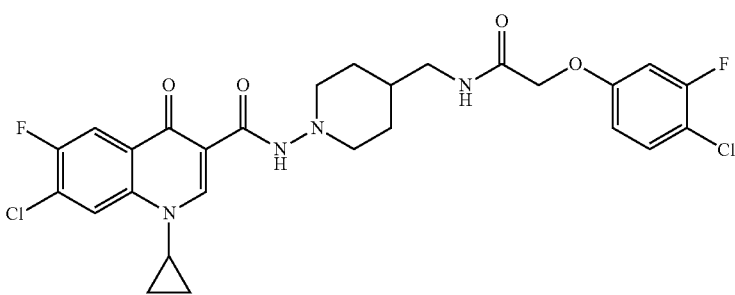 [SMILES: O=C(COc1ccc(Cl)c(F)c1)NCC1CCN(NC(=O)c2cn(C3CC3)c3cc(Cl)c(F)cc3c2=O)CC1] |

/ TABLE 1-continued
| Cpd No. | Structure |
|---|---|
| 102 | 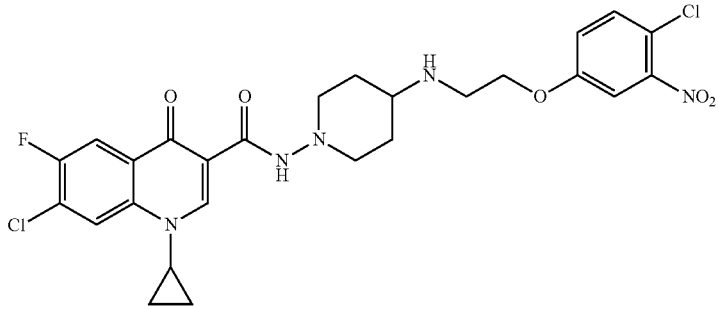 [SMILES: O=C(NN1CCC(NCCOc2ccc(Cl)c([N+](=O)[O-])c2)CC1)c1cn(C2CC2)c2cc(Cl)c(F)cc2c1=O] |
| 103 | 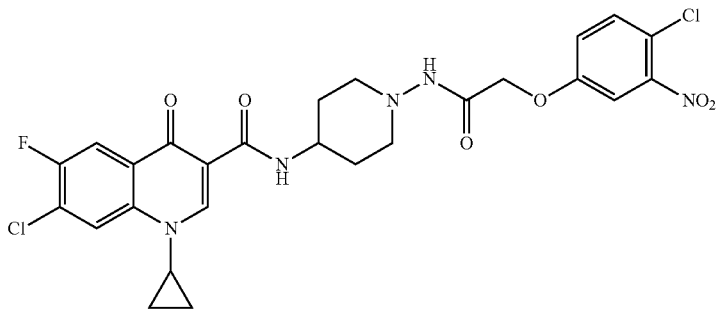 [SMILES: O=C(COc1ccc(Cl)c([N+](=O)[O-])c1)NN1CCC(NC(=O)c2cn(C3CC3)c3cc(Cl)c(F)cc3c2=O)CC1] |
| 104 | 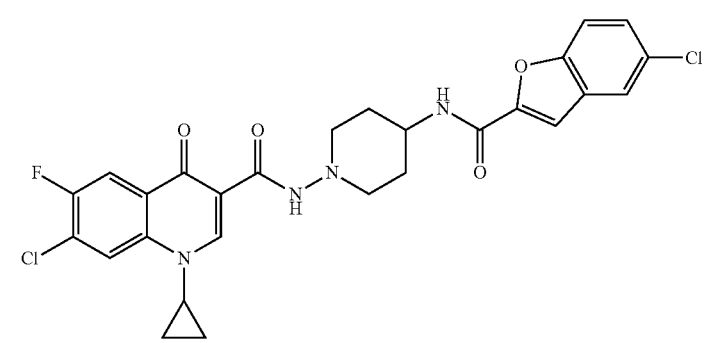 [SMILES: O=C(NC1CCN(NC(=O)c2cn(C3CC3)c3cc(Cl)c(F)cc3c2=O)CC1)c1cc2cc(Cl)ccc2o1] |
| 105 | 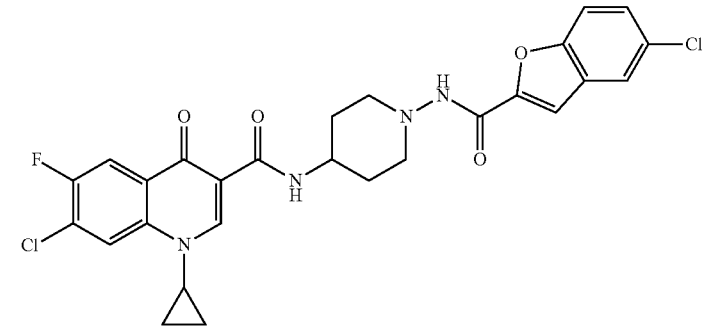 [SMILES: O=C(NN1CCC(NC(=O)c2cn(C3CC3)c3cc(Cl)c(F)cc3c2=O)CC1)c1cc2cc(Cl)ccc2o1] |

TABLE 1-continued

| Cpd No. | Structure |
|---|---|
| 106 | (6-fluoro-7-chloro-1-cyclopropyl-4-oxo-1,4-dihydroquinoline-3-carboxylic acid hydrazide linked via N-N to piperidine, 4-position bearing NH-C(O)-(5-chloro-2,3-dihydrobenzofuran-2-yl)) |
| 107 | (6-fluoro-7-chloro-1-cyclopropyl-4-oxo-1,4-dihydroquinoline-3-carboxamide linked to 4-aminopiperidine, piperidine N bearing NH-C(O)-(5-chloro-2,3-dihydrobenzofuran-2-yl)) |
| 108 | (6-fluoro-7-chloro-1-cyclopropyl-4-oxo-1,4-dihydroquinoline-3-carboxylic acid hydrazide linked via N-N to piperidine, 4-position bearing NH-C(O)-(5-chlorobenzothiazol-2-yl)) |
| 109 | (6-fluoro-7-chloro-1-cyclopropyl-4-oxo-1,4-dihydroquinoline-3-carboxamide linked to 4-aminopiperidine, piperidine N bearing NH-C(O)-(5-chlorobenzothiazol-2-yl)) |

TABLE 1-continued

| Cpd No. | Structure |
|---|---|
| 110 | (structure) |
| 111 | (structure) |
| 112 | (structure) |

Compositions and Formulations

Compositions of any of the compounds detailed herein are embraced by this disclosure. Thus, the present disclosure includes agricultural compositions comprising a compound as detailed herein or a agriculturally acceptable salt thereof and a agriculturally acceptable carrier or excipient. In one aspect, the agriculturally acceptable salt is an acid addition salt, such as a salt formed with an inorganic or organic acid. Agricultural compositions may take a form suitable for applying to a plant, such as a for suitable for spraying, chemigation (applying the composition through an irrigation system), granular application, or applying to fertilizer.

Agricultural compositions disclosed herein may comprise excipients or adjuvants, such as solvents, anti-caking agents, stabilizers, defoamers, slip agents, humectants, dispersants, wetting agents, thickening agents, emulsifiers, and preservatives. The agricultural composition may be a concentrated formulation or a ready-to-use formulation.

Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a pharmaceutically acceptable salt thereof are provided, such as compositions of substantially pure compounds. In some embodiments, a composition containing a compound as detailed herein or a pharmaceutically acceptable salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or pharmaceutically acceptable salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or pharmaceutically acceptable salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a pharmaceutically acceptable salt thereof can be used in the preparation of a formulation, such as a pharmaceutical formulation, by combining the compound or compounds, or a pharmaceutically acceptable salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or pharmaceutically acceptable salt thereof and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use and Uses

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease or disorder in an individual in need thereof comprising administering a compound describes herein or any embodiment, variation, or aspect thereof, or a pharmaceutically acceptable salt thereof. In some embodiments, the compound, pharmaceutically acceptable salt thereof, or composition is administered to the individual according to a dosage and/or method of administration described herein.

The compounds or salts thereof described herein and compositions described herein are believed to be effective for treating a variety of diseases and disorders. In some embodiments, a compound or salt thereof described herein or a composition described herein may be used in a method of treating a disease or disorder mediated by an integrated stress response (ISR) pathway. In some embodiments, the disease or disorder is mediated by eukaryotic translation initiation factor 2α (eIF2α) or eukaryotic translation initiation factor 2B (eIF2B). In some embodiments, the disease or disorder is mediated by phosphorylation of eIF2α and/or the guanine nucleotide exchange factor (GEF) activity of eIF2B.

In some embodiments, a compound or salt thereof described herein or a composition described herein may be used in a method of treating a disease or disorder, wherein the disease or disorder is a neurodegenerative disease, an inflammatory disease, an autoimmune disease, a metabolic syndrome, a cancer, a vascular disease, a musculoskeletal disease (such as a myopathy), an ocular disease, or a genetic disorder.

In some embodiments, the disease or disorder is a neurodegenerative disease. In some embodiments, the neurodegenerative disease is vanishing white matter disease, childhood ataxia with CNS hypomyelination, intellectual disability syndrome, Alzheimer's disease, prion disease, Creutzfeldt-Jakob disease, Parkinson's disease, amyotrophic lateral sclerosis (ALS) disease, Pelizaeus-Merzbacher disease, a cognitive impairment, a traumatic brain injury, a postoperative cognitive dysfunction (PCD), a neuro-otological syndrome, hearing loss, Huntington's disease, stroke, chronic traumatic encephalopathy, spinal cord injury, dementia, frontotemporal dementia (FTD), depression, or a social behavior impairment. In some embodiments, the cognitive impairment is triggered by ageing, radiation, sepsis, seizure, heart attack, heart surgery, liver failure, hepatic encephalopathy, anesthesia, brain injury, brain surgery, ischemia, chemotherapy, cancer treatment, critical illness, concussion, fibromyalgia, or depression. In some embodiments, the neurodegenerative disease is Alzheimer's disease. In some embodiments, the neurodegenerative disease is ageing-related cognitive impairment. In some embodiments, the neurodegenerative disease is a traumatic brain injury.

In some embodiments, a compound or salt thereof described herein or a composition described herein may be used in a method of treating Alzheimer's disease. In some embodiments, neurodegeneration, cognitive impairment, and/or amyloidogenesis is decreased.

In some embodiments, the disease or disorder is an inflammatory disease. In some embodiments, the inflammatory disease is arthritis, psoriatic arthritis, psoriasis, juvenile idiopathic arthritis, asthma, allergic asthma, bronchial asthma, tuberculosis, chronic airway disorder, cystic fibrosis, glomerulonephritis, membranous nephropathy, sarcoidosis, vasculitis, ichthyosis, transplant rejection, interstitial cystitis, atopic dermatitis, or inflammatory bowel disease. In some embodiments, the inflammatory bowel disease is Crohn' disease, ulcerative colitis, or celiac disease.

In some embodiments, the disease or disorder is an autoimmune disease. In some embodiments, the autoimmune disease is systemic lupus erythematosus, type 1 diabetes, multiple sclerosis, or rheumatoid arthritis.

In some embodiments, the disease or disorder is a metabolic syndrome. In some embodiments, the metabolic syndrome is acute pancreatitis, chronic pancreatitis, alcoholic liver steatosis, obesity, glucose intolerance, insulin resistance, hyperglycemia, fatty liver, dyslipidemia, hyperlipidemia, hyperhomocysteinemia, or type 2 diabetes. In some embodiments, the metabolic syndrome is alcoholic liver steatosis, obesity, glucose intolerance, insulin resistance, hyperglycemia, fatty liver, dyslipidemia, hyperlipidemia, hyperhomocysteinemia, or type 2 diabetes.

In some embodiments, the disease or disorder is a cancer. In some embodiments, the cancer is pancreatic cancer, breast cancer, kidney cancer, bladder cancer, prostate cancer, testicular cancer, urothelial cancer, endometrial cancer, ovarian cancer, cervical cancer, renal cancer, esophageal cancer, gastrointestinal stromal tumor (GIST), multiple myeloma, cancer of secretory cells, thyroid cancer, gastrointestinal carcinoma, chronic myeloid leukemia, hepatocellular carcinoma, colon cancer, melanoma, malignant glioma, glioblastoma, glioblastoma multiforme, astrocytoma, dysplastic gangliocytoma of the cerebellum, Ewing's sarcoma, rhabdomyosarcoma, ependymoma, medulloblastoma, ductal adenocarcinoma, adenosquamous carcinoma, nephroblastoma, acinar cell carcinoma, neuroblastoma, or lung cancer. In some embodiments, the cancer of secretory cells is non-Hodgkin's lymphoma, Burkitt's lymphoma, chronic lymphocytic leukemia, monoclonal gammopathy of undetermined significance (MGUS), plasmacytoma, lymphoplasmacytic lymphoma or acute lymphoblastic leukemia.

In some embodiments, the disease or disorder is a musculoskeletal disease (such as a myopathy). In some embodiments, the musculoskeletal disease is a myopathy, a muscular dystrophy, a muscular atrophy, a muscular wasting, or sarcopenia. In some embodiments, the muscular dystrophy is Duchenne muscular dystrophy (DMD), Becker's disease, myotonic dystrophy, X-linked dilated cardiomyopathy, spinal muscular atrophy (SMA), or metaphyseal chondrodysplasia, Schmid type (MCDS). In some embodiments, the myopathy is a skeletal muscle atrophy. In some embodiments, the musculoskeletal disease (such as the skeletal muscle atrophy) is triggered by ageing, chronic diseases, stroke, malnutrition, bedrest, orthopedic injury, bone fracture, cachexia, starvation, heart failure, obstructive lung disease, renal failure, Acquired Immunodeficiency Syndrome (AIDS), sepsis, an immune disorder, a cancer, ALS, a burn injury, denervation, diabetes, muscle disuse, limb immobilization, mechanical unload, myositis, or a dystrophy.

In some embodiments, the disease or disorder is a genetic disorder, such as Down syndrome or MEHMO syndrome (Mental retardation, Epileptic seizures, Hypogenitalism, Microcephaly, and Obesity).

In some embodiments, a compound or salt thereof described herein or a composition described herein may be used in a method of treating musculoskeletal disease. In some embodiments, skeletal muscle mass, quality and/or strength are increased. In some embodiments, synthesis of muscle proteins is increased. In some embodiments, skeletal muscle fiber atrophy is inhibited.

In some embodiments, the disease or disorder is a vascular disease. In some embodiments, the vascular disease is atherosclerosis, abdominal aortic aneurism, carotid artery disease, deep vein thrombosis, Buerger's disease, chronic venous hypertension, vascular calcification, telangiectasia or lymphoedema.

In some embodiments, the disease or disorder is an ocular disease. In some embodiments, the ocular disease is glaucoma, age-related macular degeneration, inflammatory retinal disease, retinal vascular disease, diabetic retinopathy, uveitis, rosacea, Sjogren's syndrome, or neovascularization in proliferative retinopathy.

In some embodiments, provided herein is a method of modulating an ISR pathway. The compounds or salts thereof described herein and compositions described herein are believed to be effective for modulating an ISR pathway. In some embodiments, the method of modulating an ISR pathway comprises modulating the ISR pathway in a cell by administering or delivering to the cell a compound described herein, or a pharmaceutically acceptable salt thereof, or a pharmaceutical composition described herein. In some embodiments, the method of modulating an ISR pathway comprises modulating the ISR pathway in an individual by administering to the individual a compound described herein, or a pharmaceutically acceptable salt thereof, or a pharmaceutical composition described herein. modulating of the ISR pathway can be determined by methods known in the art, such as western blot, immunohistochemistry, or reporter cell line assays.

In some embodiments, the modulation of the ISR pathway comprises binding eIF2B. In some embodiments, the modulation of the ISR pathway comprises increasing protein translation, increasing guanine nucleotide exchange factor (GEF) activity of eIF2B, delaying or preventing apoptosis in a cell, and/or modulating translation of one or more mRNAs comprising a 5' untranslated region (5'UTR) comprising at least one upstream open reading frame (uORF).

In some embodiments, provided herein are methods of increasing protein production using a compound or salt described herein. The protein production is increased relative to the same condition without the compound or salt. Protein production can be increased either in vivo or in vitro. For example, protein production can be increased in vivo by administering the compound or salt to an individual. In some embodiments, protein production is increased in vitro using the compound or salt with a cell-free protein synthesis system (CFPS) or a cell-based protein expression system. The protein produced can be a heterologous protein (e.g., a recombinant protein) or a native protein. Heterologous protein production can be achieved using a recombinant nucleic acid encoding the protein. In some embodiments, the protein produced is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. The increase in protein production can be determined by methods known in the art, such as western blot or immunohistochemistry.

Cell-free protein synthesis (CFPS) systems are generally known, and include cellular machinery for protein expression in an in vitro environment. In some embodiments, the CFPS system includes a cellular extract (such as a eukaryotic cellular extract), which includes protein expression machinery. In some embodiment, the cellular machinery in the CFPS system comprises eukaryotic cellular machinery, such as eukaryotic initiation factor 2 (eIF2) and/or eukaryotic initiation factor 2B (eIF2B), or one or more subunits thereof.

In some embodiments, there is a cell-free protein synthesis (CFPS) system comprising eukaryotic initiation factor 2 (eIF2) and a nucleic acid encoding a protein with a compound or salt as described herein. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the CFPS system comprises a cell extract comprising the eIF2. In some embodiments, the CFPS system further comprises eIF2B.

In some embodiments, there is a method of producing a protein, comprising contacting a cell-free protein synthesis (CFPS) system comprising eukaryotic initiation factor 2 (eIF2) and a nucleic acid encoding a protein with a compound or salt thereof as described herein. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the CFPS system comprises a cell extract comprising the eIF2. In some embodiments, the CFPS system further comprises eIF2B. In some embodiments, the method comprises purifying the protein.

In some embodiments, there is a method of producing a protein, comprising contacting a eukaryotic cell comprising a nucleic acid encoding the protein with a compound or salt as described herein. In some embodiments, the method comprises culturing the cell in an in vitro culture medium comprising the compound or salt. In some embodiments, the nucleic acid encoding the protein is a recombinant nucleic acid. In some embodiments, the eukaryotic cell is a human embryonic kidney (HEK) cell or a Chinese hamster ovary (CHO) cell. In other embodiments, the eukaryotic cell is a yeast cell (such as *Saccharomyces cerevisiae* or *Pichia pastoris*), a wheat germ cell, an insect cell, a rabbit reticulocyte, a cervical cancer cell (such as a HeLa cell), a baby hamster kidney cell (such as BHK21 cells), a murine myeloma cell (such as NSO or Sp2/0 cells), an HT-1080 cell, a PER.C6 cell, a plant cell, a hybridoma cell, or a human blood derived leukocyte. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the method comprises purifying the protein.

In some embodiments, there is a method of culturing a eukaryotic cell comprising a nucleic acid encoding a protein, comprising contacting the eukaryotic cell with an in vitro culture medium comprising a compound or salt as described herein. In some embodiments, the nucleic acid encoding the protein is a recombinant nucleic acid. In some embodiments, the eukaryotic cell is a human embryonic kidney (HEK) cell or a Chinese hamster ovary (CHO) cell. In other embodiments, the eukaryotic cell is a yeast cell (such as *Saccharomyces cerevisiae* or *Pichia pastoris*), a wheat germ cell, an insect cell, a rabbit reticulocyte, a cervical cancer cell (such as a HeLa cell), a baby hamster kidney cell (such as BHK21 cells), a murine myeloma cell (such as NSO or Sp2/0 cells), an HT-1080 cell, a PER.C6 cell, a plant cell, a hybridoma cell, or a human blood derived leukocyte. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the method comprises purifying the protein.

In some embodiments, there is an in vitro cell culture medium, comprising the compound or salt described herein, and nutrients for cellular growth. In some embodiments, the culture medium comprises a eukaryotic cell comprising a nucleic acid encoding a protein. In some embodiments, the culture medium further comprises a compound for inducing protein expression. In some embodiments, the nucleic acid encoding the protein is a recombinant nucleic acid. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the eukaryotic cell is a human embryonic kidney (HEK) cell or a Chinese hamster ovary (CHO) cell. In other embodiments, the eukaryotic cell is a yeast cell (such as *Saccharomyces cerevisiae* or *Pichia pastoris*), a wheat germ cell, an insect cell, a rabbit reticulocyte, a cervical cancer cell (such as a HeLa cell), a baby hamster kidney cell (such as BHK21 cells), a murine myeloma cell (such as NSO or Sp2/0 cells), an HT-1080 cell, a PER.C6 cell, a plant cell, a hybridoma cell, or a human blood derived leukocyte.

In some embodiments, provided herein is a method of increasing protein translation in a cell or cell free expression system. In some embodiments, the cell was stressed prior to administration of the compound, salt thereof, or composition. In some embodiments, protein translation is increased by at least about 10%, 20%, 30%, 40%, 50%, 60%, 70%, 80%, 90%, 95%, 98%, 100%, 125%, 150%, 175%, 200%, 250%, or 300% or more. In some embodiments, protein translation is increased by about 10% to about 300% (such as about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, or about 250% to about 300%) In some embodiments, protein translation is increased as compared to prior to the administration of the compounds, salt thereof, or composition. In some embodiments, protein translation is increased as compared to an unstressed cell, a basal condition where cells are not subjected to a specific stress that activates the ISR. In some embodiments, protein translation is increased as compared to a stressed cell where ISR is active.

The compounds described herein increase protein synthesis in a cell without full inhibition of ATF4 translation, under ISR-stressed or non-ISR stressed conditions. Despite ATF4 participation in various pathologies, the ATF4 protein is an important factor for restoring cellular homeostasis in stressed cells, for example during oxidative stress response, cholesterol metabolism, protein folding amino acid synthesis, and autophagy. Thus, for certain treatments, it may be preferable to limit or avoid ATF4 inhibition. In some embodiments, the compound is used to increase protein synthesis by about 10% or more, about 20% or more, about 30% or more, about 40% or more, about 50% or more, about 60% or more, about 70% or more, about 80% or more, about 90% or more, about 100% or more, about 125% or more, about 150% or more, about 175% or more, about 200% or more, about 250% or more, or about 300% or more wherein ATF4 protein expression is not substantially inhibited or is inhibited by about 75% or less, about 50% or less, about 40% or less, about 30% or less, about 20% or less, about 10% or less, or about 5% or less. In some embodiments the compound is used to increase protein synthesis by about 10% to about 1000% (such as about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, about 250% to about 300%, about 300% to about 350%, about 350% to about 400%, about 400% to about 450%, about 450% to about 500%, about 500% to about 600%, about 600% to about 700%, about 700% to about 800%, about 800% to about 900%, or about 900% to about 1000%), wherein ATF4 protein expression is not substantially inhibited or is inhibited by about 75% or less (such as about 50% or less, about 40% or less, about 30% or less, about 20% or less, about 10% or less, or about 5% or less).

In some embodiments, provided herein is a method of increasing protein translation in a cell. In some embodiments, the cell was stressed prior to administration of the compound, salt thereof, or composition. In some embodiments, protein translation is increased by at least about 10%, 20%, 30%, 40%, 50%, 60%, 70%, 80%, 90%, 95%, 98%, 100%, 125%, 150%, 175%, 200%, 250%, or 300% or more. In some embodiments, protein translation is increased as compared to prior to the administration of the compounds, salt thereof, or composition. In some embodiments, protein translation is increased as compared to an unstressed cell, a basal condition where cells are not subjected to a specific stress that activates the ISR. In some embodiments, protein translation is increased as compared to a stressed cell where ISR is active.

In some embodiments, provided herein is a method of increasing guanine nucleotide exchange factor (GEF) activity of eIF2B in cells. In some embodiments, provided herein is a method of delaying or preventing apoptosis in a cell. In some embodiments, provided herein is a method of inhibiting translation of one or more mRNAs comprising a 5' untranslated region (5'UTR) that contains at least one upstream open reading frame (uORF), encoding proteins with translational preferences, including but not limited to ATF4, ATF2, ATF5, ATF3, FGF-21, CHOP, GADD34, BACE-1, C/EBPα, or MAP1LC3B. In some embodiments, the mRNA encodes ATF4, ATF3, FGF-21, BACE-1, GADD34, or CHOP. In some embodiments, the mRNA encodes ATF4, ATF2, ATF5, CHOP, GADD34, BACE-1, C/EBPα, or MAP1LC3B. In some embodiments, the mRNA encodes ATF4, BACE-1, GADD34, or CHOP. In some embodiments, the mRNA encodes ATF4.

In some embodiments, expression of ATF4, BACE-1, GADD34 or CHOP is inhibited. In some embodiments, expression of ATF4 is inhibited. In some embodiments, expression of Aβ is inhibited. ATF4 increases expression of, among others, GADD45A, CDKN1A, and EIF4EBP1, which encode DDIT-1, p21, and 4E-BP1, respectively. These proteins induce musculoskeletal disease (such as skeletal muscle atrophy), and can be modulated by inhibiting expression of ATF4. Accordingly, in some embodiments, expression of one or more of CDKN1A, GADD45A, or EIF4EBP1 is inhibited.

In some embodiments, the compound, salt thereof, or composition inhibits translation of one or more mRNAs comprising a 5' untranslated region (5'UTR) comprising at least one upstream open reading frame (uORF) with an $IC_{50}$ of less than about 100 µM, such as less than about 75 µM, about 50 µM, about 25 µM, about 20 µM, about 10 µM, about 5 µM, about 1 µM, about 750 nM, 600 nM, 500 nM, 300 nM, 200 nM, 100 nM, 80 nM, 60 nM, 40 nM, 25 nM, or less. In some embodiments, the compound, salt thereof, or composition inhibits translation of one or more mRNAs comprising a 5' untranslated region (5'UTR) comprising at least one upstream open reading frame (uORF) with an $IC_{50}$ between about 1 nM and 100 µM, such as between about 10 nM and 600 nM, 15 nM and 200 nM, or 20 nM and 180 nM.

In some embodiments, the compound, salt thereof, or composition inhibits expression of ATF4 with an $IC_{50}$ of less than about 100 µM, such as less than about 75 µM, about 50 µM, about 25 µM, about 20 µM, about 10 µM, about 5 µM, about 1 µM, about 750 nM, 600 nM, 500 nM, 300 nM, 200 nM, 100 nM, 80 nM, 60 nM, 40 nM, 25 nM, or less. In some embodiments, the compound, salt thereof, or composition inhibits expression of ATF4 with an $IC_{50}$ between about 1 nM and 100 µM, such as between about 2 nM and 800 nM, 10 nM and 600 nM, 15 nM and 200 nM, or 20 nM and 180 nM.

In some aspects, the half maximal inhibitory concentration ($IC_{50}$) is a measure of the effectiveness of a substance in inhibiting a specific biological or biochemical function. In some aspects, the $IC_{50}$ is a quantitative measure that indicates how much of an inhibitor is needed to inhibit a given biological process or component of a process such as an enzyme, cell, cell receptor or microorganism by half. Methods of determining $IC_{50}$ in vitro and in vivo are known in the art.

In some embodiments, the individual is a mammal. In some embodiments, the individual is a primate, bovine, ovine, porcine, equine, canine, feline, rabbit, or rodent. In some embodiments, the individual is a human. In some embodiments, the individual has any of the diseases or disorders disclosed herein. In some embodiments, the individual is a risk for developing any of the diseases or disorders disclosed herein.

In some embodiments, the individual is human. In some embodiments, the human is at least about or is about any of 21, 25, 30, 35, 40, 45, 50, 55, 60, 65, 70, 75, 80, or 85 years old. In some embodiments, the human is a child. In some embodiments, the human is less than about or about any of 21, 18, 15, 12, 10, 8, 6, 5, 4, 3, 2, or 1 years old.

Also provided herein are uses of a compound described herein or a pharmaceutically acceptable salt thereof, or a pharmaceutical composition described herein, in the manufacture of a medicament. In some embodiments, the manufacture of a medicament is for the treatment of a disorder or disease described herein. In some embodiments, the manufacture of a medicament is for the prevention and/or treatment of a disorder or disease mediated by an ISR pathway. In some embodiments, the manufacture of a medicament is for the prevention and/or treatment of a disorder or disease mediated by eIF2α or eIF2B. In some embodiments, the manufacture of a medicament is for the prevention and/or treatment of a disorder or disease mediated by phosphorylation of eIF2α and/or the GEF activity of eIF2B.

In some embodiments, there is a method for enhancing protein synthesis in a living organism, comprising administering to the living organism an effective amount of a compound or salt thereof as provided herein. In some embodiments, the living organism is selected from the group consisting of a cell suspension, a hairy root culture, moss protonema, an aquatic plant (including but not limited to duckweed and microalgae), and a terrestrial plant. In some embodiments, the living organism is a terrestrial plant. In some embodiments, the terrestrial plant is selected from soybean, sunflower, grain legume, rice, wheat germ, maize, tobacco, a cereal, and a lupin crop. In some embodiments, the terrestrial plant is tobacco.

In some embodiments, provided is a method for producing a protein in a living organism, comprising contacting the living organism with a compound described herein or a salt thereof (such as an agriculturally acceptable salt thereof), and wherein the protein is selected from the group consisting of a biopolymer, an industrial protein, an industrial enzyme, and a therapeutic protein. In some embodiments, the living organism is selected from the group consisting of a cell suspension, a hairy root culture, moss protonema, an aquatic plant (including but not limited to duckweed and microalgae), and a terrestrial plant. In some embodiments, the living organism is a terrestrial plant. In some embodiments, the terrestrial plant is tobacco. In some embodiments, the protein is an industrial protein selected from the group consisting of a hydrolase, a glycosidase (such as a cellulase, and α-amylase, a β-glucuronidase, and the likes), a protease (such as trypsin), and the likes. In some embodiments, the protein is a therapeutic protein selected from the group consisting of an antibody, a vaccine, a human growth-factor, a cytokine, and the likes.

In some embodiments, there is a method for accelerating growth of a plant, comprising administering to the plant an effective amount of a compound or salt thereof as provided herein. In some embodiments, the plant is an aquatic plant. In some embodiments, the plant is a terrestrial plant. In some embodiments, the terrestrial plant is selected from soybean, sunflower, grain legume, rice, wheat germ, maize, tobacco, a cereal, and a lupin crop. In some embodiments, the terrestrial plant is tobacco.

In some embodiments, there is a method for improving protein yield or quality in a plant, comprising administering to the plant an effective amount of a compound or salt thereof as provided herein. In some embodiments, the plant is an aquatic plant. In some embodiments, the plant is a terrestrial plant. In some embodiments, the terrestrial plant is selected from soybean, sunflower, grain legume, rice, wheat germ, maize, tobacco, a cereal, and a lupin crop. In some embodiments, the terrestrial plant is tobacco.

Combinations

In certain aspects, a compound described herein is administered to an individual for treatment of a disease in combination with one or more additional pharmaceutical agents that can treat the disease. For example, in some embodiments, an effective amount of the compound is administered to an individual for the treatment of cancer in combination with one or more additional anticancer agents.

In some embodiments, activity of the additional pharmaceutical agent (such as additional anticancer agent) is inhibited by an activated ISR pathway. An ISR inhibitor, such as one of the compounds described herein, can inhibit the ISR pathway to enhance functionality of the additional pharmaceutical agent. By way of example, certain BRAF inhibitors (e.g., vemurafenib or dabrafenib) activate the ISR pathway in BRAF-mutated melanoma cells (e.g., BRAF with a V600F mutation) through the expression of ATF4. In some embodiments, there is a method of treating cancer comprising administering to an individual with cancer an effective amount of a compound described herein in combination with an effective amount of a BRAF inhibitor. In some embodiments, there is a method of treating a BRAF-mutated melanoma comprising administering to an individual with a BRAF-mutated melanoma an effective amount of a compound described herein in combination with an effective amount of a BRAF inhibitor. In some embodiments, there is a method of treating a BRAF-mutated melanoma comprising administering to an individual with a BRAF-mutated melanoma an effective amount of a compound described herein in combination with an effective amount of vemurafenib or dabrafenib.

As another example, certain anticancer agents (such as ubiquitin-proteasome pathway inhibitors (such as bortezomib), Cox-2 inhibitors (e.g., celecoxib), platinum-based antineoplastic drugs (e.g., cisplatin), anthracyclines (e.g. doxorubicin), or topoisomerase inhibitors (e.g., etoposide)) are used to treat cancer, but may have limited functionality against solid tumors. Resistance in certain solid tumors (e.g., breast cancers) has been associated with ATF4 stabilization and induction of autophagy. In some embodiments, an effective amount of an ISR inhibitor compound as described herein is administered to an individual with cancer to increase sensitivity to one or more anticancer agents.

In some embodiments, there is a method of treating a refractory cancer (such as a solid tumor) in an individual, comprising administering to the individual an effective amount of a compound described herein in combination with an effective amount of an anticancer agent. In some embodiments, there is a method of treating a refractory cancer (such as a solid tumor) in an individual, comprising administering to the individual an effective amount of a compound described herein in combination with an effective amount of an ubiquitin-proteasome pathway inhibitor (e.g., bortezomib), a Cox-2 inhibitor (e.g., celecoxib), a platinum-based antineoplastic drug (e.g., cisplatin), an anthracycline (e.g. doxorubicin), or a topoisomerase inhibitor (e.g., etoposide). In some embodiments, the refractory cancer is breast cancer. In some embodiments, the refractory cancer is melanoma.

In some embodiments, a compound described herein is used to treat cancer in combination with one or more anti-cancer agents, such as an anti-neoplastic agent, an immune checkpoint inhibitor, or any other suitable anticancer agent. Exemplary immune checkpoint inhibitors include anti-PD-1, anti-PD-L1, anti GITR, anti-OX-40, anti-LAG3, anti-TIM-3, anti-41BB, anti-CTLA-4 antibodies. Exemplary anti-neoplastic agents can include, for example, anti-microtubule agents, platinum coordination complexes, alkylating agents, topoisomerase II inhibitors, topoisomerase I inhibitors, antimetabolites, antibiotic agents, hormones and hormonal analogs, signal transduction pathway inhibitors, non-receptor tyrosine kinase angiogenesis inhibitors, proteasome inhibitors, and inhibitors of cancer metabolism. Other anti-cancer agents can include one or more of an immuno-stimulant, an antibody or fragment thereof (e.g., an anti-CD20, anti-HER2, anti-CD52, or anti-VEGF antibody or fragment thereof), or an immunotoxin (e.g., an anti-CD33 antibody or fragment thereof, an anti- CD22 antibody or fragment thereof, a calicheamicin conjugate, or a *pseudomonas* exotoxin conjugate).

ATF4-mediated expression of CHOP has also been shown to regulate the function and accumulation of myeloid-derived suppressor cells (MDSCs) in tumors. MDSCs in tumors reduce the ability to prime T cell function and reduce antitumoral or anticancer responses. Certain immunotherapeutic agents (such as anti-PD-1, anti PD-L, anti-GITR, anti-OX-40, anti-LAG3, anti-TIM-3, anti-41BB, or anti-CTLA-4 antibodies) have been used to boost the immune response against cancer. ATF4-mediated expression of AXL has been associated with poor response to anti-PD1 therapy in melanoma. In some embodiments, an effective amount of an ISR inhibitor compound as described herein is administered to an individual with cancer to increase sensitivity to one or more immunotherapeutic agents. In some embodiments, there is a method of treating a refractory cancer (such as a melanoma) in an individual, comprising administering to the individual an effective amount of a compound described herein in combination with an effective amount of an immunotherapeutic agent (e.g. anti-PD-1, anti PD-L1, anti-GITR, anti-OX-40, anti-LAG3, anti-TIM-3, anti-41BB, or anti-CTLA-4 antibodies). In some embodiments, the refractory cancer is melanoma.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more).

Any of the dosing frequencies can employ any of the compounds described herein together with any of the dosages described herein.

Articles of Manufacture and Kits

The present disclosure further provides articles of manufacture comprising a compound described herein or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment of any disease or described herein, for example for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

General Synthetic Methods

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High-Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Chromatography, recrystallization and other conventional separation procedures may also be used with intermediates or final products where it is desired to obtain a particular isomer of a compound or to otherwise purify a product of a reaction.

Enumerated Embodiments

Embodiment 1. A compound of formula (I):

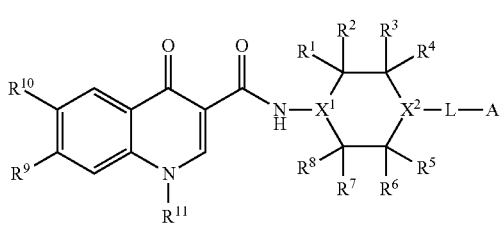

(I)

or a salt thereof,
wherein:
$X^1$ is N or $CR^{X1}$;
$X^2$ is N or $CR^{X2}$;
when present, $R^{X1}$ is selected from the group consisting of hydrogen, $C_1$-$C_6$ alkyl, $C_1$-$C_6$ haloalkyl, —C(O)OH, —C(O)O($C_1$-$C_6$ alkyl), —C(O)O($C_1$-$C_6$ haloalkyl), and halogen;
when present, $R^{X2}$ is selected from the group consisting of hydrogen, $C_1$-$C_6$ alkyl, $C_1$-$C_6$ haloalkyl, —C(O)OH, —C(O)O($C_1$-$C_6$ alkyl), —C(O)O($C_1$-$C_6$ haloalkyl), and halogen;
$R^1$, $R^2$, $R^3$, $R^4$, $R^5$, $R^6$, $R^7$, and $R^8$, independently from each other, are selected from the group consisting of hydrogen, $C_1$-$C_6$ alkyl, $C_1$-$C_6$ haloalkyl, —C(O)OH, —C(O)O($C_1$-$C_6$ alkyl), —C(O)O($C_1$-$C_6$ haloalkyl), and halogen;
or, one of $R^1$, $R^2$, $R^3$, $R^4$, $R^5$, $R^6$, $R^7$, and $R^8$, and another one of $R^1$, $R^2$, $R^3$, $R^4$, $R^5$, $R^6$, $R^7$, and $R^8$, are taken together to form a $C_1$-$C_6$ alkylene moiety;
or, two geminal substituents selected from the group consisting of $R^1$, $R^2$, $R^3$, $R^4$, $R^5$, $R^6$, $R^7$, and $R^8$ are taken together to form an oxo group;
or, one of $R^1$, $R^2$, $R^3$, $R^4$, $R^5$, $R^6$, $R^7$, and $R^8$, and $R^{X1}$, when present, are taken together to form a $C_1$-$C_6$ alkylene moiety;
$R^9$ and $R^{10}$, independently from each other, are selected from the group consisting of hydrogen, halogen, $NO_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{B-a}R^{B-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{B-a}R^{B-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{B-a}R^{B-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O) ($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C (O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$ ($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{B-a}$ and $R^{B-b}$ are taken together with the nitrogen atom to which they are attached to form a 3-10 membered heterocycle;
$R^{11}$ is selected from the group consisting of $C_3$-$C_{10}$ cycloalkyl optionally substituted with 1 to 17 $R^{12}$ substituents and 3-10 membered heterocycloalkyl optionally substituted with 1 to 17 $R^{12}$ substituents;
$R^{12}$, independently at each occurrence, is selected from the group consisting of oxo, halogen, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{C-a}R^{C-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{C-a}R^{C-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{C-a}R^{C-b}$, —OC(O)H, —OC(O)($C_1$-$C_6$ alkyl), —OC(O) ($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl) C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$ ($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S (O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{C-a}$ and $R^{C-b}$ are taken together with the nitrogen atom to which they are attached to form a 3-10 membered heterocycle;

L is a linker selected from the group consisting of @-$C_1$-$C_6$ alkylene-#, @—$NR^N$—($C_1$-$C_6$ alkylene)-#, @—$NR^N$—$NR^N$—($C_1$-$C_6$ alkylene)-#, @-$CH_2$—$NR^N$—($C_1$-$C_6$ alkylene)-#, @-$CH_2$—$NR^N$—$NR^N$—($C_1$-$C_6$ alkylene)-#, @—$NR^N$—($C_1$-$C_6$ alkylene)-O-#, @—$NR^N$—$NR^N$—($C_1$-$C_6$ alkylene)-O-#, @-$CH_2$—$NR^N$—($C_1$-$C_6$ alkylene)-O-#, @-$CH_2$—$NR^N$—$NR^N$—($C_1$-$C_6$ alkylene)-O-#, and @—($C_1$-$C_6$ alkylene)-O-#;
wherein @ represents the attachment point to $X^2$ and # represents the attachment point to A;
the $C_1$-$C_6$ alkylene moiety of each of the @-$C_1$-$C_6$ alkylene-#, @—$NR^N$—($C_1$-$C_6$ alkylene)-#, @—$NR^N$—$NR^N$—($C_1$-$C_6$ alkylene)-#, @-$CH_2$—$NR^N$—($C_1$-$C_6$ alkylene)-#, @-$CH_2$—$NR^N$—$NR^N$—($C_1$-$C_6$ alkylene)-#, @—$NR^N$—($C_1$-$C_6$ alkylene)-O-#, @—$NR^N$—$NR^N$—($C_1$-$C_6$ alkylene)-O-#, @-$CH_2$—$NR^N$—($C_1$-$C_6$ alkylene)-O-#, @-$CH_2$—$NR^N$—$NR^N$—($C_1$-$C_6$ alkylene)-O-#, and @—($C_1$-$C_6$ alkylene)-O-# is optionally substituted with 1 to 12 $R^{13}$;
$R^N$, independently at each occurrence, is selected from the group consisting of hydrogen, $C_1$-$C_6$ alkyl, and $C_1$-$C_6$ haloalkyl,
$R^{13}$, independently at each occurrence, is selected from the group consisting of oxo, halogen, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{L-a}R^{L-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{L-a}R^{L-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{L-a}R^{L-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{L-a}$ and $R^{L-b}$ are taken together with the nitrogen atom to which they are attached to form a 3-10 membered heterocycle;
A is selected from the group consisting of:
a substituent of formula (A-1)

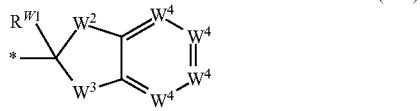

(A-1)

$W^2$ is selected from the group consisting of —C($R^{W2-1}R^{W2-2}$)—, —N($R^{W2-2}$)—, —C($R^{W2-1}R^{W2-1}$)N($R^{W2-2}$)—, —N($R^{W2-1}$)C($R^{W2-1}R^{W2-2}$)—, —C($R^{W2-1}$)=N—, —N=C($R^{W2-1}$)—, —O—, —C($R^{W2-1}R^{W2-1}$)O—, —OC($R^{W2-1}R^{W2-2}$)—, —S—, —C($R^{W2-1}R^{W2-1}$)S—, —SC($R^{W2-1}R^{W2-2}$)—, —C($R^{W2-1}R^{W2-1}$)C($R^{W2-1}R^{W2-2}$)—, and —C$R^{W2-1}$=C$R^{W2-1}$—,
wherein $R^{W2-1}$ is H or $R^A$, and $R^{W2-2}$ is H or $R^A$;
$W^3$ is selected from the group consisting of —C($R^{W3-1}R^{W3-2}$)—, —N($R^{W3-2}$)—, —C($R^{W3-1}R^{W3-1}$)N($R^{3-2}$)—, —N($R^{W3-1}$)C($R^{W3-1}R^{W3-2}$)—, —C($R^{W3-1}$)=N—, —N=C($R^{W3-1}$)—, —O—, —C($R^{W3-1}R^{W3-1}$)O—, —OC($R^{W3-1}R^{W3-2}$)—, —S—, —C($R^{W3-1}R^{W3-1}$)S—, —SC($R^{W3-1}R^{W3-2}$)—, —C($R^{W3-1}R^{W3-1}$)C($R^{W3-1}R^{W3-2}$)—, and —C$R^{W3-1}$=C$R^{W3-1}$—,
wherein $R^{W3-1}$ is H or $R^A$, and $R^{W3-2}$ is H or $R^A$;
$W^4$, independently at each occurrence, is C$R^{W4}$ or N, wherein $R^{W4}$ is H or $R^A$;
$R^{W1}$ is hydrogen or $R^A$, or $R^{W1}$ and $R^{W2-2}$ are taken together to form a double bond between the carbon atom bearing $R^{W1}$ and the atom bearing $R^{W2-2}$, or $R^{W1}$ and $R^{W3-2}$ are taken together to form a double bond between the carbon atom bearing $R^{W1}$ and the atom bearing $R^{W3-2}$;
$C_6$-$C_{14}$ aryl optionally substituted with 1, 2, 3, 4, 5, 6, 7, 8, or 9 $R^A$ substituents; and 5-14 membered heteroaryl optionally substituted with 1, 2, 3, 4, 5, 6, 7, 8, or 9 $R^A$ substituents;
$R^A$, independently at each occurrence, is selected from the group consisting of halogen, $NO_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{A-a}R^{A-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{A-a}R^{A-b}$, —S(O)$_2$H, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{A-a}R^{A-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{A-a}$ and $R^{A-b}$ are taken together with the nitrogen atom to which they are attached to form a 3-10 membered heterocycle;
provided that when $X^2$ is N, then L is a linker selected from the group consisting of @-$C_1$-$C_6$ alkylene-#, @—$NR^N$—($C_1$-$C_6$ alkylene)-#, @—$NR^N$—($C_1$-$C_6$ alkylene)-O-#, and @—($C_1$-$C_6$ alkylene)-O-#.

Embodiment 2. The compound of embodiment 1, or a salt thereof, wherein the compound of formula (I) is a compound of formula (II):

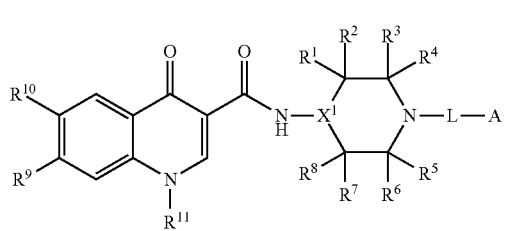

(II)

or a salt thereof,
wherein $R^1$, $R^2$, $R^3$, $R^4$, $R^5$, $R^6$, $R^7$, $R^8$, $R^9$, $R^{10}$, $R^{11}$, $X^1$, L, and A are as defined in embodiment 1.

Embodiment 3. The compound of embodiment 1, or a salt thereof, wherein the compound of formula (I) is a compound of formula (III):

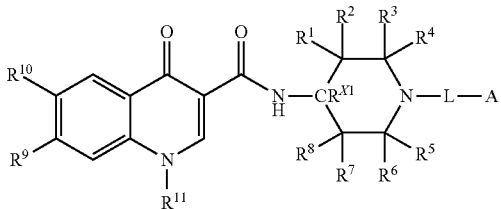

(III)

or a salt thereof,
wherein $R^1$, $R^2$, $R^3$, $R^4$, $R^5$, $R^6$, $R^7$, $R^8$, $R^9$, $R^{10}$, $R^{11}$, $CR^{X1}$, L, and A are as defined in embodiment 1.

Embodiment 4. The compound of embodiment 1, or a salt thereof, wherein the compound of formula (I) is a compound of formula (IV):

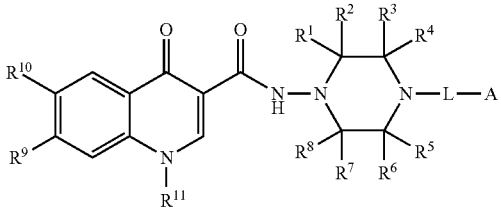

(IV)

or a salt thereof,
wherein $R^1$, $R^2$, $R^3$, $R^4$, $R^5$, $R^6$, $R^7$, $R^8$, $R^9$, $R^{10}$, $R^{11}$, L, and A are as defined in embodiment 1.

Embodiment 5. The compound of embodiment 1, or a salt thereof, wherein the compound of formula (I) is a compound of formula (V):

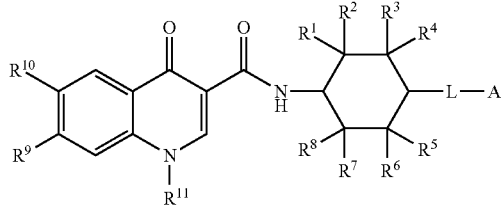

(V)

or a salt thereof,
wherein $R^1$, $R^2$, $R^3$, $R^4$, $R^5$, $R^6$, $R^7$, $R^8$, $R^9$, $R^{10}$, $R^{11}$, L, and A are as defined in embodiment 1.

Embodiment 6. The compound of embodiment 1, or a salt thereof, wherein the compound of formula (I) is a compound of formula (VI):

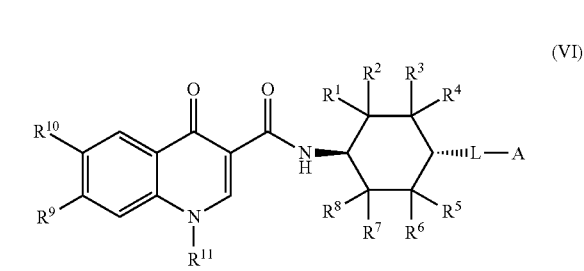

(VI)

or a salt thereof,
wherein $R^1$, $R^2$, $R^3$, $R^4$, $R^5$, $R^6$, $R^7$, $R^8$, $R^9$, $R^{10}$, $R^{11}$, L, and A are as defined in embodiment 1.

Embodiment 7. The compound of embodiment 1, or a salt thereof, wherein the compound of formula (I) is a compound of formula (VII):

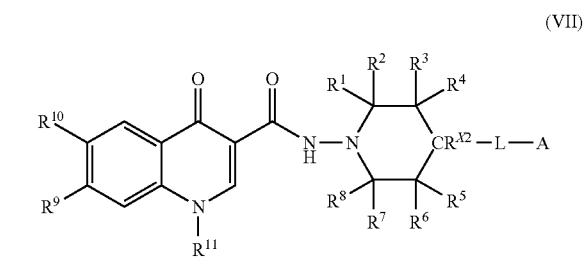

(VII)

or a salt thereof,
wherein $R^1$, $R^2$, $R^3$, $R^4$, $R^5$, $R^6$, $R^7$, $R^8$, $R^9$, $R^{10}$, $R^{11}$, $CR^{X2}$, L, and A are as defined in embodiment 1.

Embodiment 8. The compound of embodiment 1, or a salt thereof, wherein the compound of formula (I) is a compound of formula (VIII):

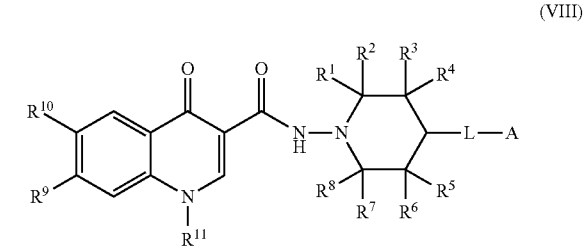

(VIII)

or a salt thereof,
wherein $R^1$, $R^2$, $R^3$, $R^4$, $R^5$, $R^6$, $R^7$, $R^8$, $R^9$, $R^{10}$, $R^{11}$, L, and A are as defined in embodiment 1.

Embodiment 9. The compound of any of the preceding embodiments, or a salt thereof, wherein L is

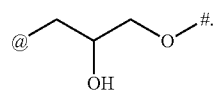

Embodiment 10. The compound of embodiment 9, or a salt thereof, wherein L is

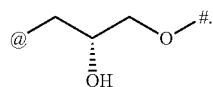

Embodiment 11. The compound of embodiment 9, or a salt thereof, wherein L is

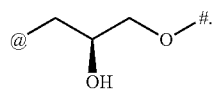

Embodiment 12. The compound of any of the preceding embodiments, or a salt thereof, wherein $R^1$, $R^2$, $R^3$, $R^4$, $R^5$, $R^6$, $R^7$, and $R^8$ are each hydrogen.

Embodiment 13 The compound of any of the preceding embodiments, or a salt thereof, wherein $R^9$ and $R^{10}$ are each halogen.

Embodiment 14. The compound of any of the preceding embodiments, or a salt thereof, wherein $R^9$ is chloro and $R^{10}$ is fluoro.

Embodiment 15. The compound of any of the preceding embodiments, or a salt thereof, wherein A is *

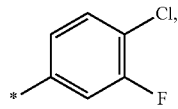

wherein * represents that attachment point to the remainder of the molecule.

Embodiment 16. A compound selected from the group consisting of:

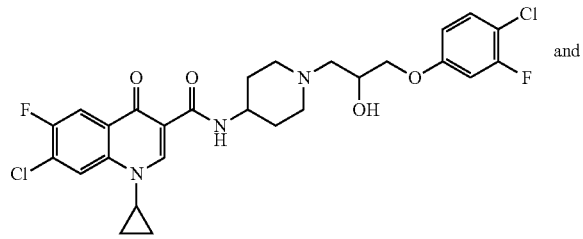

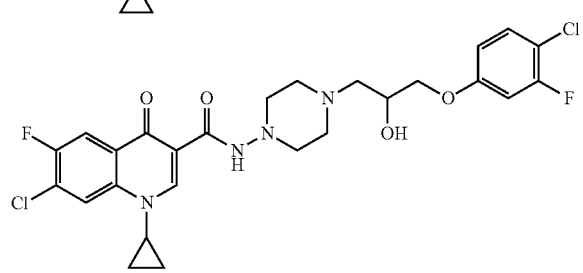

or a salt thereof.

Embodiment 17. A compound selected from the group consisting of:

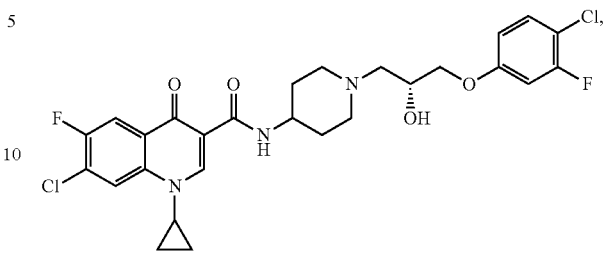

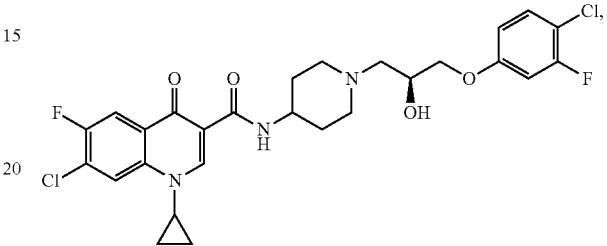

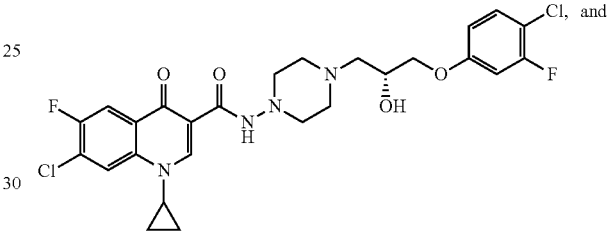

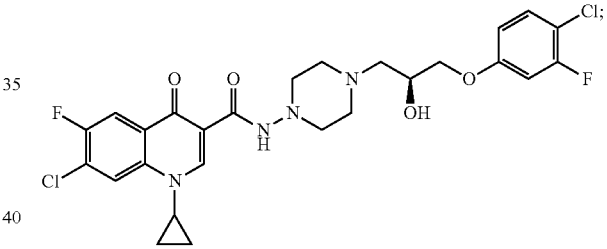

or a salt thereof.

Embodiment 18. A compound selected from the group consisting of a compound of Table 1, or a salt thereof.

Embodiment 19 A pharmaceutical composition comprising a compound of any one of the preceding embodiments, or a pharmaceutically acceptable salt thereof, and a pharmaceutically acceptable carrier.

Embodiment 20. A method for enhancing protein synthesis in a living organism, comprising administering to the living organism an effective amount of a compound of any one of embodiments 1-13, or a salt thereof.

Embodiment 21. A method for accelerating growth of a plant, comprising administering to the plant an effective amount of a compound of any one of embodiments 1-18, or a salt thereof.

Embodiment 22. A method for improving protein yield or quality in a plant, comprising administering to the plant an effective amount of a compound of any one of embodiments 1-18, or a salt thereof.

Embodiment 23. The method of embodiment 22, wherein the plant is selected from soybean, sunflower, grain legume, rice, wheat germ, maize, tobacco, a cereal, and a lupin crop.

Embodiment 24. A method of treating a disease or disorder mediated by an integrated stress response (ISR) pathway in an individual in need thereof comprising administering to the individual a therapeutically effective amount of a compound of any one of embodiments 1-18, or a pharmaceutically acceptable salt thereof, or a therapeutically effective amount of a pharmaceutical composition of embodiment 10.

Embodiment 25. The method of embodiment 24, wherein the compound, the pharmaceutically acceptable salt, or the pharmaceutical composition is administered in combination with a therapeutically effective amount of one or more additional anti-cancer agents.

Embodiment 26. The method of embodiment 24, wherein the disease or disorder is mediated by phosphorylation of eIF2α and/or the guanine nucleotide exchange factor (GEF) activity of eIF2B.

Embodiment 27. The method of any one of embodiments 24-26, wherein the disease or disorder is mediated by a decrease in protein synthesis.

Embodiment 28. The method of any one of embodiments 25-27, wherein the disease or disorder is mediated by the expression of ATF4, CHOP or BACE-1.

Embodiment 29. The method of any of embodiments 24-28, wherein the disease or disorder is a neurodegenerative disease, an inflammatory disease, an autoimmune disease, a metabolic syndrome, a cancer, a vascular disease, an ocular disease, a musculoskeletal disease, or a genetic disorder.

Embodiment 30. The method of embodiment 29, wherein the disease is vanishing white matter disease, childhood ataxia with CNS hypomyelination, intellectual disability syndrome, Alzheimer's disease, prion disease, Creutzfeldt-Jakob disease, Parkinson's disease, amyotrophic lateral sclerosis (ALS) disease, cognitive impairment, frontotemporal dementia (FTD), traumatic brain injury, postoperative cognitive dysfunction (PCD), neuro-otological syndromes, hearing loss, Huntington's disease, stroke, chronic traumatic encephalopathy, spinal cord injury, dementias or cognitive impairment, arthritis, psoriatic arthritis, psoriasis, juvenile idiopathic arthritis, asthma, allergic asthma, bronchial asthma, tuberculosis, chronic airway disorder, cystic fibrosis, glomerulonephritis, membranous nephropathy, sarcoidosis, vasculitis, ichthyosis, transplant rejection, interstitial cystitis, atopic dermatitis or inflammatory bowel disease, Crohn's disease, ulcerative colitis, celiac disease, systemic lupus erythematosus, type 1 diabetes, multiple sclerosis, rheumatoid arthritis, alcoholic liver steatosis, obesity, glucose intolerance, insulin resistance, hyperglycemia, fatty liver, dyslipidemia, hyperlipidemia, type 2 diabetes, pancreatic cancer, breast cancer, kidney cancer, bladder cancer, prostate cancer, testicular cancer, urothelial cancer, endometrial cancer, ovarian cancer, cervical cancer, renal cancer, esophageal cancer, gastrointestinal stromal tumor (GIST), multiple myeloma, cancer of secretory cells, thyroid cancer, gastrointestinal carcinoma, chronic myeloid leukemia, hepatocellular carcinoma, colon cancer, melanoma, malignant glioma, glioblastoma, glioblastoma multiforme, astrocytoma, dysplastic gangliocytoma of the cerebellum, Ewing's sarcoma, rhabdomyosarcoma, ependymoma, medulloblastoma, ductal adenocarcinoma, adenosquamous carcinoma, nephroblastoma, acinar cell carcinoma, lung cancer, non-Hodgkin's lymphoma, Burkitt's lymphoma, chronic lymphocytic leukemia, monoclonal gammopathy of undetermined significance (MGUS), plasmocytoma, lymphoplasmacytic lymphoma, acute lymphoblastic leukemia, Pelizaeus-Merzbacher disease, atherosclerosis, abdominal aortic aneurism, carotid artery disease, deep vein thrombosis, Buerger's disease, chronic venous hypertension, vascular calcification, telangiectasia or lymphoedema, glaucoma, age-related macular degeneration, inflammatory retinal disease, retinal vascular disease, diabetic retinopathy, uveitis, rosacea, Sjogren's syndrome or neovascularization in proliferative retinopathy, hyperhomocysteinemia, skeletal muscle atrophy, myopathy, muscular dystrophy, muscular wasting, sarcopenia, Duchenne muscular dystrophy (DMD), Becker's disease, myotonic dystrophy, X-linked dilated cardiomyopathy, spinal muscular atrophy (SMA), Down syndrome, MEHMO syndrome, metaphyseal chondrodysplasia, Schmid type (MCDS), depression, or social behavior impairment.

Embodiment 31. A method of producing a protein, comprising contacting a eukaryotic cell comprising a nucleic acid encoding the protein with the compound or salt of any one of embodiments 1-18.

Embodiment 32. The method of embodiment 31, comprising culturing the cell in an in vitro culture medium comprising the compound or salt.

Embodiment 33. A method of culturing a eukaryotic cell comprising a nucleic acid encoding a protein, comprising contacting the eukaryotic cell with an in vitro culture medium comprising a compound or salt of any one of embodiments 1-18.

Embodiment 34. The method of any one of embodiments 31-33, wherein the nucleic acid encoding the protein is a recombinant nucleic acid.

Embodiment 35. The method of any one of embodiments 31-34, wherein the cell is a human embryonic kidney (HEK) cell or a Chinese hamster ovary (CHO) cell.

Embodiment 36. A method of producing a protein, comprising contacting a cell-free protein synthesis (CFPS) system comprising eukaryotic initiation factor 2 (eIF2) and a nucleic acid encoding a protein with the compound or salt of any one of embodiments 1-18.

Embodiment 37. The method of any one of embodiments 31-36, wherein the protein is an antibody or a fragment thereof.

Embodiment 38. The method of any one of embodiments 31-37, comprising purifying the protein.

Embodiment 39. An in vitro cell culture medium, comprising the compound or salt of any one of embodiments 1-18 and nutrients for cellular growth.

Embodiment 40. The cell culture medium of embodiment 39, comprising a eukaryotic cell comprising a nucleic acid encoding a protein.

Embodiment 41. The cell culture medium of embodiment 39 or 40, further comprising a compound for inducing protein expression.

Embodiment 42. The cell culture medium of any one of embodiments 39-41, wherein the nucleic acid encoding the protein is a recombinant nucleic acid.

Embodiment 43. The cell culture medium of any one of embodiments 39-42, wherein the protein is an antibody or a fragment thereof.

Embodiment 44. The cell culture medium of any one of embodiments 39-43, wherein the eukaryotic cell is a human embryonic kidney (HEK) cell or a Chinese hamster ovary (CHO) cell.

Embodiment 45. A cell-free protein synthesis (CFPS) system comprising eukaryotic initiation factor 2 (eIF2) and a nucleic acid encoding a protein with the compound or salt of any one of embodiments 1-18.

Embodiment 46. The CFPS system of embodiment 45, comprising a eukaryotic cell extract comprising eIF2.

Embodiment 47. The CFPS system of embodiment 45 or 46, further comprising eIF2B.

Embodiment 48. The CFPS system of any one of embodiments 45-47, wherein the protein is an antibody or a fragment thereof.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure.

In some cases, stereoisomers are separated to give single enantiomers or diastereomers as single, unknown stereoisomers, and are arbitrarily drawn as single isomers. Where appropriate, information is given on separation method and elution time and order. In the biological examples, compounds tested were prepared in accordance to the synthetic procedures described therein. For any given compound of unknown absolute stereochemistry for which specific rotation is available, biological data for that compound was obtained using the enantiomer or diastereoisomer associated with said specific rotation.

In some cases, optical rotation was determined on Jasco DIP-360 digital polarimeter at a wavelength of 589 nm (sodium D line) and are reported as $[\alpha]_D^T$ for a given temperature T (expressed in ° C.). Where appropriate, information is given on solvent and concentration (expressed as g/100 mL).

Abbreviations br. s. Broad singlet
chloroform-d Deuterated chloroform
methanol-$d_4$ Deuterated methanol
DIAD Diisopropyl azodicarboxylate
DCM Dichloromethane
DEA Diethylamine
DIPEA Diisopropylethylamine
DMF N,N-Dimethylformamide
DMSO-$d_6$ Deuterated dimethylsulfoxide
d Doublet
EDC.HCl 1-Ethyl-3-(3-dimethylaminopropyl)carbodiimide hydrochloric acid
EtOAc Ethyl acetate
EtOH Ethanol
g Gram
HATU (O-(7-azabenzotriazol-1-yl)-N,N,N',N'-tetramethyluronium hexafluorophosphate)
HOBT Hydroxybenzotriazole
HPLC High Performance Liquid Chromatography
L Litre
LCMS Liquid Chromatography Mass Spectrometry
MeCN Acetonitrile
MeOH Methanol
mg Milligram
mL Millilitre
mmol Millimoles
m multiplet
NMR Nuclear Magnetic Resonance
iPrOH Isopropanol
q quartet
RT Room temperature
s singlet
SFC Supercritical Fluid Chromatography
TFA trifluoroacetic acid
THF Tetrahydrofuran
TLC Thin layer chromatography
t triplet

Example 1

Synthesis of 7-chloro-N-(1-(3-(4-chloro-3-fluorophenoxy)-2-hydroxypropyl)piperidin-4-yl)-1-cyclopropyl-6-fluoro-4-oxo-1,4-dihydroquinoline-3-carboxamide

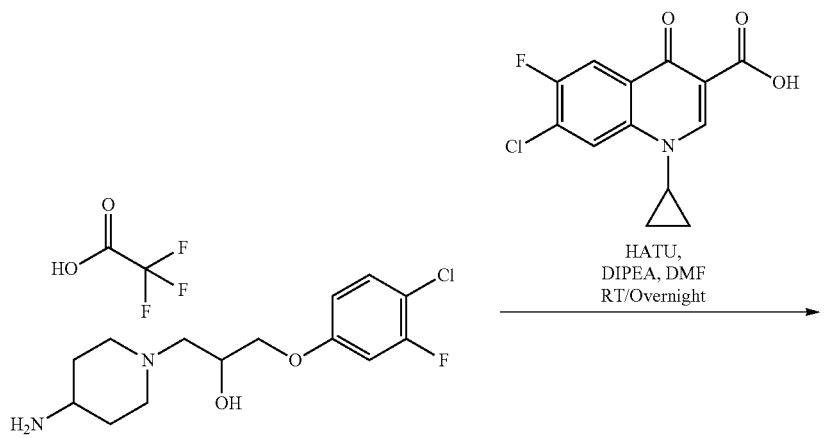

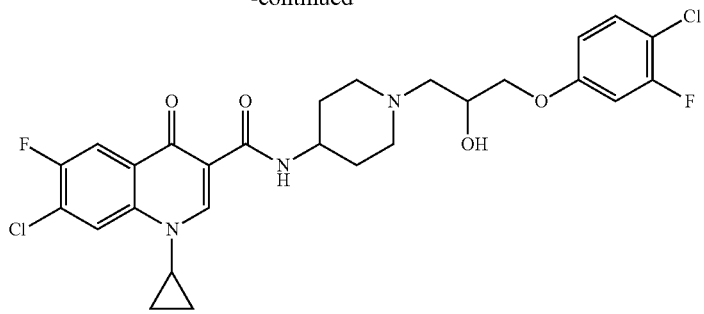

To a stirred solution of 1-(4-aminopiperidin-1-yl)-3-(4-chloro-3-fluorophenoxy)propan-2-ol 2,2,2-trifluoroacetate (0.200 g, 0.480 mmol, 1.0 equiv) and 7-chloro-1-cyclopropyl-6-fluoro-4-oxo-1,4-dihydroquinoline-3-carboxylic acid (0.136 g, 0.480 mmol, 1.0 equiv) in DMF (5 mL) was added HATU (0.366 g, 0.960 mmol, 2.0 equiv) followed by the addition of DIPEA (0.3 mL) at RT. The resulting reaction mixture was allowed to stir at RT for overnight. Product formation was confirmed by LCMS. The reaction mixture was diluted with water (100 mL). The resulting solid was filtered off, washed with water (25 mL×2) and dried under vacuum. The crude product was purified by reversed phase HPLC to obtain 7-chloro-N-(1-(3-(4-chloro-3-fluorophenoxy)-2-hydroxypropyl)piperidin-4-yl)-1-cyclopropyl-6-fluoro-4-oxo-1,4-dihydroquinoline-3-carboxamide (Compound 1-0.050 g, 18% Yield) as an off-white solid. LCMS 566.4 [M+H]$^+$; $^1$H NMR (400 MHz, DMSO-d$_6$) δ 9.80 (d, J=7.45 Hz, 1H), 8.69 (s, 1H), 8.39 (d, J=6.14 Hz, 1H), 8.14 (d, J=9.21 Hz, 1H), 7.46 (t, J=8.99 Hz, 1H), 7.08 (dd, J=11.84, 2.63 Hz, 1H), 6.85 (dd, J=8.77, 1.75 Hz, 1H), 4.91 (br. s., 1H), 4.02 (d, J=6.58 Hz, 1H), 3.73-3.97 (m, 3H), 3.33 (br. s., 3H), 2.76 (br. s., 2H), 2.19-2.48 (m, 4H), 1.85 (d, J=8.77 Hz, 2H), 1.42-1.58 (m, 2H), 1.31 (d, J=6.14 Hz, 2H), 1.12 (br. s., 2H).

Example 2

Synthesis of (R)-7-chloro-N-(1-(3-(4-chloro-3-fluorophenoxy)-2-hydroxypropyl)piperidin-4-yl)-1-cyclopropyl-6-fluoro-4-oxo-1,4-dihydroquinoline-3-carboxamide

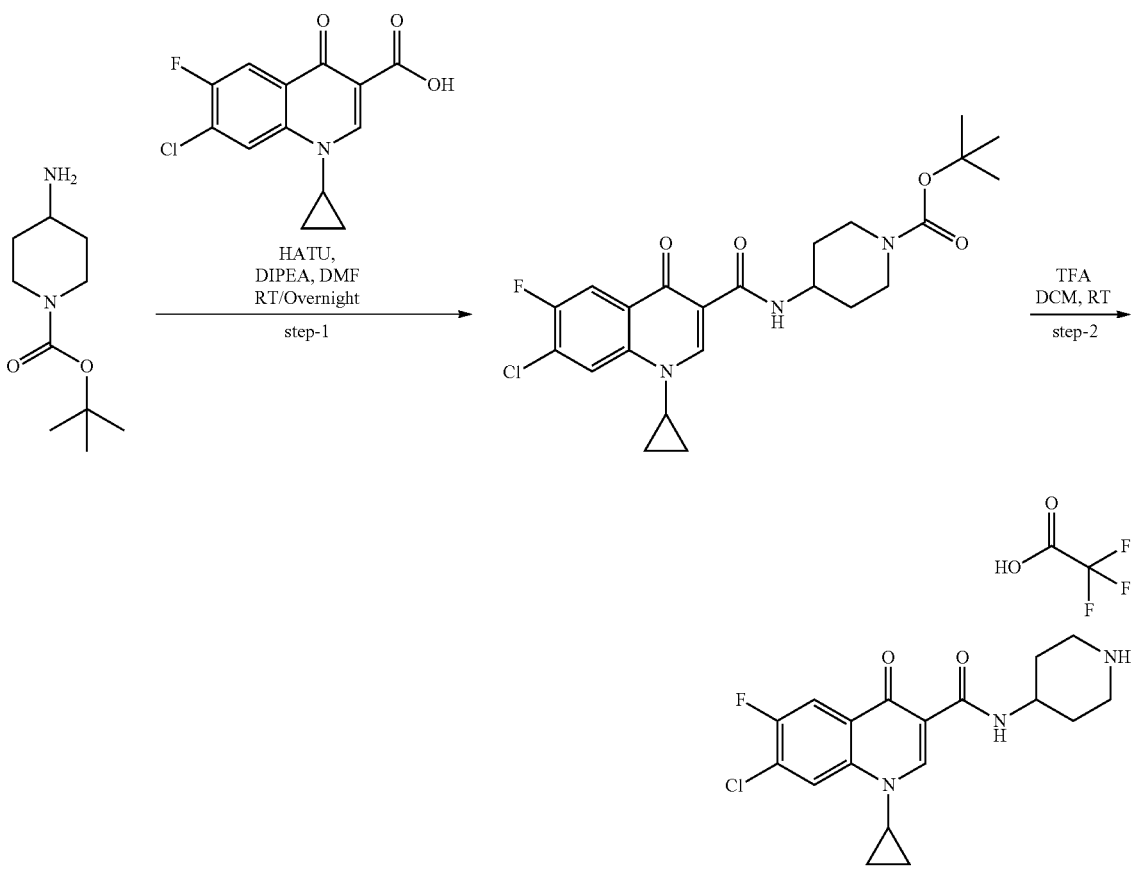

123

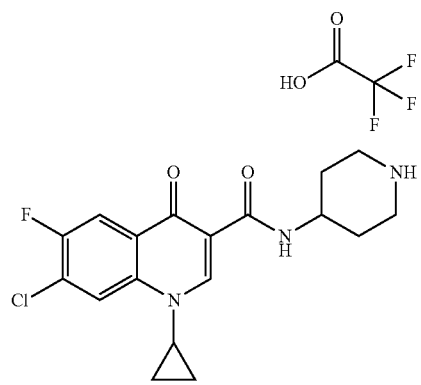

-continued

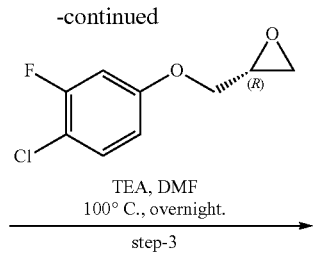

TEA, DMF
100° C., overnight.
———————→
step-3

124

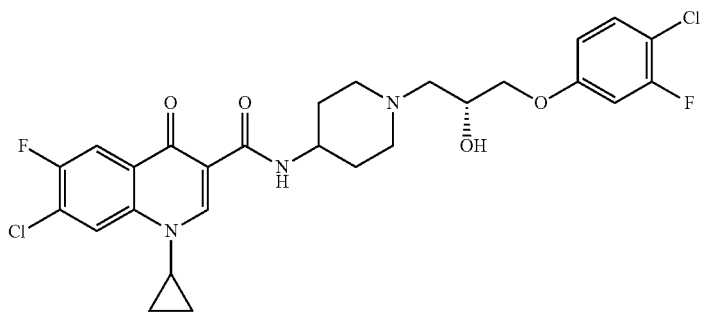

Step 1—Synthesis of tert-butyl 4-(7-chloro-1-cyclopropyl-6-fluoro-4-oxo-1,4-dihydroquinoline-3-carboxamido)piperidine-1-carboxylate To a stirred solution of 7-chloro-1-cyclopropyl-6-fluoro-4-oxo-1,4-dihydroquinoline-3-carboxylic acid (0.705 g, 2.50 mmol, 1.0 equiv) in DMF (10 mL) was added HATU (1.90 g, 5.00 mmol, 2.0 equiv) at RT and stirred for 10 minutes. Then tert-butyl 4-aminopiperidine-1-carboxylate (0.500 g, 1.492 mmol, 1.0 equiv) was added followed by the addition of DIPEA (1.4 mL, 7.50 mmol, 3.0 equiv). The resulting reaction mixture was allowed to stir at RT for overnight. Product formation was confirmed by LCMS. The reaction mixture was diluted with water (100 mL). The resulting solid was filtered off, washed with water (25 mL×2) and dried under vacuum to obtain tert-butyl 4-(7-chloro-1-cyclopropyl-6-fluoro-4-oxo-1,4-dihydroquinoline-3-carboxamido)piperidine-1-carboxylate (1.00 g, 87% Yield) as an off-white solid. LCMS 464.2 [M+H]$^+$; $^1$H NMR (400 MHz, DMSO-d$_6$) δ 9.81 (d, J=7.45 Hz, 1H), 8.69 (s, 1H), 8.39 (d, J=6.14 Hz, 1H), 8.13 (d, J=9.21 Hz, 1H), 3.99 (d, J=7.89 Hz, 1H), 3.67-3.84 (m, 3H), 3.01 (br. s., 2H), 1.86 (d, J=9.21 Hz, 2H), 1.41 (s, 7H), 1.36 (br. s., 1H), 1.31 (d, J=6.58 Hz, 2H), 1.12 (br. s., 2H).

Step 2—Synthesis of 7-chloro-1-cyclopropyl-6-fluoro-4-oxo-N-(piperidin-4-yl)-1,4-dihydroquinoline-3-carboxamide 2,2,2-trifluoroacetate To a stirred solution of tert-butyl 4-(7-chloro-1-cyclopropyl-6-fluoro-4-oxo-1,4-dihydroquinoline-3-carboxamido)piperidine-1-carboxylate (1.00 g, 2.15 mmol, 1.0 equiv) in DCM (50 mL), was added TFA (1 mL) and the resultant reaction mixture was stirred at RT for overnight under nitrogen atmosphere. Product formation was confirmed by $^1$HNMR. After completion of reaction, the reaction mixture was concentrated under reduced pressure to obtain crude product which was crystallized in diethyl ether to obtain 7-chloro-1-cyclopropyl-6-fluoro-4-oxo-N-(piperidin-4-yl)-1,4-dihydroquinoline-3-carboxamide 2,2,2-trifluoroacetate (1.00 g, 97% Yield) as an off-white solid. LCMS 364.2 [M+H]$^+$; $^1$H NMR (400 MHz, DMSO-d$_6$) δ 9.86 (d, J=7.45 Hz, 1H), 8.70 (s, 1H), 8.60 (br. s., 1H), 8.41 (d, J=6.14 Hz, 1H), 8.33 (br. s., 1H), 8.13 (d, J=9.21 Hz, 1H), 4.09 (d, J=7.45 Hz, 1H), 3.78 (d, J=3.51 Hz, 1H), 3.29 (d, J=11.84 Hz, 2H), 3.07 (d, J=10.52 Hz, 2H), 2.07 (d, J=11.40 Hz, 2H), 1.58-1.74 (m, 2H), 1.32 (d, J=6.58 Hz, 2H), 1.03-1.19 (m, 2H).

Step 3—Synthesis of (R)-7-chloro-N-(1-(3-(4-chloro-3-fluorophenoxy)-2-hydroxypropyl)piperidin-4-yl)-1-cyclopropyl-6-fluoro-4-oxo-1,4-dihydroquinoline-3-carboxamide To a stirred solution of 7-chloro-1-cyclopropyl-6-fluoro-4-oxo-N-(piperidin-4-yl)-1,4-dihydroquinoline-3-carboxamide 2,2,2-trifluoroacetate (0.200 g, 0.418 mmol, 1.0 equiv) in DMF (2 mL) was added TEA (0.127 g, 1.255 mmol, 3.0 equiv) followed by the addition of (R)-2-((4-chloro-3-fluorophenoxy)methyl)oxirane (0.102 g, 0.502 mmol, 1.2 equiv). The resulting reaction mixture was heated at 100° C. for overnight. Product formation was monitored by LCMS and TLC. After completion of reaction, the reaction mixture was diluted with water (50 mL) and extracted with EtOAc (50 mL×2). The combined organic layer was washed with water (30 mL×4), dried over anhydrous sodium sulfate and concentrated under reduced pressure. The crude product which was purified flash chromatography (0-5% MeOH in DCM as an eluent) to obtain (R)-7-chloro-N-(1-(3-(4-chloro-3-fluorophenoxy)-2-hydroxypropyl)piperidin-4-yl)-1-cyclopropyl-6-fluoro-4-oxo-1,4-dihydroquinoline-3-carboxamide (Compound 2-0.060 g, 25% Yield) as an off-white solid. LCMS 566.4 [M+H]$^+$; $^1$H NMR (400 MHz, DMSO-d$_6$) δ 9.81 (d, J=7.89 Hz, 1H), 8.69 (s, 1H), 8.39 (d, J=6.58 Hz, 1H), 8.15 (d, J=9.21 Hz, 1H), 7.46 (t, J=8.77 Hz, 1H), 7.08 (dd, J=11.62, 2.85 Hz, 1H), 6.79-6.92 (m, 1H), 4.89 (br. s., 1H), 4.02 (d, J=7.02 Hz, 1H), 3.85-3.97 (m, 2H), 3.71-3.85 (m, 1H), 2.75 (br. s., 1H), 2.36-2.44 (m, 2H), 2.12-2.36 (m, 3H), 1.85 (br. s., 2H), 1.50 (d, J=9.65 Hz, 2H), 1.31 (d, J=5.70 Hz, 2H), 1.06-1.17 (m, 2H).

Example 3

Synthesis of (S)-7-chloro-N-(1-(3-(4-chloro-3-fluorophenoxy)-2-hydroxypropyl)piperidin-4-yl)-1-cyclopropyl-6-fluoro-4-oxo-1,4-dihydroquinoline-3-carboxamide

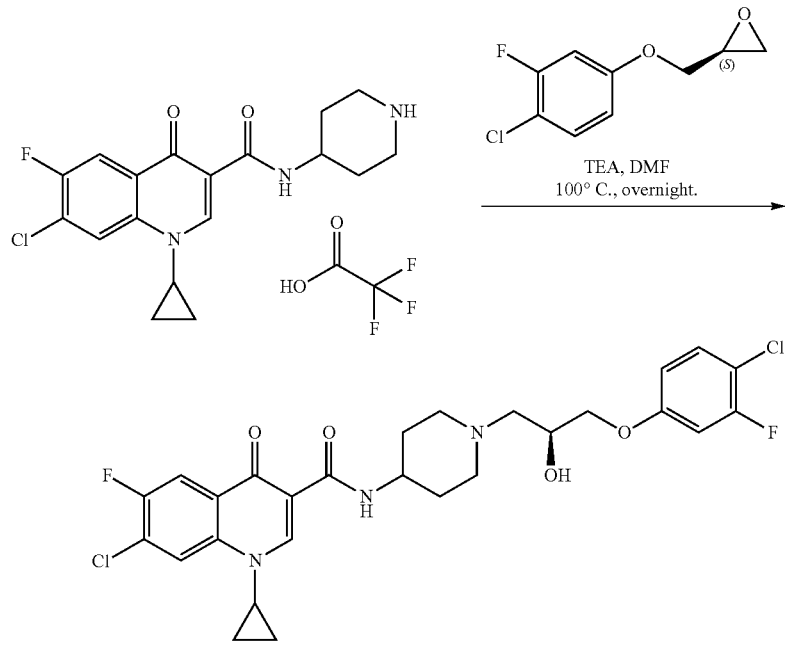

To a stirred solution of 7-chloro-1-cyclopropyl-6-fluoro-4-oxo-N-(piperidin-4-yl)-1,4-dihydroquinoline-3-carboxamide 2,2,2-trifluoroacetate (0.200 g, 0.418 mmol, 1.0 equiv) in DMF (2 mL) was added TEA (0.127 g, 1.255 mmol) followed by the addition of (S)-2-((4-chloro-3-fluorophenoxy)methyl)oxirane (0.102 g, 0.502 mmol, 1.2 equiv). The resulting reaction mixture was heated at 100° C. for overnight. Product formation was monitored by LCMS and TLC. After completion of reaction, the reaction mixture was diluted with water (50 mL) and extracted with EtOAc (50 mL×2). The combined organic layer was washed with water (30 mL×4), dried over anhydrous sodium sulfate and concentrated under reduced pressure. The crude product which was purified flash chromatography (0-5% MeOH in DCM as an eluent) to obtain (S)-7-chloro-N-(1-(3-(4-chloro-3-fluorophenoxy)-2-hydroxypropyl)piperidin-4-yl)-1-cyclopropyl-6-fluoro-4-oxo-1,4-dihydroquinoline-3-carboxamide (Compound 3-0.080 g, 33% Yield) as an off-white solid. LCMS 566.4 [M+H]$^+$; $^1$H NMR (400 MHz, DMSO-$d_6$) δ 9.81 (d, J=7.89 Hz, 1H), 8.69 (s, 1H), 8.39 (d, J=6.58 Hz, 1H), 8.15 (d, J=9.21 Hz, 1H), 7.46 (t, J=8.77 Hz, 1H), 7.08 (dd, J=11.62, 2.85 Hz, 1H), 6.79-6.92 (m, 1H), 4.89 (br. s., 1H), 4.02 (d, J=7.02 Hz, 1H), 3.85-3.97 (m, 2H), 3.71-3.85 (m, 1H), 2.75 (br. s., 1H), 2.36-2.44 (m, 2H), 2.12-2.36 (m, 3H), 1.85 (br. s., 2H), 1.50 (d, J=9.65 Hz, 2H), 1.31 (d, J=5.70 Hz, 2H), 1.06-1.17 (m, 2H).

Example 4

Synthesis of (R)-7-chloro-N-(4-(3-(4-chloro-3-fluorophenoxy)-2-hydroxypropyl)piperazin-1-yl)-1-cyclopropyl-6-fluoro-4-oxo-1,4-dihydroquinoline-3-carboxamide

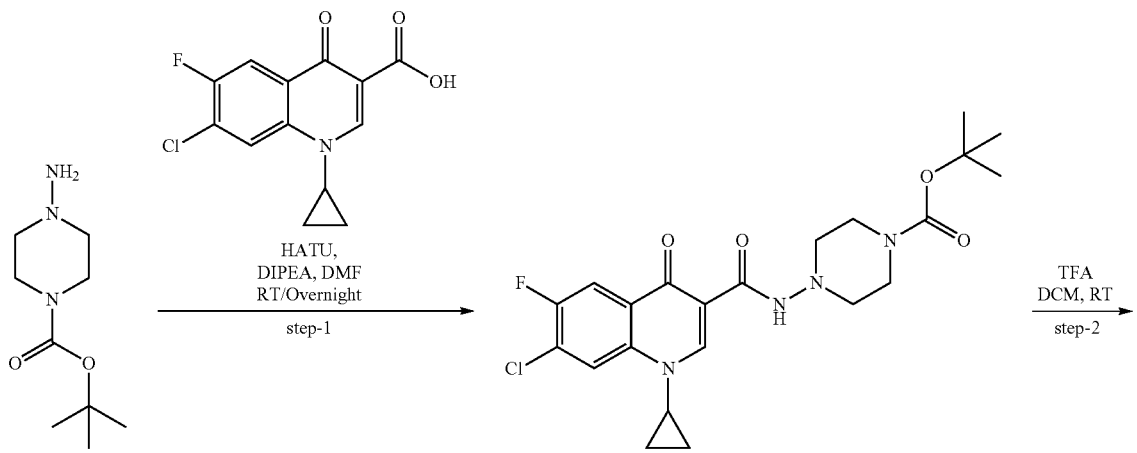

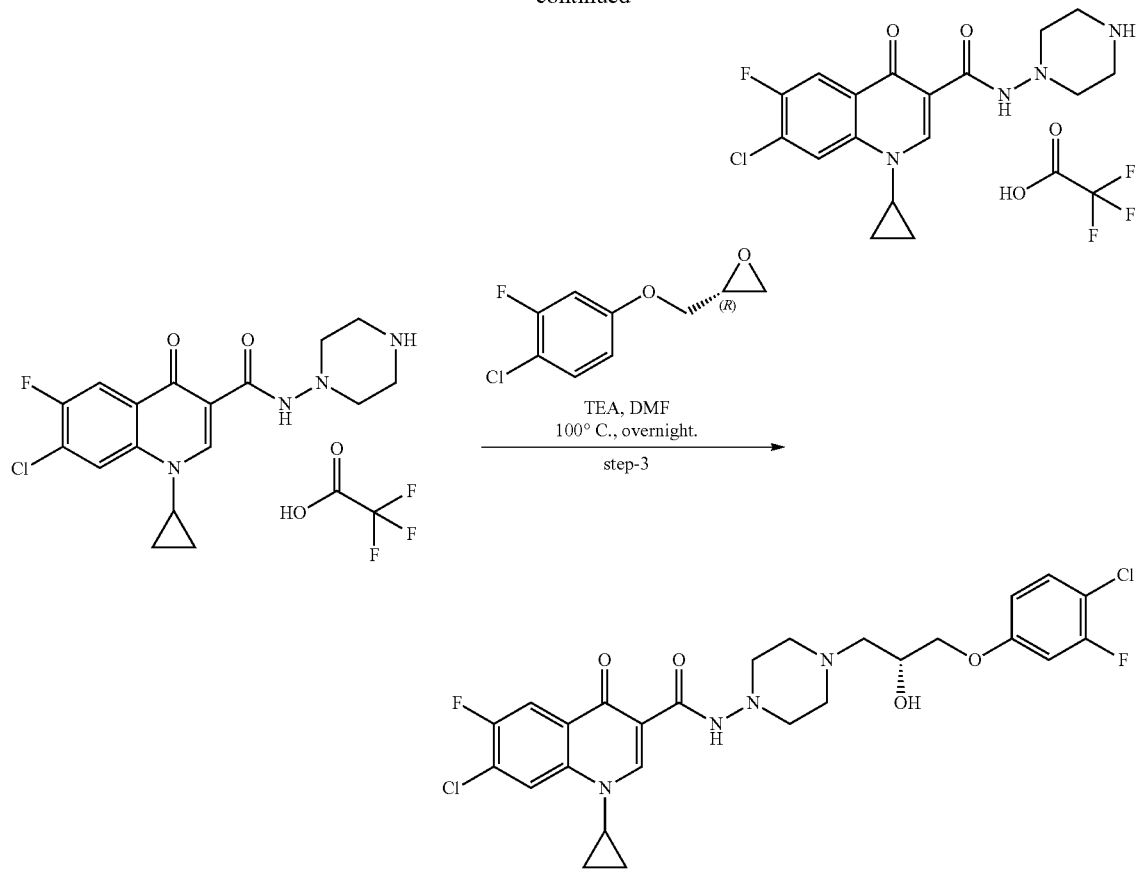

Step 1—Synthesis of tert-butyl 4-(7-chloro-1-cyclopropyl-6-fluoro-4-oxo-1,4-dihydroquinoline-3-carboxamido)piperazine-1-carboxylate To a stirred solution of 7-chloro-1-cyclopropyl-6-fluoro-4-oxo-1,4-dihydroquinoline-3-carboxylic acid (0.420 g, 1.492 mmol, 1.0 equiv) in DMF (10 mL) was added HATU (1.20 g, 2.985 mmol, 2.0 equiv) at RT and stirred for 10 minutes. Then tert-butyl 4-aminopiperazine-1-carboxylate (0.300 g, 1.492 mmol, 1.0 equiv) was added followed by the addition of DIPEA (0.8 mL, 4.472 mmol, 3.0 equiv). The resulting reaction mixture was allowed to stir at RT for overnight. Product formation was confirmed by LCMS. The reaction mixture was diluted with water (50 mL) and extracted with EtOAc (100 mL×2). The combined organic layer was washed with water (50 mL×5), dried over anhydrous sodium sulfate and concentrated under reduced pressure. The crude product which was enriched by flash chromatography (0-5% MeOH in DCM as an eluent) to obtain tert-butyl 4-(7-chloro-1-cyclopropyl-6-fluoro-4-oxo-1,4-dihydroquinoline-3-carboxamido)piperazine-1-carboxylate (0.150 g, 22% Yield) as an off-white solid. LCMS 465.2 [M+H]$^+$.

Step 2—Synthesis of 7-chloro-1-cyclopropyl-6-fluoro-4-oxo-N-(piperazin-1-yl)-1,4-dihydroquinoline-3-carboxamide 2,2,2-trifluoroacetate To a stirred solution of tert-butyl 4-(7-chloro-1-cyclopropyl-6-fluoro-4-oxo-1,4-dihydroquinoline-3-carboxamido)piperazine-1-carboxylate (0.150 g, 0.323 mmol, 1.0 equiv) in DCM (5 mL), was added TFA (0.2 mL) and the resultant reaction mixture was stirred at RT for overnight under nitrogen atmosphere. Product formation was confirmed by $^1$HNMR. After completion of reaction, the reaction mixture was concentrated under reduced pressure to obtain crude product which was crystallized in diethyl ether to obtain 7-chloro-1-cyclopropyl-6-fluoro-4-oxo-N-(piperazin-1-yl)-1,4-dihydroquinoline-3-carboxamide 2,2,2-trifluoroacetate (0.150 g, 97% Yield) as an off-white solid. LCMS 365.2 [M+H]$^+$; $^1$H NMR (400 MHz, DMSO-d$_6$) δ 10.83 (s, 1H), 8.67 (s, 3H), 8.41 (d, J=6.14 Hz, 1H), 8.13 (d, J=9.21 Hz, 1H), 3.73-3.82 (m, 1H), 3.23 (br. s., 4H), 3.16 (d, J=4.39 Hz, 4H), 1.32 (d, J=5.70 Hz, 2H), 1.12 (br. s., 2H).

Step 3—Synthesis of (R)-7-chloro-N-(4-(3-(4-chloro-3-fluorophenoxy)-2-hydroxypropyl)piperazin-1-yl)-1-cyclopropyl-6-fluoro-4-oxo-1,4-dihydroquinoline-3-carboxamide To a stirred solution of 7-chloro-1-cyclopropyl-6-fluoro-4-oxo-N-(piperazin-1-yl)-1,4-dihydroquinoline-3-carboxamide 2,2,2-trifluoroacetate (0.150 g, 0.313 mmol, 1.0 equiv) in DMF (2 mL) was added TEA (0.095 g, 0.939 mmol) followed by the addition of (R)-2-((4-chloro-3-fluorophenoxy)methyl)oxirane (0.077 g, 0.375 mmol, 1.0 equiv). The resulting reaction mixture was heated at 100° C. for overnight. Product formation was monitored by LCMS and TLC. After completion of reaction, the reaction mixture was diluted with water (50 mL) and extracted with EtOAc (50 mL×2). The combined organic layer was washed with water (30 mL×4), dried over anhydrous sodium sulfate and concentrated under reduced pressure. The crude product which was purified flash chromatography (0-5% MeOH in DCM as an eluent) to obtain (R)-7-chloro-N-(4-(3-(4-chloro-3-fluorophenoxy)-2-hydroxypropyl)piperazin-1-yl)-1-cyclopropyl-6-fluoro-4-oxo-1,4-dihydroquinoline-3-carboxamide (Compound 5-0.070 g, 40% Yield) as a white solid. LCMS 567.4 [M+H]+; 1H NMR (400 MHz, DMSO-d6) δ 10.59 (s, 1H), 8.67 (s, 1H), 8.39 (d, J=6.14 Hz, 1H), 8.14 (d, J=9.21 Hz, 1H), 7.46 (t, J=8.77 Hz, 1H), 7.08 (dd, J=11.40, 2.63 Hz, 1H), 6.85 (dd, J=8.77, 1.75 Hz, 1H), 4.94 (d, J=4.82 Hz, 1H), 4.02 (d, J=6.58 Hz, 1H), 3.87-3.99 (m, 2H), 3.74-3.81 (m, 1H), 2.86 (br. s., 4H), 2.67 (br. s., 1H), 2.55 (d, J=12.72 Hz, 4H), 1.27-1.36 (m, 2H), 1.23 (s, 1H), 1.12 (br. s., 2H).

Example 5

Synthesis of (S)-7-chloro-N-(4-(3-(4-chloro-3-fluorophenoxy)-2-hydroxypropyl)piperazin-1-yl)-1-cyclopropyl-6-fluoro-4-oxo-1,4-dihydroquinoline-3-carboxamide

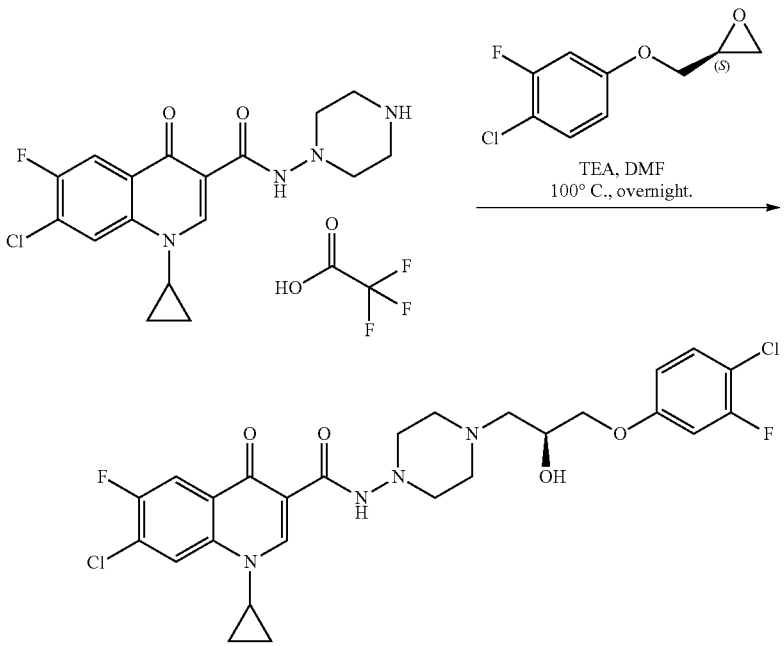

To a stirred solution of 7-chloro-1-cyclopropyl-6-fluoro-4-oxo-N-(piperazin-1-yl)-1,4-dihydroquinoline-3-carboxamide 2,2,2-trifluoroacetate (0.400 g, 0.835 mmol, 1.0 equiv) in DMF (10 mL) was added TEA (0.4 mL, 2.505 mmol) followed by the addition of (S)-2-((4-chloro-3-fluorophenoxy)methyl)oxirane (0.203 g, 1.000 mmol, 1.0 equiv). The resulting reaction mixture was heated at 100° C. for overnight. Product formation was monitored by LCMS and TLC. After completion of reaction, the reaction mixture was diluted with water (50 mL) and extracted with EtOAc (50 mL×2). The combined organic layer was washed with water (30 mL×4), dried over anhydrous sodium sulfate and concentrated under reduced pressure. The crude product which was enriched by flash chromatography (0-5% MeOH in DCM as an eluent) followed by the reversed phase HPLC purification to obtain (S)-7-chloro-N-(4-(3-(4-chloro-3-fluorophenoxy)-2-hydroxypropyl)piperazin-1-yl)-1-cyclopropyl-6-fluoro-4-oxo-1,4-dihydroquinoline-3-carboxamide (Compound 6-0.150 g, 31% Yield) as a white solid. LCMS 567.4 [M+H]+; 1H NMR (400 MHz, DMSO-d6) δ 10.59 (s, 1H), 8.67 (s, 1H), 8.39 (d, J=6.14 Hz, 1H), 8.13 (d, J=9.21 Hz, 1H), 7.46 (t, J=8.99 Hz, 1H), 7.08 (dd, J=11.62, 2.85 Hz, 1H), 6.85 (dd, J=8.99, 1.97 Hz, 1H), 4.94 (br. s., 1H), 4.02 (d, J=6.58 Hz, 1H), 3.86-3.97 (m, 2H), 3.73-3.84 (m, 1H), 2.86 (br. s., H), 2.57 (br. s., 4H), 1.31 (d, J=6.14 Hz, 2H), 1.12 (br. s., 2H).

Example 6

Synthesis of 7-chloro-N-(1-(3-(4-chloro-3-fluoro-phenoxy)propyl)piperidin-4-yl)-1-cyclopropyl-6-fluoro-4-oxo-1,4-dihydroquinoline-3-carboxamide

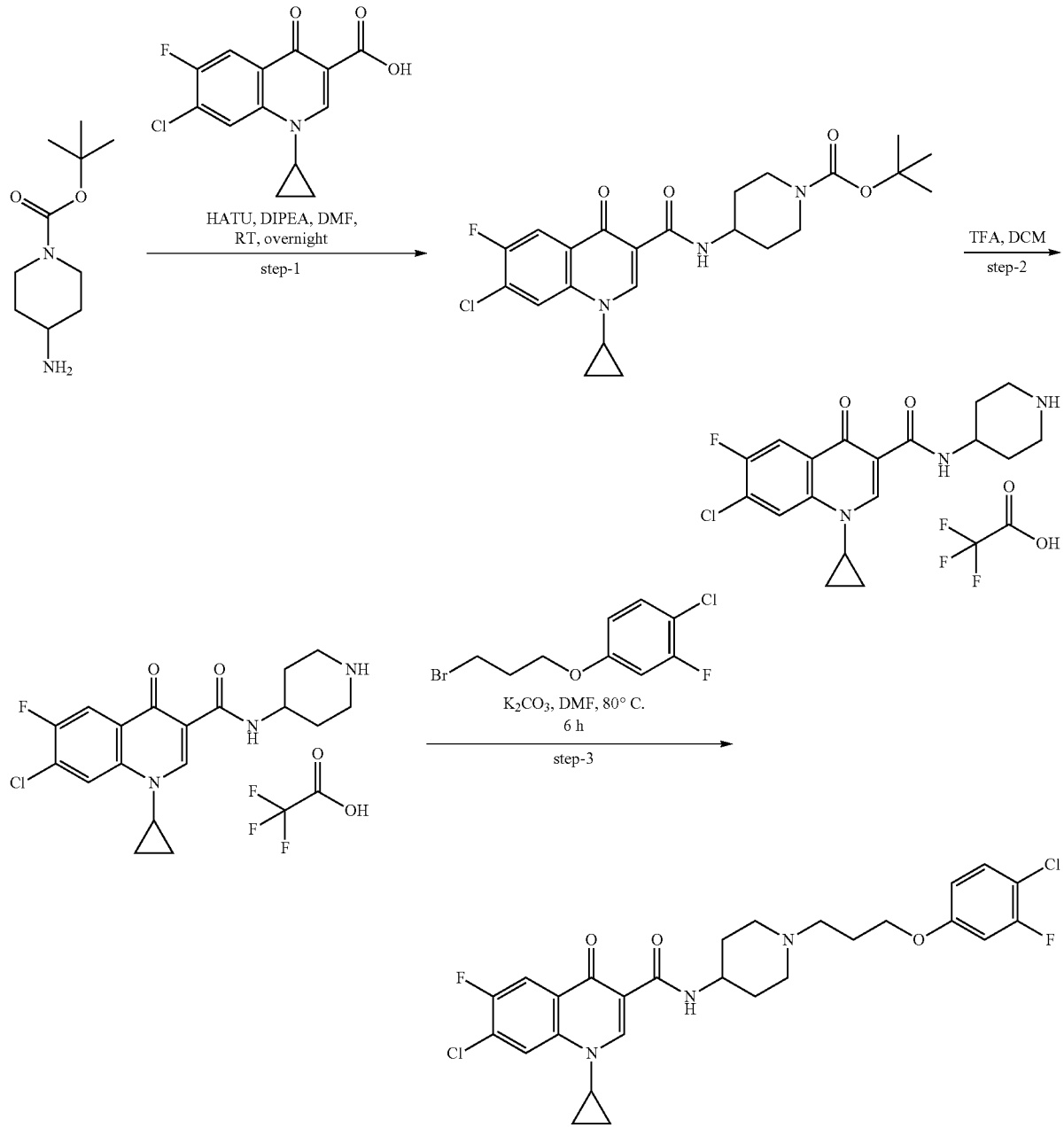

Step 1—Synthesis of tert-butyl 4-(7-chloro-1-cyclopropyl-6-fluoro-4-oxo-1,4-dihydroquinoline-3-carboxamido)piperidine-1-carboxylate To a solution of 7-chloro-1-cyclopropyl-6-fluoro-4-oxo-1,4-dihydroquinoline-3-carboxylic acid (0.300 g, 1.064 mmol, 1.0 equiv) in DMF (5 mL) was added tert-butyl 4-aminopiperidine-1-carboxylate (0.234 g, 1.17 mmol, 1.1 equiv) and HATU (0.808 g, 2.12 mmol, 2.0 equiv) at RT. The reaction mixture was stirred for 10 minutes and then DIPEA (0.5 mL, 3.19 mmol, 3.0 equiv) was added. The resultant reaction mixture was allowed to stir at RT for overnight. Progress of the reaction was monitored by LCMS. The reaction mixture was diluted with water (30 mL) and extracted with ethyl acetate (100 mL×2). Combined organic layer was washed with water (50 mL×4), dried over anhydrous $Na_2SO_4$ and concentrated under reduced pressure to obtain the crude compound which was purified by flash chromatography (0-5% MeOH in DCM as aneluent) to obtain tert-butyl 4-(7-chloro-1-cyclopropyl-6-fluoro-4-oxo-1,4-dihydroquinoline-3-carboxamido)piperidine-1-carboxylate (0.360 g, 73% Yield) as an off-white solid. LCMS 464.1 $[M+H]^+$ Step 2—Synthesis of 7-chloro-1-cyclopropyl-6-fluoro-4-oxo-N-(piperidin-4-yl)-1,4-dihydroquinoline-3-carboxamide 2,2,2-trifluoroacetate To a stirred solution tert-butyl 4-(7-chloro-1-cyclopropyl-6-fluoro-4-oxo-1,4-dihydroquinoline-3-carboxamido)piperidine-1-carboxylate (0.350 g, 0.75 mmol, 1.0 equiv) in DCM (15 mL) was added trifluoroacetic acid (1 mL) at RT. The reaction mixture was allowed to stir at RT overnight. DCM and excess of trifluoroacetic acid was removed under reduced pressure to obtain 7-chloro-1-cyclopropyl-6-fluoro-4-oxo-N-(piperidin-4-yl)-1,4-dihydroquinoline-3-carboxamide 2,2,2-trifluoroacetate (0.300 g, Quant. Yield) as an off white solid. LCMS 364.2 [M+H]$^+$; $^1$H NMR (400 MHz, DMSO-d$_6$) δ 9.86 (d, J=7.45 Hz, 1H) 8.69 (s, 1H) 8.63 (br. s., 1H) 8.41 (d, J=6.14 Hz, 2H) 8.12 (d, J=9.21 Hz, 1H) 4.00-4.17 (m, 1H) 3.78 (dt, J=6.91, 3.34 Hz, 1H) 3.29 (d, J=12.72 Hz, 2H) 3.07 (q, J=11.11 Hz, 2H) 2.07 (d, J=10.96 Hz, 2H) 1.53-1.74 (m, 2H) 1.20-1.41 (m, 2H) 1.01-1.19 (m, 2H).

Step 3—Synthesis of 7-chloro-N-(1-(3-(4-chloro-3-fluorophenoxy)propyl)piperidin-4-yl)-1-cyclopropyl-6-fluoro-4-oxo-1,4-dihydroquinoline-3-carboxamide To solution of 7-chloro-1-cyclopropyl-6-fluoro-4-oxo-N-(piperidin-4-yl)-1,4-dihydroquinoline-3-carboxamide 2,2,2-trifluoroacetate (0.100 g, 0.275 mmols, 1.0 equiv) in DMF (3 mL) was added K$_2$CO$_3$ (0.072 g, 0.50 mmols, 2.0 equiv) followed by the addition of 4-(3-bromopropoxy)-1-chloro-2-fluorobenzene (0.081 g, 0.303 mmols, 1.1 equiv). The resulting reaction mixture was heated at 120° C. for 6 h. Product formation was confirmed by NMR spectroscopy. After completion of reaction the reaction mixture was diluted with water (50 mL) and extracted with ethyl acetate (100 mL×2). Combined organic layer was washed with water (20 mL×4), dried over anhydrous Na$_2$SO$_4$ and concentrated under reduced pressure. The crude product was purified by reversed phase HPLC to obtain 7-chloro-N-(1-(3-(4-chloro-3-fluorophenoxy)propyl)piperidin-4-yl)-1-cyclopropyl-6-fluoro-4-oxo-1,4-dihydroquinoline-3-carboxamide (Compound 22-0.060 g, 40% Yield) as an off-white solid. LCMS 550.5 [M+H]$^+$; $^1$H NMR (400 MHz, DMSO-d$_6$) δ 9.82 (d, J=7.45 Hz, 1H) 8.69 (s, 1H) 8.39 (d, J=6.14 Hz, 1H) 8.08-8.18 (m, 1H) 7.46 (t, J=8.77 Hz, 1H) 7.07 (dd, J=11.62, 2.41 Hz, 1H) 6.83 (d, J=7.02 Hz, 1H) 4.04 (t, J=6.14 Hz, 2H) 3.85 (br. s., 1H) 3.77 (br. s., 1H) 2.76 (br. s., 2H) 2.33 (br. s., 1H) 2.25 (br. s., 3H) 1.89 (br. s., 4H) 1.52 (d, J=10.52 Hz, 2H) 1.31 (d, J=5.70 Hz, 2H) 1.11 (br. s., 2H).

Example 7

Synthesis of trans-7-chloro-N-(4-(2-(4-chloro-3-fluorophenoxy)acetamido)cyclohexyl)-1-cyclopropyl-6-fluoro-4-oxo-1,4-dihydroquinoline-3-carboxamide

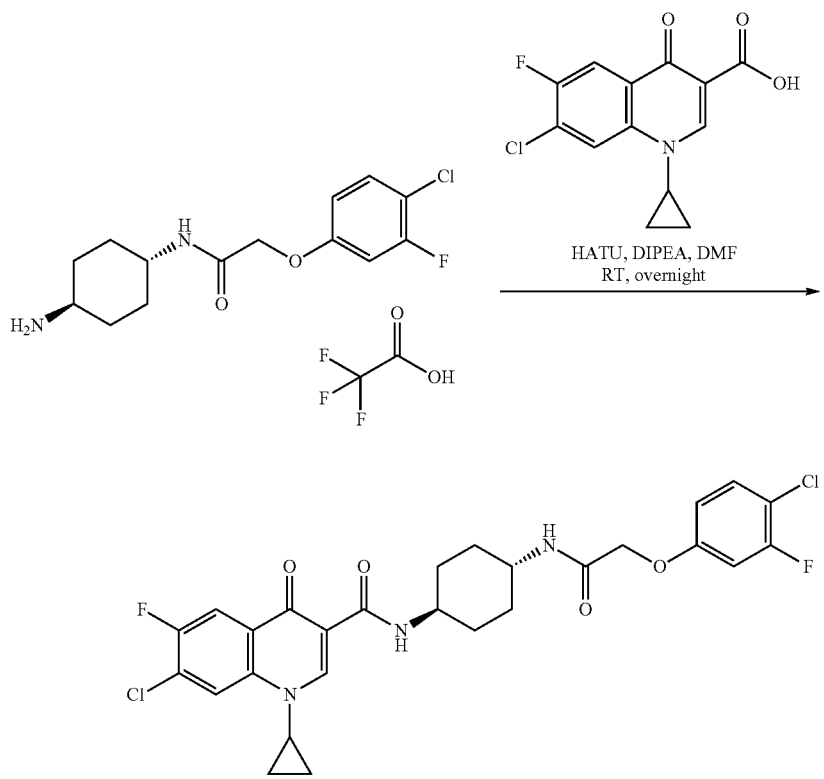

To a solution of trans-N-(4-aminocyclohexyl)-2-(4-chloro-3-fluorophenoxy)acetamide 2,2,2-trifluoroacetate (0.100 g, 0.252 mmol, 1.0 equiv) in DMF (3 mL) was added 7-chloro-1-cyclopropyl-6-fluoro-4-oxo-1,4-dihydroquinoline-3-carboxylic acid (0.078 g, 0.278 mmol, 1.1 equiv) and HATU (0.192 g, 0.505 mmol, 2.0 equiv) at RT. The reaction mixture was stirred for 10 minutes and then DIPEA (0.5 mL, 3.19 mmol, 3.0 equiv) was added. The resultant reaction mixture was allowed to stir at RT for overnight. Progress of the reaction was monitored by LCMS. The reaction mixture was diluted with water (30 mL) and extracted with ethyl acetate (100 mL×2). Combined organic layer was washed with water (50 mL×4), dried over anhydrous $Na_2SO_4$ and concentrated under reduced pressure to obtain the crude product which was purified by flash chromatography (0-5% MeOH in DCM as an eluent) to obtain trans-7-chloro-N-(4-(2-(4-chloro-3-fluorophenoxy)acetamido)cyclohexyl)-1-cyclopropyl-6-fluoro-4-oxo-1,4-dihydroquinoline-3-carboxamide (Compound 32-0.080 g, 56% Yield) as a white solid. LCMS 564.4 [M+H]$^+$; $^1$H NMR (400 MHz, DMSO-d$_6$) δ 9.69 (d, J=7.45 Hz, 1H) 8.68 (s, 1H) 8.38 (d, J=6.14 Hz, 1H) 8.12 (d, J=9.21 Hz, 1H) 7.50 (t, J=8.99 Hz, 1H) 7.07 (d, J=10.09 Hz, 1H) 6.85 (d, J=9.21 Hz, 1H) 4.51 (s, 2H) 3.77 (br. s., 2H) 3.68 (br. s., 1H) 1.96 (br. s., 2H) 1.80 (br. s., 2H) 1.34-1.50 (m, 3H) 1.31 (d, J=5.70 Hz, 3H) 1.11 (br. s., 2H).

Example 8

Synthesis of trans-7-chloro-N-(4-(2-(4-chlorophenoxy)acetamido)cyclohexyl)-1-cyclopropyl-6-fluoro-4-oxo-1,4-dihydroquinoline-3-carboxamide cyclopropyl-6-fluoro-4-oxo-1,4-dihydroquinoline-3-carboxylic acid (0.082 g, 0.290 mmol, 1.1 equiv) and HATU (0.201 g, 0.528 mmol, 2.0 equiv) at RT. The reaction mixture was stirred for 10 minutes and then DIPEA (0.13 mL, 0.800 mmol, 3.0 equiv) was added. The resultant reaction mixture was allowed to stir at RT for overnight. Progress of the reaction was monitored by LCMS. The reaction mixture was diluted with water (30 mL) and extracted with ethyl acetate (100 mL×2). Combined organic layer was washed with water (50 mL×4), dried over anhydrous $Na_2SO_4$ and concentrated under reduced pressure to obtain the crude product which was purified by flash chromatography (0-5% MeOH in DCM as an eluent) to obtain trans-7-chloro-N-(4-(2-(4-chlorophenoxy)acetamido)cyclohexyl)-1-cyclopropyl-6-fluoro-4-oxo-1,4-dihydroquinoline-3-carboxamide (Compound 112-0.045 g, 31% Yield) as a white solid. LCMS 546.4 [M+H]$^+$; $^1$H NMR (400 MHz, DMSO-d$_6$) δ 9.69 (d, J=7.45 Hz, 1H) 8.69 (s, 1H) 8.38 (d, J=6.14 Hz, 1H) 8.13 (d, J=8.77 Hz, 1H) 7.96 (d, J=7.89 Hz, 1H) 7.35 (m, J=8.33 Hz, 2H) 6.98 (m, J=8.77 Hz, 2H) 4.46 (s, 2H) 3.77 (br. s., 3H) 3.38 (d, J=6.58 Hz, 1H) 1.95 (d, J=10.09 Hz, 2H) 1.79 (br. s., 2H) 1.25-1.47 (m, 4H) 1.00-1.19 (m, 2H).

BIOLOGICAL EXAMPLES

Example B1—ATF4 Expression Inhibition Assay

The ATF4 reporter was prepared by fusing the human full length 5'UTR of ATF4 (NCBI Accession No. BC022088.2) upstream of the firefly luciferase coding sequence lacking the initiator methionine. The fused sequence was cloned into pLenti-EF1a-C-Myc-DDK-IRES-Puro cloning vector (Ori-

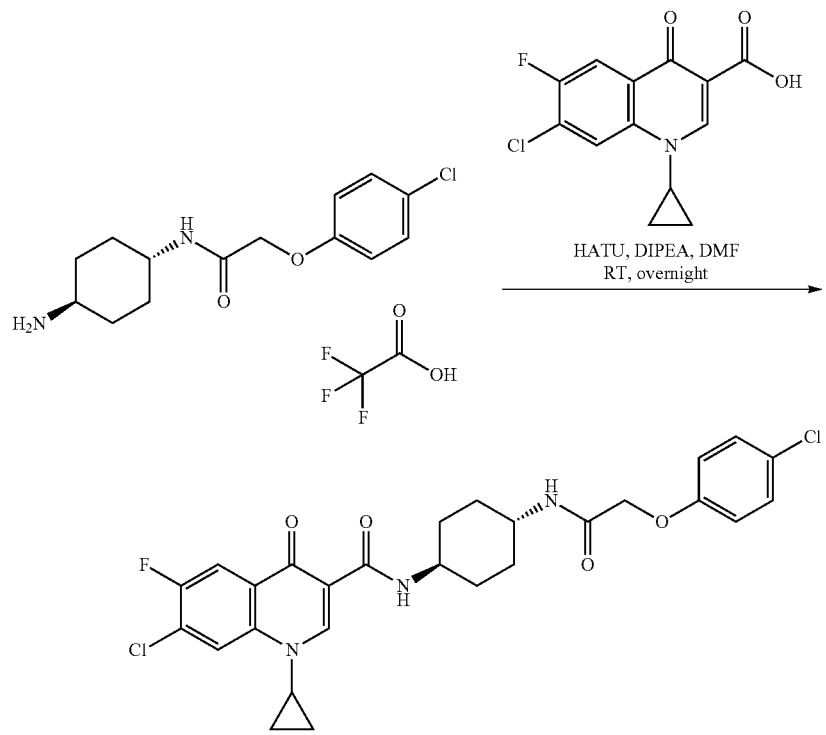

gen #PS100085) using standard methods. Virus production was carried out by using Lenti-X™ Packaging Single Shots Protocol (Clonetech #631276). Viral particles were used to transduce HEK293T cells (ATCC #CRL-3216, ATCC Manassas, Va.), which were subsequently selected with puromycin to generate stable cell line. Cells were maintained at 37° C. and 5% $CO_2$ in DMEM-F12 (Hyclone #SH30023.02) supplemented with 10% heat-inactivated fetal bovine serum (Gibco #16000-044), 2 mM L-glutamine (Gibco #25030-081), 100 U/ml penicillin, and 100 μg/ml streptomycin (Gibco #15140-122).

HEK293T cells carrying the ATF4 luciferase reporter were plated on 96-well plates (Nunc) at 10,000 cells per well. Cells were treated two days after seeding with 100 nM thapsigargin (Tg) (Sigma-Aldrich #T9033) in the presence of different concentrations of selected compounds ranging from 1 nM to 10 M. Cells without treatment or cells treated with Tg alone were used as controls. Assay plates containing cells were incubated for 3 hours at 37° C.

Luciferase reactions were performed using Luciferase Assay System (Promega #E1501) as specified by the manufacturer. Luminescence was read with an integration time of 1 s and a gain of 110 using a Cytation-5 multi-mode microplate reader (BioTek). Relative luminescence units were normalized to Tg treatment (0% inhibition) and untreated cells (100% inhibition) and the percentage of ATF4 inhibition was calculated.

The half-maximal inhibitory concentration ($IC_{50}$) for the increasing of ATF4 protein levels is shown in Table 2. Under ISR stressed conditions (resulting from treatment with Tg), ATF4 expression is generally upregulated. Accordingly, inhibition of ATF4 expression as a result of the test compound indicates suppression of the ISR pathway.

TABLE 2

| Compound No. | ATF4 inhibition $IC_{50}$ (nM) |
| --- | --- |
| 1 | >10,000 |
| 2 | >10,000 |
| 3 | >10,000 |
| 5 | >10,000 |
| 6 | >10,000 |

Example B2—Protein Synthesis Assay

Chinese hamster ovary (CHO) cells were maintained at 37° C. and 5% $CO_2$ in Dulbecco's Modified Eagle's Media (DMEM) supplemented with 10% fetal bovine serum, 2 mM L-glutamine, 100 U/ml penicillin, and 100 μg/ml streptomycin. After reaching 80% of confluence, cells were detached and seeded on 6 well plates in complete media, allowed to recover overnight and treated for 2 hours with 1 μM of the test compound (to assess protein synthesis levels in unstressed condition), or for 2 hours with 300 nM Tg in the presence of 1 μM of the test compound (to assess the recovery of protein synthesis in a stressed condition). Cells with Tg alone were used as controls.

After the 2 hours treatments, media were replaced by adding 10 μg/ml puromycin (Sigma Aldrich #P8833) in complete media for 30 min. Media were removed and cells were lysed with SDS-PAGE lysis buffer. Lysates were transferred to 1.5 ml tubes and sonicated for 3 min and total protein amount were quantified using BCA Protein Assay Kit (Pierce). Equal amount of protein (30 μg) was loaded on SDS-PAGE gels. Proteins were transferred onto 0.2 m PVDF membranes (BioRad) and probed with primary antibodies diluted in Tris-buffered saline supplemented with 0.1% Tween 20 (Merck #S6996184 505) and 3% bovine serum albumin (Rockland #BSA-50).

Puromycin (12D10) (Merck #MABE343) and 3-actin (Sigma Aldrich #A5441) antibodies were used as primary antibody. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Percent increase of protein synthesis in unstressed cells (without Tg treatment) in the presence of media alone or certain test compounds is shown in Table 3. The percentage levels were normalized to the media alone condition, which correspond to 100% protein synthesis. Certain compounds stimulated protein synthesis above baseline, indicating that these test compounds result in increased protein synthesis in unstressed cells.

Percent recovery of protein synthesis in stressed cells (with Tg treatment) due to the test compounds at 1 μM is also shown in Table 3. The levels were normalized to the media alone and Tg alone conditions, which correspond to 100% and 0% respectively.

TABLE 3

| Compound No. | % Protein synthesis in unstressed cells (1 μM test compound) | % Recovery of protein synthesis (1 μM test compound) |
| --- | --- | --- |
| 1 | 336.9 | 351.1 |
| 2 | 336.3 | 306.9 |
| 3 | 397.3 | 324 |
| 5 | 173.2 | 116.9 |
| 6 | 244.5 | 140.4 |

Data summarized in Tables 2 and 3 show that some compounds have differential activity in ATF4 inhibition and protein synthesis under ISR-inducing conditions. That is, compounds effectively restore protein synthesis but do not inhibit ATF4 expression under ISR-inducing conditions. This differential modulation of activities represents a unique characteristic that can be exploited when selecting specific compounds for a desired use.

Example B3—Fasting-Induced Muscle Atrophy

Wild type eight-weeks-old male Balb/c mice obtained from the vivarium Fundación Ciencia & Vida Chile (Santiago, Chile) are used. Mice were housed in independent plastic cages in a room maintained at 25° C. with a 12-h:12-h light:dark cycle.

Twenty-four hours before and during the 2 days of fasted procedures, animals received oral administration via feeding tubes (15 gauge) of vehicle (50% Polyethylene glycol 400 (Sigma-Aldrich P3265) in distilled water or 10 mg/kg of test compound formulated in vehicle solution. After 2 days of fasting the animals were sacrificed and muscles were removed from both hindlimbs. Mice with feed and water ad libitum were used as control. During muscle atrophy, protein synthesis was reduced and protein degradation was increased as known in the art. For in vivo measurements of protein synthesis, puromycin (Sigma-Aldrich, P8833) was prepared at 0.04 μmol/g body weight in a volume of 200 μL of PBS, and subsequently administered into the animals via IP injection, 30 min prior to muscle collection.

Upon collection, muscles were immediately frozen in liquid nitrogen and then stored at −80° C. The frozen muscles were then homogenized with a T 10 basic ULTRA- TURRAX (IKa) in ice-cold buffer lysis (Cell Signaling 9803) and protease and phosphatase inhibitors (Roche). Lysates were sonicated for 3 min and centrifuged at 13,000 rpm for 20 minutes at 4° C. Protein concentration in supernatants was determined using BCA Protein Assay Kit (Pierce). Equal amount of proteins was loaded on SDS-PAGE gels. Proteins were transferred onto 0.2 µm PVDF membranes (BioRad) and probed with primary antibodies diluted in Tris-buffered saline supplemented with 0.1% Tween 20 and 3% bovine serum albumin.

Puromycin (12D10) (Merck Millipore, and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Percent of protein synthesis in tibialis anterior of each mouse from fed or fasted animals treated with vehicle or compound 3 is shown in FIG. 1. The levels were normalized to β-actin expression and percentage was calculated as the percent relative to protein synthesis levels from control mice (Fed) which correspond to 100%. Treatment of fasted mice with compound 3 resulted in an improvement in protein synthesis in muscles compared to vehicle-treated fasted mice suggesting a reduction in muscle atrophy.

Example B4—Protein Synthesis with a Cell-Free System

The expression of the green fluorescence protein (GFP) was evaluated using the 1-Step Human In vitro Protein Expression Kit based on HeLa cell lysates (ThermoFisher Scientific). HeLa lysate, accessory proteins, reaction mix and pCFE-GFP plasmid from the kit are thawed in ice. Reactions were prepared at room temperature in a 96-well optical plate by adding 12.5 µL of HeLa lysate, 2.5 µL accessory proteins, 5 µL reaction mix, 1 µg of pCFE-GFP plasmid and 1 µM of test compound in 5 µL or vehicle (distilled $H_2O$). A well with $dH2O$ instead of pCFE-GFP plasmid was used as basal autofluorescence of the reaction. All reactions were made in duplicate. Fluorescence intensity was measured by a multi-mode microplate reader (Synergy-4; Biotek) during 6-hour treatments and capturing fluorescence at 15-minute intervals with 485/20 and 528/20 excitation and emission filters.

Figure 2:
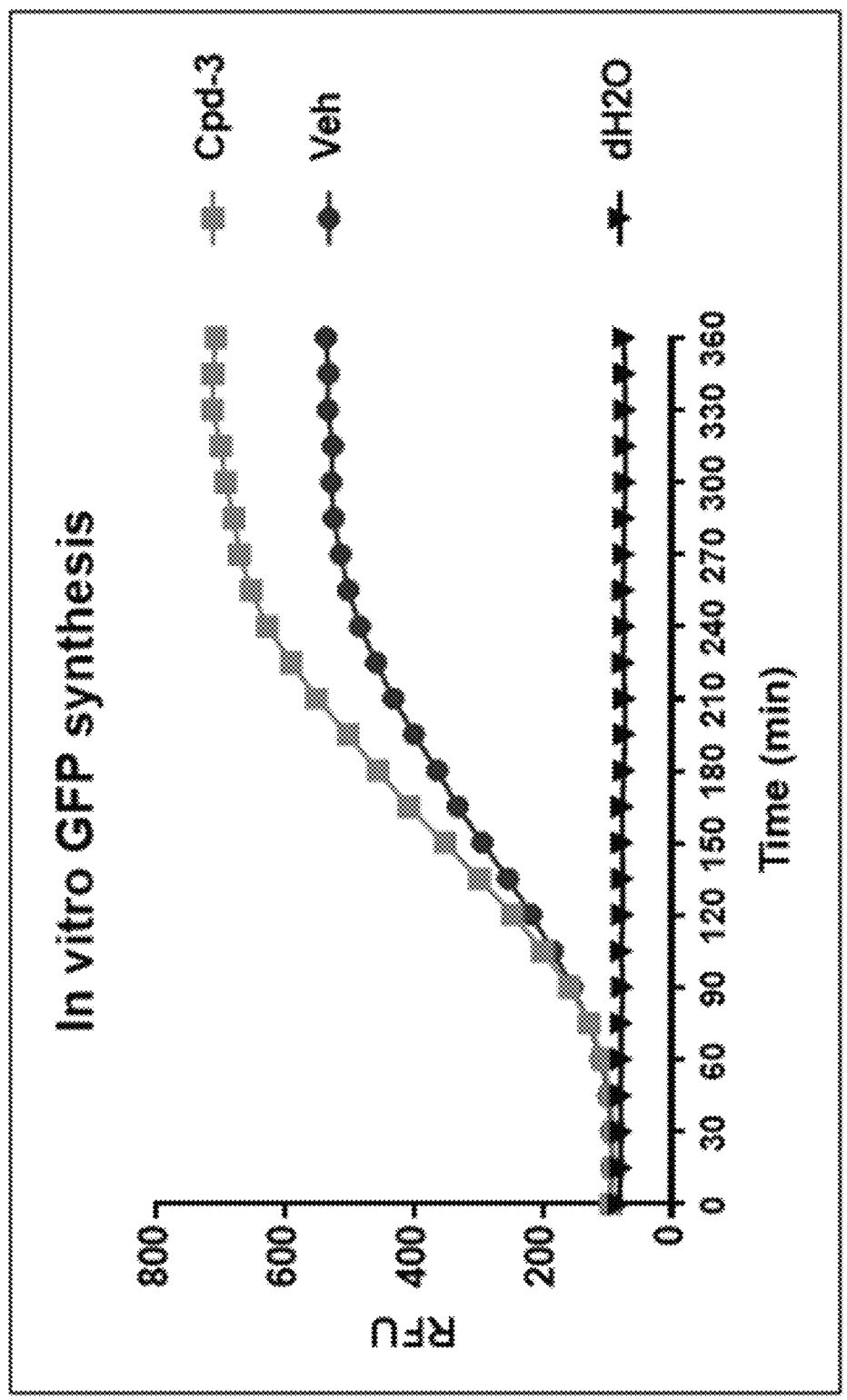
FIG. 2 shows relative fluorescence intensity (RFU) of GFP treated with either vehicle or compound 3 in a cell-free expression system.

Relative fluorescence intensity (RFU) of GFP treated with either vehicle or test compound is shown in FIG. 2. The addition of tested compound to the kit's reaction mix increased the expression of GFP and hence its fluorescence compared to the expression obtained using the kit's reagents alone.

Example B5—Secretion of Ig-Kappa by ARH Cells

ARH cells were maintained at 37° C. and 5% $CO_2$ and seeded at a density of 500,000 cell/well in RPMI supplemented with, 100 U/ml penicillin, and 100 µg/ml streptomycin in a 12-well culture plate. Cells were treated either with vehicle (0.1% DMSO) or 1 µM of test compounds for 24 hours. Then, culture media with cells were recovered in microtubes and centrifuged at 500 g for 5 minutes. Supernatants (SN) which contain secreted proteins were extracted and protease and phosphatase inhibitors (Roche) were added to each sample. SN were centrifuged at 2,000 g for 10 min to discard any cellular debris and 900 µL SN were transferred to empty microtubes with 400 µL methanol by mixing well. 200 µL of chloroform was added to the mix and then samples were centrifuged at 14,000 g for 2 minutes. Top aqueous layer was discarded by pipetting off and 400 µL methanol was added to each sample by mixing well. Samples were then centrifuged at 17,000 g for 8 minutes and methanol was discarded by pipetting off without disturbing the protein pellet. Samples were left dry at room temperature and pellets were resuspended with SDS-PAGE sample buffer. Secreted proteins were loaded on SDS-PAGE gels. Proteins were transferred onto 0.2 µm PVDF membranes (BioRad) and probed with anti Ig-kappa light chain (Abcam) primary antibody diluted in Tris-buffered saline supplemented with 0.1% Tween 20 and 3% bovine serum albumin. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 3:
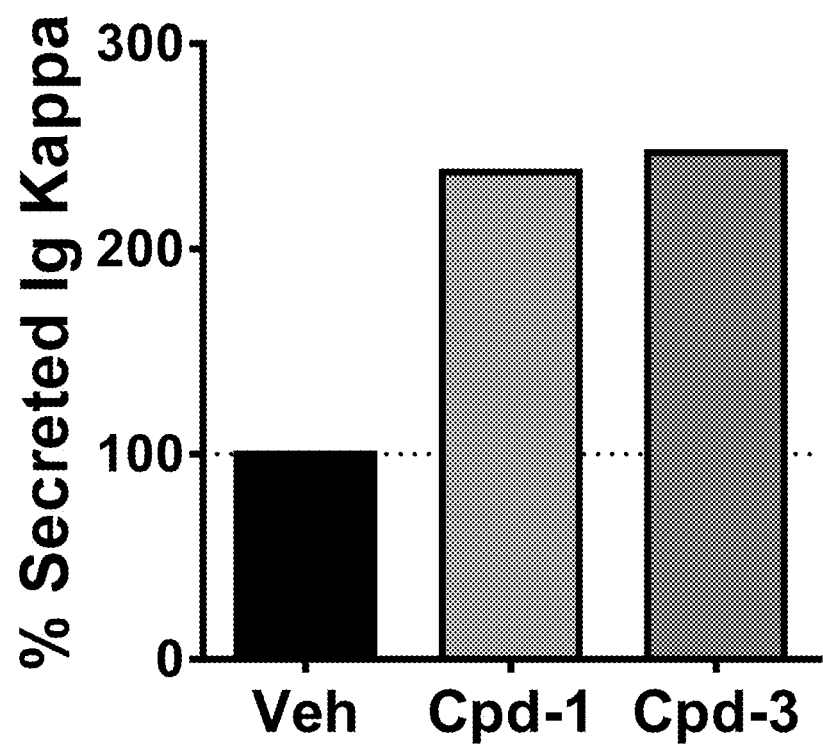
FIG. 3 shows percent of secreted Ig kappa light chain by ARH cells treated with vehicle or with compounds 1 or 3.

Percent of secreted Ig kappa light chain by ARH cells treated with vehicle or test compounds is shown in FIG. 3. Percentage was calculated as the percent relative to Ig kappa secretion levels from ARH cells treated with vehicle which correspond to 100%. Tested compounds increased the secretion of the immunoglobulin light chain kappa in the lymphoblastic ARH cell line.

Example B6—Secretion of EGF in Yeast

*Saccharomyces cerevisiae* stable expressing the recombinant human EGF protein (S.c-EGF) were obtained from ANGO Inc. S.c-EGF were cultured in 50 mL flask in SD-Leu-Glu medium (Sunrise Science Products) in agitation and at 30° C. At the final period of the exponential phase, 100 µL inocula were seeded in 48-well plates in 1 mL of complete medium with vehicle (0.1% DMSO) or 1 µM test compounds and incubated in continuous agitation (200 rpm) for 72° C. at 30° C. using a microplate spectrophotometer reader (Epoch, BioTek). After 72 hours treatments, culture media with cells were recovered in microtubes and centrifuged at 13,000 g for 5 minutes. Supernatants (SN) which contained secreted proteins were used to quantify the concentration of secreted human EGF by ELISA (ThermoFisher, Cat No. KHG0062) according to the manufacturer instructions. Final reaction was measured at 450 nm in the microplate Epoch (BioTek) and an internal calibration curve was used to calculate the amount of human EGF.

Figure 4:
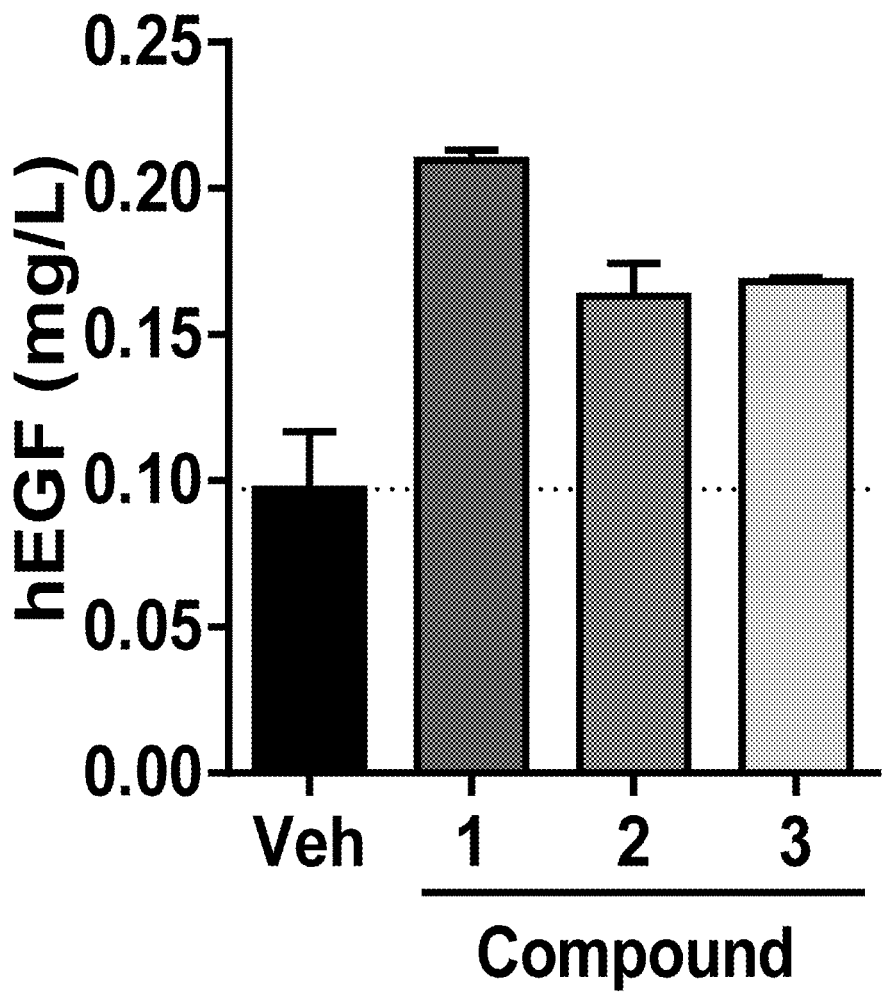
FIG. 4 shows the amount of secreted human EGF protein by *Saccharomyces cerevisiae* stable expressing the recombinant human EGF protein treated with either vehicle or with 1 µM of compounds 1, 2, or 3.

The amount of secreted human EGF protein by S.c-EGF treated with either vehicle or 1 µM test compounds is shown in FIG. 4. Tested compounds increased the secretion of a recombinant protein (hEGF) expressed in yeast.

Example B7—Expression of a Recombinant Intracellular Protein in CHO

CHO cells were maintained at 37° C. and 5% CO2 in DMEM supplemented with 10% fetal bovine serum (FBS), 2 mM L-glutamine, 100 U/ml penicillin, and 100 µg/ml streptomycin. After reaching 80% of confluence, cells were detached and seeded on 6-well plates in complete media, allowed to recover for 48 h. Cells were transfected with 1 µg DNA of the plasmid pIRES2-AcGFP1 (Clontech) using Lipofectamine LTX (Thermo Fisher Scientific) according to manufacturer instructions and test compounds were added to the medium at 1 or 5 µM concentration. 0.1% DMSO was used as vehicle control and a well without plasmidial DNA was used as a control of baseline expression (Empty). After 24 hours of treatments, media were removed and cells were lysed with SDS-PAGE lysis buffer. Lysates were transferred to 1.5 ml tubes and sonicated for 3 min and total protein amount were quantified using BCA Protein Assay Kit (Pierce). Equal amount of protein (30 μg) was loaded on SDS-PAGE gels. Proteins were transferred onto 0.2 μm PVDF membranes (BioRad) and probed with primary antibodies diluted in Tris-buffered saline supplemented with 0.1% Tween 20 (Merck #S6996184 505) and 3% bovine serum albumin (Rockland #BSA-50).

GFP (Cell Signaling #2956) and β-actin (Sigma Aldrich #A5441) antibodies were used as primary antibody. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 5A:
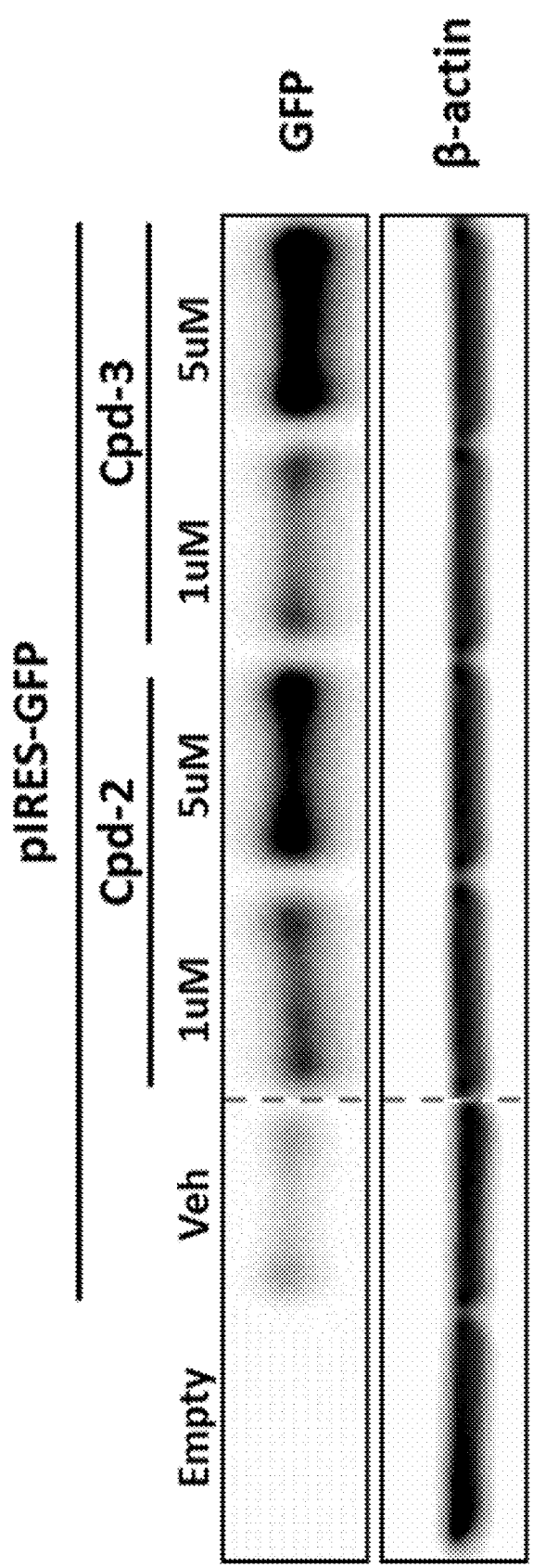
FIG. 5A shows GFP expression in transiently-transfected CHO cells treated with vehicle or with 1 µM or 5 µM of compounds 2 or 3.
Figure 5B:
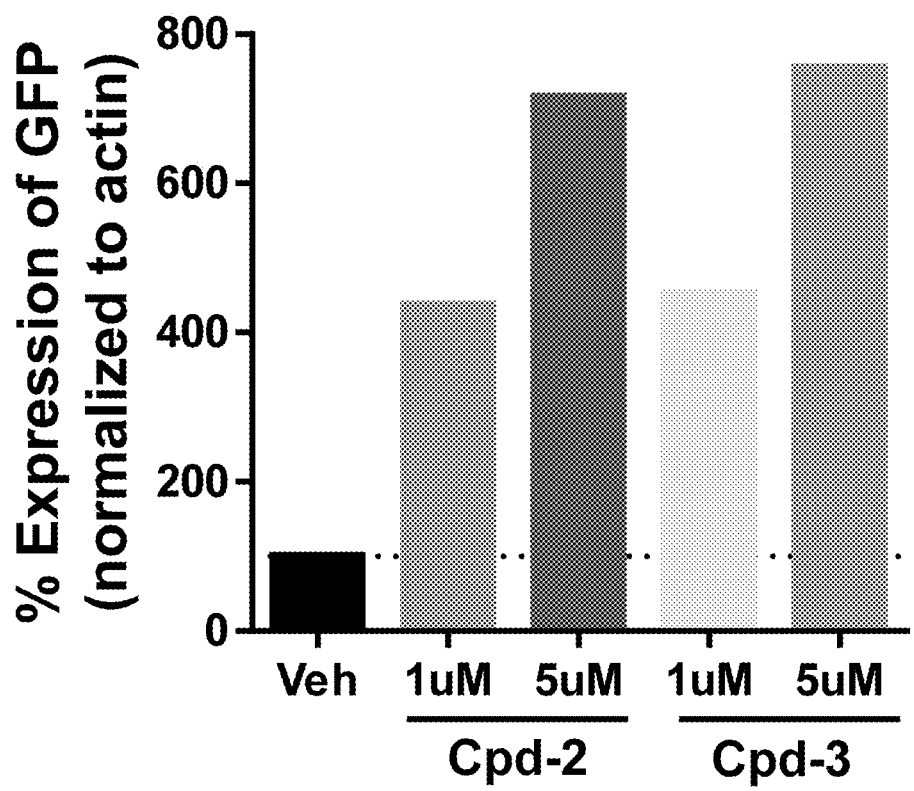
FIG. 5B shows percent of GFP expression in transiently-transfected CHO cells treated with vehicle or with 1 µM or 5 µM of compounds 2 or 3.

Photographs of the gels were taken in a gel imaging system (Chemidoc—BioRad) and are shown in FIG. 5A. Dotted lines indicate that pictures of the same gel was cut in order to plot the lanes corresponding to control lanes and test compound-treatments one beside the other. Percent of GFP expression in CHO cells treated with vehicle or tested compounds is shown in FIG. 5B. Percentage was calculated as the percent relative to GFP levels from CHO cells treated with vehicle which correspond to 100%. Tested compounds increased the expression of an intracellular protein expressed in CHO cells.

All references throughout, such as publications, patents, patent applications and published patent applications, are incorporated herein by reference in their entireties.

The invention claimed is:

1. A compound of formula (I):

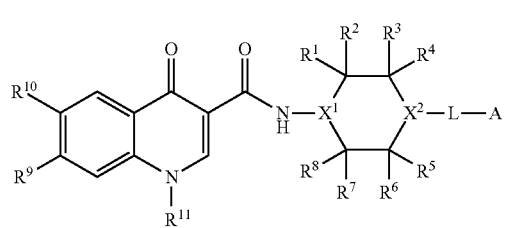

(I)

or a salt thereof,
wherein:
X$^1$ is N or CR$^{X1}$;
X$^2$ is N or CR$^{X2}$;
when present, R$^{X1}$ is selected from the group consisting of hydrogen, C$_1$-C$_6$ alkyl, C$_1$-C$_6$ haloalkyl, —C(O)OH, —C(O)O(C$_1$-C$_6$ alkyl), —C(O)O(C$_1$-C$_6$ haloalkyl), and halogen;
when present, R$^{X2}$ is selected from the group consisting of hydrogen, C$_1$-C$_6$ alkyl, C$_1$-C$_6$ haloalkyl, —C(O)OH, —C(O)O(C$_1$-C$_6$ alkyl), —C(O)O(C$_1$-C$_6$ haloalkyl), and halogen;
R$^1$, R$^2$, R$^3$, R$^4$, R$^5$, R$^6$, R$^7$, and R$^8$, independently from each other, are selected from the group consisting of hydrogen, C$_1$-C$_6$ alkyl, C$_1$-C$_6$ haloalkyl, —C(O)OH, —C(O)O(C$_1$-C$_6$ alkyl), —C(O)O(C$_1$-C$_6$ haloalkyl), and halogen;
or, one of R$^1$, R$^2$, R$^3$, R$^4$, R$^5$, R$^6$, R$^7$, and R$^8$, and another one of R$^1$, R$^2$, R$^3$, R$^4$, R$^5$, R$^6$, R$^7$, and R$^8$, are taken together to form a C$_1$-C$_6$ alkylene moiety;
or, two geminal substituents selected from the group consisting of R$^1$, R$^2$, R$^3$, R$^4$, R$^5$, R$^6$, R$^7$, and R$^8$ are taken together to form an oxo group;
or, one of R$^1$, R$^2$, R$^3$, R$^4$, R$^5$, R$^6$, R$^7$, and R$^8$, and R$^{X1}$, when present, are taken together to form a C$_1$-C$_6$ alkylene moiety;
R$^9$ and R$^{10}$, independently from each other, are selected from the group consisting of hydrogen, halogen, NO$_2$, C$_1$-C$_6$ alkyl, C$_2$-C$_6$ alkenyl, C$_2$-C$_6$ alkynyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{B-a}$R$^{B-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{B-a}$R$^{B-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{B-a}$R$^{B-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);
wherein R$^{B-a}$ and R$^{B-b}$ are taken together with the nitrogen atom to which they are attached to form a 3-10 membered heterocycle;
R$^{11}$ is selected from the group consisting of C$_3$-C$_{10}$ cycloalkyl optionally substituted with 1 to 17 R$^{12}$ substituents and 3-10 membered heterocycloalkyl optionally substituted with 1 to 17 R$^{12}$ substituents;
R$^{12}$, independently at each occurrence, is selected from the group consisting of oxo, halogen, C$_1$-C$_6$ alkyl, C$_2$-C$_6$ alkenyl, C$_2$-C$_6$ alkynyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{C-a}$R$^{C-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{C-a}$R$^{C-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{C-a}$R$^{C-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S $(O)_2(C_1$-$C_6$ alkyl), —N($C_1$-$C_6$ alkyl)S$(O)_2$($C_1$-$C_6$ haloalkyl), —N($C_1$-$C_6$ haloalkyl)S$(O)_2$($C_1$-$C_6$ alkyl), and —N($C_1$-$C_6$ haloalkyl)S$(O)_2$($C_1$-$C_6$ haloalkyl);

wherein $R^{C-a}$ and $R^{C-b}$ are taken together with the nitrogen atom to which they are attached to form a 3-10 membered heterocycle;

L is a linker selected from the group consisting of @-$C_1$-$C_6$ alkylene-#, @—$NR^N$—($C_1$-$C_6$ alkylene)-#, @—$NR^N$—$NR^N$—($C_1$-$C_6$ alkylene)-#, @-$CH_2$—$NR^N$—($C_1$-$C_6$ alkylene)-#, @-$CH_2$—$NR^N$—$NR^N$—($C_1$-$C_6$ alkylene)-#, @—$NR^N$—($C_1$-$C_6$ alkylene)-O-#, @—$NR^N$—$NR^N$—($C_1$-$C_6$ alkylene)-O-#, @-$CH_2$—$NR^N$—($C_1$-$C_6$ alkylene)-O-#, @-$CH_2$—$NR^N$—$NR^N$—($C_1$-$C_6$ alkylene)-O-#, and @—($C_1$-$C_6$ alkylene)-O-#;

wherein @ represents the attachment point to $X^2$ and # represents the attachment point to A;

the $C_1$-$C_6$ alkylene moiety of each of the @-$C_1$-$C_6$ alkylene-#, @—$NR^N$—($C_1$-$C_6$ alkylene)-#, @—$NR^N$—$NR^N$—($C_1$-$C_6$ alkylene)-#, @-$CH_2$—$NR^N$—($C_1$-$C_6$ alkylene)-#, @-$CH_2$—$NR^N$—$NR^N$—($C_1$-$C_6$ alkylene)-#, @—$NR^N$—($C_1$-$C_6$ alkylene)-O-#, @—$NR^N$—$NR^N$—($C_1$-$C_6$ alkylene)-O-#, @-$CH_2$—$NR^N$—($C_1$-$C_6$ alkylene)-O-#, @-$CH_2$—$NR^N$—$NR^N$—($C_1$-$C_6$ alkylene)-O-#, and @—($C_1$-$C_6$ alkylene)-O-# is optionally substituted with 1 to 12 $R^{13}$;

$R^N$, independently at each occurrence, is selected from the group consisting of hydrogen, $C_1$-$C_6$ alkyl, and $C_1$-$C_6$ haloalkyl, $R^{13}$, independently at each occurrence, is selected from the group consisting of oxo, halogen, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{L-a}R^{L-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{L-a}R^{L-b}$, —S$(O)_2$OH, —S$(O)_2$O($C_1$-$C_6$ alkyl), —S$(O)_2$O($C_1$-$C_6$ haloalkyl), —S$(O)_2NH_2$, —S$(O)_2$NH($C_1$-$C_6$ alkyl), —S$(O)_2$NH($C_1$-$C_6$ haloalkyl), —S$(O)_2$N($C_1$-$C_6$ alkyl)$_2$, —S$(O)_2$N($C_1$-$C_6$ haloalkyl)$_2$, —S$(O)_2NR^{L-a}R^{L-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS$(O)_2$($C_1$-$C_6$ alkyl), —OS$(O)_2$($C_1$-$C_6$ haloalkyl), —N(H)S$(O)_2$($C_1$-$C_6$ alkyl), —N(H)S$(O)_2$($C_1$-$C_6$ haloalkyl), —N($C_1$-$C_6$ alkyl)S$(O)_2$($C_1$-$C_6$ alkyl), —N($C_1$-$C_6$ alkyl)S$(O)_2$($C_1$-$C_6$ haloalkyl), —N($C_1$-$C_6$ haloalkyl)S$(O)_2$($C_1$-$C_6$ alkyl), and —N($C_1$-$C_6$ haloalkyl)S$(O)_2$($C_1$-$C_6$ haloalkyl);

wherein $R^{L-a}$ and $R^{L-b}$ are taken together with the nitrogen atom to which they are attached to form a 3-10 membered heterocycle;

A is selected from the group consisting of:
a substituent of formula (A-1)

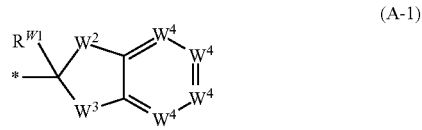

(A-1)

$W^2$ is selected from the group consisting of —C($R^{W2-1}R^{W2-2}$)—, —N($R^{W2-2}$)—, —C($R^{W2-1}R^{W2-1}$)N($R^{W2-2}$)—, —N($R^{W2-1}$)C($R^{W2-1}R^{W2-2}$)—, —C($R^{W2-1}$)=N—, —N=C($R^{W2-1}$)—, —O—, —C($R^{W2-1}R^{W2-1}$)O—, —OC($R^{W2-1}R^{W2-2}$)—, —S—, —C($R^{W2-1}R^{W2-1}$)S—, —SC($R^{W2-1}R^{W2-2}$)—, —C($R^{W2-1}R^{W2-1}$)C($R^{W2-1}R^{W2-2}$)—, and —C$R^{W2-1}$=C$R^{W2-1}$—, wherein $R^{W2-1}$ is H or $R^A$, and $R^{W2-2}$ is H or $R^A$;

$W^3$ is selected from the group consisting of —C($R^{W3-1}R^{W3-2}$)—, —N($R^{W3-2}$)—, —C($R^{W3-1}R^{W3-1}$)N($R^{W3-2}$)—, —N($R^{W3-1}$)C($R^{W3-1}R^{W3-2}$)—, —C($R^{W3-1}$)=N—, —N=C($R^{W3-1}$)—, —O—, —C($R^{W3-1}R^{W3-1}$)O—, —OC($R^{W3-1}R^{W3-2}$)—, —S—, —C($R^{W3-1}R^{W3-1}$)S—, —SC($R^{W3-1}R^{W3-2}$)—, —C($R^{W3-1}R^{W3-1}$)C($R^{W3-1}R^{W3-2}$)—, and —C$R^{W3-1}$=C$R^{W3-1}$—, wherein $R^{W3-1}$ is H or $R^A$, and $R^{W3-2}$ is H or $R^A$;

$W^4$, independently at each occurrence, is C$R^{W4}$ or N, wherein $R^{W4}$ is H or $R^A$;

$R^{W1}$ is hydrogen or $R^A$, or $R^{W1}$ and $R^{W2-2}$ are taken together to form a double bond between the carbon atom bearing $R^{W1}$ and the atom bearing $R^{W2-2}$, or $R^{W1}$ and $R^{W3-2}$ are taken together to form a double bond between the carbon atom bearing $R^{W1}$ and the atom bearing $R^{W3-2}$;

$C_6$-$C_{14}$ aryl optionally substituted with 1, 2, 3, 4, 5, 6, 7, 8, or 9 $R^A$ substituents; and 5-14 membered heteroaryl optionally substituted with 1, 2, 3, 4, 5, 6, 7, 8, or 9 $R^A$ substituents;

$R^A$, independently at each occurrence, is selected from the group consisting of halogen, $NO_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{A-a}R^{A-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{A-a}R^{A-b}$, —S$(O)_2$OH, —S$(O)_2$O($C_1$-$C_6$ alkyl), —S$(O)_2$O($C_1$-$C_6$ haloalkyl), —S$(O)_2NH_2$, —S$(O)_2$NH($C_1$-$C_6$ alkyl), —S$(O)_2$NH($C_1$-$C_6$ haloalkyl), —S$(O)_2$N($C_1$-$C_6$ alkyl)$_2$, —S$(O)_2$N($C_1$-$C_6$ haloalkyl)$_2$, —S$(O)_2NR^{A-a}R^{A-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS$(O)_2$($C_1$-$C_6$ alkyl), —OS$(O)_2$($C_1$-$C_6$ haloalkyl), —N(H)S$(O)_2$($C_1$-$C_6$ alkyl), —N(H)S$(O)_2$($C_1$-$C_6$ haloalkyl), —N($C_1$-$C_6$ alkyl)S$(O)_2$($C_1$-$C_6$ alkyl), —N($C_1$-$C_6$ alkyl)S$(O)_2$($C_1$-$C_6$ haloalkyl), —N($C_1$-$C_6$ haloalkyl)S$(O)_2$($C_1$-$C_6$ alkyl), —N($C_1$-$C_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein R$^{A-a}$ and R$^A$b are taken together with the nitrogen atom to which they are attached to form a 3-10 membered heterocycle;

provided that when X$^2$ is N, then L is a linker selected from the group consisting of @-C$_1$-C$_6$ alkylene-#, @—NR$^N$—(C$_1$-C$_6$ alkylene)-#, @—NR$^N$—(C$_1$-C$_6$ alkylene)-O-#, and @—(C$_1$-C$_6$ alkylene)-O-#.

2. The compound of claim 1, or a salt thereof, wherein the compound of formula (I) is a compound of formula (II):

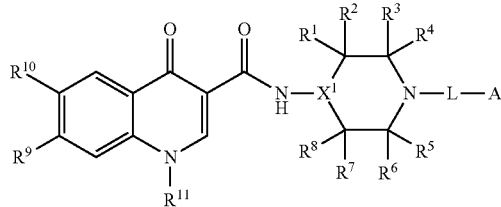

(II)

or a salt thereof, wherein R$^1$, R$^2$, R$^3$, R$^4$, R$^5$, R$^6$, R$^7$, R$^8$, R$^9$, R$^{10}$, R$^{11}$, X$^1$, L, and A are as defined in claim 1.

3. The compound of claim 1, or a salt thereof, wherein the compound of formula (I) is a compound of formula (III):

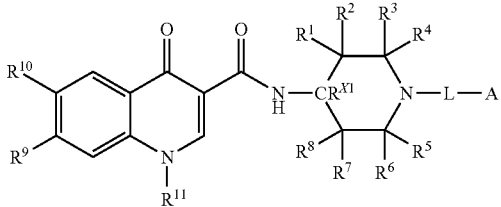

(III)

or a salt thereof, wherein R$^1$, R$^2$, R$^3$, R$^4$, R$^5$, R$^6$, R$^7$, R$^8$, R$^9$, R$^{10}$, R$^{11}$, CR$^{X1}$, L, and A are as defined in claim 1.

4. The compound of claim 1, or a salt thereof, wherein the compound of formula (I) is a compound of formula (IV):

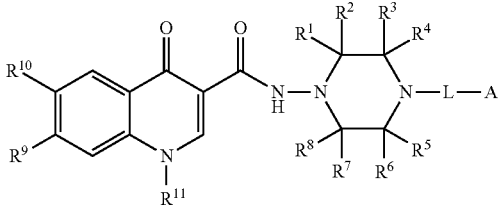

(IV)

or a salt thereof, wherein R$^1$, R$^2$, R$^3$, R$^4$, R$^5$, R$^6$, R$^7$, R$^8$, R$^9$, R$^{10}$, R$^{11}$, L, and A are as defined in claim 1.

5. The compound of claim 1, or a salt thereof, wherein the compound of formula (I) is a compound of formula (V):

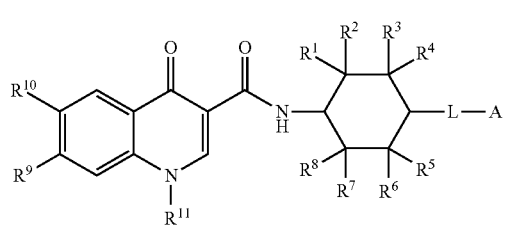

(V)

or a salt thereof, wherein R$^1$, R$^2$, R$^3$, R$^4$, R$^5$, R$^6$, R$^7$, R$^8$, R$^9$, R$^{10}$, R$^{11}$, L, and A are as defined in claim 1.

6. The compound of claim 1, or a salt thereof, wherein the compound of formula (I) is a compound of formula (VI):

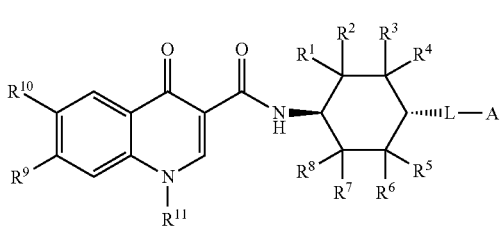

(VI)

or a salt thereof, wherein R$^1$, R$^2$, R$^3$, R$^4$, R$^5$, R$^6$, R$^7$, R$^8$, R$^9$, R$^{10}$, R$^{11}$, L, and A are as defined in claim 1.

7. The compound of claim 1, or a salt thereof, wherein the compound of formula (I) is a compound of formula (VII):

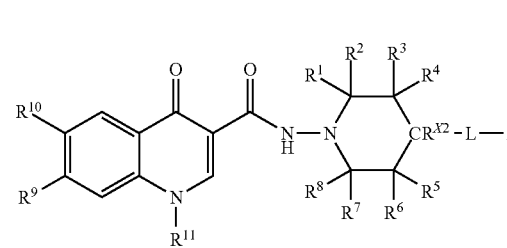

(VII)

or a salt thereof, wherein R$^1$, R$^2$, R$^3$, R$^4$, R$^5$, R$^6$, R$^7$, R$^8$, R$^9$, R$^{10}$, R$^{11}$, CR$^{X2}$, L, and A are as defined in claim 1.

8. The compound of claim 1, or a salt thereof, wherein the compound of formula (I) is a compound of formula (VIII):

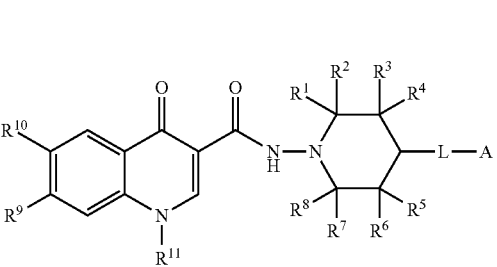

(VIII)

or a salt thereof, wherein $R^1$, $R^2$, $R^3$, $R^4$, $R^5$, $R^6$, $R^7$, $R^8$, $R^9$, $R^{10}$, $R^{11}$, L, and A are as defined in claim 1.

9. The compound of claim 1, or a salt thereof, wherein L is

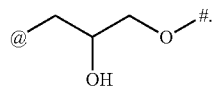

10. The compound of claim 9, or a salt thereof, wherein L is

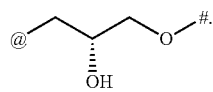

11. The compound of claim 9, or a salt thereof, wherein L is

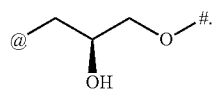

12. The compound of claim 1, or a salt thereof, wherein $R^1$, $R^2$, $R^3$, $R^4$, $R^5$, $R^6$, $R^7$, and $R^8$ are each hydrogen.

13. The compound of claim 1, or a salt thereof, wherein $R^9$ and $R^{10}$ are each halogen.

14. The compound of claim 1, or a salt thereof, wherein $R^9$ is chloro and $R^{10}$ is fluoro.

15. The compound of claim 1, or a salt thereof, wherein A is

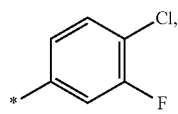 [SMILES: *c1ccc(Cl)c(F)c1]

wherein * represents that attachment point to the remainder of the molecule.

16. A compound selected from the group consisting of:

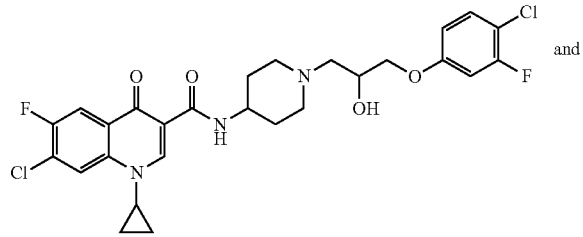

and

-continued

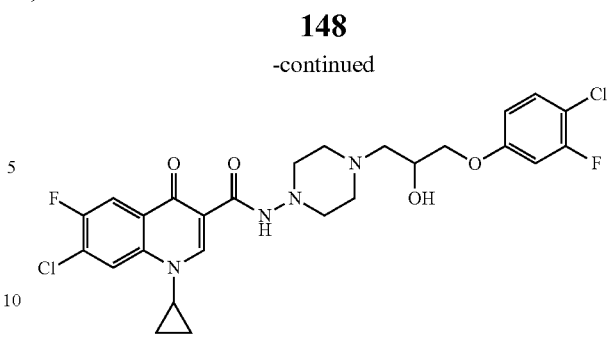

or a salt thereof.

17. A compound selected from the group consisting of:

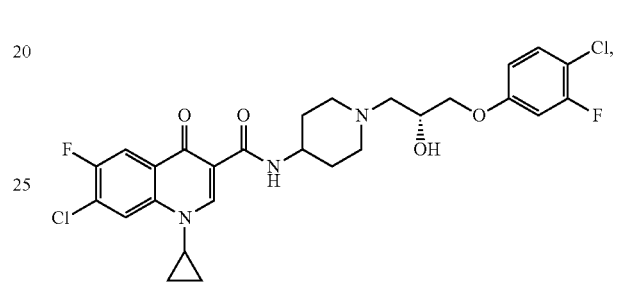

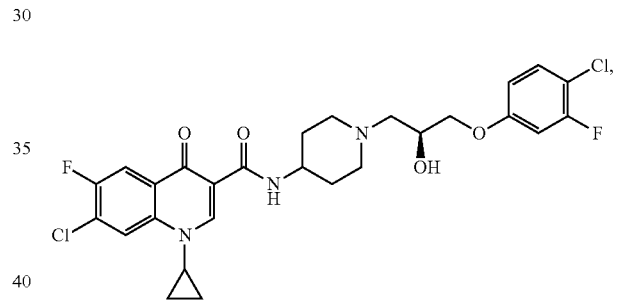

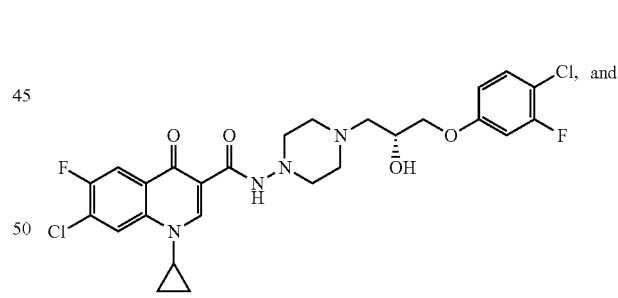

and

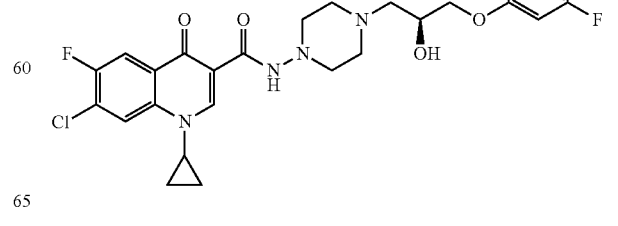

or a salt thereof.

18. A compound selected from the group consisting of
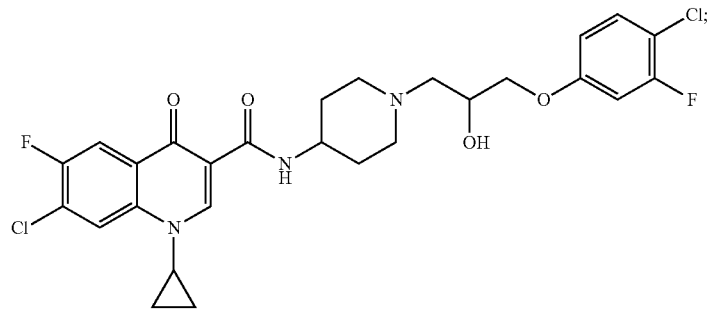
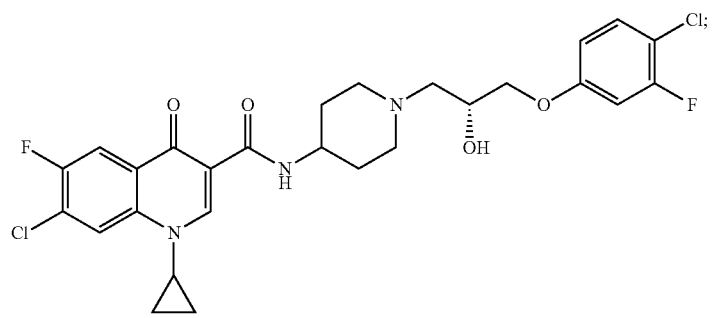
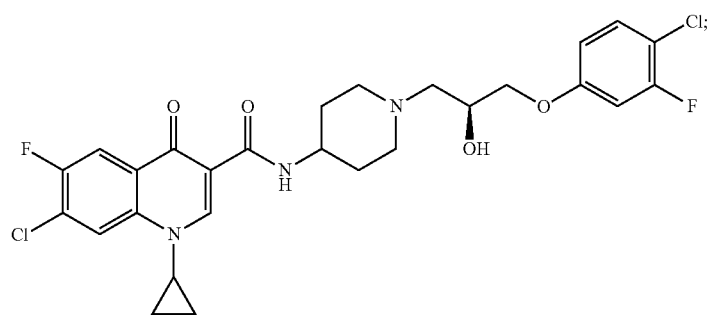
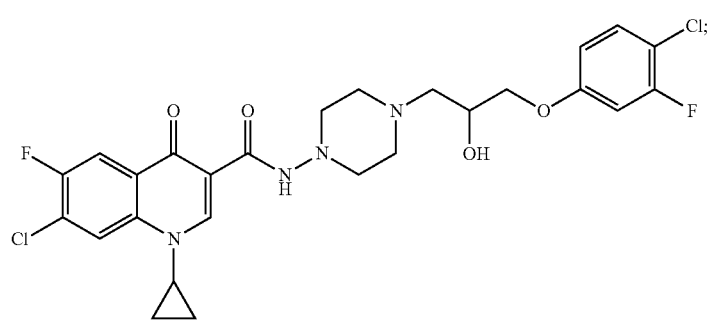
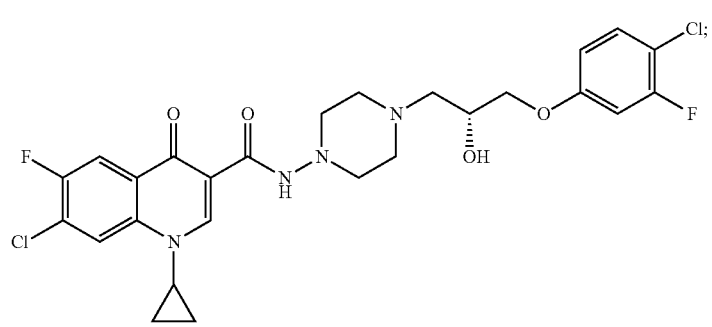

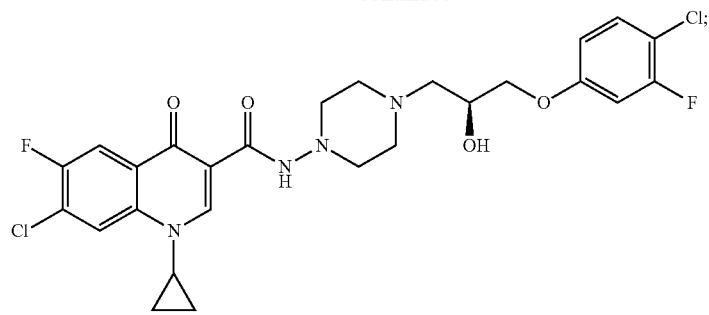
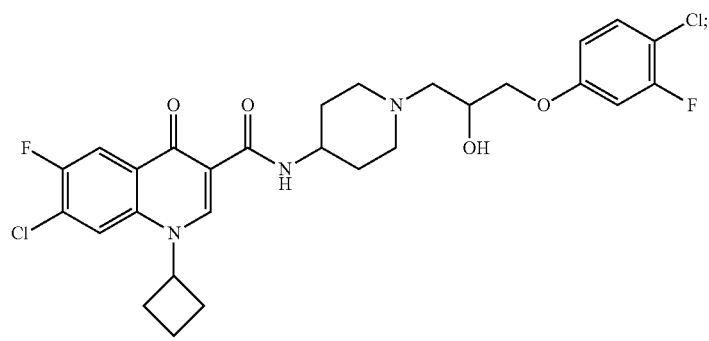
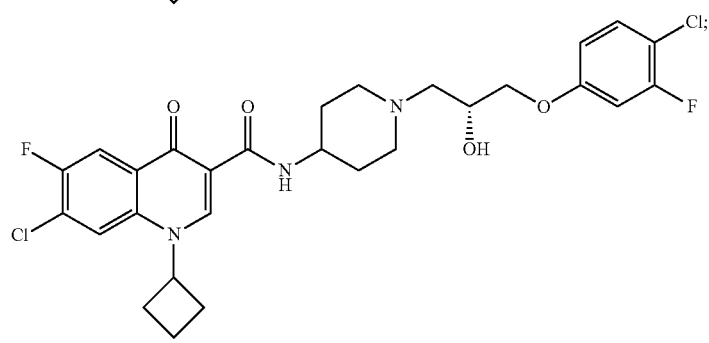
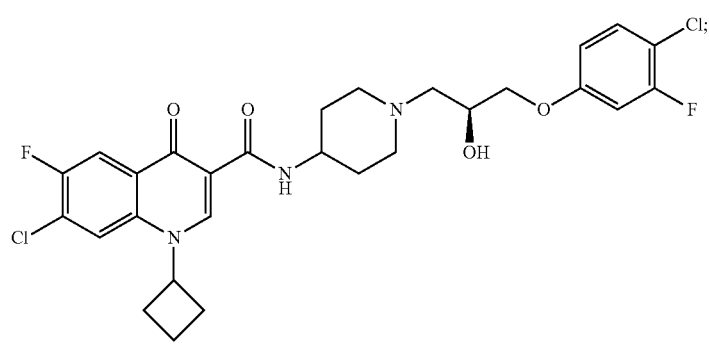
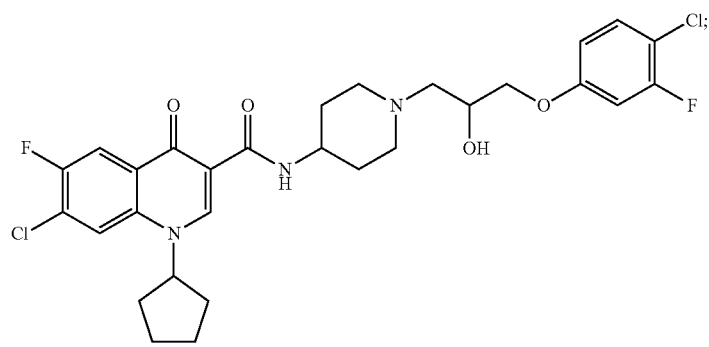

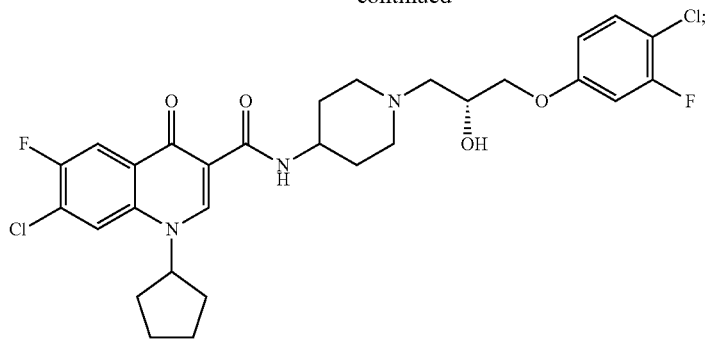
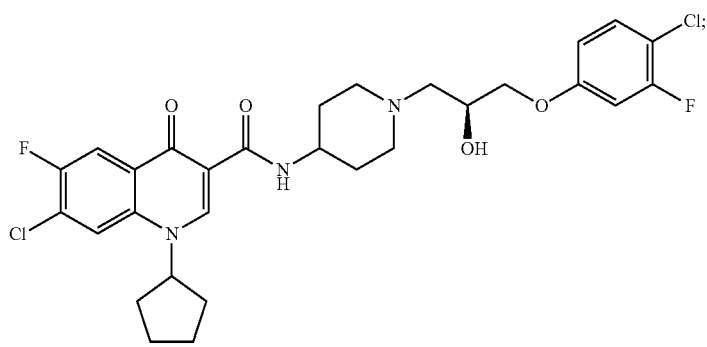
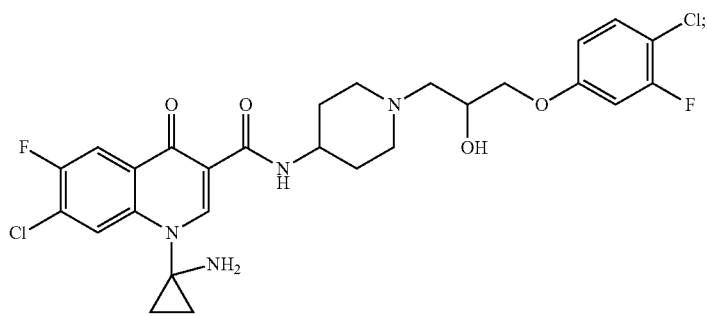
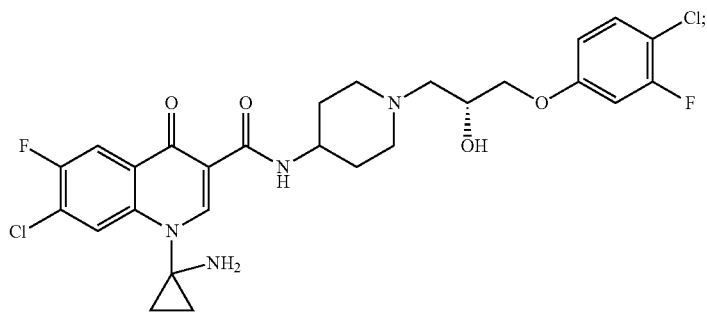
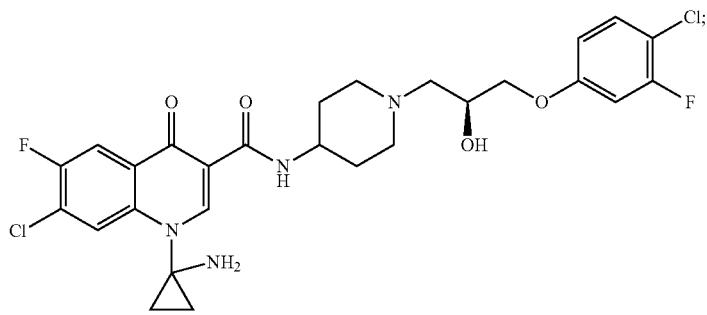

-continued
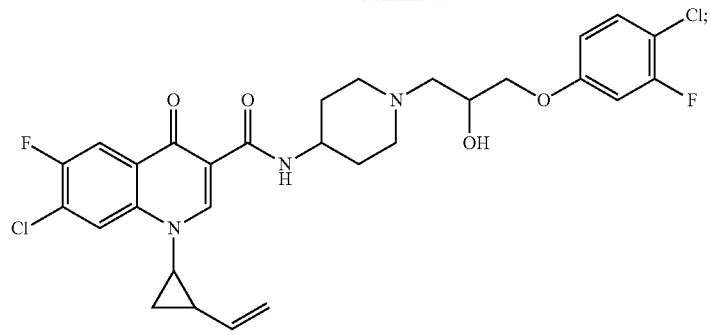
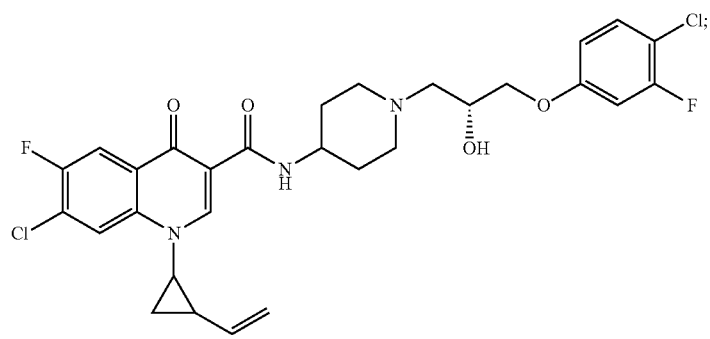
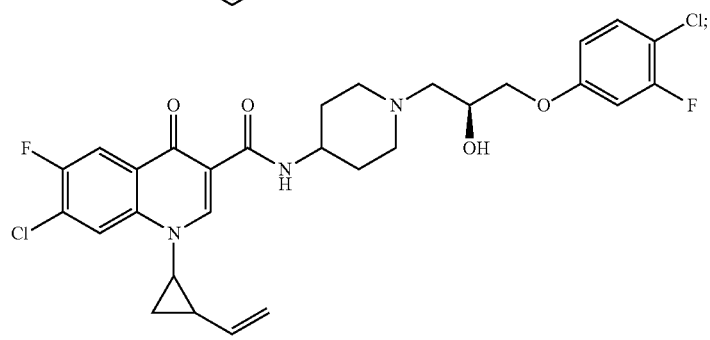
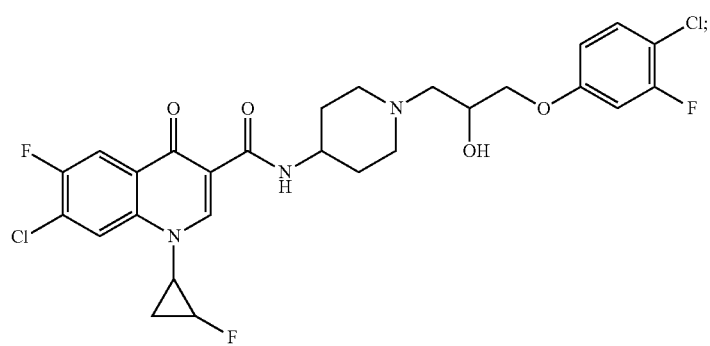
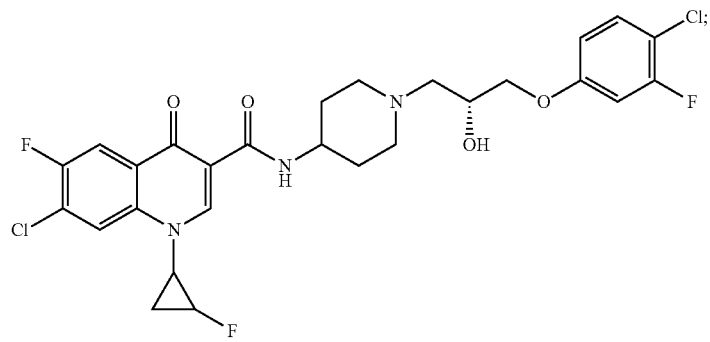

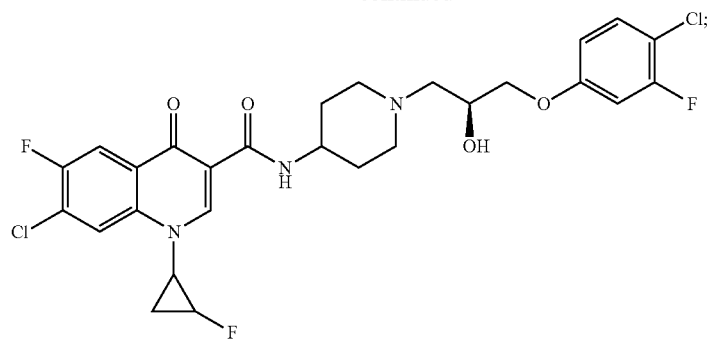
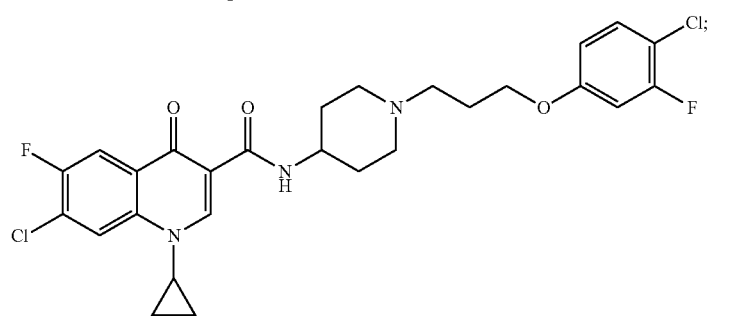
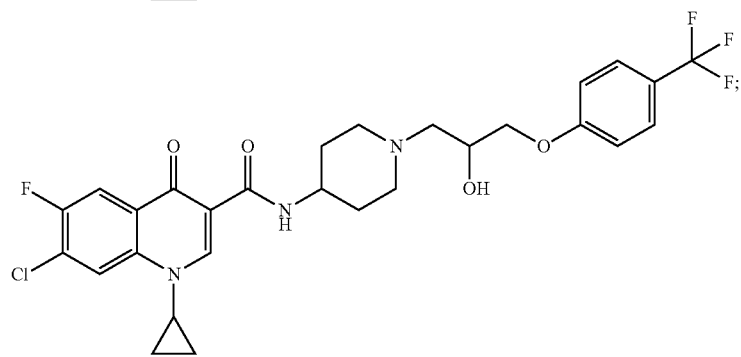
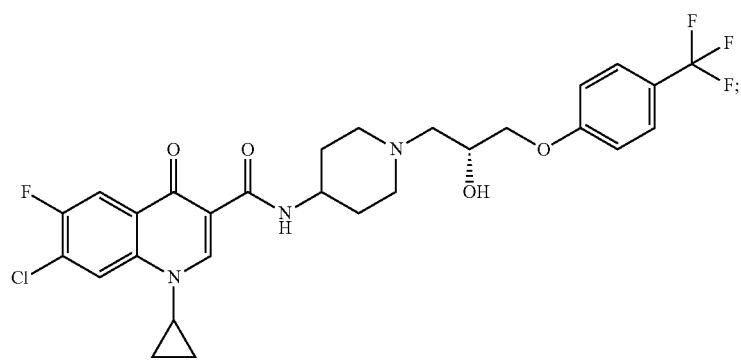
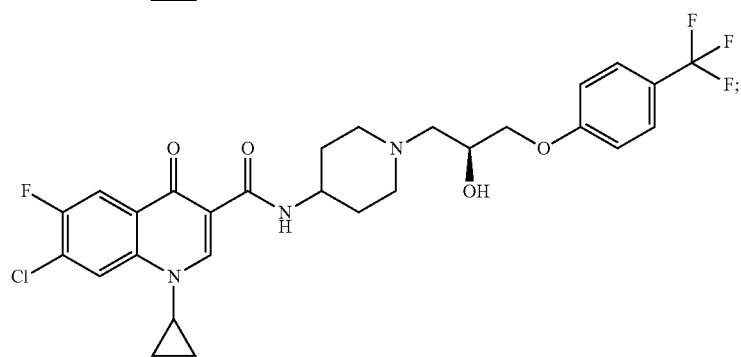

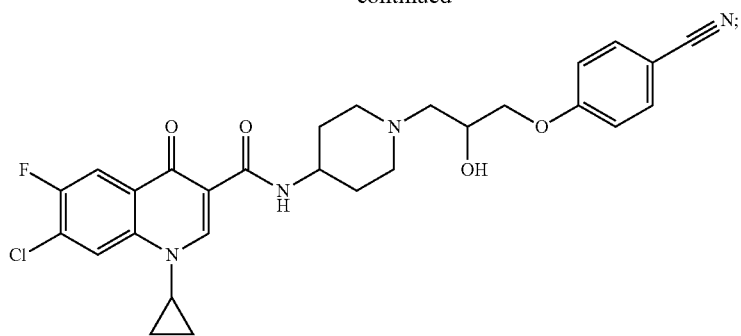
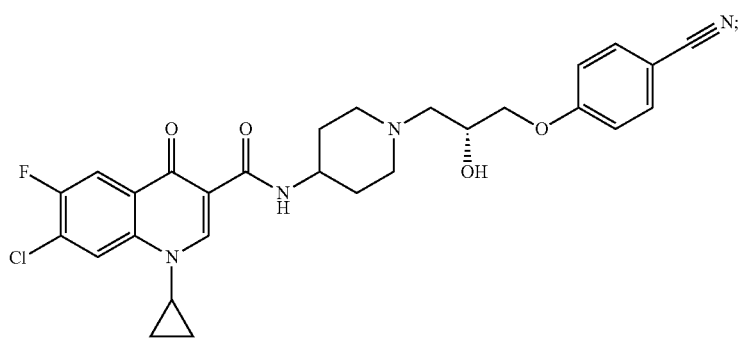
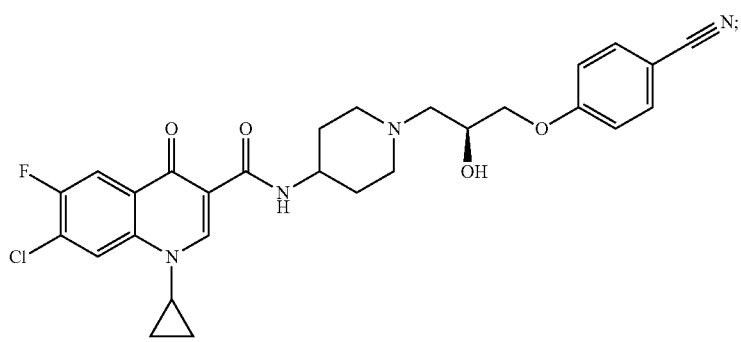
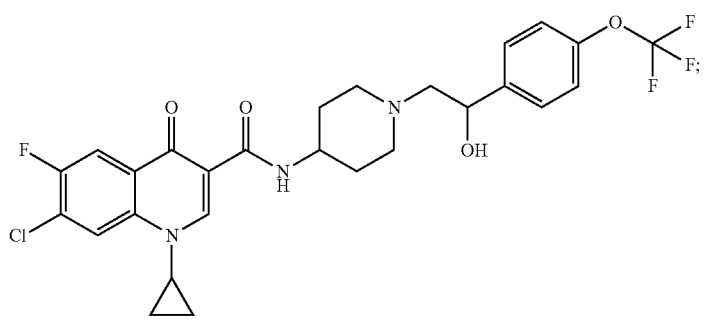
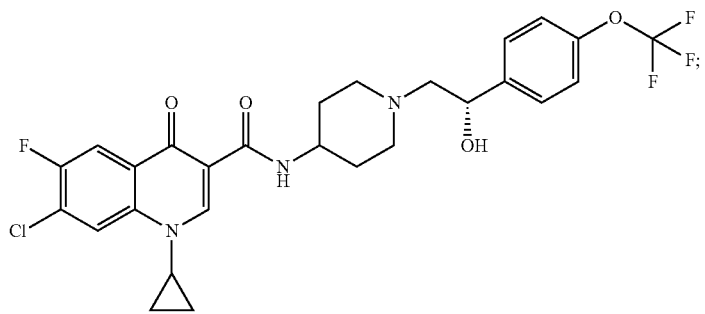

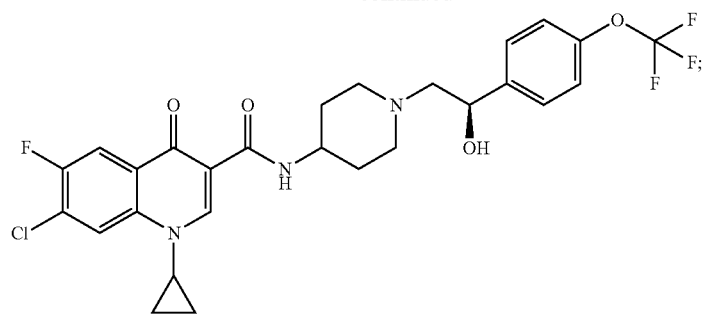
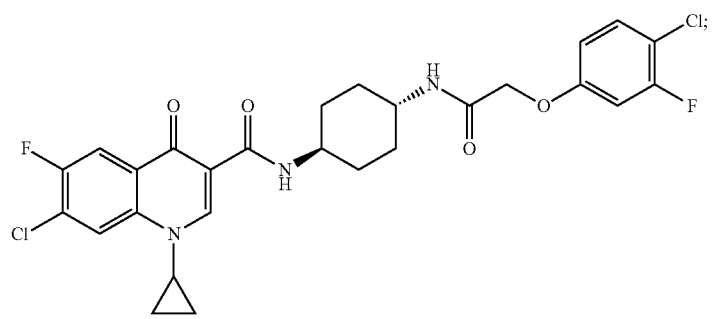
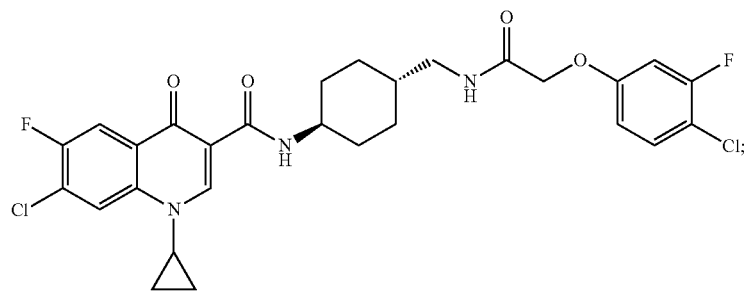
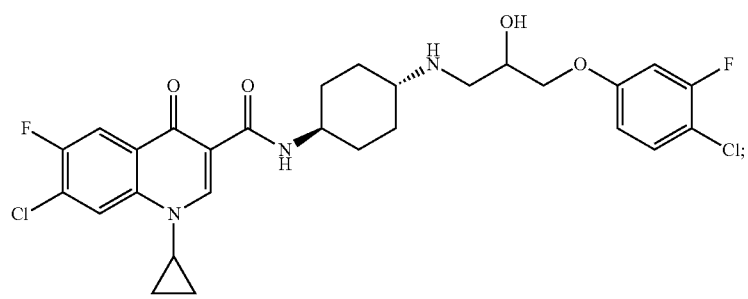
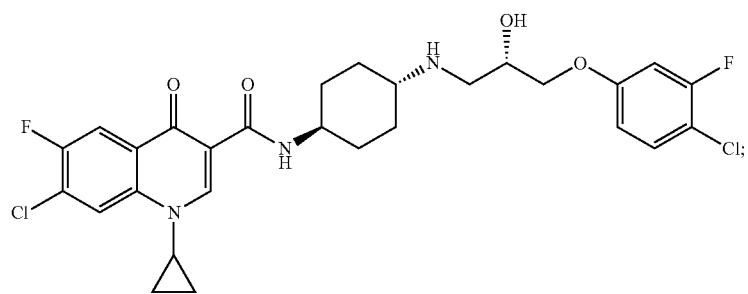

-continued
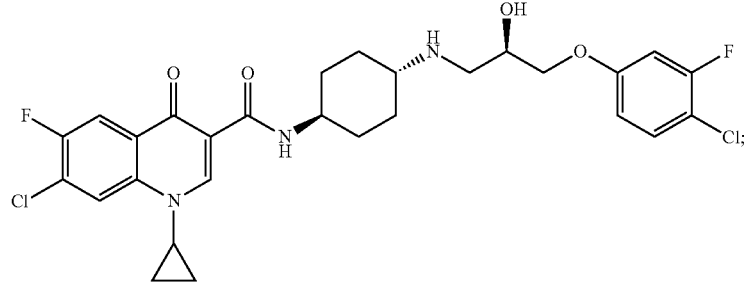
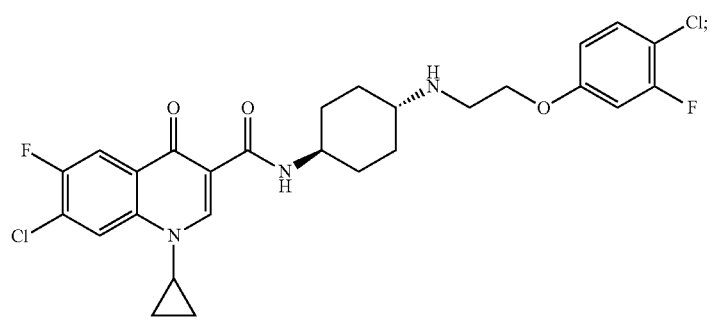
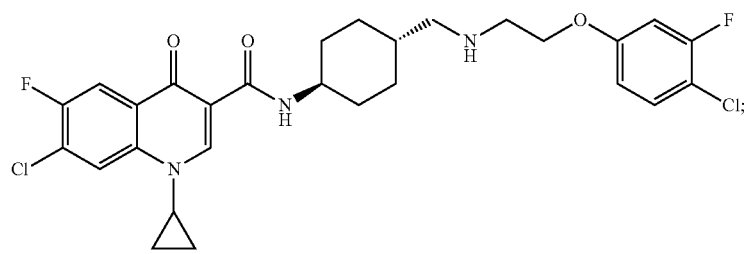
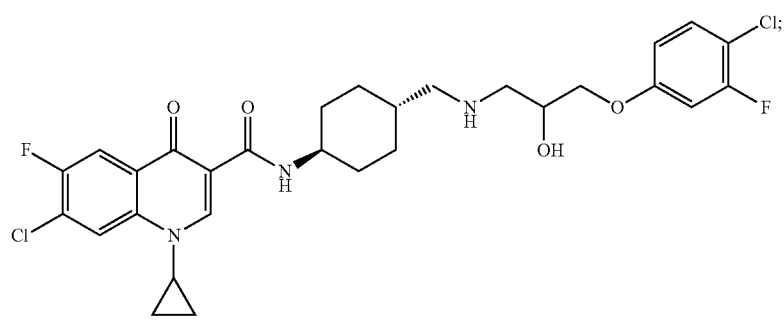
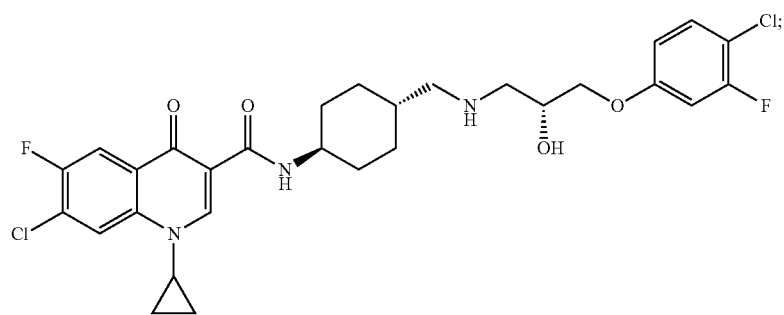

-continued
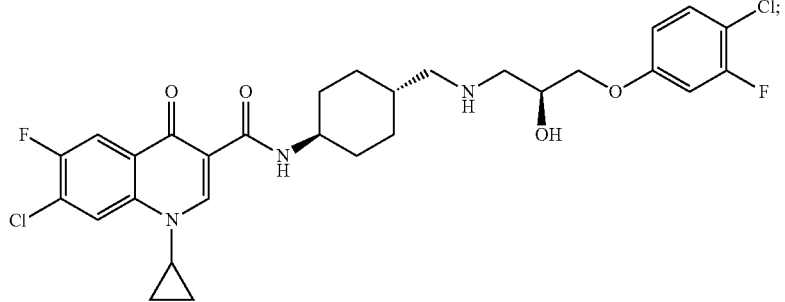
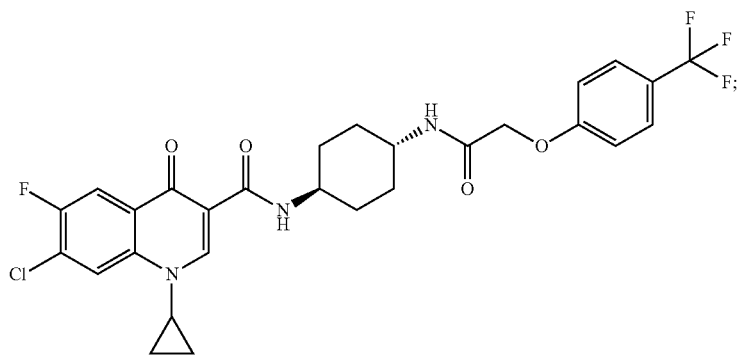
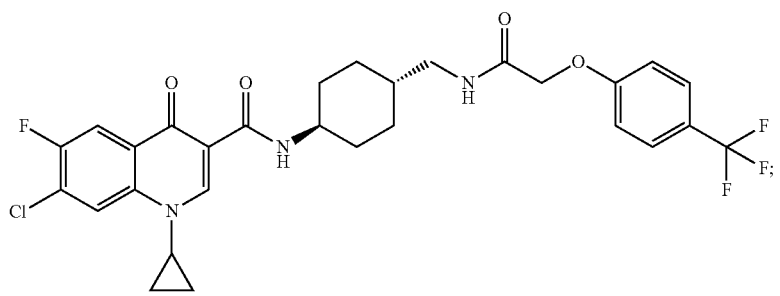
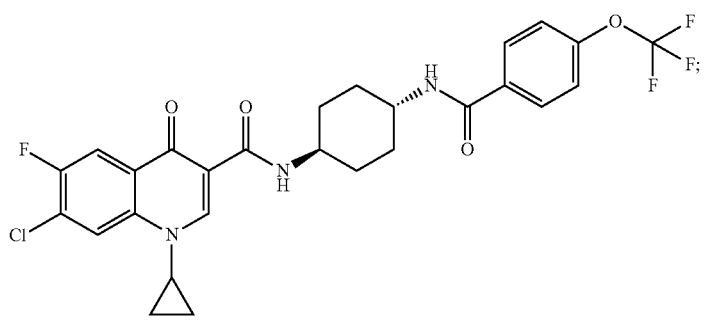
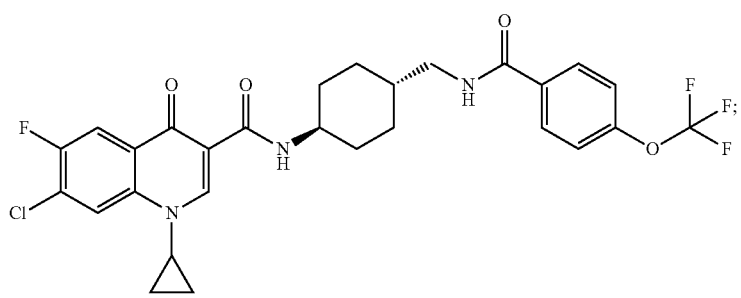

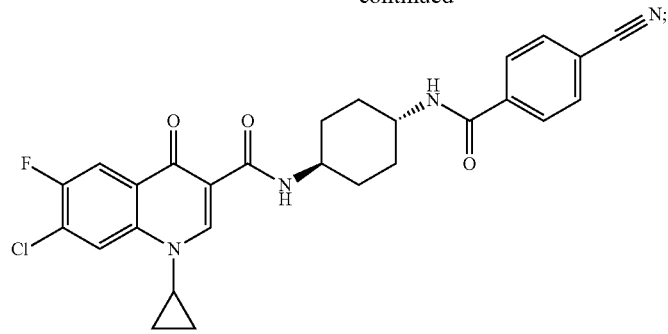
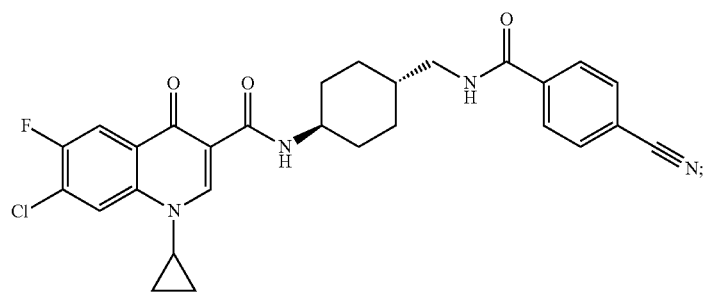
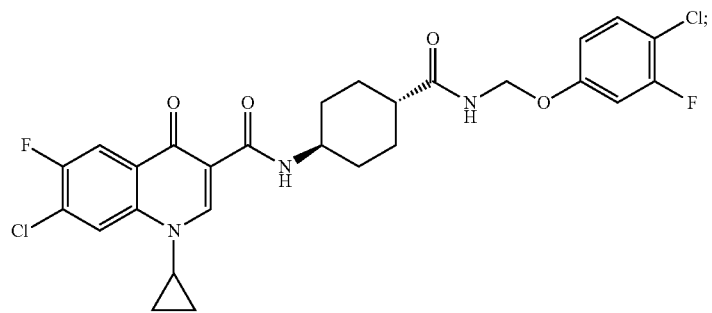
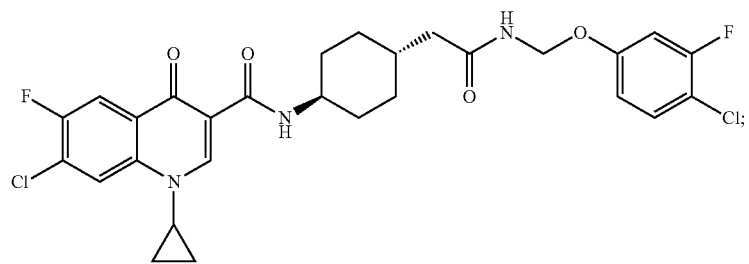
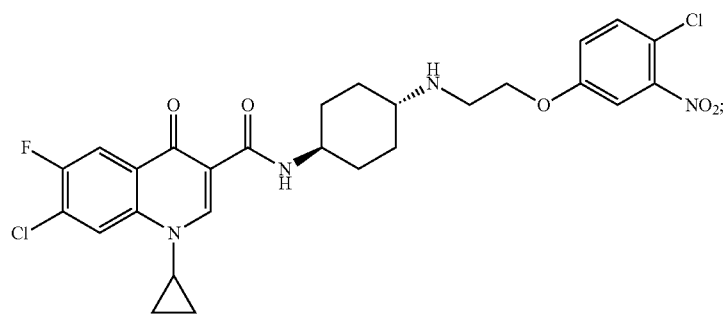

-continued
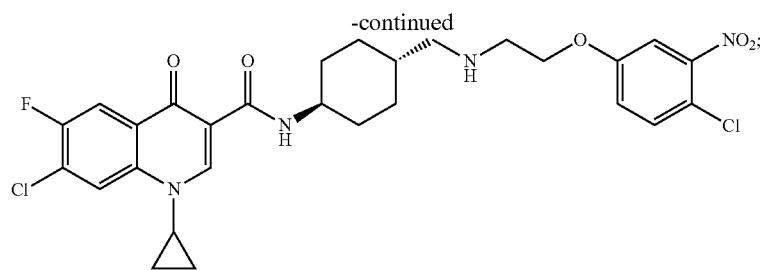
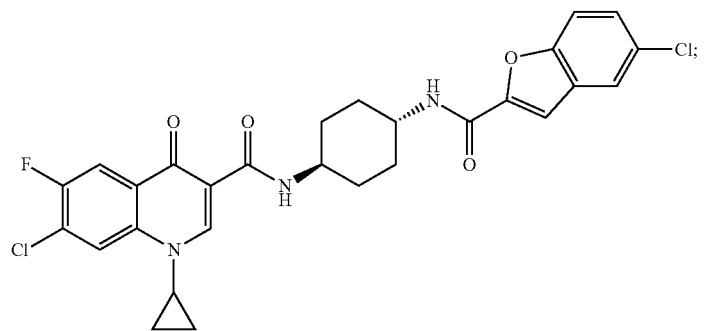
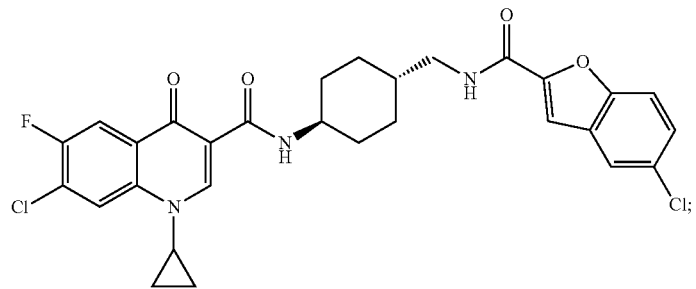
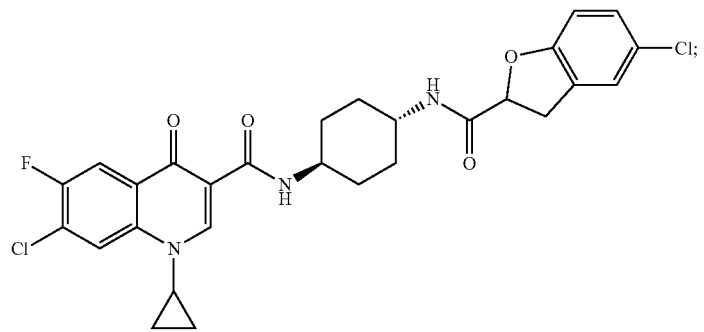
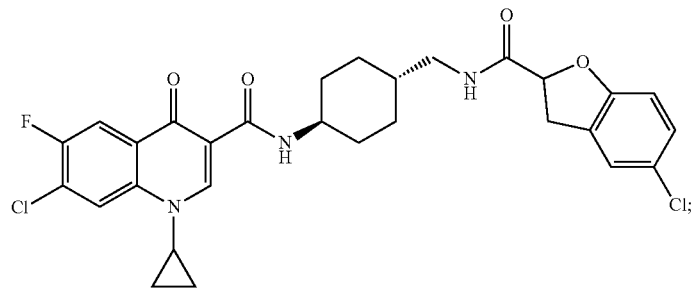

-continued
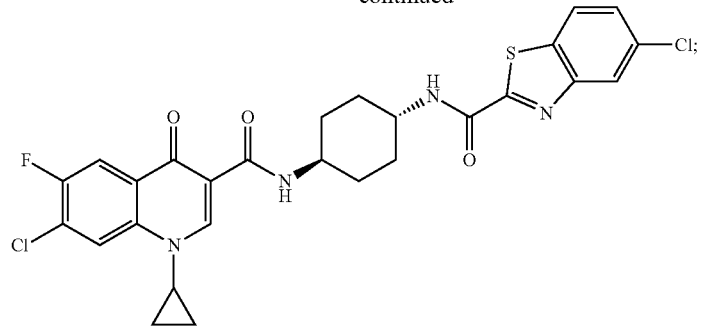
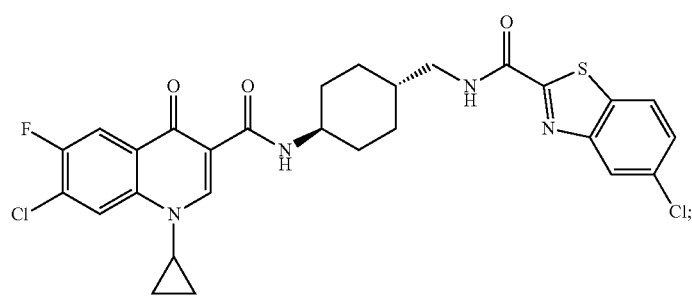
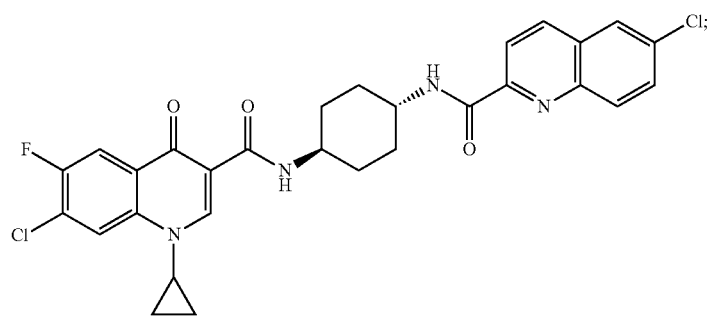
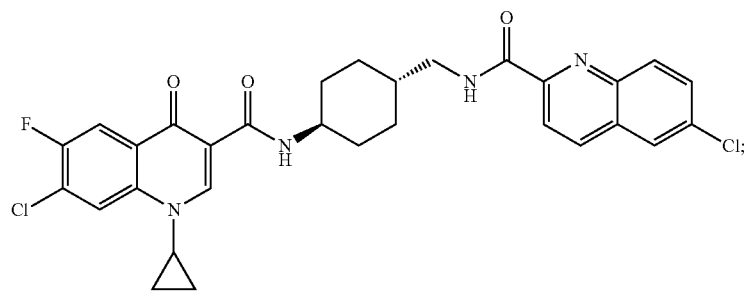
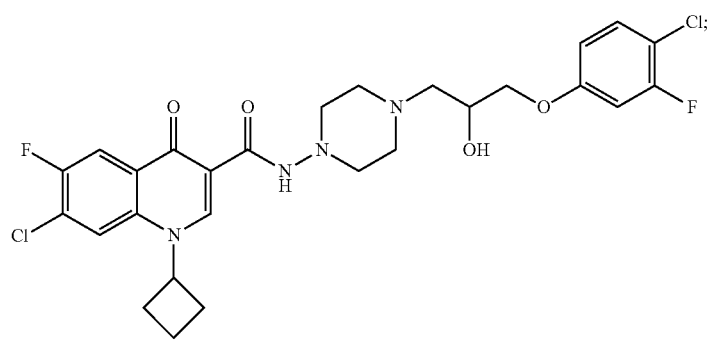

-continued
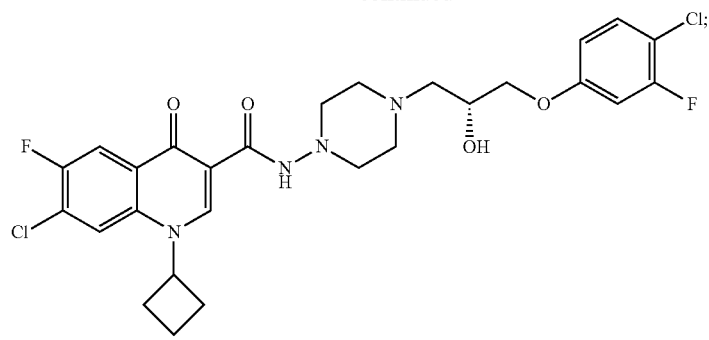
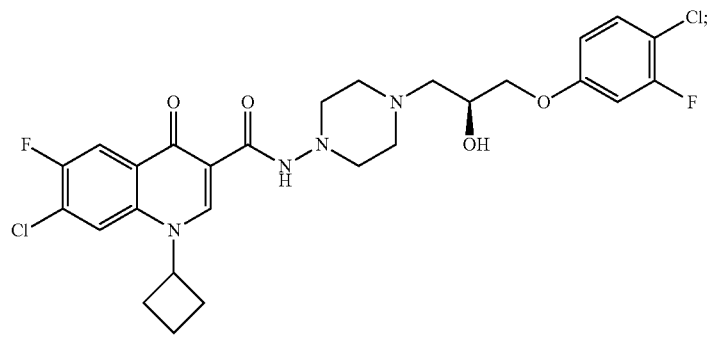
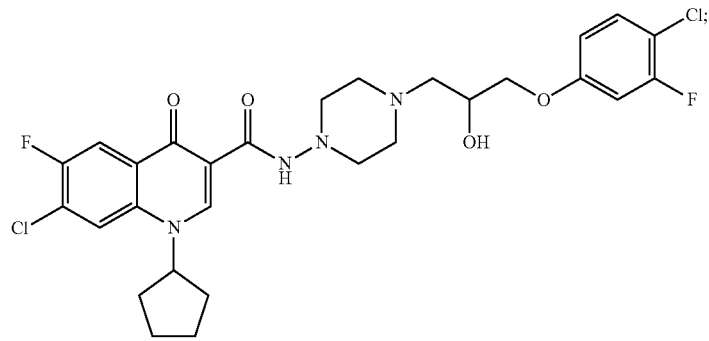
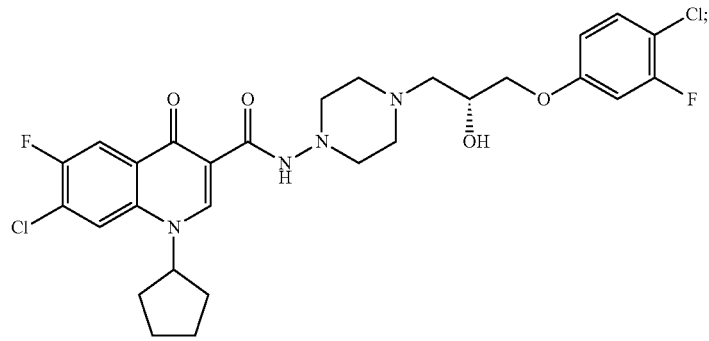
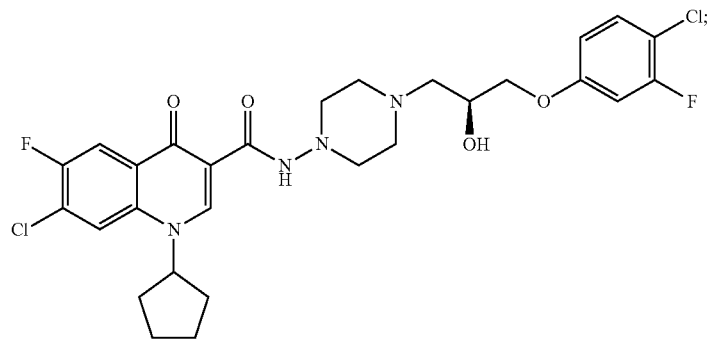

-continued
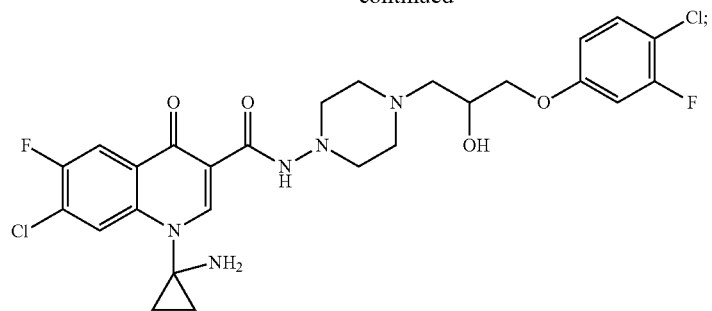
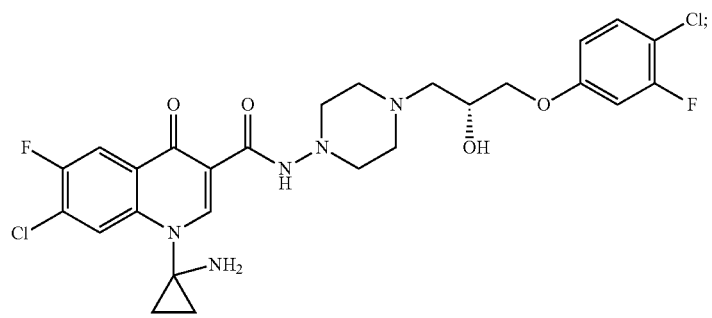
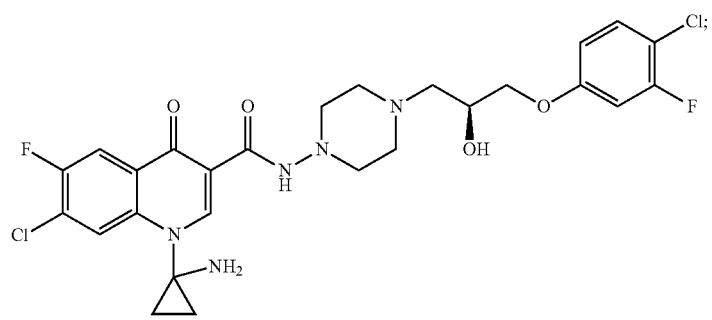
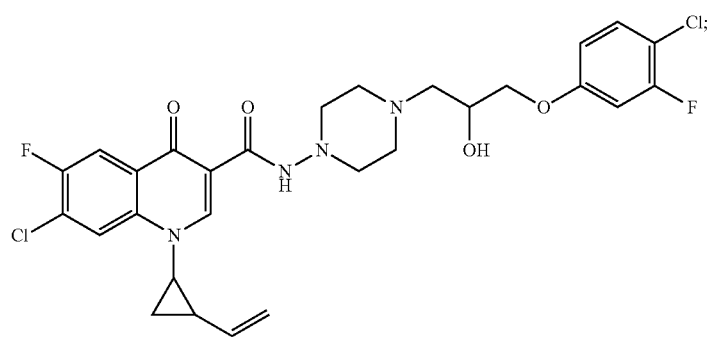
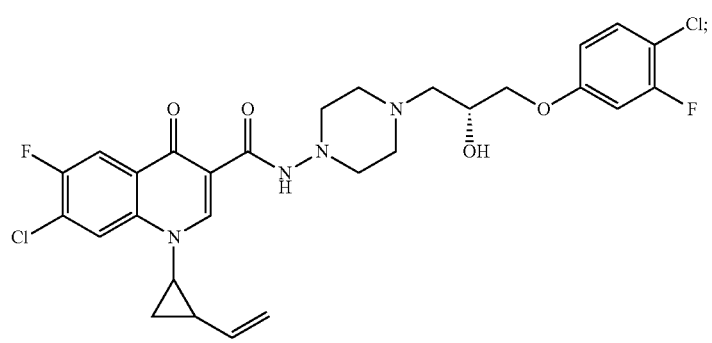

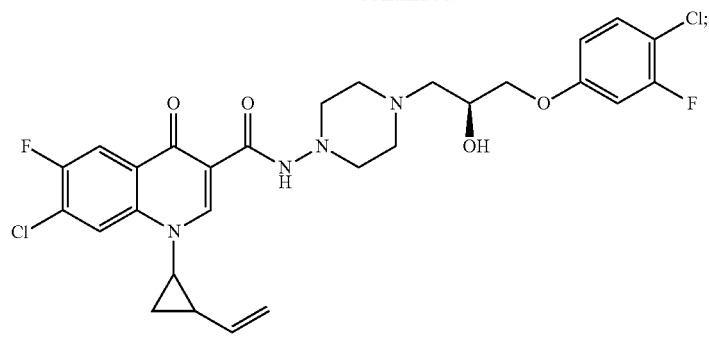
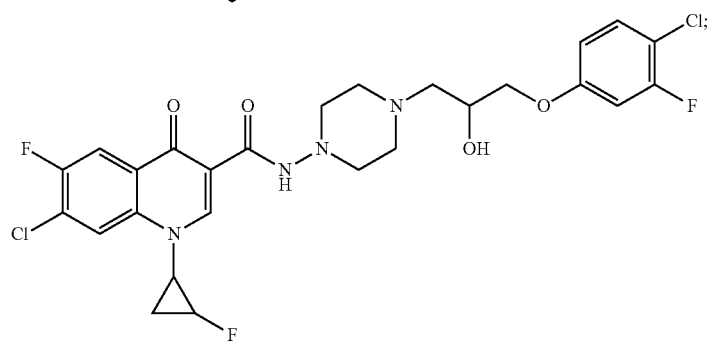
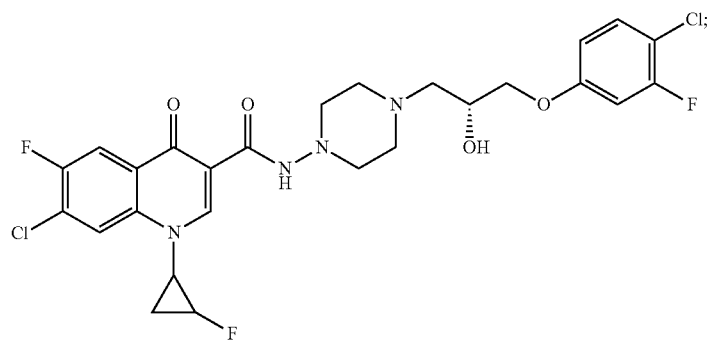
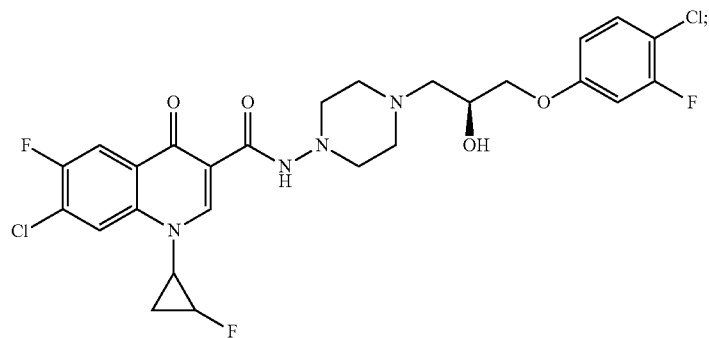
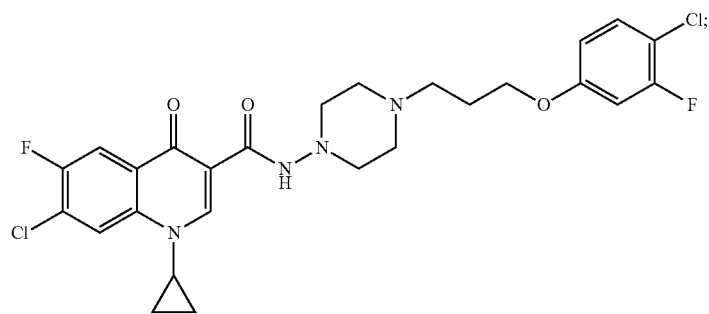

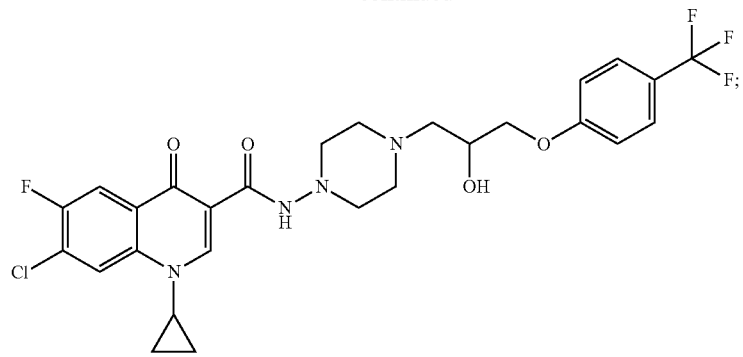
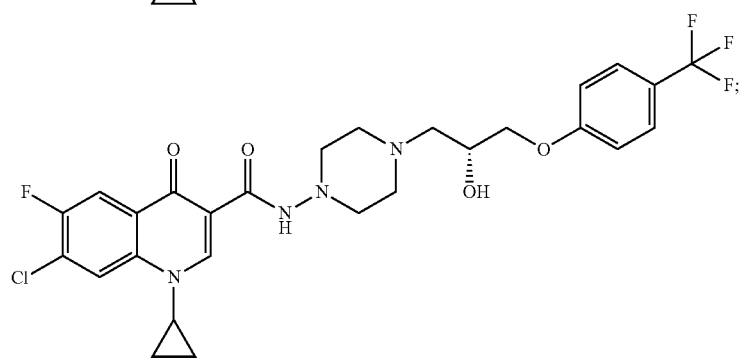
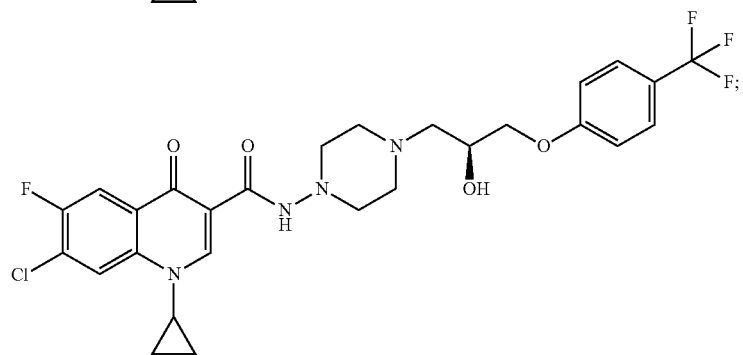
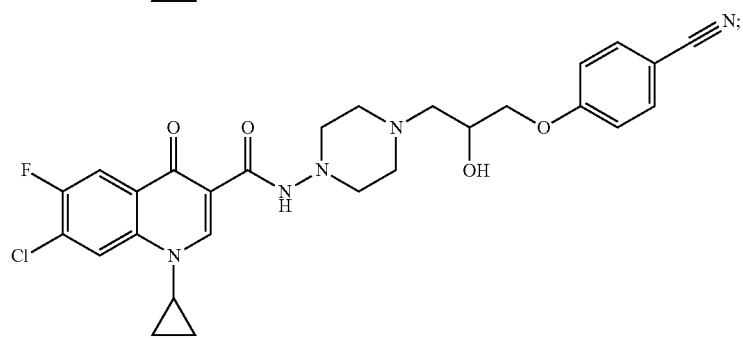
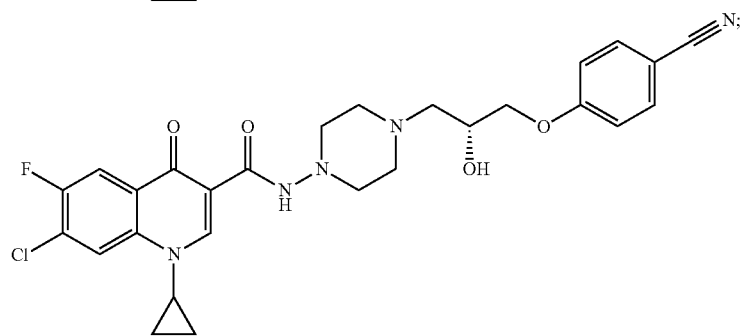

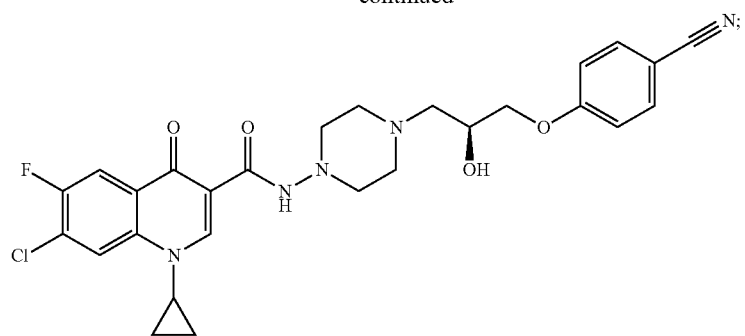
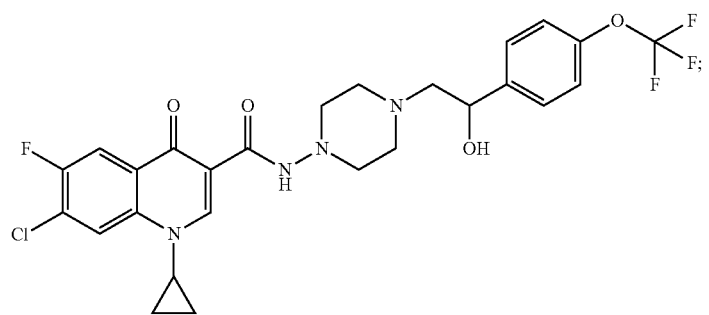
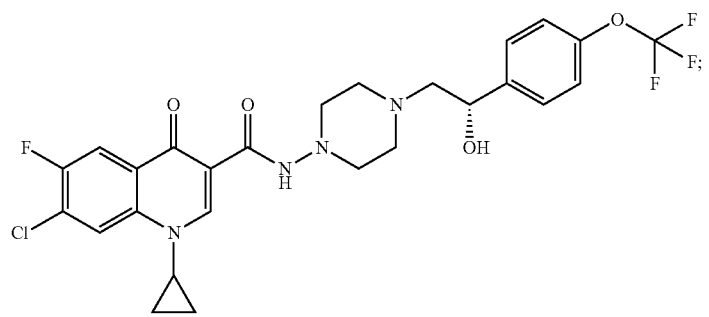
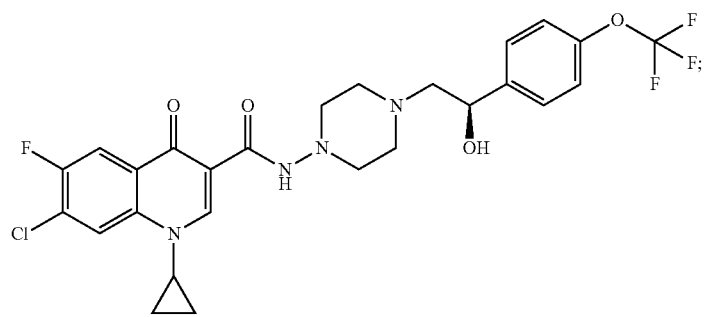
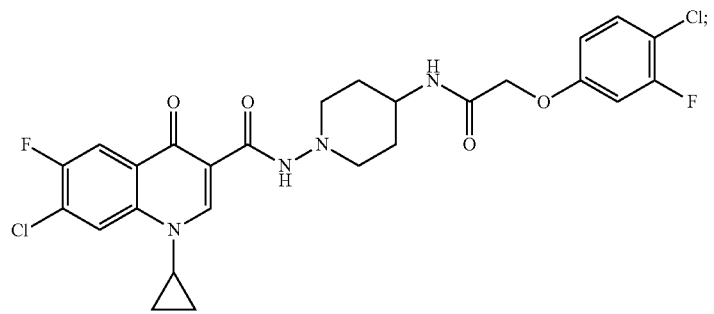

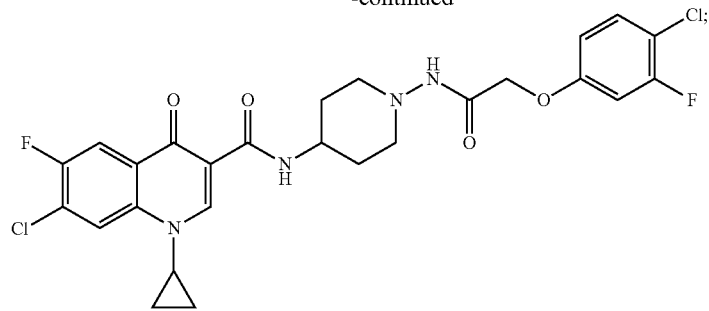
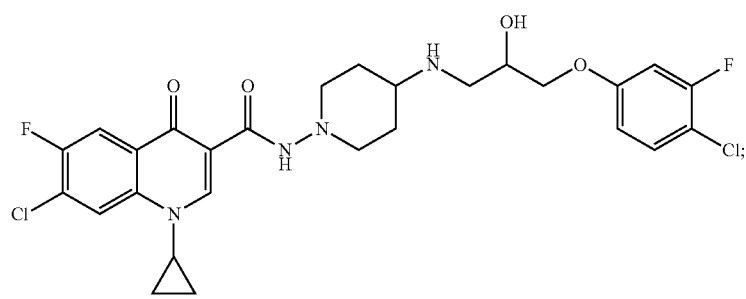
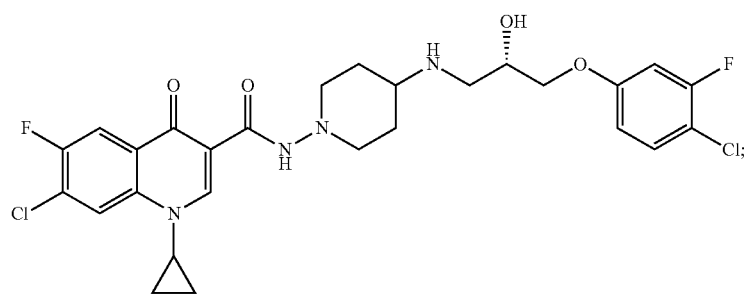
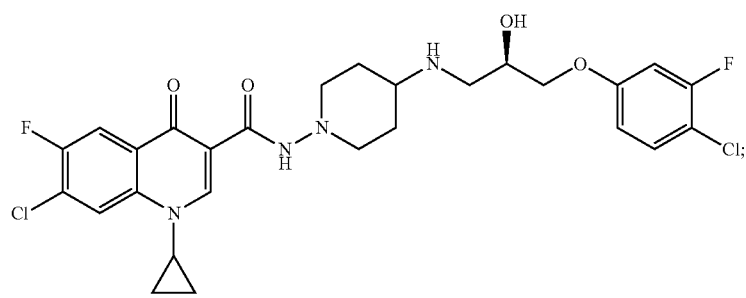
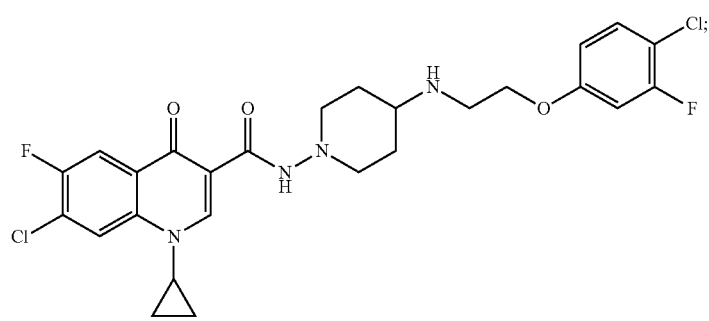

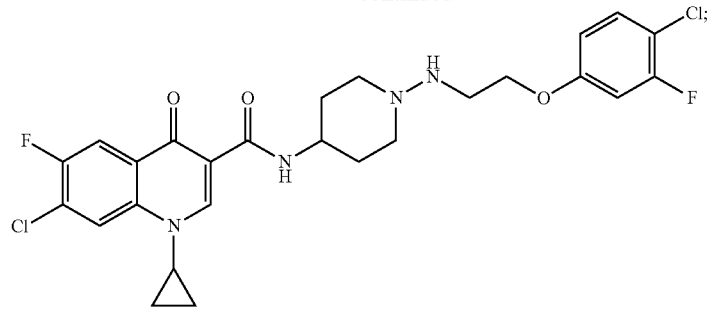
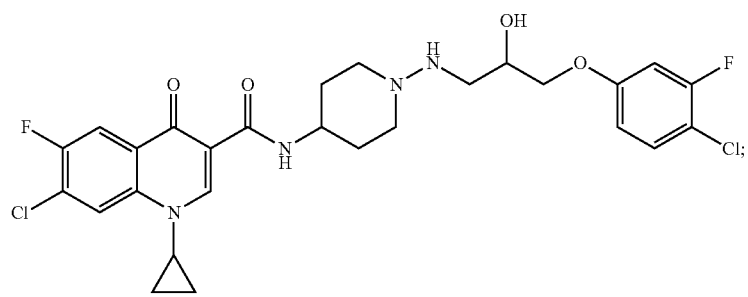
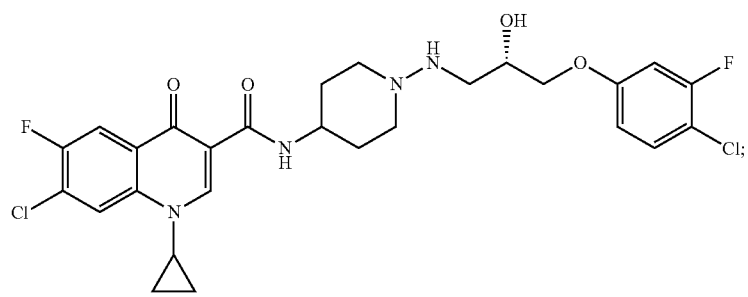
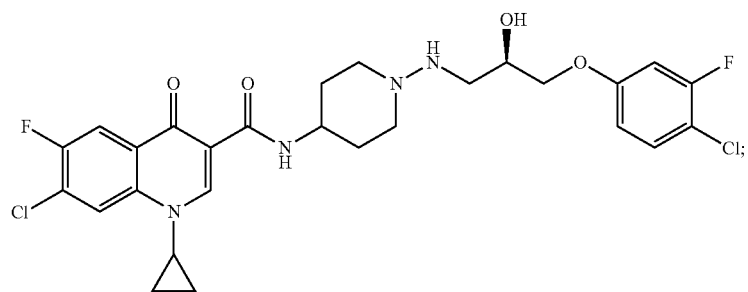
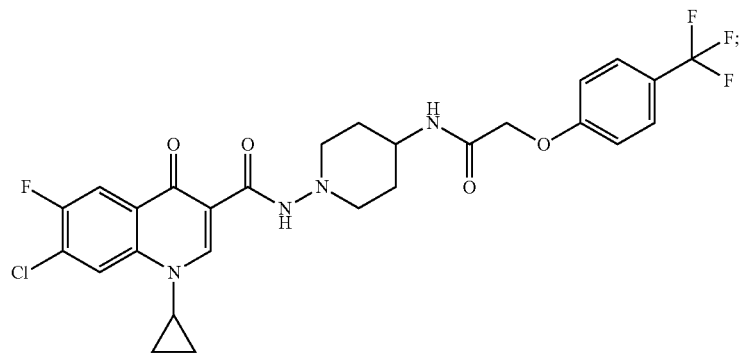

-continued
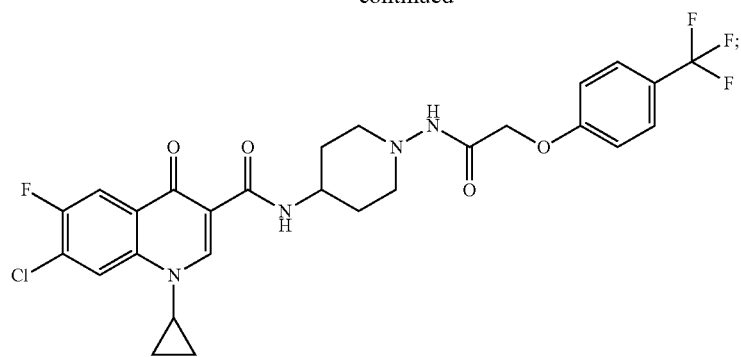
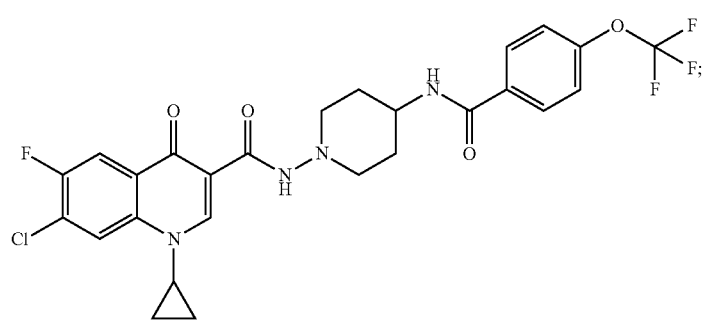
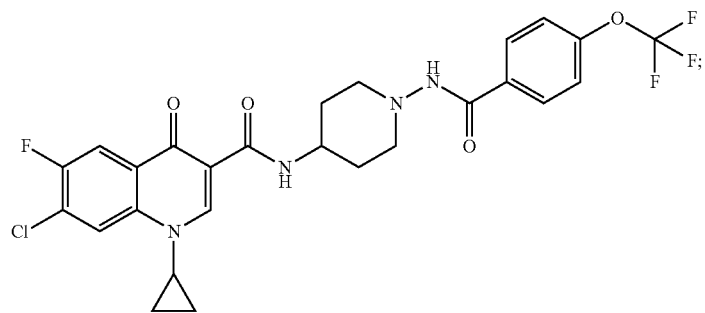
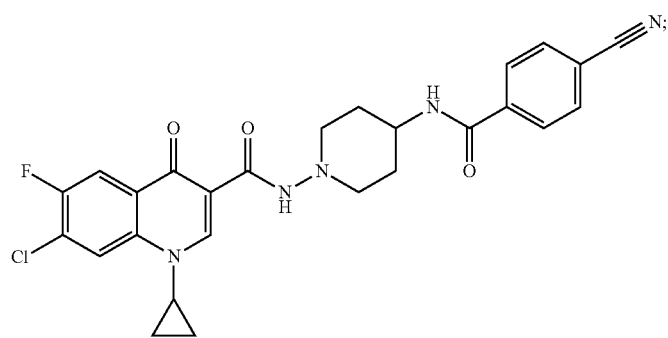
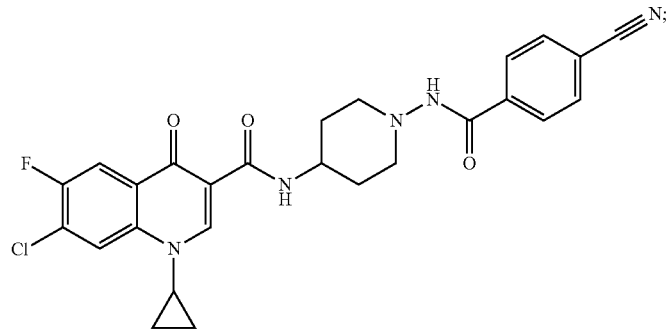

-continued
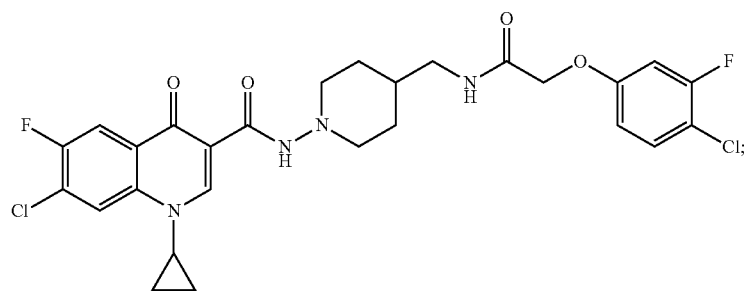
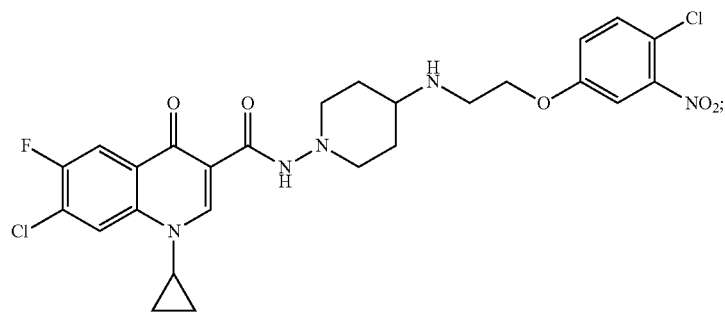
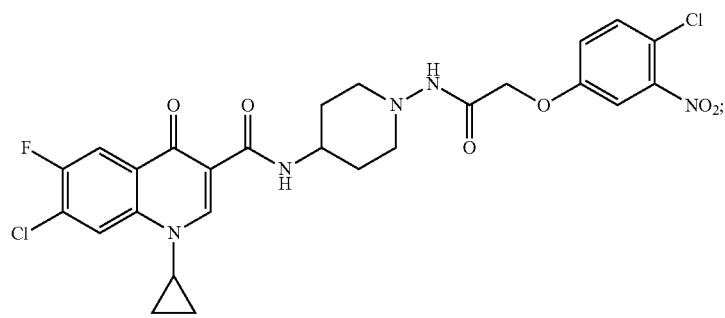
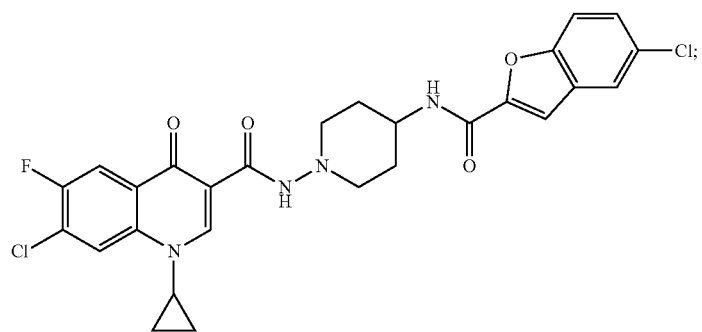
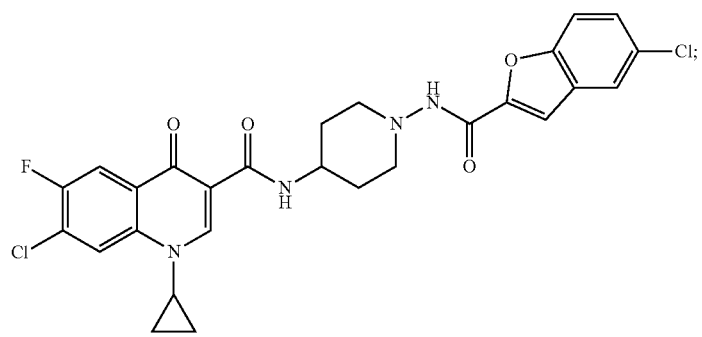

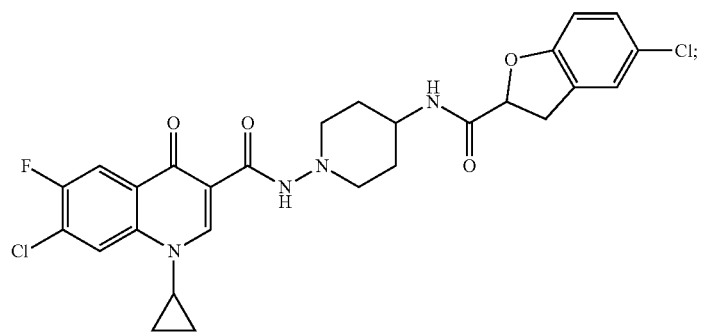
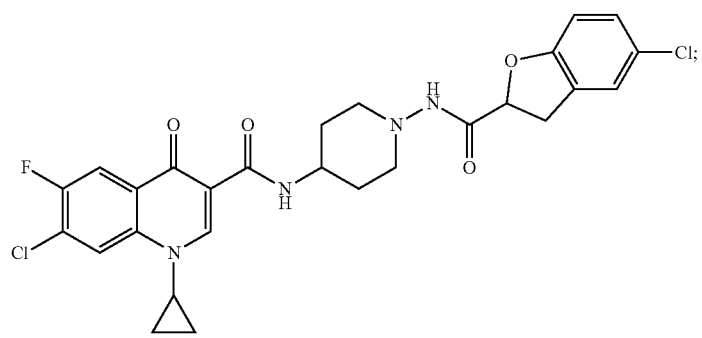
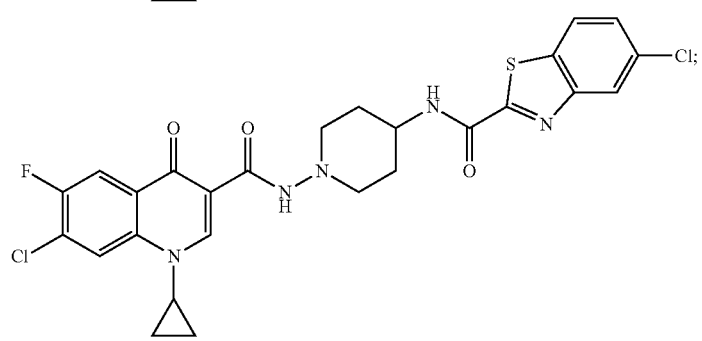
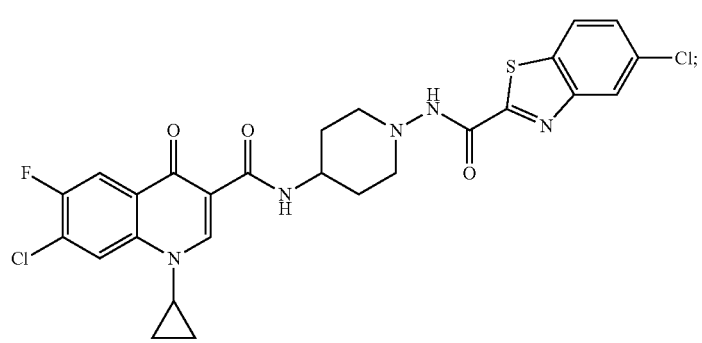
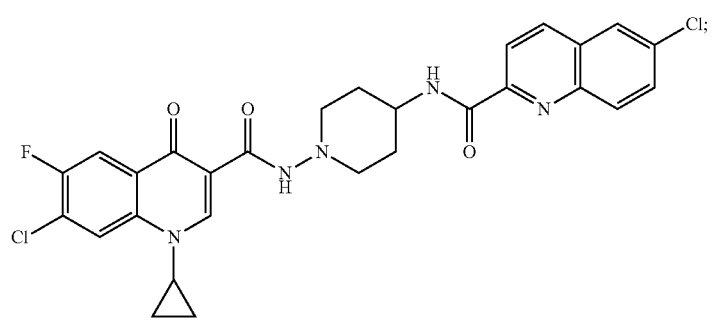

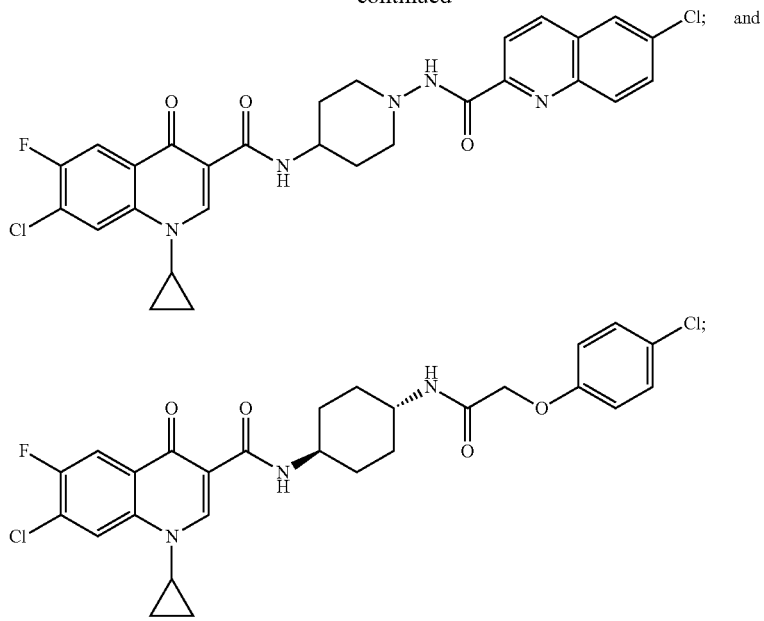

or a salt thereof.

19. A pharmaceutical composition comprising a compound of any one of the preceding claims, or a pharmaceutically acceptable salt thereof, and a pharmaceutically acceptable carrier.

20. A method of producing a protein, comprising contacting a eukaryotic cell comprising a nucleic acid encoding the protein with the compound or salt of claim 1.

21. The method of claim 20, comprising culturing the cell in an in vitro culture medium comprising the compound or salt.

22. A method of culturing a eukaryotic cell comprising a nucleic acid encoding a protein, comprising contacting the eukaryotic cell with an in vitro culture medium comprising a compound or salt of claim 1.

23. The method of claim 20, wherein the nucleic acid encoding the protein is a recombinant nucleic acid.

24. The method of claim 20, wherein the cell is a human embryonic kidney (HEK) cell or a Chinese hamster ovary (CHO) cell.

25. A method of producing a protein, comprising contacting a cell-free protein synthesis (CFPS) system comprising eukaryotic initiation factor 2 (eIF2) and a nucleic acid encoding a protein with the compound or salt of claim 1.

26. The method of claim 20, wherein the protein is an antibody or a fragment thereof.

27. The method of claim 20, comprising purifying the protein.

28. An in vitro cell culture medium, comprising the compound or salt of claim 1 and nutrients for cellular growth.

29. The cell culture medium of claim 28, comprising a eukaryotic cell comprising a nucleic acid encoding a protein.

30. The cell culture medium of claim 28, further comprising a compound for inducing protein expression.

31. The cell culture medium of claim 28, wherein the nucleic acid encoding the protein is a recombinant nucleic acid.

32. The cell culture medium of claim 28, wherein the protein is an antibody or a fragment thereof.

33. The cell culture medium of claim 28, wherein the eukaryotic cell is a human embryonic kidney (HEK) cell or a Chinese hamster ovary (CHO) cell.

34. A cell-free protein synthesis (CFPS) system comprising eukaryotic initiation factor 2 (eIF2) and a nucleic acid encoding a protein with the compound or salt of claim 1.

35. The CFPS system of claim 34, comprising a eukaryotic cell extract comprising eIF2.

36. The CFPS system of claim 34, further comprising eIF2B.

37. The CFPS system of claim 34, wherein the protein is an antibody or a fragment thereof.

38. The compound of claim 16, or salt thereof, wherein the compound is

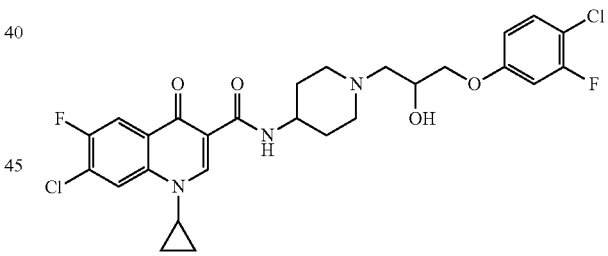

or a salt thereof.

39. The compound of claim 16, or salt thereof, wherein the compound is

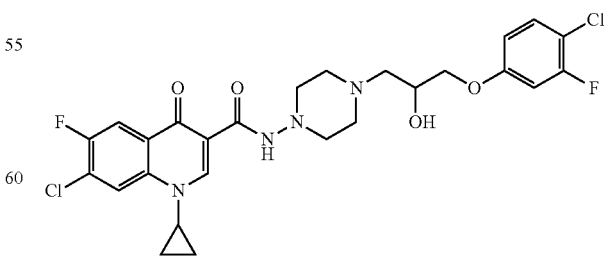

or a salt thereof.

40. The compound of claim 17, or salt thereof, wherein the compound is

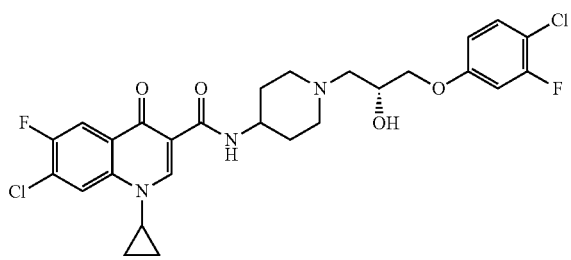 [SMILES: O=C(NC1CCN(C[C@@H](O)COc2ccc(Cl)c(F)c2)CC1)c1cn(C2CC2)c2cc(Cl)c(F)cc2c1=O]

or a salt thereof.

41. The compound of claim 17, or salt thereof, wherein the compound is

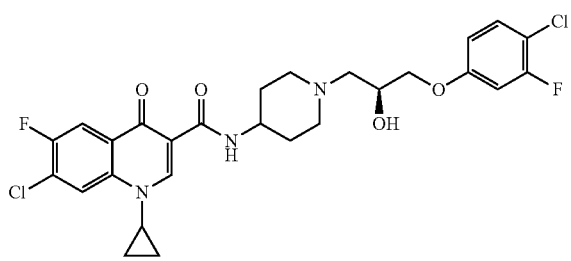 [SMILES: O=C(NC1CCN(C[C@H](O)COc2ccc(Cl)c(F)c2)CC1)c1cn(C2CC2)c2cc(Cl)c(F)cc2c1=O]

or a salt thereof.

42. The compound of claim 17, or salt thereof, wherein the compound is

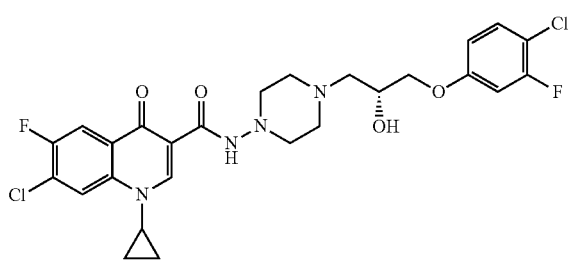 [SMILES: O=C(NN1CCN(C[C@@H](O)COc2ccc(Cl)c(F)c2)CC1)c1cn(C2CC2)c2cc(Cl)c(F)cc2c1=O]

or a salt thereof.

43. The compound of claim 17, or salt thereof, wherein the compound is

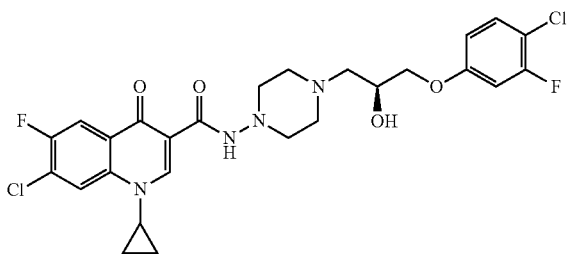 [SMILES: O=C(NN1CCN(C[C@H](O)COc2ccc(Cl)c(F)c2)CC1)c1cn(C2CC2)c2cc(Cl)c(F)cc2c1=O]

or a salt thereof.

44. The compound of claim 18, or salt thereof, wherein the compound is

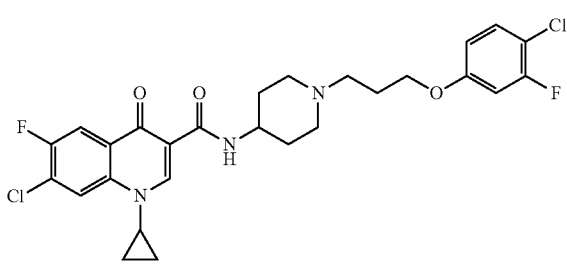 [SMILES: O=C(NC1CCN(CCCOc2ccc(Cl)c(F)c2)CC1)c1cn(C2CC2)c2cc(Cl)c(F)cc2c1=O]

or a salt thereof.

45. The compound of claim 18, or salt thereof, wherein the compound is

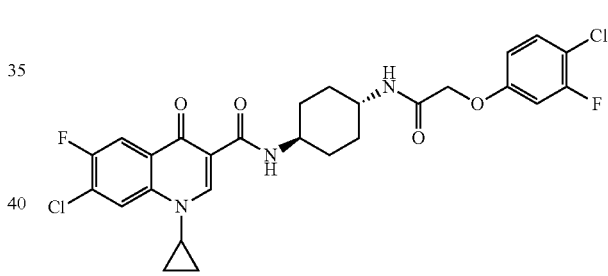

or a salt thereof.

* * * * *